(12) United States Patent
Melvin, Jr. et al.

(10) Patent No.: US 8,088,771 B2
(45) Date of Patent: Jan. 3, 2012

(54) CYCLOALKYLIDENE AND HETEROCYCLOALKYLIDENE INHIBITOR COMPOUNDS

(75) Inventors: Lawrence S. Melvin, Jr., Longmont, CO (US); Michael Graupe, Pacifica, CA (US); Chandrasekar Venkataramani, Redwood City, CA (US); Juan A. Guerrero, Concord, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 12/510,809

(22) Filed: Jul. 28, 2009

(65) Prior Publication Data

US 2010/0022543 A1    Jan. 28, 2010

Related U.S. Application Data

(60) Provisional application No. 61/084,081, filed on Jul. 28, 2008.

(51) Int. Cl.
  *A61K 31/5377* (2006.01)
  *A61K 31/4178* (2006.01)
  *A61K 31/4965* (2006.01)
  *A61K 31/497* (2006.01)
  *C07D 405/14* (2006.01)
  *C07D 417/14* (2006.01)

(52) U.S. Cl. ............. 514/236.8; 514/253.1; 514/255.05; 514/397; 544/133; 544/364; 544/405; 548/311.1

(58) Field of Classification Search .................. None
  See application file for complete search history.

(56) References Cited

U.S. PATENT DOCUMENTS

| | | | |
|---|---|---|---|
| 5,760,246 A | 6/1998 | Biller et al. | 548/309.7 |
| 6,403,588 B1 | 6/2002 | Hayakawa et al. | 514/249 |
| 7,253,204 B2 | 8/2007 | Delorme et al. | 514/422 |
| 2002/0168761 A1 | 11/2002 | Gour et al. | 435/325 |
| 2004/0006011 A1 | 1/2004 | Gour et al. | 514/9 |
| 2005/0054850 A1 | 3/2005 | Wu et al. | 544/238 |
| 2005/0187266 A1 | 8/2005 | Su | 514/359 |
| 2005/0234066 A1 | 10/2005 | Bailey et al. | 514/252.03 |
| 2005/0288282 A1 | 12/2005 | Delorme et al. | 514/228.2 |
| 2006/0293320 A1 | 12/2006 | Schmitz et al. | 514/233.2 |
| 2007/0093492 A1 | 4/2007 | Jiaang et al. | 514/249 |
| 2007/0213330 A1 | 9/2007 | Delorme et al. | 514/235.5 |
| 2009/0005374 A1 | 1/2009 | Melvin et al. | 514/233 |
| 2009/0076021 A1 | 3/2009 | Plato | 514/252 |
| 2010/0009990 A1 | 1/2010 | Venkataramani | 514/233.2 |
| 2010/0022543 A1 | 1/2010 | Melvin et al. | 514/236.8 |
| 2010/0029638 A1 | 2/2010 | Melvin et al. | 514/233.2 |
| 2010/0310500 A1 | 12/2010 | Graupe et al. | |
| 2010/0311794 A1 | 12/2010 | Venkataramani | |

FOREIGN PATENT DOCUMENTS

| | | | |
|---|---|---|---|
| CA | 2644933 | 9/2007 | 184/46 |
| EP | 0847992 A1 | 6/1998 | |
| EP | 1 277 754 | 1/2003 | |
| JP | 2003-313126 | 11/2003 | |
| JP | 2004-002826 | 1/2004 | |
| JP | 2007-001885 | 1/2007 | |
| WO | WO 97/26240 | 7/1997 | |
| WO | WO-00/18733 A1 | 4/2000 | |
| WO | WO 01/14375 | 3/2001 | |
| WO | WO 01/19788 | 3/2001 | |
| WO | WO-01/53331 A2 | 7/2001 | |
| WO | WO 01/56989 | 8/2001 | |
| WO | WO 01/83481 | 8/2001 | |
| WO | WO 02/00651 | 1/2002 | |
| WO | WO 02/26712 | 4/2002 | |
| WO | WO 02/34748 | 5/2002 | |
| WO | WO 02/46170 | 6/2002 | |
| WO | WO 02/065979 | 8/2002 | |
| WO | WO 02/066480 | 8/2002 | |
| WO | WO 02/066481 | 8/2002 | |
| WO | WO 03/000682 | 1/2003 | |
| WO | WO 03/000689 | 1/2003 | |
| WO | WO 03/002524 | 1/2003 | |
| WO | WO 03/031446 | 4/2003 | |
| WO | WO 03/041649 | 5/2003 | |
| WO | WO 03/084948 | 10/2003 | |
| WO | WO 03/084997 | 10/2003 | |
| WO | WO 03/099221 | 12/2003 | |
| WO | WO 03/099817 | 12/2003 | |
| WO | WO-03/103151 A1 | 12/2003 | |
| WO | WO 2004/021989 | 3/2004 | |
| WO | WO 2004/035525 | 4/2004 | |
| WO | WO 2004/039325 | 5/2004 | |

(Continued)

OTHER PUBLICATIONS

Termin et al., caplus an 2003:57901.* U.S. Appl. No. 61/185,126, filed Jun. 8, 2009, Gaupe et al.
U.S. Appl. No. 61/185,134, filed Jun. 8, 2009, Gaupe et al.
Acharya et al., "Rational Development of Histone Deacetylase Inhibitors as Anticancer Agents: A Review", *Molecular Pharmacology*, 2005, 68:917-932.
Alam et al., "Synthesis and SAR of aminopyridines as novel c-Jun N-terminal kinase (JNK) inhibitors", *Bioorg. Med. Chem. Lett.*, 2007, 17:3463-3467.

(Continued)

*Primary Examiner* — Sun Jae Loewe
(74) *Attorney, Agent, or Firm* — J. Elin Hartrum

(57) ABSTRACT

The present invention provides a compound of general Formula (I) having histone deacetylase (HDAC) inhibitory activity, a pharmaceutical composition comprising the compound, and a method useful to treat diseases using the compound.

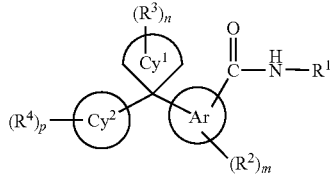

Formula (I)

9 Claims, No Drawings

FOREIGN PATENT DOCUMENTS

| WO | WO 2004/041191 | 5/2004 |
| --- | --- | --- |
| WO | WO 2004/048343 | 6/2004 |
| WO | WO-2004/060318 A2 | 7/2004 |
| WO | WO 2004/069133 | 8/2004 |
| WO | WO 2004/069803 | 8/2004 |
| WO | WO 2004/076452 | 9/2004 |
| WO | WO 2004/080390 | 9/2004 |
| WO | WO 2004/084901 | 10/2004 |
| WO | WO 2004/092115 | 10/2004 |
| WO | WO 2004/092145 | 10/2004 |
| WO | WO 2004/110350 | 12/2004 |
| WO | WO 2005/006945 | 1/2005 |
| WO | WO 2005/030140 | 4/2005 |
| WO | WO-2005/030705 A1 | 4/2005 |
| WO | WO 2005/046594 | 5/2005 |
| WO | WO-2005/054850 A2 | 6/2005 |
| WO | WO 2005/060571 | 7/2005 |
| WO | WO-2005/070180 A2 | 8/2005 |
| WO | WO 2005/077368 | 8/2005 |
| WO | WO 2005/077373 | 8/2005 |
| WO | WO 2005/082871 | 9/2005 |
| WO | WO 2005/092899 | 10/2005 |
| WO | WO 2005/102318 | 11/2005 |
| WO | WO 2005/102325 | 11/2005 |
| WO | WO-2005/102326 A2 | 11/2005 |
| WO | WO 2005/102346 | 11/2005 |
| WO | WO 2005/102455 | 11/2005 |
| WO | WO 2005/103022 | 11/2005 |
| WO | WO 2005/112920 | 12/2005 |
| WO | WO 2005/115304 | 12/2005 |
| WO | WO 2005/115385 | 12/2005 |
| WO | WO 2006/010750 | 2/2006 |
| WO | WO 2006/038001 | 4/2006 |
| WO | WO 2006/044509 | 4/2006 |
| WO | WO 2006/058007 | 6/2006 |
| WO | WO 2006/058905 | 6/2006 |
| WO | WO-2006/064251 A1 | 6/2006 |
| WO | WO 2006/070943 | 7/2006 |
| WO | WO 2006/077401 | 7/2006 |
| WO | WO 2006/108059 | 10/2006 |
| WO | WO 2006/104983 | 11/2006 |
| WO | WO 2006/122011 | 11/2006 |
| WO | WO 2007/008664 | 1/2007 |
| WO | WO 2007/026251 | 3/2007 |
| WO | WO 2007/030362 | 3/2007 |
| WO | WO 2007/036732 | 4/2007 |
| WO | WO 2007/037187 | 4/2007 |
| WO | WO-2007/040440 A1 | 4/2007 |
| WO | WO 2007/055941 | 5/2007 |
| WO | WO 2007/076034 | 7/2007 |
| WO | WO 2007/076035 | 7/2007 |
| WO | WO 2007/079185 | 7/2007 |
| WO | WO 2007/087129 | 8/2007 |
| WO | WO 2007/087717 | 8/2007 |
| WO | WO-2007/093492 A1 | 8/2007 |
| WO | WO 2007/095124 | 8/2007 |
| WO | WO 2007/106192 | 8/2007 |
| WO | WO 2007/100795 | 9/2007 |
| WO | WO-2007/127137 A2 | 11/2007 |
| WO | WO 2007/135036 | 11/2007 |
| WO | WO 2008/033743 | 3/2008 |
| WO | WO 2009/002534 | 12/2008 |
| WO | WO 2009/079391 | 6/2009 |
| WO | WO 2010/009139 | 1/2010 |
| WO | WO 2010/009155 | 1/2010 |
| WO | WO 2010/009166 | 1/2010 |
| WO | WO 2010/014611 | 2/2010 |

OTHER PUBLICATIONS

Buggy et al,. "CRA-024781: a novel synthetic inhibitor of histone deacetylase enzymes with antitumor activity in vitro and in vivo", *Mol. Cancer Ther.*, 2006, 5:1309-1317.

Bush & McKinsey, "Targeting Histone Deacetylases for Heart Failure," *Expert Opin. Ther. Targets*, 2009, 13(7): 767-784.

Feng et al., "Synthesis and SAR of 2-(4-fluorophenyl)-3-pyrimidin-4-ylimidazo[1,2-α]pyridine derivatives as anticoccidial agents", *Bioorg. Med. Chem. Lett.*, 2006, 5978-5981.

Gudmundsson et al., "Imidazo[1,2-α]pyridines with potent activity against herpesviruses", *Bioorg. Med. Chem. Lett.*, 2007, 17:2735-2739.

Hayakawa et al., "Synthesis and biological evaluation of imidazo[1,2-α]pyridine derivatives as novel PI3 kinase p110α inhibitors", *Bioorg. Med. Chem. Lett.*, 2007, 15:403-412.

Liang et al., "Synthesis and SAR studies of potent imidazopyridine anticoccidial agents", *Bioorg. Med. Chem. Lett.*, 2007, 17:3558-3561.

Mahboobi et al., "2-Aroylindoles and ω-Aroylbenzofurans with N-Hydroxyacrylamide Substructures as a Novel Series of Rationally Designed Histone Deacetylase Inhibitors," *J. Chem. Soc.*, 2007, 50(18): 4405-4418.

Marcou et al., "Optimizing Fragment and Scaffold Docking by Use of Molecular Interaction Fingerprints", *J. Chem. Inf. Model*, 2007, 47(1):195-207.

Moradei et al., "Histone Deacetylase Inhibitors: Latest Developments, Trends, and Prospects", *Current Med. Chem.—Anti-Cancer Agents*, 2005, 529-560.

Paris et al., "Histone Deacetylase Inhibitors: From Bench to Clinic", *J. Med. Chem*, 2008, 51(6):1505-1529.

Park et al., "A Simple and Efficient Docking Method to the Cyclin-Dependent Kinase 2", *Bull. Korean Chem. Soc.*, 2007, 28(2):211-219.

Price et al., "Histone deacetylase inhibitors: an analysis of recent patenting activity", *Expert Opinion, Ther. Patents*, 2007, 745-765.

Rosato et al., *Cancer Research*, 2003, 63:3637-3645.

Vadivelan et al., "Virtual Screening Studies to Design Potent CDK2-Cyclin A Inhibitors", *J. Chem. Inf. Model*, 2007, 47(4): 1526-1535.

Vigushin et al., "Targeted Histone Deacetylase Inhibition for Cancer Therapy", *Current Cancer Drug Targets*, 2004, 4(2):205-218.

International Search Report, dated Oct. 1, 2008, issued in PCT/US2008/007963.

International Search Report, dated Mar. 23, 2009, issued in PCT/US2008/086643.

International Search Report, dated Oct. 2, 2009, issued in PCT/US2009/051964.

International Search Report, dated Oct. 12, 2009, issued in PCT/US2009/050558.

International Search Report, dated Nov. 11, 2009, issued in PCT/US2009/050577.

International Search Report and Written Opinion, dated Nov. 18, 2009, issued in PCT/US2009/050595.

Office Action for Election/Restrictions, dated Jan. 22, 2010, issued in U.S. Appl. No. 12/146,894.

Arbiser, J.L. (2007) "Why Targeted Therapy Hasn't Worked in Advanced Cancer", *The Journal of Clinical Investigation*, vol. 17, No. 10 pp. 2762-2765.

Fischer, B. et al. (2007) "Targeting Receptor Tyrosine Kinase Signalling in Small Cell Lung Cancer (SCLC): What Have We Learned So Far?", *Cancer Treatment Reviews*, vol. 33, pp. 391-406.

International Search Report for PCT/US2009/051964, International Filing Date Jul. 28, 2009, mailed Oct. 2, 2009.

International Search Report for PCT/US2010/037647, International Filing Date Jun. 7, 2010, mailed Nov. 9, 2010.

Madhusudan, S. et al. (2004) "Tyrosine Kinase Inhibitors in Cancer Therapy", *Clinincal Biochemistry*, vol. 37, 00.618-635.

U.S. Office Action for U.S. Appl. No. 12/747,159, mailed Dec. 10, 2010.

U.S. Appl. No. 12/943,799, filed Nov. 10, 2010.

Lee, M. et al. (2003) "Molecular Targets for Cell Cycle Inhibition and Cancer Therapy", *Expert opinion on Therapeutic Patents*. 13(3):329-346.

* cited by examiner

CYCLOALKYLIDENE AND HETEROCYCLOALKYLIDENE INHIBITOR COMPOUNDS

CROSS REFERENCE TO RELATED APPLICATION

This application claims the benefit of U.S. provisional application Ser. No. 61/084,081 filed Jul. 28, 2008. The disclosure of the application is hereby incorporated by reference.

FIELD

The present invention generally relates to a compound having enzyme inhibitory activity, pharmaceutical compositions comprising the compound, and methods useful for treating diseases.

BACKGROUND

Histones are protein components making up chromatin in association with DNA. Histones are subject to covalent modifications of various enzymes such as, for example, histone deacetylase (HDAC), histone methyltransferase (HMT) and histone acetyltransferase (HAT). Covalent modifications of core histones influence protein-protein interaction and protein access to DNA.

HDACs catalyze deacetylation of lysine residues on histones and other proteins. It is known that low levels of histone-acetylation are associated with repression of gene expression. Therefore, abnormal HDAC activities could destroy the delicate balance in cell regulation. The HDACs belong to four structurally and functionally different phylogenetic classes: class I (HDAC-1, -2, -3, and -8) compounds are closely related to yeast RPD3; class IIa (HDAC-4, -5, -7, and -9) and class IIb (HDAC-6 and -10) share domains with yeast HDAC-1; class IV, recently described (comprising HDAC-11), exhibits properties of both class I and class II HDACs. All the above HDACs are zinc dependent proteases. Class III HDACs have been identified on the basis of sequence similarity with Sir2, a yeast transcription repressor, and require the cofactor NAD$^+$ for their deacetylase function. See, for example, Marielle Paris et al., *Histone Deacetylase Inhibitors: From Bench to Clinic*, JOURNAL OF MEDICINAL CHEMISTRY 51(11): 3330-3330 (2008).

It has been reported that HDAC activities play an important role in a variety of human disease states. Accordingly, an HDAC inhibitor can provide therapeutic benefits to a broad range of patients. Due to the therapeutic significance, various types of HDAC inhibitors have been developed to date. See, for example, Moradei et al., *Histone Deacetylase Inhibitors: Latest Developments, Trends, and Prospects*, CURR. MED. CHEM.: ANTI-CANCER AGENTS 5(5):529-560 (2005).

WO 2005/092899 mentions a series of compounds useful for inhibiting HDAC enzymatic activity where the compounds are amino or hydroxyl substituted aniline derivatives attached to various cyclic groups.

There is a continued need to develop new inhibitors to provide appropriate therapy for a variety of disease conditions implicated in HDAC activity.

SUMMARY

In various embodiments, a compound having HDAC inhibitory activity, a composition comprising the compound, and a method useful to treat diseases arising from abnormal cell proliferation or differentiation are provided.

The compound is of Formula (I) or a pharmaceutically acceptable salt thereof:

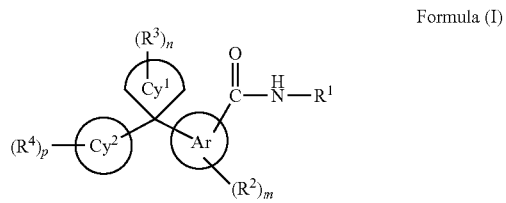

Formula (I)

wherein
$Cy^1$ is cycloalkylidene or heterocycloalkylidene;
$Cy^2$ is cycloalkyl, aryl or heterocyclyl;
Ar is aryl or heteroaryl;
m is an integer from 0 to the maximum number of substitutable positions on Ar;
n is an integer from 0 to the maximum number of substitutable positions on $Cy^1$;
p is an integer equal to the number of substitutable positions on $Cy^2$, wherein a substitutable position is one that, based on the valence of the ring atom occupying the position, can contain H or other substituent. Carbon ring atoms are substitutable, while O and S ring atoms are not substitutable. N ring atoms are substitutable or not, depending on valence. Further, the ring position of $Cy^2$ occupied by $Cy^1$ is not substitutable;
$R^1$ is hydroxyl, aryl or heteroaryl, wherein aryl or heteroaryl is substituted with —$NH_2$ or —OH and aryl or heteroaryl is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl;
each $R^2$ is independently selected from the group consisting of hydroxyl, oxo, halo, nitro, cyano, trifluoromethyl, trifluoromethoxy, amino, carboxyl, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—($C_{1-10}$ alkyl)amino, N,N—($C_{1-10}$ alkyl)$_2$ amino, $C_{1-10}$ alkanoylamino, N—($C_{1-10}$ alkyl)carbamoyl, N,N—($C_{1-10}$ alkyl)$_2$ carbamoyl, $C_{1-10}$ alkyl-S(O)$_a$ wherein a is 0, 1 or 2, $NH_2$—S(O)$_2$NH—, N—($C_{1-10}$ alkyl)sulphamoyl, N,N—($C_{1-10}$ alkyl)$_2$sulphamoyl, cycloalkyl, heterocyclyl and aryl;
each $R^3$ is independently selected from the group consisting of hydroxyl, oxo, halo, nitro, cyano, trifluoromethyl, trifluoromethoxy, amino, carboxyl, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—($C_{1-10}$ alkyl)amino, N,N—($C_{1-10}$ alkyl)$_2$ amino, $C_{1-10}$ alkanoylamino, N—($C_{1-10}$ alkyl)carbamoyl, N,N—($C_{1-10}$ alkyl)$_2$ carbamoyl, $C_{1-10}$ alkyl-S(O)$_a$ wherein a is 0, 1 or 2, $NH_2$—S(O)$_2$NH—, N—($C_{1-10}$ alkyl)sulphamoyl, N,N—($C_{1-10}$ alkyl)$_2$sulphamoyl, cycloalkyl, heterocyclyl and aryl, wherein each $R^3$ is optionally substituted by one or more A where such an optional substitution is chemically feasible; and alternatively or in addition two groups $R^3$ are substituted on the same carbon ring atom of $Cy^1$ and together with the carbon ring atom of $Cy^1$ form a ring situated on $Cy^1$ in a spiro configuration; in various embodiments the spiro-ring on $Cy^1$ is cycloalkyl or heterocycloalkyl, containing from 3 to 7 ring atoms, and is optionally substituted by one or more A;

each $R^4$ is independently selected from the group consisting of H, halo, nitro, cyano, hydroxyl, oxo, hydroxy ($C_{1-10}$ alkyl), amino($C_{1-10}$ alkyl), haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, hydroxy($C_{1-10}$ alkoxy)($C_{1-10}$ alkoxy), ($C_{1-10}$ alkoxy)($C_{1-10}$ alkoxy), ($C_{1-10}$ alkoxy)($C_{1-10}$ alkyl), $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, NH$_2$—S(O)$_2$NH—, NH$_2$—CO—NH—, N—($C_{1-10}$ alkyl)sulphamoyl, N,N—($C_{1-10}$ alkyl)$_2$sulphamoyl, aryl, arylalkyl, aryloxy, arylthio, cycloalkyl, cycloalkylalkyl, cycloalkyloxy, heterocyclyl, heterocyclylalkyl, heterocyclyl(C=O)—, heterocyclyloxy and heterocyclylthio, wherein if $R^4$ is not aryl, cycloalkyl or heterocyclyl, each $R^4$ is optionally substituted by one or more B where such an optional substitution is chemically feasible, and if $R^4$ is aryl, cycloalkyl or heterocyclyl, $R^4$ is optionally further substituted by one or more $R^5$ where such an optional substitution is chemically feasible, or when p is 2 or greater, two $R^4$ groups together can form a 5- or 6-membered cyclic moiety to make a fused ring with $Cy^2$ ring, wherein the cyclic moiety can contain one or more heteroatoms selected from N, O and S and the fused ring is optionally substituted by one or more $R^5$ where such an optional substitution is chemically feasible;

each $R^5$ is independently selected from halo, nitro, cyano, hydroxyl, oxo, hydroxy($C_{1-10}$ alkyl), amino($C_{1-10}$ alkyl), haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, hydroxy($C_{1-10}$ alkoxy)($C_{1-10}$ alkoxy), ($C_{1-10}$ alkoxy)($C_{1-10}$ alkoxy), ($C_{1-10}$ alkoxy)($C_{1-10}$ alkyl), $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, NH$_2$—S(O)$_2$NH—, NH$_2$—CO—NH—, N—($C_{1-10}$ alkyl)sulphamoyl, N,N—($C_{1-10}$ alkyl)$_2$sulphamoyl, aryl, arylalkyl, aryloxy, arylthio, cycloalkyl, cycloalkylalkyl, cycloalkyloxy, heterocyclyl, heterocyclylalkyl, heterocyclyl(C=O)—, heterocyclyloxy and heterocyclylthio, wherein each $R^5$ is optionally substituted by one or more D where such an optional substitution is chemically feasible; and A, B and D are independently selected from halo, nitro, cyano, hydroxyl, oxo, hydroxyalkyl, haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, N—($C_{1-10}$ alkyl)sulphamoyl, N,N—($C_{1-10}$ alkyl)$_2$sulphamoyl, H$_2$NS(O)$_2$NH—, N—($C_{1-10}$ alkyl)NHS(O)$_2$NH—, N,N—($C_{1-10}$ alkyl)$_2$NS(O)$_2$NH—, aryl, aryloxy, arylthio, cycloalkyl, cycloalkyloxy, heterocyclyl, heterocyclyl(C=O)—, heterocyclyloxy and heterocyclylthio.

Pharmaceutical compositions comprise an HDAC-inhibitory effective amount of one or more compounds described herein and a pharmaceutically-acceptable carrier.

Methods of inhibiting or treating diseases arising from abnormal cell proliferation and differentiation comprise administering to a subject a therapeutically effective amount of one or more compounds described herein. Other methods involve co-therapies by administering one or more of the compounds together with other anti-cancer agents.

The compounds above are more fully described in the detailed description that follows.

DETAILED DESCRIPTION

The following description is merely exemplary in nature and is not intended to limit the present disclosure, application, or uses.

Definitions

"Alkenyl" refers to a straight or branched hydrocarbyl group with at least one site of unsaturation, i.e. a carbon-carbon, sp$^2$ double bond. In an embodiment, alkenyl has from 2 to 12 carbon atoms. In some embodiments, alkenyl is a $C_2$-$C_{10}$ alkenyl group or a $C_2$-$C_6$ alkenyl group. Examples of alkenyl group include, but are not limited to, ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkanoyl" is the group RC(O)—; "alkanoyloxy" is RC(O)O—; and "alkanoylamino" is RC(O)NR'—; where R is an alkyl group as defined herein, and R' is H or alkyl. In various embodiments, R is a $C_1$-$C_{10}$ alkyl group or a $C_1$-$C_6$ alkyl group.

"Alkoxy" is RO— where R is alkyl. Non-limiting examples of alkoxy groups include methoxy, ethoxy and propoxy.

"Alkoxyalkyl" refers to an alkyl moiety substituted with an alkoxy group. Examples of alkoxyalkyl groups include methoxymethyl, methoxyethyl, methoxypropyl and ethoxyethyl.

"Alkoxycarbonyl" is ROC(O)—, where R is an alkyl group as defined herein. In various embodiments, R is a $C_1$-$C_{10}$ alkyl group or a $C_1$-$C_6$ alkyl group.

"Alkyl" refers to a straight or branched chain saturated hydrocarbyl group. In an embodiment, alkyl has from 1 to 12 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

"Alkylamino" refers to an amino group substituted with one or more alkyl groups. "N-(alkyl)amino" is RNH— and "N,N-(alkyl)$_2$amino" is R$_2$N—, where the R groups are alkyl as defined herein and are the same or different. In various embodiments, R is a $C_1$-$C_{10}$ alkyl group or a $C_1$-$C_6$ alkyl group. Examples of alkylamino groups include methylamino, ethylamino, propylamino, butylamino, dimethylamino, diethylamino, and methylethylamino.

"Alkylaminoalkyl" refers to an alkyl moiety substituted with an alkylamino group, wherein alkylamino is as defined herein. Examples of alkylaminoalkyl groups include methylaminomethyl and ethylaminomethyl.

"Alkynyl" refers to a straight or branched carbon-chain group with at least one site of unsaturation, i.e. a carbon-carbon, sp triple bond. In an embodiment, alkynyl has from 2 to 12 carbon atoms. In some embodiments, alkynyl is a $C_2$-$C_{10}$ alkynyl group or a $C_2$-$C_6$ alkynyl group. Examples of alkynyl groups include acetylenic (—C≡CH) and propargyl (—CH$_2$C≡CH).

"Aryl" refers to a monocyclic, bicyclic or tricyclic carbon ring system of up to 7 atoms in each ring, wherein at least one ring is aromatic. In various embodiments, aryl encompasses a ring system of up to 14 carbons atoms. Aryl includes a carbocyclic aromatic ring fused with a 5- or 6-membered cycloalkyl group. Examples of aryl groups include, but are not limited to, phenyl, naphthyl, tetrahydronaphthyl and indanyl.

"Aryloxy" is RO—, where R is aryl. "Arylthio" is RS—, where R is aryl.

"Carbamoyl" is the group NH$_2$—C(O)—; the nitrogen can be substituted with alkyl groups. N-(alkyl)carbamoyl is RNH—C(O)— and N,N-(alkyl)$_2$ carbamoyl is R$_2$N—C(O)—, where the R groups are alkyl as defined herein and are the same or different. In various embodiments, R is a $C_1$-$C_{10}$ alkyl group or a $C_1$-$C_6$ alkyl group.

"Cycloalkyl" is a hydrocarbyl group containing at least one saturated or partially unsaturated ring structure, and attached via a ring carbon. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

"Cycloalkyloxy" is RO—, where R is cycloalkyl.

"Cycloalkylalkyl" refers to an alkyl moiety substituted with a cycloalkyl group, wherein cycloalkyl is as defined herein. Examples of cycloalkylalkyl groups include, but are not limited to, cyclopropylmethyl, cyclobutylmethyl, cyclopentylethyl and cyclohexylmethyl.

"Cycloalkylidene" refers to a divalent group formed from cycloalkane having two substituents on a single carbon of the cycloalkane. It can be represented in illustrative fashion by the following formula,

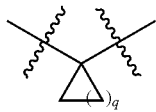

wherein q determines the size of the ring and is one or greater. For example, q=2 makes cyclobutylidene. In various embodiments, cycloalkylidene is a divalent $C_3$-$C_{12}$ cyclic moiety. Examples of cycloalkylidene groups include cyclopropylidene, cyclobutylidene, cyclopentylidene and cyclohexylidene.

"Dialkylamino" refers to an RR'N— group where R and R' are independently alkyl as defined herein. Examples of dialkylamino groups include, but are not limited to, dimethylamino, diethylamino, methylethylamino and methylpropylamino. In various embodiments, R and R' are independently a $C_1$-$C_{10}$ alkyl group or a $C_1$-$C_6$ alkyl group.

"Dialkylaminoalkyl" refers to an alkyl moiety substituted with a dialkylamino group, wherein dialkylamino is as defined herein. Examples of dialkylaminoalkyl groups include, but are not limited to, dimethylaminomethyl and diethylaminomethyl.

"Feasible" refers to a structure or process that is capable of being accomplished; one that is possible, suitable, or logical. When a structure or process is "chemically feasible", that structure or process is synthetically attainable, chemically stable to the typical ambient conditions and/or contributes to favorable biological properties such as efficacy, bioavailability and minimal toxicity for the intended use. Chemically feasible structures are bound by the rules of electron bonding, whereby bonds can only be formed between atoms that are capable of forming bonds with one another. Likewise, chemically feasible processes can only produce structures that are themselves chemically feasible.

"Halo" refers to chloro (—Cl), bromo (—Br), fluoro (—F) or iodo (—I).

"Haloalkoxy" refers to an alkoxy group substituted with one or more halo groups. Examples of haloalkoxy groups include, but are not limited to, —OCF$_3$, —OCHF$_2$ and —OCH$_2$F.

"Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl.

"Haloalkyl" refers to an alkyl moiety substituted with one or more halo groups. Examples of haloalkyl groups include —CF$_3$ and —CHF$_2$.

"Heterocyclyl" includes heteroaryl and heterocycloalkyl defined below and refers to an unsaturated, saturated, or partially unsaturated heterocyclic group. In various embodiments, it is a monocyclic, bicyclic or tricyclic group of 2 to 14 ring-carbon atoms. In addition to ring-carbon atoms, at least one ring has one or more heteroatoms selected from P, N, O and S. In various embodiments, the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

"Heterocyclylalkyl" is an alkyl group substituted with a heterocyclyl.

"Heterocyclyloxy" is RO—, where R is heterocyclyl.
"Heterocyclylthio" is RS—, where R is heterocyclyl.

"Heteroaryl" is a heterocyclyl where at least one ring is aromatic. In various embodiments, it refers to a monocyclic, bicyclic or tricyclic ring having up to 7 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroaryloxy" is RO—, where R is heteroaryl.

"Heterocycloalkyl" is a heterocyclyl where no rings are aromatic.

"Heterocycloalkylidene" refers to a divalent group formed from a heterocyclyl with two substituents on a single ring carbon. It can be represented in illustrative fashion by the formula

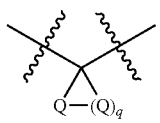

where q determines the size of the ring and is one or greater. Each Q is independently —$CH_2$— or a heteroatom selected from —NH—, —O— and —S—, and when Q is methylene (—$CH_2$—) or imino (—NH—), Q is optionally substituted with a group $R^3$ as defined herein.

"Hydroxyalkoxy" refers to an alkoxy group substituted with a hydroxyl group (—OH), wherein alkoxy is as defined herein. An example of hydroxyalkoxy is hydroxyethoxy.

"Hydroxyalkyl" refers to a linear or branched monovalent $C_1$-$C_{10}$ hydrocarbon group substituted with at least one hydroxyl group. Examples of hydroxyalkyl groups include, but are not limited to, hydroxymethyl, hydroxyethyl, hydroxypropyl and hydroxybutyl.

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less.

"Sulphamoyl" is $NH_2$—$S(O)_2$—; "N-(alkyl)sulphamoyl" is RNH—$S(O)_2$—; and "N,N-(alkyl)$_2$ sulphamoyl" is $R_2N$—$S(O)_2$—, where the R groups are alkyl as defined herein and are the same or different. In various embodiments, R is a $C_1$-$C_{10}$ alkyl group or a $C_1$-$C_6$ alkyl group.

"Pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically-acceptable carrier" refers to a diluent, adjuvant, excipient, carrier, other ingredient, or combination of ingredients that is pharmaceutically-acceptable and with which a compound of the invention is administered.

"Pharmaceutically-acceptable salt" refers to a salt that may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid (p-TsOH), camphorsulfonic acid, 4-methyl-bicyclo[2.2.2]oct-2-ene1-carboxylic acid, glucoheptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

"Therapeutically-effective amount" refers to an amount of a compound that, when administered to a subject for treating a disease, is sufficient to effect treatment for the disease. "Therapeutically effective amount" can vary depending on the compound, the disease and its severity, and the age, the weight, etc. of the subject to be treated.

Embraced herein, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants.

In one embodiment, the invention provides a compound of Formula (I) or a pharmaceutically acceptable salt thereof:

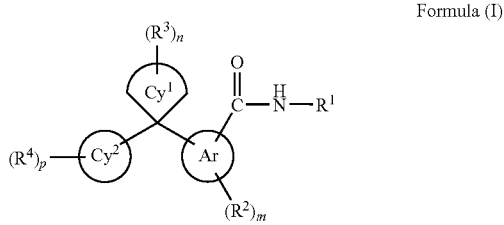

Formula (I)

wherein m, n, p, $Cy^1$, $Cy^2$, Ar, $R^1$, $R^2$, $R^3$ and $R^4$ are as defined above.

In various embodiments, the substitution with —$NH_2$ or —OH on aryl or heteroaryl of $R^1$ is adjacent to the attachment of the Ar—C(O)—NH— group to the aryl or heteroaryl.

In an embodiment, $R^1$ is hydroxyl and the compounds are characterized as hydroxamates. In another embodiment, $R^1$ is substituted aryl or heteroaryl and the compounds are characterized as arylamides.

In an embodiment, Ar is phenyl. In various embodiments, the $Cy^1$ and —C(O)NH—$R^1$ groups are disposed on the phenyl in a 1,4-configuration, where $Cy^1$ is considered as the 1-position.

In an embodiment, Ar is thiophene. In various embodiments, the $Cy^1$ and —C(O)NH—$R^1$ groups are disposed on the thiophene in a 2,5-configuration, where $Cy^1$ is considered as the 2-position (with the S atom of the thiophene ring taken as the 1-position).

In an embodiment, Ar is pyridine. In various embodiments, the $Cy^1$ and —C(O)NH—$R^1$ groups are disposed on the pyridine in a 2,5-configuration, where $Cy^1$ is considered as the 2-position, or in a 3,6-configuration, where $Cy^1$ is considered as the 3-position (in all cases, the N atom of the pyridine ring is taken as the 1-position).

In an embodiment, Ar is thiazole. In various embodiments, the $Cy^1$ and —C(O)NH—$R^1$ groups are disposed on the thiazole in a 2,4- or 2,5-configuration, where the $Cy^1$ is considered as the 2-position (with the S atom of the thiazole ring taken as the 1-position).

In an embodiment, $Cy^1$ is $C_{3-7}$ cycloalkylidene, where the Ar and $Cy^2$ groups are substituted in a 1,1-configuration on the $C_{3-7}$ ring. The ring of cycloalkylidene is optionally substituted with one or more groups $R^3$ as further defined herein. In various embodiments, the ring is completely saturated with H so that the variable n in Formula (I) is zero. In particular embodiments, $Cy^1$ is cyclopropylidene, cyclobutylidene, or cyclopentylidene.

In an embodiment, $Cy^1$ is a heterocyclic group with 1,1-disubstitution by the Ar and $Cy^2$ rings. Examples include 5- to 7-membered rings containing at least one heteroatom selected from N, O, and S. In preferred embodiments, there is no heteroatom substitution in $Cy^1$ adjacent the 1,1-attachment of Ar and $Cy^2$. Carbon atoms in the 1,1-disubstituted heterocyclic ring are optionally substituted with one or more oxo groups (i.e., 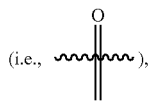), and substitutable positions on the ring are optionally substituted with 1 or more groups $R^3$. In various embodiments, the only substituent $R^3$ is an oxo group on carbon. In other embodiments, all substitutable positions contain H, so that the variable n in Formula (I) is zero. A non-limiting example of $Cy^1$ is tetrahydropyran-4,4-diyl (i.e., 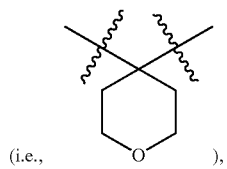), where Ar and $Cy^2$ are attached to the 4-position of tetrahydropyran, with the oxygen position taken as position 1.

In an embodiment, the ring $Cy^2$ is a nitrogen containing heterocyclyl. In various embodiments, $Cy^2$ is a 5-membered or 6-membered heterocyclyl. Examples include pyrrole, imidazole, pyrazole, triazole, tetrazole, thiazole, isothiazole, oxazole, isoxazole, pyridine, dihydropyridine, pyrimidine, pyrazine, pyridazine, and triazines. In various embodiments, $Cy^2$ is a fused bicyclic ring system containing a 5- or 6-membered nitrogen containing heteroaryl ring fused to another ring.

In an embodiment, $Cy^2$ is selected from

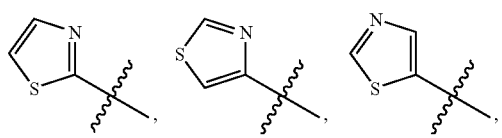

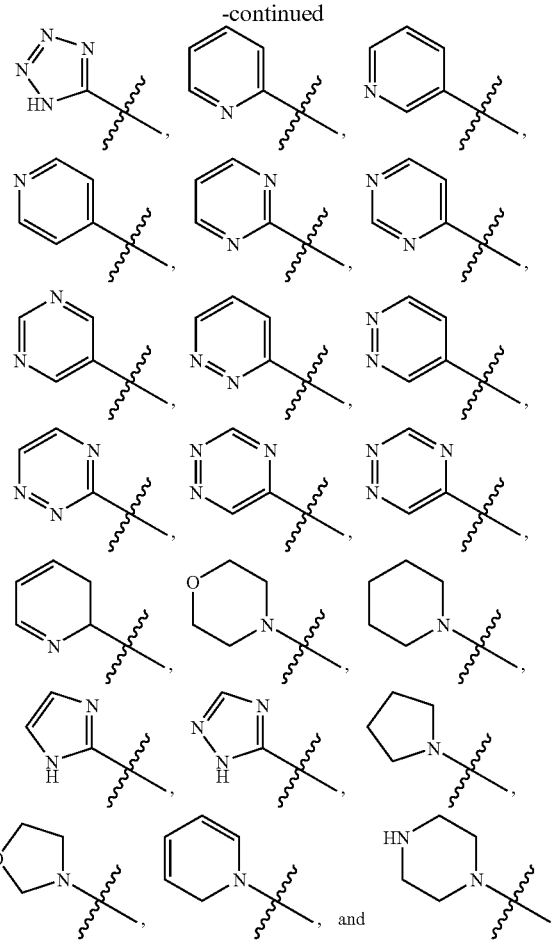

where the wavy lines show a position of attachment of the $Cy^1$ group and each optional $R^4$ group is attached to any other available positions on the $Cy^2$ ring.

In some embodiments, $Cy^2$ is a heterocyclic group substituted by one or more oxo groups. Non-limiting examples of such $Cy^2$ include:

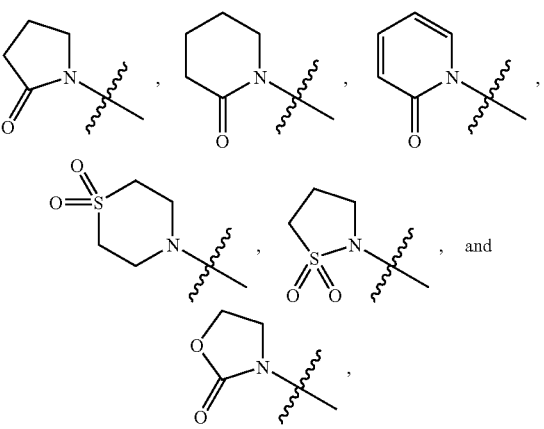

where the wavy lines show a position of attachment of the $Cy^1$ group and each optional $R^4$ group is attached to any other available positions on the $Cy^2$ ring.

In various embodiments, at least one of the substituents on ring $Cy^2$ is a cyclic group. In various embodiments, the cyclic group $R^4$ is a 5- or 6-membered ring nitrogen containing heteroaryl, optionally fused. The cyclic group optionally contains one or more substituents $R^5$, as further defined herein.

In an embodiment, A, B and D are independently selected from the group consisting of halo, alkyl, nitro, cyano, hydroxyl, oxo, cycloalkyl, trifluoromethoxy, trifluoromethyl, trifluoroethyl, amino, carboxyl, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, aryl, and heterocyclyl.

In the definitions herein of $R^1$, $R^2$, $R^3$, $R^4$, $R^5$, A, B and D, the carbon ranges for the groups alkyl, alkenyl, alkynyl, alkoxy, alkanoyl, alkanoyloxy, alkanoylamino, and the like include all ranges encompassed in the recited ranges $C_{1-10}$ and $C_{2-10}$. For example, in non-limiting fashion $C_{1-10}$ and $C_{2-10}$ include a disclosure of $C_{1-6}$ and $C_{1-3}$. In various embodiments, $C_{1-10}$ carbon-chain containing groups such as $C_{1-10}$ alkyl, $C_{2-10}$ alkenyl, $C_{2-10}$ alkynyl and so forth include the respective $C_{1-6}$ and $C_{1-3}$ shorter carbon-chains such as $C_{1-6}$ alkyl, $C_{1-3}$ alkyl, $C_{2-6}$ alkenyl, $C_{2-3}$ alkenyl, $C_{2-6}$ alkynyl and $C_{2-3}$ alkynyl.

In an embodiment when Ar is phenyl or 5- or 6-member heteroaryl, m is 0; in another embodiment, m is 1; in another embodiment, m is 2.

In the Tables that follow, examples are given with m=0 or m=1. When m=0, the entry in the $R^2$ column reads H (hydrogen) to indicate that all substituents are H. When m=1, the entry in the $R^2$ column gives the identity and position of the single non-hydrogen substituent. In particular embodiments, the variables are further exemplified as follows:

each $R^4$ is independently H, halo, hydroxyl, oxo, nitro, cyano, trifluoromethyl, trifluoromethoxy, amino, carboxyl, carbamoyl, sulphamoyl, $C_{1-3}$ alkyl, $C_{2-3}$ alkenyl, $C_{2-3}$ alkynyl, $C_{1-3}$ alkoxy, $C_{1-3}$ alkanoyl, N—($C_{1-3}$ alkyl) amino, N,N—($C_{1-3}$ alkyl)$_2$ amino, $C_{1-3}$ alkanoylamino, N—($C_{1-3}$ alkyl)carbamoyl, N,N—($C_{1-3}$ alkyl)$_2$ carbamoyl, $C_{1-3}$ alkyl-S(O)$_a$ wherein a is 0, 1 or 2, NH$_2$—S(O)$_2$NH—, N—($C_{1-3}$ alkyl)sulphamoyl, N,N—($C_{1-3}$ alkyl)$_2$ sulphamoyl, imidazolyl, triazolyl, pyridinyl, imidazopyridinyl, pyrazolopyridinyl, imidazopyridazinyl, imidazopyrimidinyl, imidazopyrazinyl, aryl, cycloalkyl or heterocyclyl, wherein if $R^4$ is not aryl, cycloalkyl or heterocyclyl, each $R^4$ is optionally substituted by one or more B where such an optional substitution is chemically feasible, and if $R^4$ is aryl, cycloalkyl or heterocyclyl, $R^4$ is optionally further substituted by one or more $R^5$ where such an optional substitution is chemically feasible;

each $R^5$ is independently selected from the group consisting of halo, nitro, cyano, hydroxyl, oxo, hydroxyalkyl, haloalkyl, haloalkoxy, amino, azido, carboxyl, carbamoyl, mercapto, sulphamoyl, $C_{1-3}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkyl-S(O)$_a$ wherein a is 0, 1 or 2, $C_{1-6}$ alkoxycarbonyl, NH$_2$—S(O)$_2$NH—, N—($C_{1-6}$ alkyl)sulphamoyl, N,N—($C_{1-6}$ alkyl)$_2$sulphamoyl, aryl, aryloxy, arylthio, cycloalkyl, cycloalkyloxy, heterocyclyl, heterocyclyl(C=O)—, heterocyclyloxy and heterocyclylthio, wherein $R^5$ is optionally substituted by one or more D where such an optional substitution is chemically feasible;

Ar is phenyl, 5-member heteroaryl, or 6-member heteroaryl, wherein the heteroaryl contains one or more heteroatoms selected from N, S and O; and A, B and D are independently selected from halo, nitro, cyano, hydroxyl, oxo, hydroxyalkyl, haloalkyl, haloalkoxy, amino, azido, carboxyl, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkyl-S(O)$_a$ wherein a is 0, 1 or 2, $C_{1-6}$ alkoxycarbonyl, N—($C_{1-6}$ alkyl)sulphamoyl, N,N—($C_{1-6}$ alkyl)$_2$sulphamoyl, H$_2$NS(O)$_2$NH—, N—($C_{1-6}$ alkyl)NHS(O)$_2$NH—, N,N—($C_{1-6}$ alkyl)$_2$NS(O)$_2$NH—, aryl, aryloxy, arylthio, cycloalkyl, cycloalkyloxy, heterocyclyl, heterocyclyl(C=O)—, heterocyclyloxy and heterocyclylthio.

A compound of Formula (I) contains a divalent $Cy^1$ linking a substituted or unsubstituted $Cy^2$ to —Ar—CONH—$R^1$. Each Ar, $Cy^1$ and $Cy^2$ can be optionally substituted with various substituents as defined as $R^2$, $R^3$ and $R^4$, respectively. Formula (I) indicates that the attachment of substituents on $Cy^1$, $Cy^2$ and Ar rings is variable. In particular embodiments, compounds are selected from those of Formulae (I-a), (I-b), (I-c), (I-d), (I-e), (I-f), (I-g), (I-h), (I-i), (I-j), (I-k), (I-l), (I-m), (I-n), (I-o), (I-p), (I-q), and (I-r) with substituents defined as in Formula (I):

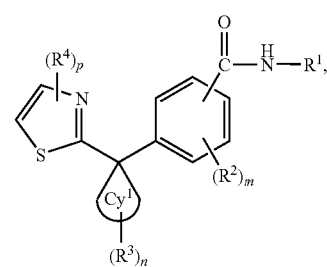

Formula (I-a)

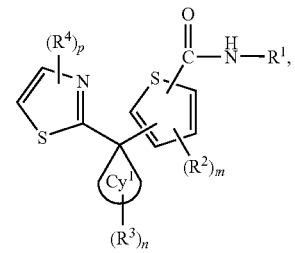

Formula (I-b)

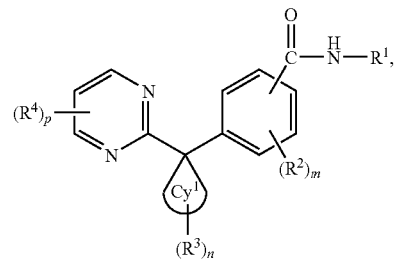

Formula (I-c)

Formula (I-d)
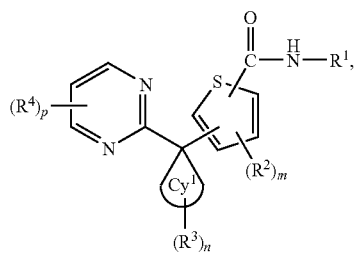
Formula (I-e)
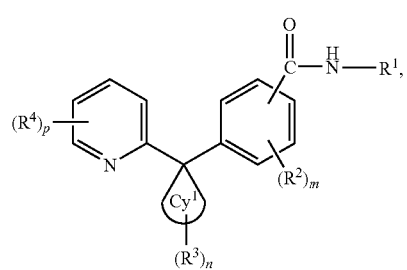
Formula (I-f)
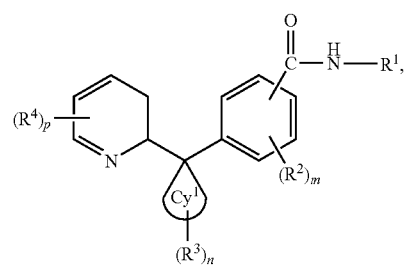
Formula (I-g)
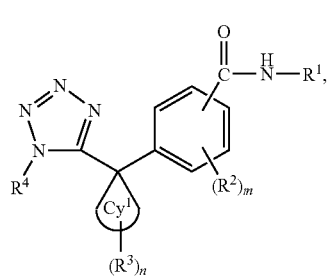
Formula (I-h)
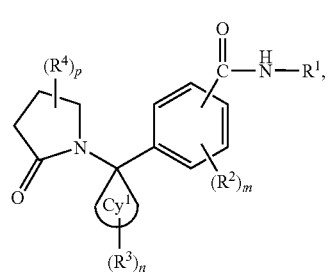
Formula (I-i)
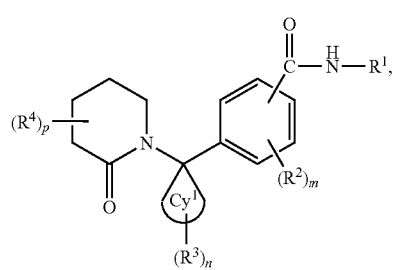
Formula (I-j)
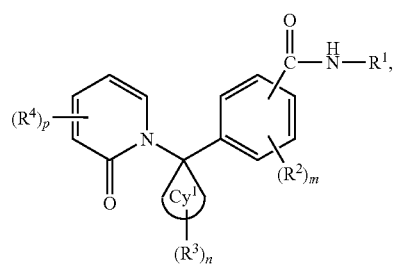
Formula (I-k)
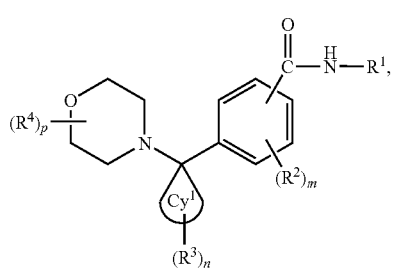
Formula (I-l)
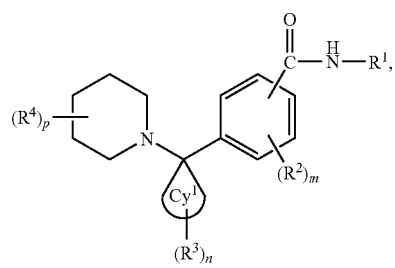
Formula (I-m)
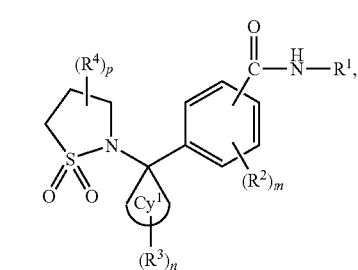
Formula (I-n)

Formula (I-o)

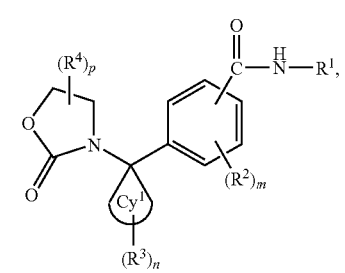

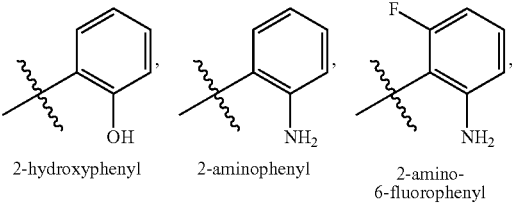

2-hydroxyphenyl, 2-aminophenyl, 2-amino-6-fluorophenyl

Formula (I-p)

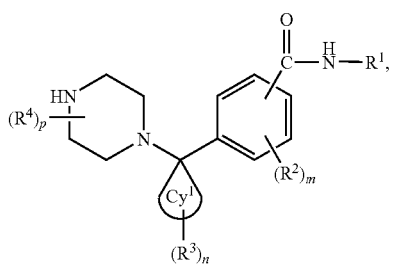

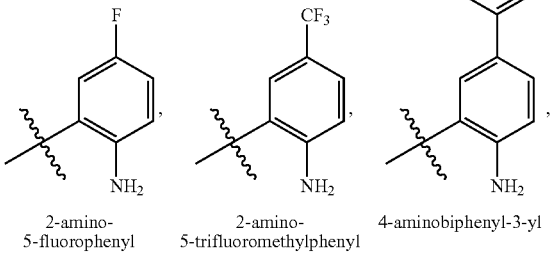

2-amino-5-fluorophenyl, 2-amino-5-trifluoromethylphenyl, 4-aminobiphenyl-3-yl

Formula (I-q)

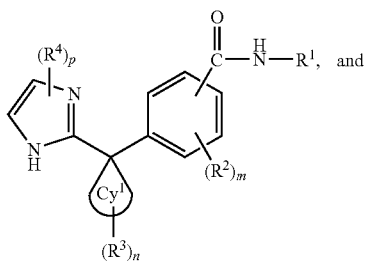

Formula (I-r)

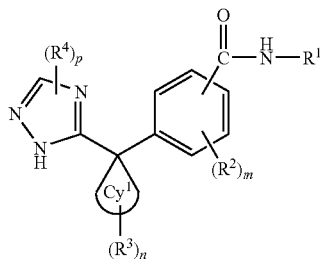

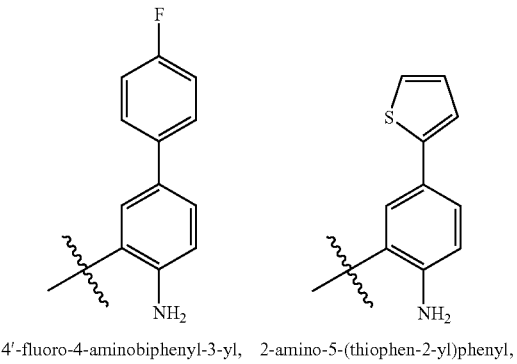

4'-fluoro-4-aminobiphenyl-3-yl, 2-amino-5-(thiophen-2-yl)phenyl,

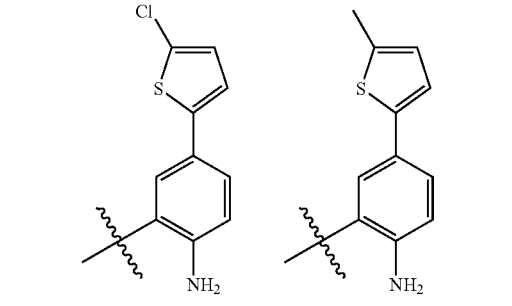

5'-chloro-2-amino-5-(thiophen-2-yl)phenyl, 5'-methyl-2-amino-5-(thiophen-2-yl)phenyl,

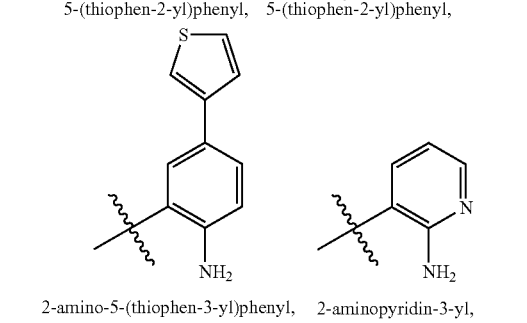

2-amino-5-(thiophen-3-yl)phenyl, 2-aminopyridin-3-yl,

Compounds defined above are useful to inhibit HDACs. In one embodiment, therefore, a compound of the invention is used in inhibiting HDAC enzymes such as, for example, mammalian HDACs. More specifically, a compound of the invention can be used to treat or inhibit HDAC-mediated diseases or abnormalities.

In an embodiment of the compounds of Formulae (I), (I-a), (I-b), (I-c), (I-d), (I-e), (I-f), (I-g), (I-h), (I-i), (I-j), (I-k), (I-l), (I-m), (I-n), (I-o), (I-p), (I-q), and (I-r), one or more (including all) of the substituents $R^1$, $R^2$, $R^3$, $R^4$ and $R^5$ are further limited as follows:

$R^1$ is hydroxyl, aryl or heteroaryl, wherein aryl or heteroaryl is substituted with —$NH_2$ or —OH at a ring position adjacent to attachment of the —CONH-moiety, and $R^1$ is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl. In particular embodiments, $R^1$ is hydroxyl,

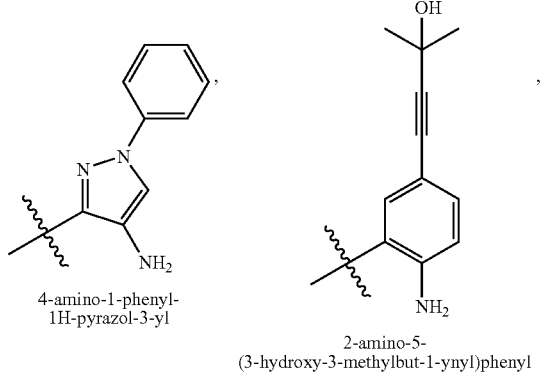

4-amino-1-phenyl-
1H-pyrazol-3-yl 2-amino-5-
(3-hydroxy-3-methylbut-1-ynyl)phenyl

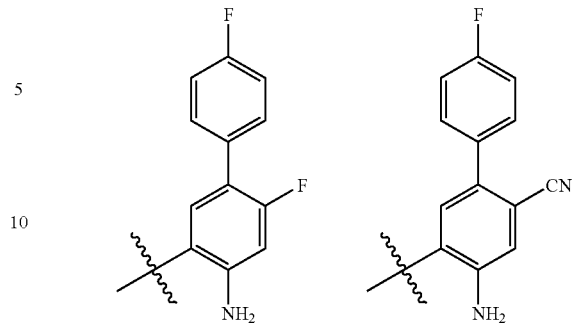

4',6-difluoro-4-aminobiphenyl-3-yl,   4-amino-4'-fluoro-
6-cyanobiphenyl-3-yl

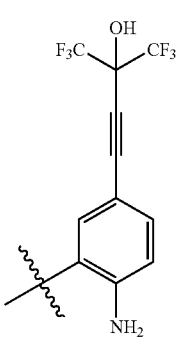

2-amino-5-(4,4,4-trifluoro-3-hydroxy-3-
(trifluoromethyl)but-1-ynyl)phenyl

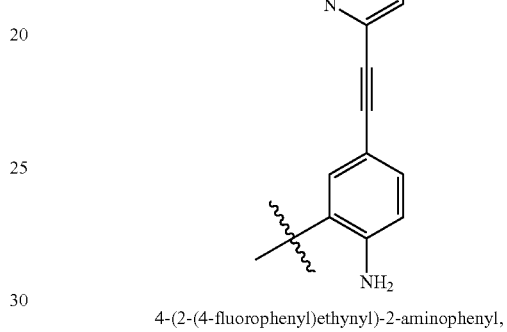

4-(2-(4-fluorophenyl)ethynyl)-2-aminophenyl,

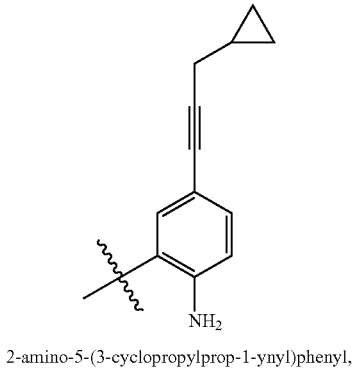

2-amino-5-(3-cyclopropylprop-1-ynyl)phenyl,

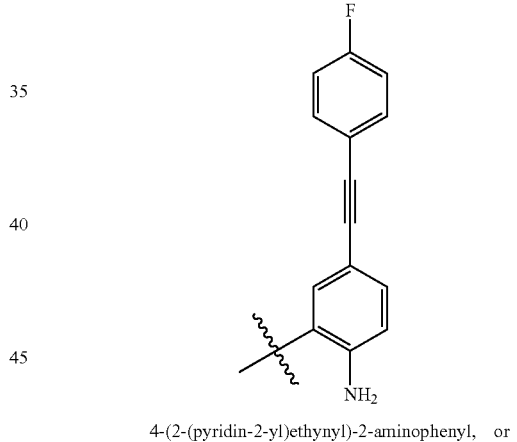

4-(2-(pyridin-2-yl)ethynyl)-2-aminophenyl,   or

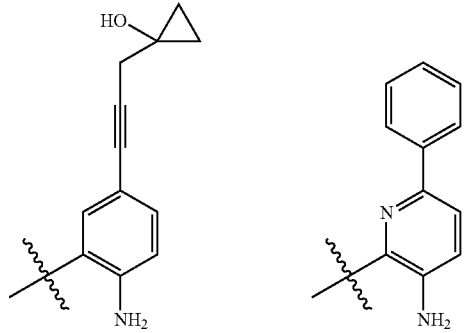

2-amino-5-(3-(1-hydroxycyclopropyl)
prop-1-ynyl)phenyl,   3-amino-6-phenylpyridin-2-yl,

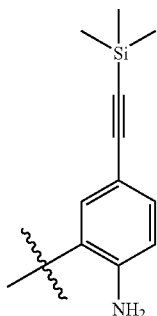

4-(2-(trimethylsilyl)ethynyl)-2-aminophenyl m is 0, 1 or 2 and each $R^2$ is independently fluoro, chloro, bromo, or methyl.

n is 0, 1 or 2 and each $R^3$ is, if present, a non-hydrogen substituent selected independently from methyl, ethyl, bromo, and trifluoromethyl, or two $R^3$ together form a spiro-ring on $Cy^1$ selected from

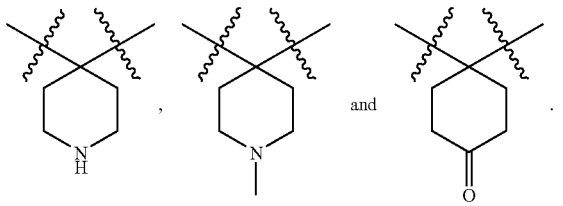

For example, compounds containing such a spiro moiety include

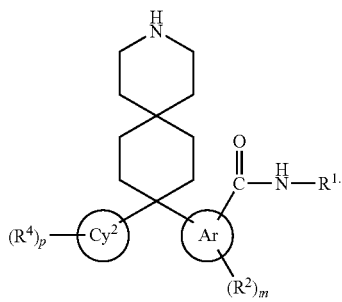

Each $R^4$ is independently selected from H, chloro, hydroxyl, methyl, ethyl, propyl, acetyl, propanoyl, butanoyl, methoxy, ethoxy, methoxymethyl, ethoxyethyl, propoxyethyl, methoxyethoxy, trifluoromethyl, hydroxyethoxy, dimethylamino, diethylamino, dimethylaminomethyl, diethylaminomethyl, dimethylaminoethoxy, trifluoromethoxymethyl, trifluoroethoxymethyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, pyridyl, thienyl, furanyl, pyrimidyl, imidazolyl, pyridinyl, triazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, imidazopyridinyl, pyrazolopyridinyl, imidazopyridazinyl, imidazopyrimidinyl, imidazopyrazinyl, benzothiazolyl, benzooxazolyl, benzimidazolyl, isoindolyl, benzotriazolyl, purinyl, thianaphthenyl, 1-methylcyclopropyl, trifluoroethyl, methoxypropyl, N,N-dimethylaminopropyl, 1-carboxycyclopropyl, N,N-dimethylcarbamoylcyclopropyl, pyridin-2-ylmethyl, 5-trifluoromethylpyridin-2-ylmethyl, N,N-dimethylcarbamoyl, morpholinylcarbonyl, t-butylcarbamoyl, morpholinoethoxycarbonyl, benzoyl, picolinoyl, quinoxa-6-linylcarbonyl, cyclopropylcarbonyl, propionyl, methoxypropanoyl, N,N-dimethylaminopropanoyl, 5-trifluoromethylpyridin-2-yl, 5-chloropyridin-2-yl, 5-cyclopropylpyridin-2-yl, 5-chloropyrimidin-2-yl, 2-methoxyphenyl, 4-carboxyphenyl, N,N-dimethylcarbamoylphenyl, 2-chlorophenyl, 1-methylcyclopropoxycarbonyl, t-butoxycarbonyl, 2-trifluoromethylprop-2-oxycarbonyl, methylsulfonyl, trifluoroethylsulfonyl, 5-trifluoromethylpyridin-3-ylsulfonyl, pyridin-3-ylsulfonyl, phenylsulfonyl, cyclopropylsulfonyl, pyridin-2-yl, 5-trifluoromethylpyridin-2-yl, phenyl, and cyclopropyl; or p is 2 or greater and two $R^4$ groups are substituted at adjacent positions of $Cy^2$ and form a 5- or 6-membered cyclic moiety to make a fused ring with $Cy^2$, wherein the cyclic moiety can be carbocyclic or contain one or more heteroatoms selected from N, O and S; and the cyclic moiety is optionally substituted by one or more $R^5$ where such an optional substitution is chemically feasible. Examples of such fused rings include, but are not limited to:

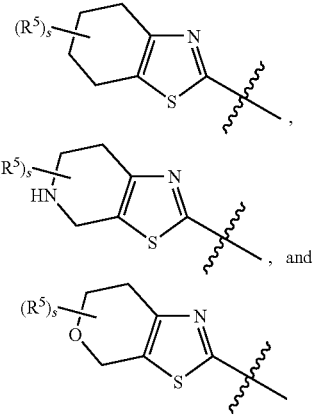

wherein s is 0, 1, 2 or 3.

If $R^4$ is not aryl, cycloalkyl or heterocyclyl, each $R^4$ is optionally substituted by one or more B where such an optional substitution is chemically feasible, and if $R^4$ is aryl, cycloalkyl or heterocyclyl, $R^4$ is optionally further substituted by one or more $R^5$ where such an optional substitution is chemically feasible.

$R^5$ is independently selected from chloro, hydroxyl, oxo, methyl, ethyl, propyl, methoxy, ethoxy, methoxymethyl, ethoxyethyl, propoxyethyl, methoxyethoxy, trifluoromethyl, hydroxyethoxy, dimethylamino, diethylamino, dimethylaminomethyl, diethylaminomethyl, dimethylaminoethoxy, trifluoromethoxymethyl, trifluoroethoxymethyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-2-ylethoxy, morpholin-3-ylethoxy and morpholin-4-ylethoxy.

In various embodiments, the $Cy^1$ linker and the —CONHR$^1$ moiety are disposed about the phenyl ring of Formulae (I-a), (I-c) and (I-e) through (I-r) in either a 1,3-

(meta) or a 1,4-(para) configuration. $R^2$ can be attached to any ring position of the phenyl ring which is not occupied by the $Cy^1$ linker and —$CONHR^1$ moiety and such attachment includes 1,2-(ortho), 1,3-(meta) and 1,4-(para) configurations wherein the $Cy^1$ linker is at position 1. In the Tables that follow, ortho-, meta- and para-configurations of $R^2$ mean attachment to positions 2, 3 and 4 of the phenyl ring as shown in Formulas (I-a) and (I-c), respectively. Where $R^2$ is an ortho-substitution (i.e., position 2), meta-$CONHR^1$ moiety is intended to be at position 5.

In one embodiment, the invention provides a compound of Formula (I-a) and a pharmaceutically acceptable salt thereof:

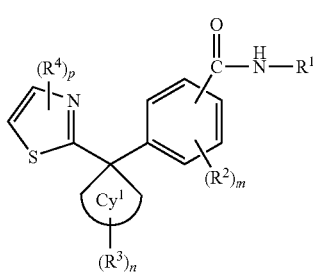

Formula (I-a)

wherein $Cy^1$, $R^1$, $R^2$, $R^3$ and $R^4$ are as defined above for various aspects of Formula (I).

In an embodiment of Formula (I-a), $Cy^1$ is cyclopropylidene; $R^1$ is hydroxyl, aryl or heteroaryl, wherein aryl or heteroaryl is substituted with —$NH_2$ or —OH at a ring position adjacent to attachment of the —CONH-moiety, wherein $R^1$ is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl; m is 0 or 1 and $R^2$ is halo, $C_{1-10}$ alkyl or haloalkyl; n is 0, 1 or 2 and each $R^3$ is independently methyl, ethyl, bromo, trifluoromethyl; p is 2 and each $R^4$ is independently selected from the group consisting of H, halo, nitro, cyano, hydroxyl, hydroxyalkyl, haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, $NH_2$—S(O)$_2$ NH—, N—($C_{1-10}$ alkyl)sulphamoyl and N,N—($C_{1-10}$ alkyl)$_2$ sulphamoyl, or p is 2 or greater and two $R^4$ groups form a 5- or 6-membered cyclic moiety to make a fused ring with the thiazole ring ($Cy^2$), wherein the cyclic moiety can contain one or more heteroatoms selected from N, O and S, wherein each $R^4$ is optionally substituted by one or more B where such an optional substitution is chemically feasible.

Non-limiting examples of such compounds include compounds of Formula (I-a0) and pharmaceutically acceptable salts thereof:

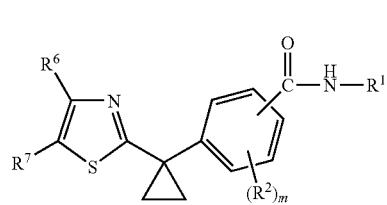

Formula (I-a0)

wherein $R^6$ and $R^7$ are independently selected from the functional groups of $R^4$ defined herein. Table 1 provides non-limiting examples of compounds of Formula (I-a0) where m is zero where $R^6$ and $R^7$ together can form a cyclic moiety to make a fused ring with the thiazole ring ($Cy^2$), that fused ring is shown in the $R^6$ and $R^7$ columns of the table.

TABLE 1

Examples of Formula (I-a0)

| Compound No. | —$CONHR^1$ attachment | $R^1$ | $R^6$ | $R^7$ |
|---|---|---|---|---|
| a0-01 | para | —OH | $CH_3$— | $CH_3C(O)$— |
| a0-02 | para | —OH | | H |
| a0-03 | para | —OH | N-pyridin-2-ylaminomethyl | H |
| a0-04 | para | —OH | pyridin-2-yloxymethyl | H |
| a0-05 | para | —OH | | H |
| a0-06 | para | —OH | | H |
| a0-07 | para | —OH | | H |

TABLE 1-continued

Examples of Formula (I-a0)

| Compound No. | —CONHR[1] attachment | R[1] | R[6] | R[7] |
|---|---|---|---|---|
| a0-08 | para | —OH | CH$_3$— | (CH$_3$)$_2$NC(O)— |
| a0-09 | para | —OH | | 4,5,6,7-tetrahydrobenzothiazol-2-yl |
| a0-10 | para | —OH | | 4,5,6,7-tetrahydrothiazolo[5,4-c]pyridin-2-yl (NH) |
| a0-11 | para | —OH | | 5-methyl-4,5,6,7-tetrahydrothiazolo[5,4-c]pyridin-2-yl |
| a0-12 | para | —OH | | 5-ethyl-4,5,6,7-tetrahydrothiazolo[5,4-c]pyridin-2-yl |
| a0-13 | para | —OH | | 5-isopropyl-4,5,6,7-tetrahydrothiazolo[5,4-c]pyridin-2-yl |
| a0-14 | para | —OH | | 5-(2-methoxyethyl)-4,5,6,7-tetrahydrothiazolo[5,4-c]pyridin-2-yl |
| a0-15 | para | —OH | | 5-acetyl-4,5,6,7-tetrahydrothiazolo[5,4-c]pyridin-2-yl |
| a0-16 | para | —OH | | 5-(N,N-dimethylglycyl)-4,5,6,7-tetrahydrothiazolo[5,4-c]pyridin-2-yl |
| a0-17 | para | —OH | | 5-valyl-4,5,6,7-tetrahydrothiazolo[5,4-c]pyridin-2-yl |

TABLE 1-continued
Examples of Formula (I-a0)
| Compound No. | —CONHR¹ attachment | R¹ | R⁶ | R⁷ |
|---|---|---|---|---|
| a0-18 | para | —OH | 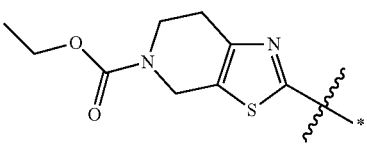 | |
| a0-19 | para | —OH | 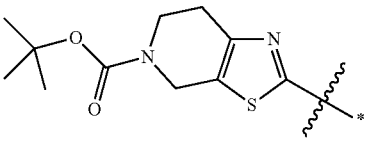 | |
| a0-20 | meta | —OH | CH₃— | CH₃C(O)— |
| a0-21 | meta | —OH | 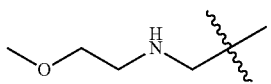 | H |
| a0-22 | meta | —OH | N-pyridin-2-ylaminomethyl | H |
| a0-23 | meta | —OH | pyridin-2-yloxymethyl | H |
| a0-24 | meta | —OH | 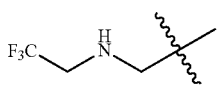 | H |
| a0-25 | meta | —OH | 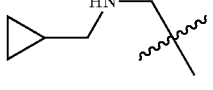 | H |
| a0-26 | para | —OH | 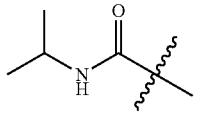 | H |
| a0-27 | meta | —OH | CH₃— | (CH₃)₂NC(O)— |
| a0-28 | meta | —OH | 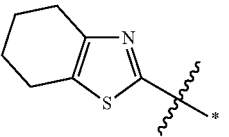 | |
| a0-29 | meta | —OH | 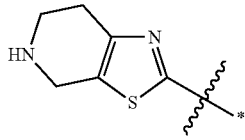 | |
| a0-30 | meta | —OH | 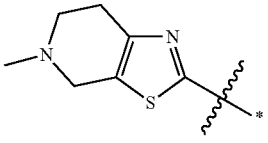 | |
| a0-31 | meta | —OH | 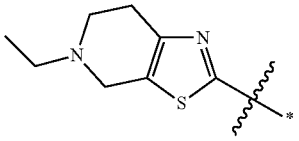 | |

TABLE 1-continued

Examples of Formula (I-a0)

| Compound No. | —CONHR¹ attachment | R¹ | R⁶ | R⁷ |
|---|---|---|---|---|
| a0-32 | meta | —OH | (5-isopropyl-4,5,6,7-tetrahydrothiazolo[5,4-c]pyridin-2-yl) | |
| a0-33 | meta | —OH | (5-(2-methoxyethyl)-4,5,6,7-tetrahydrothiazolo[5,4-c]pyridin-2-yl) | |
| a0-34 | meta | —OH | (5-acetyl-4,5,6,7-tetrahydrothiazolo[5,4-c]pyridin-2-yl) | |
| a0-35 | meta | —OH | (5-(2-(dimethylamino)acetyl)-4,5,6,7-tetrahydrothiazolo[5,4-c]pyridin-2-yl) | |
| a0-36 | meta | —OH | (5-(2-amino-3-methylbutanoyl)-4,5,6,7-tetrahydrothiazolo[5,4-c]pyridin-2-yl) | |
| a0-37 | meta | —OH | (5-(ethoxycarbonyl)-4,5,6,7-tetrahydrothiazolo[5,4-c]pyridin-2-yl) | |
| a0-38 | meta | —OH | (5-(tert-butoxycarbonyl)-4,5,6,7-tetrahydrothiazolo[5,4-c]pyridin-2-yl) | |
| a0-39 | para | 2-aminophenyl | CH₃— | CH₃C(O)— |
| a0-40 | para | 2-aminophenyl | (2-methoxyethyl)aminomethyl | H |
| a0-41 | para | 2-aminophenyl | N-pyridin-2-ylaminomethyl | H |
| a0-42 | para | 2-aminophenyl | pyridin-2-yloxymethyl | H |
| a0-43 | para | 2-aminophenyl | (2,2,2-trifluoroethyl)aminomethyl | H |
| a0-44 | para | 2-aminophenyl | (cyclopropylmethyl)amino-dimethyl | H |

TABLE 1-continued

Examples of Formula (I-a0)

| Compound No. | —CONHR¹ attachment | R¹ | R⁶ | R⁷ |
| --- | --- | --- | --- | --- |
| a0-45 | para | 2-aminophenyl | isopropyl-NH-C(O)-C(CH₃)₂- | H |
| a0-46 | para | 2-aminophenyl | CH₃— | (CH₃)₂NC(O)— |
| a0-47 | para | 2-aminophenyl | 4,5,6,7-tetrahydrobenzothiazol-2-yl | |
| a0-48 | para | 2-aminophenyl | 4,5,6,7-tetrahydrothiazolo[5,4-c]pyridin-2-yl | |
| a0-49 | para | 2-aminophenyl | 5-methyl-4,5,6,7-tetrahydrothiazolo[5,4-c]pyridin-2-yl | |
| a0-50 | para | 2-aminophenyl | 5-ethyl-4,5,6,7-tetrahydrothiazolo[5,4-c]pyridin-2-yl | |
| a0-51 | para | 2-aminophenyl | 5-isopropyl-4,5,6,7-tetrahydrothiazolo[5,4-c]pyridin-2-yl | |
| a0-52 | para | 2-aminophenyl | 5-(2-methoxyethyl)-4,5,6,7-tetrahydrothiazolo[5,4-c]pyridin-2-yl | |
| a0-53 | para | 2-aminophenyl | 5-acetyl-4,5,6,7-tetrahydrothiazolo[5,4-c]pyridin-2-yl | |
| a0-54 | para | 2-aminophenyl | 5-(N,N-dimethylglycyl)-4,5,6,7-tetrahydrothiazolo[5,4-c]pyridin-2-yl | |

TABLE 1-continued

Examples of Formula (I-a0)

| Compound No. | —CONHR¹ attachment | R¹ | R⁶ | R⁷ |
|---|---|---|---|---|
| a0-55 | para | 2-aminophenyl | 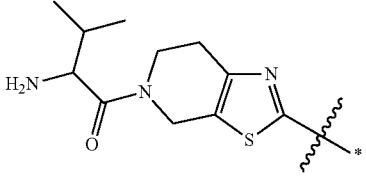 | |
| a0-56 | para | 2-aminophenyl | 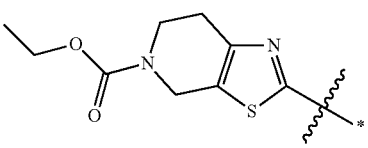 | |
| a0-57 | para | 2-aminophenyl | 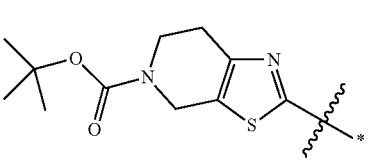 | |
| a0-58 | meta | 2-aminophenyl | CH₃— | CH₃C(O)— |
| a0-59 | meta | 2-aminophenyl | 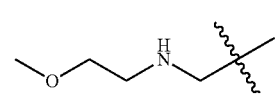 | H |
| a0-60 | meta | 2-aminophenyl | N-pyridin-2-ylaminomethyl | H |
| a0-61 | meta | 2-aminophenyl | pyridin-2-yloxymethyl | H |
| a0-62 | meta | 2-aminophenyl | 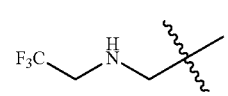 | H |
| a0-63 | meta | 2-aminophenyl | 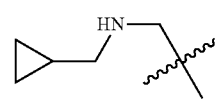 | H |
| a0-64 | meta | 2-aminophenyl | 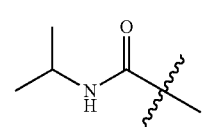 | H |
| a0-65 | meta | 2-aminophenyl | CH₃— | (CH₃)₂NC(O)— |
| a0-66 | meta | 2-aminophenyl | 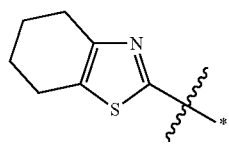 | |
| a0-67 | meta | 2-aminophenyl | 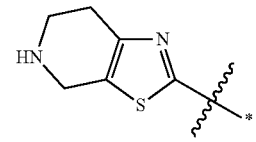 | |
| a0-68 | meta | 2-aminophenyl | 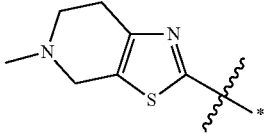 | |

TABLE 1-continued

Examples of Formula (I-a0)

| Compound No. | —CONHR¹ attachment | R¹ | R⁶ | R⁷ |
|---|---|---|---|---|
| a0-69 | meta | 2-aminophenyl | | N-ethyl tetrahydrothiazolopyridinyl group |
| a0-70 | meta | 2-aminophenyl | | N-isopropyl tetrahydrothiazolopyridinyl group |
| a0-71 | meta | 2-aminophenyl | | N-(2-methoxyethyl) tetrahydrothiazolopyridinyl group |
| a0-72 | meta | 2-aminophenyl | | N-acetyl tetrahydrothiazolopyridinyl group |
| a0-73 | meta | 2-aminophenyl | | N-(N,N-dimethylglycyl) tetrahydrothiazolopyridinyl group |
| a0-74 | meta | 2-aminophenyl | | N-valyl tetrahydrothiazolopyridinyl group |
| a0-75 | meta | 2-aminophenyl | | N-(ethoxycarbonyl) tetrahydrothiazolopyridinyl group |
| a0-76 | meta | 2-aminophenyl | | N-(tert-butoxycarbonyl) tetrahydrothiazolopyridinyl group |
| a0-77 | para | —OH | H | H |
| a0-78 | para | 2-aminophenyl | H | H |
| a0-79 | para | 4'-fluoro-4-amino-biphenyl-3-yl | H | H |

TABLE 1-continued

Examples of Formula (I-a0)

| Compound No. | —CONHR[1] attachment | R[1] | R[6] | R[7] |
|---|---|---|---|---|
| a0-80 | para | 4-amino-3-(thiophen-2-yl)phenyl (attached via position with H$_2$N on ring, thiophene at para to NH$_2$) | H | H |
| a0-81 | para | 4-amino-3-(5-methylthiophen-2-yl)phenyl | H | H |
| a0-82 | para | 2-amino-5-fluorophenyl | H | H |
| a0-83 | para | 2-aminophenyl | CH$_3$— | isopropyl |
| a0-84 | para | 4-amino-4'-fluorobiphenyl-3-yl | CH$_3$— | isopropyl |
| a0-85 | para | 2-aminophenyl | CH$_3$— | 1-hydroxyethyl (—CH(OH)CH$_3$) |
| a0-86 | para | 2-amino-5-fluorophenyl | CH$_3$— | 1-hydroxyethyl (—CH(OH)CH$_3$) |
| a0-87 | para | 4-amino-3-(thiophen-2-yl)phenyl | CH$_3$— | 1-hydroxyethyl (—CH(OH)CH$_3$) |
| a0-88 | para | 4-amino-4'-fluorobiphenyl-3-yl | CH$_3$— | 1-hydroxyethyl (—CH(OH)CH$_3$) |
| a0-89 | para | 2-aminophenyl | CH$_3$— | CH$_3$— |
| a0-90 | para | 4-amino-4'-fluorobiphenyl-3-yl | CH$_3$— | CH$_3$— |
| a0-91 | para | HO— | pyrrolidin-1-ylmethyl | H |
| a0-92 | para | 2-aminophenyl | pyrrolidin-1-ylmethyl | H |
| a0-93 | para | 2-amino-5-fluorophenyl | pyrrolidin-1-ylmethyl | H |

TABLE 1-continued

Examples of Formula (I-a0)

| Compound No. | —CONHR¹ attachment | R¹ | R⁶ | R⁷ |
|---|---|---|---|---|
| a0-94 | para | 4-amino-3-(thiophen-2-yl)phenyl (H₂N-phenyl-thiophene) | pyrrolidin-1-ylmethyl | H |
| a0-95 | para | 2-aminophenyl | 2-(2-methoxyethoxy) | H |
| a0-96 | para | 4-amino-3-(thiophen-2-yl)phenyl | 2-(2-methoxyethoxy) | H |
| a0-97 | para | 2-aminophenyl | morpholin-4-ylmethyl | H |
| a0-98 | para | 4-amino-3-(thiophen-2-yl)phenyl | morpholin-4-ylmethyl | H |
| a0-99 | para | 2-aminophenyl | ethoxy | H |
| a0-100 | para | 4-amino-3-(4-fluorophenyl)phenyl | ethoxy | H |
| a0-101 | para | 4-amino-3-(thiophen-2-yl)phenyl | ethoxy | H |
| a0-102 | para | 2-aminophenyl | 4-(4-methylpiperazin-1-yl)phenyl | H |
| a0-103 | para | 2-amino-5-fluorophenyl | 4-(4-methylpiperazin-1-yl)phenyl | H |
| a0-104 | para | 2-aminophenyl | H | CH₃— |
| a0-105 | para | 4-amino-3-(4-fluorophenyl)phenyl | H | CH₃— |

TABLE 1-continued

Examples of Formula (I-a0)

| Compound No. | —CONHR¹ attachment | R¹ | R⁶ | R⁷ |
|---|---|---|---|---|
| a0-106 | para | 4-amino-3-(thiophen-2-yl)phenyl (attached at 3-position) | H | CH₃— |
| a0-107 | para | 2-aminophenyl | H | pyridin-3-yl |
| a0-108 | para | 4-amino-3-(thiophen-2-yl)phenyl | H | pyridin-3-yl |
| a0-109 | para | 2-aminophenyl | H | pyridin-3-yl |
| a0-110 | para | 2-aminophenyl | H | 6-cyclopropyl pyridin-3-yl |
| a0-111 | para | 2-aminophenyl | CH₃— | H |
| a0-112 | para | 4-amino-4'-fluorobiphenyl-3-yl | cyclopropyl | H |
| a0-113 | para | 2-aminophenyl | cyclopropyl | H |
| a0-114 | para | 4-amino-4'-fluorobiphenyl-3-yl | CH₃— | CH₃C(O)— |
| a0-115 | para | 2-aminophenyl | CH₃— | CH₃C(O)— |
| a0-116 | para | 2-amino-5-fluorophenyl | \[5-methyl-4,5,6,7-tetrahydrothiazolo[5,4-c]pyridin-2-yl\] | |
| a0-117 | para | 4-amino-4'-fluorobiphenyl-3-yl | \[5-methyl-4,5,6,7-tetrahydrothiazolo[5,4-c]pyridin-2-yl\] | |
| a0-118 | para | 4-amino-3-(thiophen-2-yl)phenyl | \[5-methyl-4,5,6,7-tetrahydrothiazolo[5,4-c]pyridin-2-yl\] | |

TABLE 1-continued

Examples of Formula (I-a0)

| Compound No. | —CONHR¹ attachment | R¹ | R⁶ | R⁷ |
|---|---|---|---|---|
| a0-119 | para | 4-amino-3-(thiophen-2-yl)phenyl (2-amino-5-(thiophen-2-yl)phenyl) | | 5-acetyl-4,5,6,7-tetrahydrothiazolo[5,4-c]pyridin-2-yl |
| a0-120 | para | 2-aminophenyl | | 4,7-dihydro-5H-pyrano[3,4-d]thiazol-2-yl |
| a0-121 | para | 2-amino-5-(thiophen-2-yl)phenyl | | 4,7-dihydro-5H-pyrano[3,4-d]thiazol-2-yl |
| a0-122 | para | 2-amino-5-(4'-fluorobiphenyl) | | 4,7-dihydro-5H-pyrano[3,4-d]thiazol-2-yl |
| a0-123 | para | 2-aminophenyl | | 5-(tert-butylcarbamoyl)-4,5,6,7-tetrahydrothiazolo[5,4-c]pyridin-2-yl |
| a0-124 | para | 2-amino-5-fluorophenyl | | 5-(tert-butylcarbamoyl)-4,5,6,7-tetrahydrothiazolo[5,4-c]pyridin-2-yl |
| a0-125 | para | 2-aminophenyl | | 5-(morpholine-4-carbonyl)-4,5,6,7-tetrahydrothiazolo[5,4-c]pyridin-2-yl |
| a0-126 | para | 2-amino-5-fluorophenyl | | 5-(morpholine-4-carbonyl)-4,5,6,7-tetrahydrothiazolo[5,4-c]pyridin-2-yl |

*wherein R⁶ and R⁷ form a cyclic moiety. The groups R⁶ and R⁷ are illustrated with the thiazolyl group (Cy²) to show their attachments to the thiazolyl ring.

In another embodiment of Formula (I-a), $Cy^1$ is cyclopropylidene and the thiazole ring $Cy^2$ is substituted with a fused aryl, cycloalkyl, or heterocyclyl ring. Also, $R^1$ is hydroxyl, aryl or heteroaryl, wherein aryl or heteroaryl is substituted with —$NH_2$ or —OH at a ring position adjacent to attachment of the —CONH-moiety, wherein $R^1$ is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl; $R^2$ is halo, alkyl or haloalkyl; m is 0 or 1 and $R^2$ is halo, alkyl or haloalkyl; n is 0, 1 or 2 and each $R^3$ is independently methyl, ethyl, bromo, trifluoromethyl; p is 1 or greater, wherein one and only one $R^4$ is aryl, cycloalkyl or heterocyclyl, wherein aryl, cycloalkyl or heterocyclyl is a fused ring; and the other $R^4$, if present, are not aryl, cycloalkyl or heterocyclyl, optionally further substituted by one or more $R^5$ where such an optional substitution is chemically feasible; and $R^5$ is as defined above. Compounds of this embodiment include, but are not limited to, compounds of the following formulae, where $R^{6'}$, $R^{7'}$, $R^8$, $R^9$, and $R^{10}$ are independently selected from H and the functional groups of $R^5$ defined herein:

Formula (I-a1)

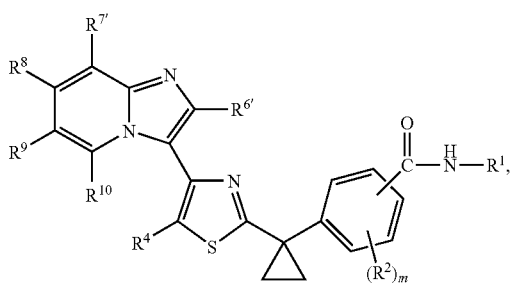

Formula (I-a2)

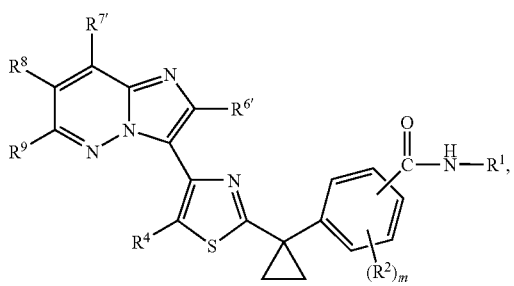

Formula (I-a3)

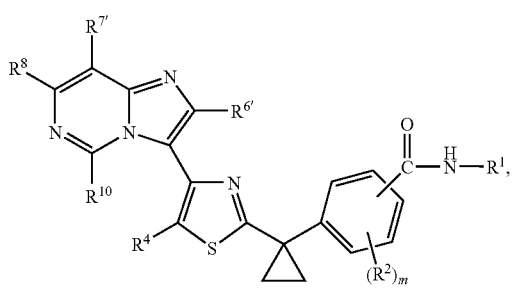

-continued

Formula (I-a4)

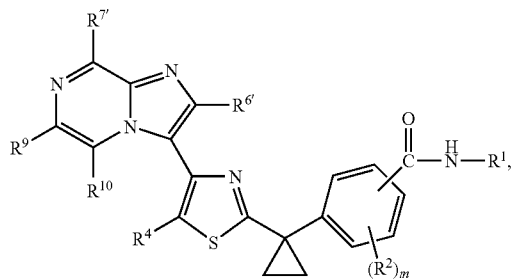

Formula (I-a5)

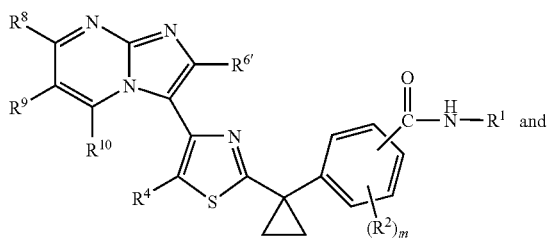

and

Formula (I-a6)

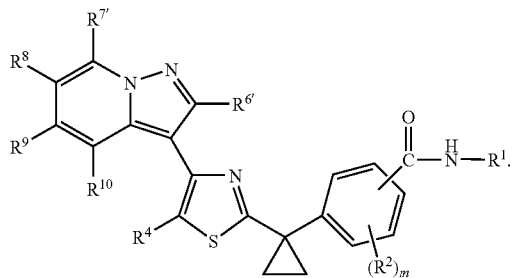

Non-limiting examples of compounds of Formula (I-a1) include the following compounds shown in Table 2 and pharmaceutically acceptable salts thereof:

TABLE 2

Examples of Formula (I-a1).

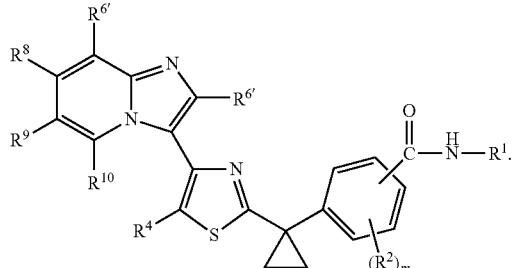

Formula (I-a1)

| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-01 | para | —OH | H | H | H | H | H | H | H |
| a1-02 | meta | —OH | H | H | H | H | H | H | H |
| a1-03 | para | —OH | H | —CH₃ | H | H | H | H | H |
| a1-04 | meta | —OH | H | —CH₃ | H | H | H | H | H |
| a1-05 | para | 2-aminophenyl | H | H | H | H | H | H | H |
| a1-06 | meta | 2-aminophenyl | H | H | H | H | H | H | H |
| a1-07 | para | 2-aminophenyl | H | —CH₃ | H | H | H | H | H |
| a1-08 | meta | 2-aminophenyl | H | —CH₃ | H | H | H | H | H |
| a1-09 | para | 2-aminopyridin-3-yl | H | H | H | H | H | H | H |
| a1-10 | meta | 2-aminopyridin-3-yl | H | H | H | H | H | H | H |
| a1-11 | para | 2-aminopyridin-3-yl | H | —CH₃ | H | H | H | H | H |
| a1-12 | meta | 2-aminopyridin-3-yl | H | —CH₃ | H | H | H | H | H |
| a1-13 | para | 1-phenyl-4-amino-pyrazol-3-yl | H | H | H | H | H | H | H |
| a1-14 | meta | 1-phenyl-4-amino-pyrazol-3-yl | H | H | H | H | H | H | H |
| a1-15 | para | 1-phenyl-4-amino-pyrazol-3-yl | H | —CH₃ | H | H | H | H | H |
| a1-16 | meta | 1-phenyl-4-amino-pyrazol-3-yl | H | —CH₃ | H | H | H | H | H |
| a1-17 | para | 2-amino-6-fluorophenyl | H | H | H | H | H | H | H |

TABLE 2-continued

Examples of Formula (I-a1).

Formula (I-a1)

| Compound No. | —CONHR$^1$ attachment | R$^1$ | R$^2$ | R$^4$ | R$^{6'}$ | R$^{7'}$ | R$^8$ | R$^9$ | R$^{10}$ |
|---|---|---|---|---|---|---|---|---|---|
| a1-18 | meta | 2-amino-6-fluorophenyl | H | H | H | H | H | H | H |
| a1-19 | para | 2-amino-6-fluorophenyl | H | —CH$_3$ | H | H | H | H | H |
| a1-20 | meta | 2-amino-6-fluorophenyl | H | —CH$_3$ | H | H | H | H | H |
| a1-21 | para | 2-amino-6-fluorophenyl | ortho-F | H | H | H | H | H | H |
| a1-22 | meta | 2-amino-6-fluorophenyl | ortho-F | H | H | H | H | H | H |
| a1-23 | para | 2-amino-6-fluorophenyl | ortho-F | —CH$_3$ | H | H | H | H | H |
| a1-24 | meta | 2-amino-6-fluorophenyl | ortho-F | —CH$_3$ | H | H | H | H | H |
| a1-25 | para | —OH | H | H | —CH$_3$ | H | H | H | H |
| a1-26 | meta | —OH | H | H | —CH$_3$ | H | H | H | H |
| a1-27 | para | —OH | H | —CH$_3$ | —CH$_3$ | H | H | H | H |
| a1-28 | meta | —OH | H | —CH$_3$ | —CH$_3$ | H | H | H | H |
| a1-29 | para | 2-aminophenyl | H | H | —CH$_3$ | H | H | H | H |
| a1-30 | meta | 2-aminophenyl | H | H | —CH$_3$ | H | H | H | H |
| a1-31 | para | 2-aminophenyl | H | —CH$_3$ | —CH$_3$ | H | H | H | H |
| a1-32 | meta | 2-aminophenyl | H | —CH$_3$ | —CH$_3$ | H | H | H | H |
| a1-33 | para | 2-aminopyridin-3-yl | H | H | —CH$_3$ | H | H | H | H |
| a1-34 | meta | 2-aminopyridin-3-yl | H | H | —CH$_3$ | H | H | H | H |
| a1-35 | para | 2-aminopyridin-3-yl | H | —CH$_3$ | —CH$_3$ | H | H | H | H |
| a1-36 | meta | 2-aminopyridin-3-yl | H | —CH$_3$ | —CH$_3$ | H | H | H | H |
| a1-37 | para | 4-amino-1-phenyl-pyrazol-3-yl | H | H | —CH$_3$ | H | H | H | H |
| a1-38 | meta | 4-amino-1-phenyl-pyrazol-3-yl | H | H | —CH$_3$ | H | H | H | H |

TABLE 2-continued

Examples of Formula (I-a1).

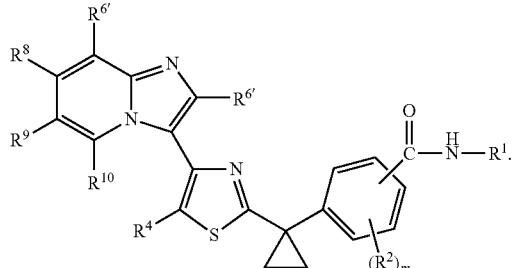

Formula (I-a1)

| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-39 | para | (1-phenyl-4-amino-pyrazol-3-yl) | H | —CH₃ | —CH₃ | H | H | H | H |
| a1-40 | meta | (1-phenyl-4-amino-pyrazol-3-yl) | H | —CH₃ | —CH₃ | H | H | H | H |
| a1-41 | para | 2-amino-6-fluorophenyl | H | H | —CH₃ | H | H | H | H |
| a1-42 | meta | 2-amino-6-fluorophenyl | H | H | —CH₃ | H | H | H | H |
| a1-43 | para | 2-amino-6-fluorophenyl | H | —CH₃ | —CH₃ | H | H | H | H |
| a1-44 | meta | 2-amino-6-fluorophenyl | H | —CH₃ | —CH₃ | H | H | H | H |
| a1-45 | para | 2-amino-6-fluorophenyl | ortho-F | H | —CH₃ | H | H | H | H |
| a1-46 | meta | 2-amino-6-fluorophenyl | ortho-F | H | —CH₃ | H | H | H | H |
| a1-47 | para | 2-amino-6-fluorophenyl | ortho-F | —CH₃ | —CH₃ | H | H | H | H |
| a1-48 | meta | 2-amino-6-fluorophenyl | ortho-F | —CH₃ | —CH₃ | H | H | H | H |
| a1-45 | para | —OH | H | H | —CH₃ | —Cl | H | H | H |
| a1-46 | para | —OH | H | H | —CH₃ | H | —Cl | H | H |
| a1-47 | para | —OH | H | H | —CH₃ | H | H | —Cl | H |
| a1-48 | para | —OH | H | H | —CH₃ | H | H | H | —Cl |
| a1-49 | meta | —OH | H | H | —CH₃ | —Cl | H | H | H |
| a1-50 | meta | —OH | H | H | —CH₃ | H | —Cl | H | H |
| a1-51 | meta | —OH | H | H | —CH₃ | H | H | —Cl | H |
| a1-52 | meta | —OH | H | H | —CH₃ | H | H | H | —Cl |
| a1-53 | para | 2-aminophenyl | H | H | —CH₃ | —Cl | H | H | H |
| a1-54 | para | 2-aminophenyl | H | H | —CH₃ | H | —Cl | H | H |
| a1-55 | para | 2-aminophenyl | H | H | —CH₃ | H | H | —Cl | H |
| a1-56 | para | 2-aminophenyl | H | H | —CH₃ | H | H | H | —Cl |
| a1-57 | para | 2-aminophenyl | H | H | —CH₃ | —Cl | H | H | H |
| a1-58 | para | 2-aminophenyl | H | H | —CH₃ | H | —Cl | H | H |
| a1-59 | para | 2-aminophenyl | H | H | —CH₃ | H | H | —Cl | H |
| a1-60 | para | 2-aminophenyl | H | H | —CH₃ | H | H | H | —Cl |
| a1-61 | para | 2-aminopyridin-3-yl | H | H | —CH₃ | —Cl | H | H | H |
| a1-62 | para | 2-aminopyridin-3-yl | H | H | —CH₃ | H | —Cl | H | H |
| a1-63 | para | 2-aminopyridin-3-yl | H | H | —CH₃ | H | H | —Cl | H |

TABLE 2-continued

Examples of Formula (I-a1).

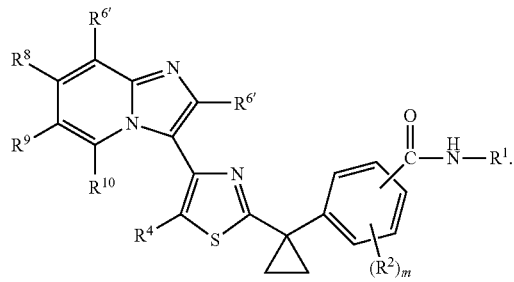

Formula (I-a1)

| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-64 | para | 2-aminopyridin-3-yl | H | H | —CH₃ | H | H | H | —Cl |
| a1-65 | para | 2-aminopyridin-3-yl | H | H | —CH₃ | —Cl | H | H | H |
| a1-66 | para | 2-aminopyridin-3-yl | H | H | —CH₃ | H | —Cl | H | H |
| a1-67 | para | 2-aminopyridin-3-yl | H | H | —CH₃ | H | H | —Cl | H |
| a1-65 | para | 2-aminopyridin-3-yl | H | H | —CH₃ | H | H | H | —Cl |
| a1-69 | para | —OH | H | H | —CH₃ | —CF₃ | H | H | H |
| a1-70 | para | —OH | H | H | —CH₃ | H | —CF₃ | H | H |
| a1-71 | para | —OH | H | H | —CH₃ | H | H | —CF₃ | H |
| a1-72 | para | —OH | H | H | —CH₃ | H | H | H | —CF₃ |
| a1-73 | para | 2-aminophenyl | H | H | —CH₃ | —CF₃ | H | H | H |
| a1-74 | para | 2-aminophenyl | H | H | —CH₃ | H | —CF₃ | H | H |
| a1-75 | para | 2-aminophenyl | H | H | —CH₃ | H | H | —CF₃ | H |
| a1-76 | para | 2-aminophenyl | H | H | —CH₃ | H | H | H | —CF₃ |
| a1-77 | para | —OH | H | H | —CH₃ | —OCH₃ | H | H | H |
| a1-75 | para | —OH | H | H | —CH₃ | H | —OCH₃ | H | H |
| a1-79 | para | —OH | H | H | —CH₃ | H | H | —OCH₃ | H |
| a1-80 | para | —OH | H | H | —CH₃ | H | H | H | —OCH₃ |
| a1-81 | para | 2-aminophenyl | H | H | —CH₃ | —OCH₃ | H | H | H |
| a1-82 | para | 2-aminophenyl | H | H | —CH₃ | H | —OCH₃ | H | H |
| a1-83 | para | 2-aminophenyl | H | H | —CH₃ | H | H | —OCH₃ | H |
| a1-84 | para | 2-aminophenyl | H | H | —CH₃ | H | H | H | —OCH₃ |
| a1-85 | para | —OH | H | H | H | ![N(CH₃)₂CH₂–] | H | H | H |
| a1-86 | para | —OH | H | H | H | H | ![N(CH₃)₂CH₂–] | H | H |
| a1-87 | para | —OH | H | H | H | H | H | ![N(CH₃)₂CH₂–] | H |
| a1-88 | para | —OH | H | H | H | H | H | H | ![N(CH₃)₂CH₂–] |

US 8,088,771 B2

TABLE 2-continued

Examples of Formula (I-a1).

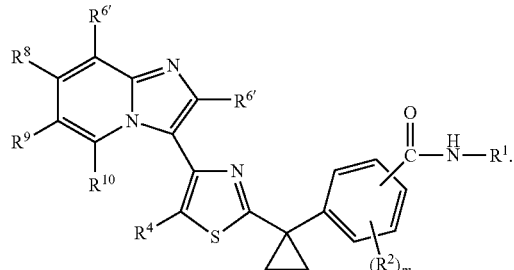

Formula (I-a1)

| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-89 | para | 2-aminophenyl | H | H | H | ‑N(CH₃)CH₂C(CH₃)₂~ | H | H | H |
| a1-90 | para | 2-aminophenyl | H | H | H | H | ‑N(CH₃)CH₂C(CH₃)₂~ | H | H |
| a1-91 | para | 2-aminophenyl | H | H | H | H | H | ‑N(CH₃)CH₂C(CH₃)₂~ | H |
| a1-92 | para | 2-aminophenyl | H | H | H | H | H | H | ‑N(CH₃)CH₂C(CH₃)₂~ |
| a1-93 | para | 2-aminophenyl | ortho-F | H | H | ‑N(CH₃)CH₂C(CH₃)₂~ | H | H | H |
| a1-94 | para | 2-aminophenyl | ortho-F | H | H | H | ‑N(CH₃)CH₂C(CH₃)₂~ | H | H |
| a1-95 | para | 2-aminophenyl | ortho-F | H | H | H | H | ‑N(CH₃)CH₂C(CH₃)₂~ | H |
| a1-96 | para | 2-aminophenyl | ortho-F | H | H | H | H | H | ‑N(CH₃)CH₂C(CH₃)₂~ |

TABLE 2-continued

Examples of Formula (I-a1).

Formula (I-a1)

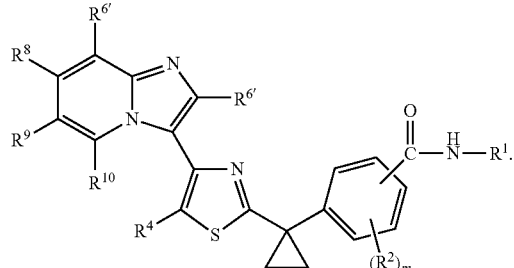

| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-97 | para | 2-amino-6-fluorophenyl | ortho-F | H | H | ~N(CH₃)CH₂– | H | H | H |
| a1-98 | para | 2-amino-6-fluorophenyl | ortho-F | H | H | H | ~N(CH₃)CH₂– | H | H |
| a1-99 | para | 2-amino-6-fluorophenyl | ortho-F | H | H | H | H | ~N(CH₃)CH₂– | H |
| a1-100 | para | 2-amino-6-fluorophenyl | ortho-F | H | H | H | H | H | ~N(CH₃)CH₂– |
| a1-101 | meta | 2-aminophenyl | H | H | H | ~N(CH₃)CH₂– | H | H | H |
| a1-102 | meta | 2-aminophenyl | H | H | H | H | ~N(CH₃)CH₂– | H | H |
| a1-103 | meta | 2-aminophenyl | H | H | H | H | H | ~N(CH₃)CH₂– | H |
| a1-104 | meta | 2-aminophenyl | H | H | H | H | H | H | ~N(CH₃)CH₂– |

TABLE 2-continued

Examples of Formula (I-a1).

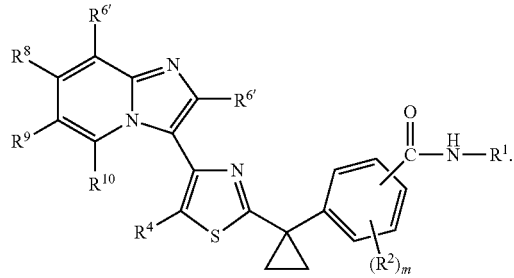

Formula (I-a1)

| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-105 | para | 2-aminophenyl | H | H | H | pyrrolidinylmethyl | H | H | H |
| a1-106 | para | 2-aminophenyl | H | H | H | H | pyrrolidinylmethyl | H | H |
| a1-107 | para | 2-aminophenyl | H | H | H | H | H | pyrrolidinylmethyl | H |
| a1-108 | para | 2-aminophenyl | H | H | H | H | H | H | pyrrolidinylmethyl |
| a1-109 | para | 2-amino-6-fluorophenyl | ortho-F | H | H | pyrrolidinylmethyl | H | H | H |
| a1-110 | para | 2-amino-6-fluorophenyl | ortho-F | H | H | H | pyrrolidinylmethyl | H | H |

TABLE 2-continued
Examples of Formula (I-a1).
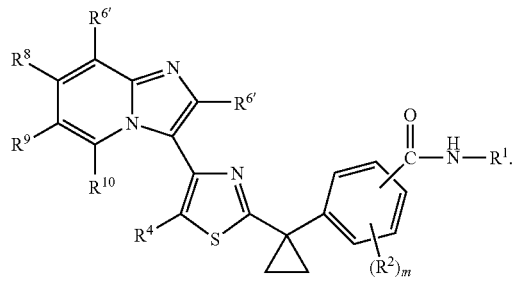
Formula (I-a1)
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-111 | para | 2-amino-6-fluorophenyl | ortho-F | H | H | H | H | pyrrolidinyl-CH₂- | H |
| a1-112 | para | 2-amino-6-fluorophenyl | ortho-F | H | H | H | H | H | pyrrolidinyl-CH₂- |
| a1-113 | para | 2-aminophenyl | H | H | H | morpholinyl-CH₂- | H | H | H |
| a1-114 | para | 2-aminophenyl | H | H | H | H | morpholinyl-CH₂- | H | H |
| a1-115 | para | 2-aminophenyl | H | H | H | H | H | morpholinyl-CH₂- | H |

TABLE 2-continued
Examples of Formula (I-a1).
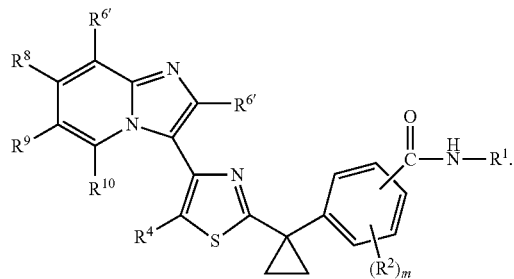
Formula (I-a1)
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-116 | para | 2-aminophenyl | H | H | H | H | H | H | 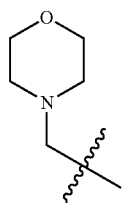 |
| a1-117 | para | 2-amino-6-fluorophenyl | ortho-F | H | H | 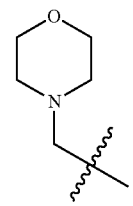 | H | H | H |
| a1-118 | para | 2-amino-6-fluorophenyl | ortho-F | H | H | H | 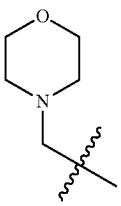 | H | H |
| a1-119 | para | 2-amino-6-fluorophenyl | ortho-F | H | H | H | H | 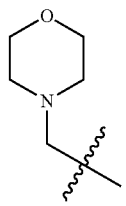 | H |
| a1-120 | para | 2-amino-6-fluorophenyl | ortho-F | H | H | H | H | H | 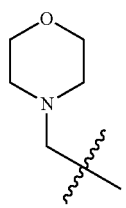 |

TABLE 2-continued
Examples of Formula (I-a1).
Formula (I-a1)
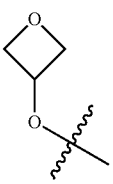
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-121 | para | 2-aminophenyl | H | H | H | 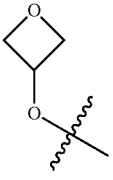 | H | H | H |
| a1-122 | para | 2-aminophenyl | H | H | H | H | 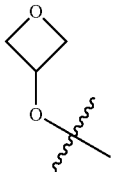 | H | H |
| a1-123 | para | 2-aminophenyl | H | H | H | H | H | 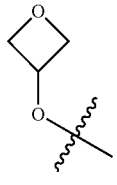 | H |
| a1-124 | para | 2-aminophenyl | H | H | H | H | H | H | 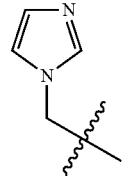 |
| a1-125 | para | 2-aminophenyl | H | H | H | 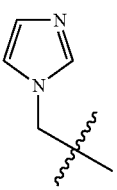 | H | H | H |
| a1-126 | para | 2-aminophenyl | H | H | H | H |  | H | H |

TABLE 2-continued
Examples of Formula (I-a1).
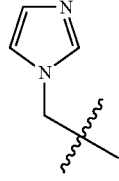
Formula (I-a1)
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-127 | para | 2-aminophenyl | H | H | H | H | H | 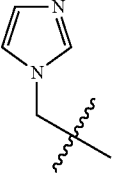 | H |
| a1-128 | para | 2-aminophenyl | H | H | H | H | H | H | 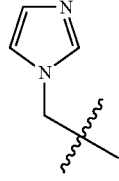 |
| a1-129 | para | 2-aminophenyl | H | H | H | 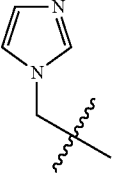 | H | H | H |
| a1-130 | para | 2-aminophenyl | H | H | H | H | 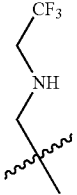 | H | H |
| a1-131 | para | 2-aminophenyl | H | H | H | H | H | 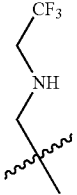 | H |

TABLE 2-continued

Examples of Formula (I-a1).

Formula (I-a1)

| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-132 | para | 2-aminophenyl | H | H | H | H | H | H | -CH₂C(CH₃)(NHCH₂CF₃)- |
| a1-133 | para | 2-aminophenyl | H | H | H | -C(CH₃)(CH₂N(CH₃)CH₂CH₂OCH₃)- | H | H | H |
| a1-134 | para | 2-aminophenyl | H | H | H | H | -C(CH₃)(CH₂N(CH₃)CH₂CH₂OCH₃)- | H | H |
| a1-135 | para | 2-aminophenyl | H | H | H | H | H | -C(CH₃)(CH₂N(CH₃)CH₂CH₂OCH₃)- | H |

TABLE 2-continued
Examples of Formula (I-a1).
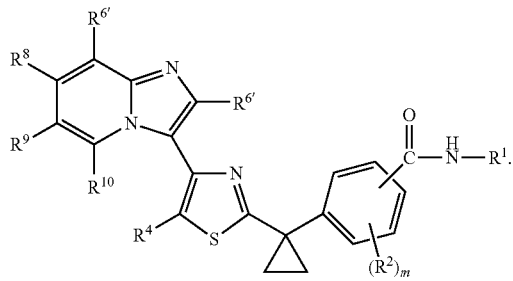
Formula (I-a1)
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-136 | para | 2-aminophenyl | H | H | H | H | H | H | (OCH2CH2N(CH3)-) |
| a1-137 | para | 2-amino-5-fluorophenyl | H | H | H | CF₃CH₂NH- | H | H | H |
| a1-138 | para | 2-amino-5-fluorophenyl | H | H | H | H | CF₃CH₂NH- | H | H |
| a1-139 | para | 2-amino-5-fluorophenyl | H | H | H | H | H | CF₃CH₂NH- | H |
| a1-140 | para | 2-amino-5-fluorophenyl | H | H | H | H | H | H | CF₃CH₂NH- |

TABLE 2-continued
Examples of Formula (I-a1).
Formula (I-a1)
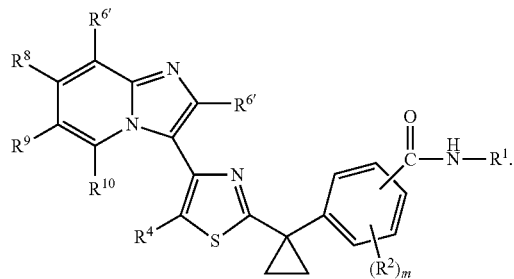
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-141 | para | 2-aminophenyl | H | H | H | 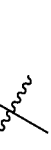 | H | H | H |
| a1-142 | para | 2-aminophenyl | H | H | H | H | 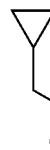 | H | H |
| a1-143 | para | 2-aminophenyl | H | H | H | H | H |  | H |
| a1-144 | para | 2-aminophenyl | H | H | H | H | H | H |  |
| a1-145 | para | 2-aminophenyl | H | H | H |  | H | H | H |
| a1-146 | para | 2-aminophenyl | H | H | H | H |  | H | H |
| a1-147 | para | 2-aminophenyl | H | H | H | H | H |  | H |

TABLE 2-continued

Examples of Formula (I-a1).

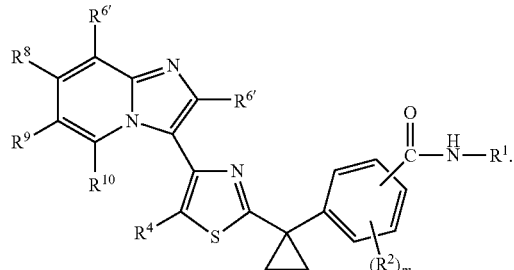

Formula (I-a1)

| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-148 | para | 2-aminophenyl | H | H | H | H | H | H | cyclopropyl |
| a1-149 | para | 2-aminophenyl | H | H | H | cyclobutyl-O- | H | H | H |
| a1-150 | para | 2-aminophenyl | H | H | H | H | cyclobutyl-O- | H | H |
| a1-151 | para | 2-aminophenyl | H | H | H | H | H | cyclobutyl-O- | H |
| a1-152 | para | 2-aminophenyl | H | H | H | H | H | H | cyclobutyl-O- |
| a1-153 | para | 2-aminophenyl | H | H | H | 1-cyclopropylethyl-O- | H | H | H |
| a1-154 | para | 2-aminophenyl | H | H | H | H | 1-cyclopropylethyl-O- | H | H |

US 8,088,771 B2
TABLE 2-continued
Examples of Formula (I-a1).
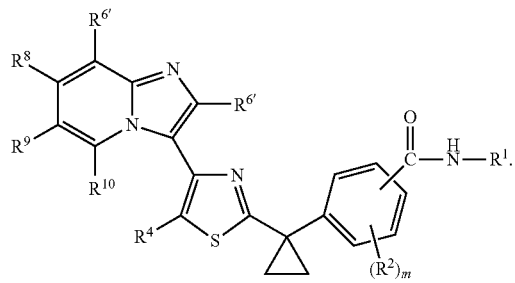
Formula (I-a1)
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-155 | para | 2-aminophenyl | H | H | H | H | H | 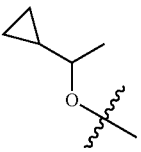 | H |
| a1-156 | para | 2-aminophenyl | H | H | H | H | H | H | 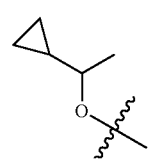 |
| a1-157 | para | 2-aminophenyl | H | H | H | 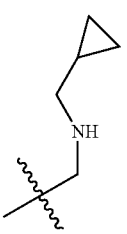 | H | H | H |
| a1-158 | para | 2-aminophenyl | H | H | H | H | H | 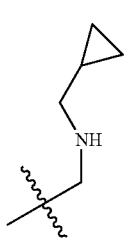 | H |
| a1-159 | para | 2-aminophenyl | H | H | H | H | H | H | 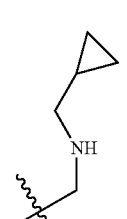 |

TABLE 2-continued
Examples of Formula (I-a1).
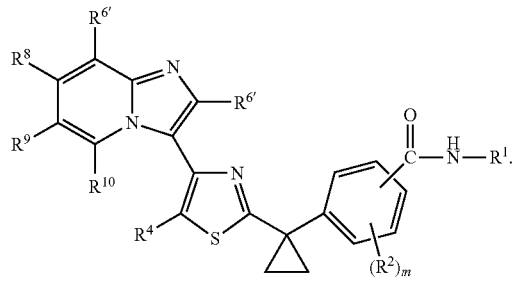
Formula (I-a1)
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-160 | para | 2-aminophenyl | H | H | H | H | H | H | ![cyclopropylmethylaminoethyl] |
| a1-161 | para | 2-aminophenyl | H | H | H | ![4-methylpiperazinyl-CO-C(CH3)2-] | H | H | H |
| a1-162 | para | 2-aminophenyl | H | H | H | H | ![4-methylpiperazinyl-CO-C(CH3)2-] | H | H |
| a1-163 | para | 2-aminophenyl | H | H | H | H | H | ![4-methylpiperazinyl-CO-C(CH3)2-] | H |

TABLE 2-continued
Examples of Formula (I-a1).
Formula (I-a1)
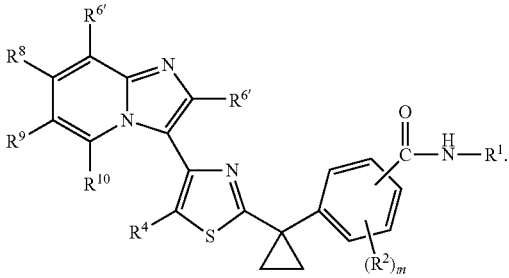
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-164 | para | 2-aminophenyl | H | H | H | H | H | H | 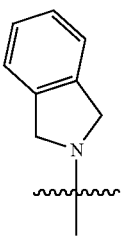 |
| a1-165 | para | 2-aminophenyl | H | H | H | 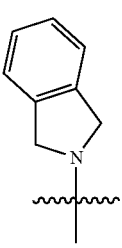 | H | H | H |
| a1-166 | para | 2-aminophenyl | H | H | H | H | 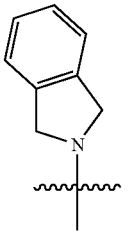 | H | H |
| a1-167 | para | 2-aminophenyl | H | H | H | H | H |  | H |

TABLE 2-continued

Examples of Formula (I-a1).

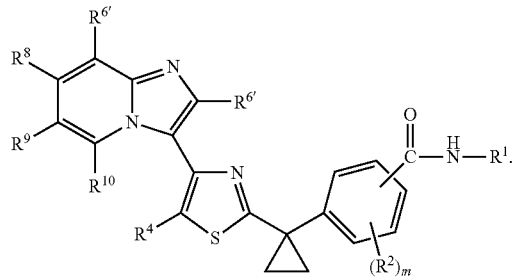

Formula (I-a1)

| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-168 | para | 2-aminophenyl | H | H | H | H | H | H | ![isoindoline] |
| a1-169 | para | —OH | H | H | —CH₃ | —F | H | H | H |
| a1-170 | para | 2-aminophenyl | H | H | —CH₃ | —F | H | H | H |
| a1-171 | para | —OH | H | H | —CH₃ | H | H | —Br | H |
| a1-172 | para | 2-aminophenyl | H | H | —CH₃ | H | H | —Br | H |
| a1-173 | para | —OH | H | H | —CH₃ | H | ![methoxyethylamide] | H | H |
| a1-174 | para | 2-aminophenyl | H | H | —CH₃ | H | ![methoxyethylamide] | H | H |
| a1-175 | para | —OH | H | H | —CH₃ | H | H | ![methoxyethylamide] | H |

TABLE 2-continued
Examples of Formula (I-a1).
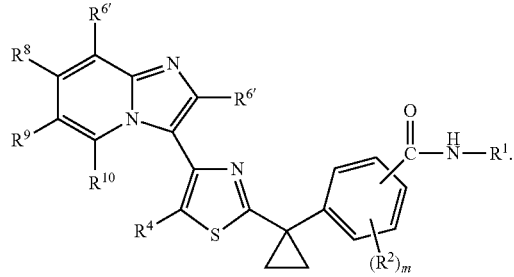
Formula (I-a1)
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-176 | para | 2-aminophenyl | H | H | —CH₃ | H | H | ![methoxyethyl amide] | H |
| a1-177 | para | —OH | H | H | —CH₃ | H | H | ![morpholinoethyl amide] | H |
| a1-178 | para | 2-aminophenyl | H | H | —CH₃ | H | H | ![morpholinoethyl amide] | H |
| a1-179 | para | —OH | H | H | —CH₃ | H | H | ![morpholinoethyl amide] | H |

TABLE 2-continued
Examples of Formula (I-a1).
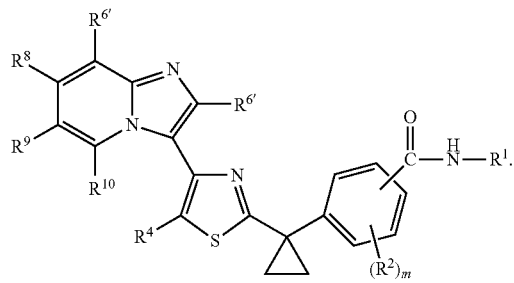
Formula (I-a1)
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-180 | para | 2-aminophenyl | H | H | —CH₃ | H | H | 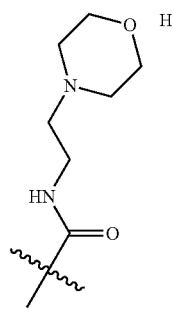 | H |
| a1-181 | para | —OH | H | H | —CH₃ | H | 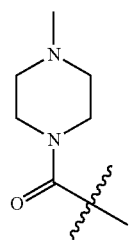 | H | H |
| a1-182 | para | 2-aminophenyl | H | H | —CH₃ | H | 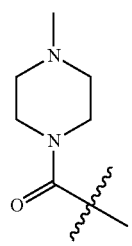 | H | H |
| a1-183 | para | —OH | H | H | —CH₃ | H | H | 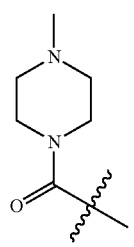 | H |

TABLE 2-continued
Examples of Formula (I-a1).
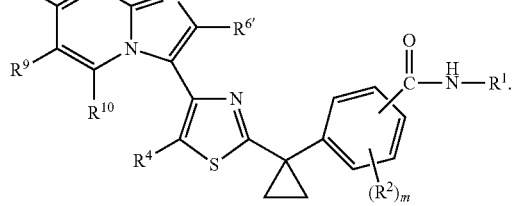
Formula (I-a1)
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-184 | para | 2-aminophenyl | H | H | —CH₃ | H | H | 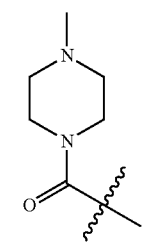 | H |
| a1-185 | para | —OH | H | H | —CH₃ | H | 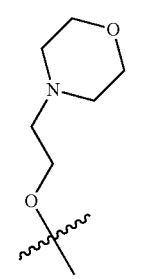 | H | H |
| a1-186 | para | 2-aminophenyl | H | H | —CH₃ | H | 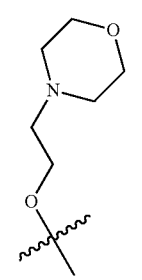 | H | H |
| a1-187 | para | —OH | H | H | —CH₃ | H | 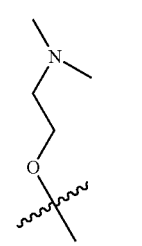 | H | H |

TABLE 2-continued
Examples of Formula (I-a1).
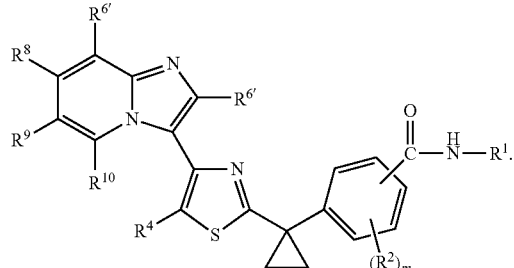
Formula (I-a1)
| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-188 | para | 2-aminophenyl | H | H | —CH₃ | H | | H | H |
| a1-189 | para | —OH | H | H | —CH₃ | H | | H | H |
| a1-190 | para | 2-aminophenyl | H | H | —CH₃ | H | | H | H |
| a1-191 | para | —OH | H | H | —CH₃ | H | H | | H |
| a1-192 | para | 2-aminophenyl | H | H | —CH₃ | H | H | | H |

TABLE 2-continued

Examples of Formula (I-a1).

Formula (I-a1)

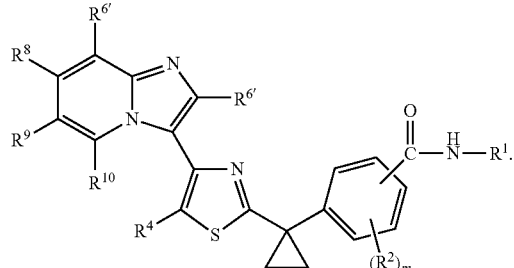

| Compound No. | —CONHR¹ attachment | R¹ | R² | R⁴ | R⁶' | R⁷' | R⁸ | R⁹ | R¹⁰ |
|---|---|---|---|---|---|---|---|---|---|
| a1-193 | para | —OH | H | H | —CH₃ | H | ₂) | H | H |
| a1-194 | para | 2-aminophenyl | H | H | —CH₃ | H | ₂) | H | H |
| a1-195 | para | —OH | H | H | —CH₃ | H | H | —OCH₃ | H |
| a1-196 | para | 2-aminophenyl | H | H | —CH₃ | H | H | —OCH₃ | H |
| a1-197 | para | —OH | H | H | —CF₃ | H | H | —OCH₃ | H |
| a1-198 | para | 2-aminophenyl | H | H | —CF₃ | H | H | —OCH₃ | H |
| a1-199 | para | —OH | H | H | —CH₃ | H | ₂) | H | H |
| a1-200 | para | 2-aminophenyl | H | H | —CH₃ | H | ₂) | H | H |

In particular embodiments of Formulae (I-a2) to (I-a6), the groups R¹, R⁴, R⁶', R⁷', R⁸, R⁹ and R¹⁰ can be selected to have the same combination of substituents given in the table for Compounds a1-01 to a1-200 where such combinations are chemically feasible.

In yet another embodiment of Formula (I-a), Cy¹ is cyclopropylidene and Cy² is substituted by R⁴ being a monocyclic aryl, cycloalkyl or heterocyclyl. Further, R¹ is hydroxyl, aryl or heteroaryl, wherein aryl or heteroaryl is substituted with —NH₂ or —OH at a ring position adjacent to attachment of the —CONH-moiety, wherein R¹ is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl; R² is halo, alkyl or haloalkyl; m is 0 or 1 and R² is halo, alkyl or haloalkyl; n is 0, 1 or 2 and each R³ is independently methyl, ethyl, bromo, trifluoromethyl; p is 1 or greater; and one and only one R⁴ is aryl, cycloalkyl or heterocyclyl, wherein aryl, cycloalkyl or heterocyclyl is a monocyclic ring while other R⁴, if present, are not aryl, cycloalkyl, or heterocyclyl. When $R^4$ is a ring, $R^4$ is optionally further substituted by one or more $R^5$ where such an optional substitution is chemically feasible; and $R^5$ is as defined above.

Compounds of this embodiment include, but are not limited to, the following formulae where the groups $R^{6\prime}$, $R^{7\prime}$, $R^8$, $R^9$, and $R^{10}$ are independently selected from H and the functional groups of $R^5$ defined herein:

Formula (I-a7)

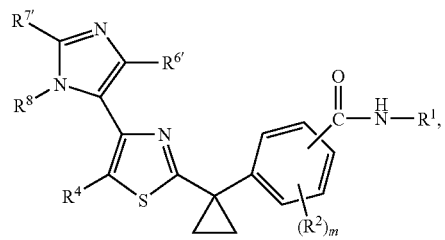

Formula (I-a8)

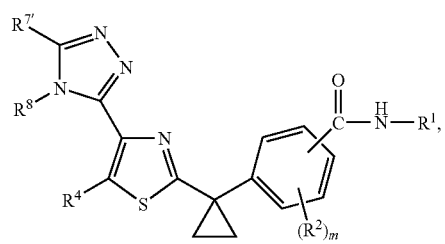

Formula (I-a9)

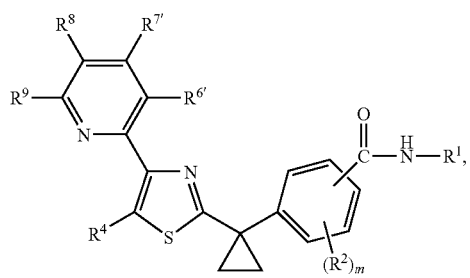

Formula (I-a10)

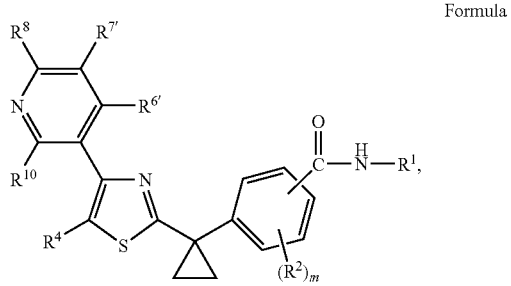

Formula (I-a11)

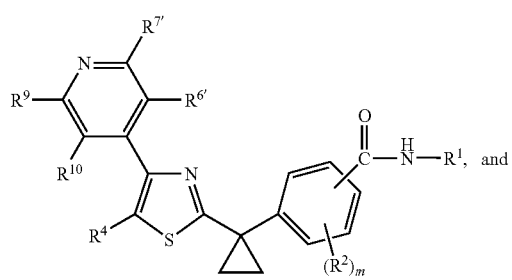

Formula (I-a12)

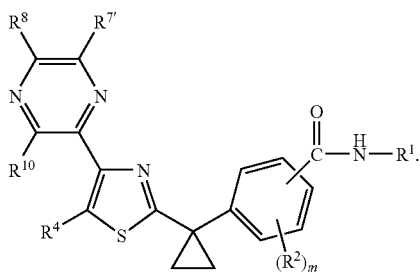

Non-limiting examples of Formulae (I-a7), (I-a8), (I-a9), (I-a11), and (I-a12) include the following compounds and pharmaceutically acceptable salts thereof:

Compound a7-01

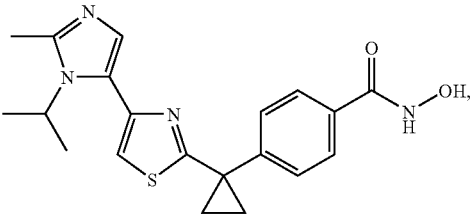

Compound a7-02

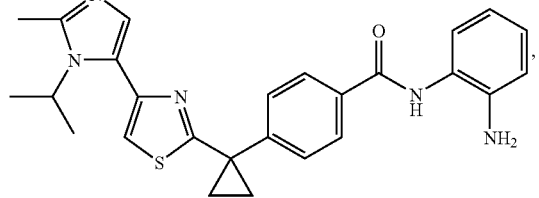

Compound a7-03

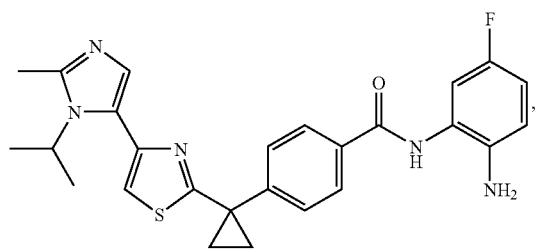

Compound a8-01

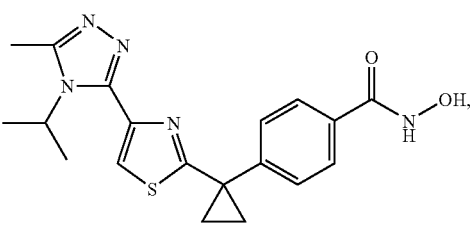

Compound a8-02
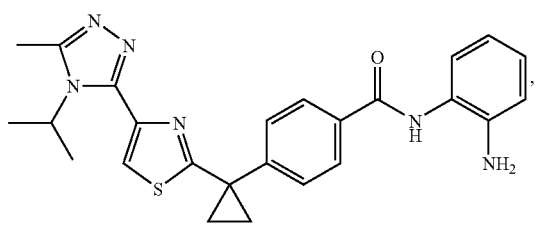
Compound a8-03
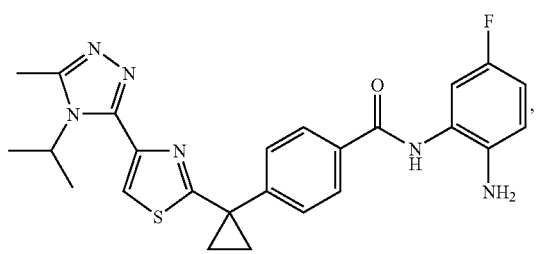
Compound a9-01
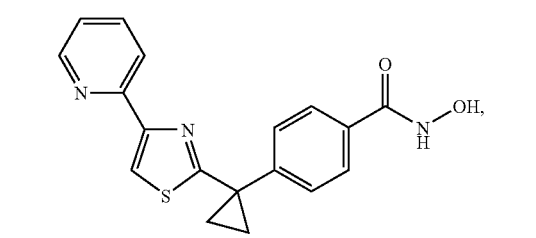
Compound a9-02
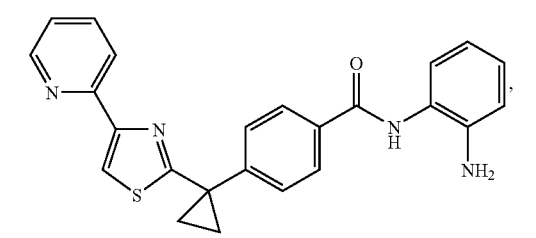
Compound a9-03
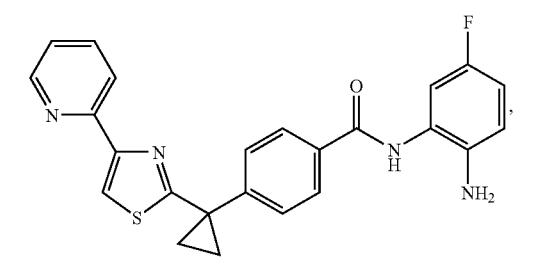
Compound a11-01
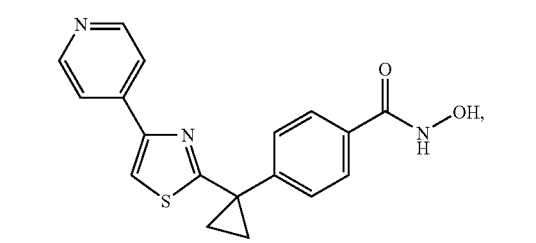
Compound a11-02
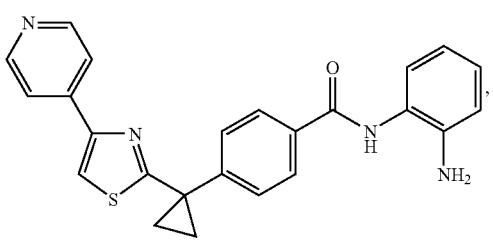
Compound a11-03
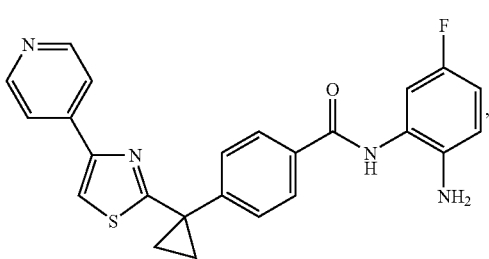
Compound a12-01
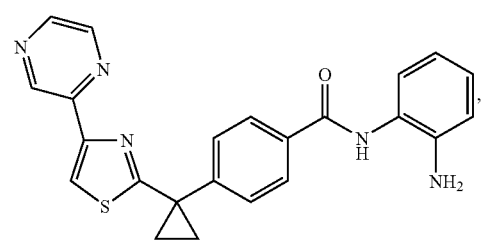
Compound a12-02
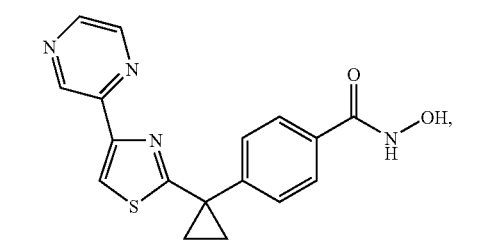
Compound a12-03
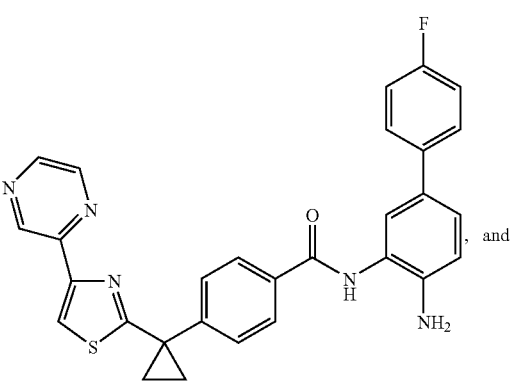
and -continued Compound a12-04

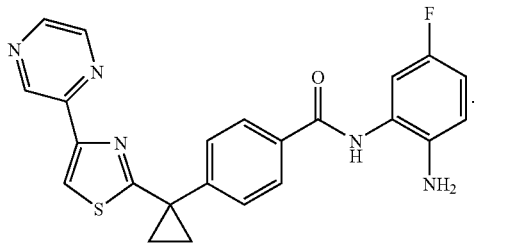

Table 3 provides non-limiting examples of compounds of Formula (I-a10) where m is zero and $R^4$, $R^{6'}$, $R^{7'}$, and $R^{10}$ are H, as shown in Structure (A10).

TABLE 3

Examples of Structure (A10).

Structure (A10)

| Compound No. | $R^1$ | $R^8$ |
|---|---|---|
| a10-01 | HO— | H |
| a10-02 | 2-aminophenyl | H |
| a10-03 | 2-amino-5-fluorophenyl | H |
| a10-04 | ![H2N-phenyl-thiophene] | H |
| a10-05 | ![H2N-phenyl-methylthiophene] | H |
| a10-06 | HO— | Cl— |
| a10-07 | 2-aminophenyl | Cl— |
| a10-08 | HO— | pyrrolidin-1-yl |
| a10-09 | 2-aminophenyl | pyrrolidin-1-yl |
| a10-10 | HO— | 2-methoxy-ethoxy |
| a10-11 | 2-aminophenyl | 2-methoxy-ethoxy |
| a10-12 | HO— | piperazin-1-yl |
| a10-13 | 2-aminophenyl | piperazin-1-yl |
| a10-14 | HO— | 4-methyl-piperazin-1-yl |
| a10-15 | 2-aminophenyl | 4-methyl-piperazin-1-yl |
| a10-16 | HO— | 4-cyclopropyl-piperazin-1-yl |
| a10-17 | 2-aminophenyl | 4-cyclopropyl-piperazin-1-yl |

In an embodiment of Formula (I-a), $Cy^1$ is cyclobutylidene, cyclopentylidene, cyclohexylidene or cycloheptylidene; $R^1$ is hydroxyl, aryl or heteroaryl, wherein aryl or heteroaryl is substituted with —$NH_2$ or —OH at a ring position adjacent to attachment of the —CONH-moiety, wherein $R^1$ is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl; m is 0 or 1 and $R^2$ is halo, alkyl or haloalkyl; n is 0, 1 or 2 and each $R^3$ is independently methyl, ethyl, bromo, trifluoromethyl; p is 0, 1 or 2 and each $R^4$ is independently selected from the group consisting of halo, nitro, cyano, hydroxyl, hydroxyalkyl, haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, $NH_2$—S(O)$_2$NH—, N—($C_{1-10}$ alkyl)sulphamoyl and N,N—($C_{1-10}$ alkyl)$_2$ sulphamoyl, wherein each $R^4$ is optionally substituted by one or more B where such an optional substitution is chemically feasible. In a particular embodiment, $Cy^1$ is cyclopentylidene.

Non-limiting examples of such compounds include compounds of Formula (I-a'0) and pharmaceutically acceptable salts thereof:

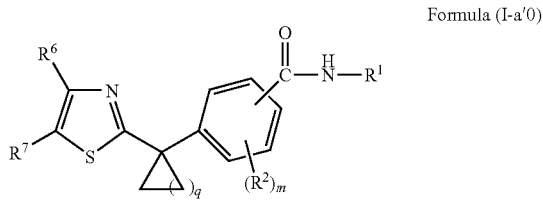

Formula (I-a'0)

wherein q is 2, 3, 4 or 5; $R^1$ and $R^2$ are as defined above; and $R^6$ and $R^7$ are selected from groups $R^4$. In specific embodiments, $R^1$, $R^4$, $R^6$ and $R^7$ can be selected to have the same combination of substituents given in the table for Compounds a0-01 to a0-126.

In another embodiment of Formula (I-a), $Cy^1$ is cyclobutylidene, cyclopentylidene, cyclohexylidene or cycloheptylidene and $Cy^2$ is substituted with a fused ring $R^4$. Further, $R^1$ is hydroxyl, aryl or heteroaryl, wherein aryl or heteroaryl is substituted with —$NH_2$ or —OH at a ring position adjacent to attachment of the —CONH-moiety, wherein $R^1$ is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl; $R^2$ is halo, alkyl or haloalkyl; m is 0 or 1 and $R^2$ is halo, alkyl or haloalkyl; n is 0, 1 or 2 and each $R^3$ is independently methyl, ethyl, bromo, trifluoromethyl; p is 1 or greater; and one and only one $R^4$ is aryl, cycloalkyl or heterocyclyl, wherein aryl, cycloalkyl or heterocyclyl is a fused ring optionally further substituted by one or more $R^5$ where such an optional substitution is chemically feasible; and $R^5$ is as defined above. In a particular embodiment, $Cy^1$ is cyclopentylidene.

Non-limiting examples of such compounds include compounds of Formulae (I-a'1) to (I-a'6) and pharmaceutically acceptable salts thereof:

Formula (I-a'1)

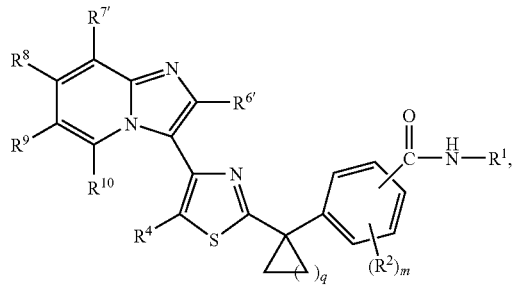

Formula (I-a'2)

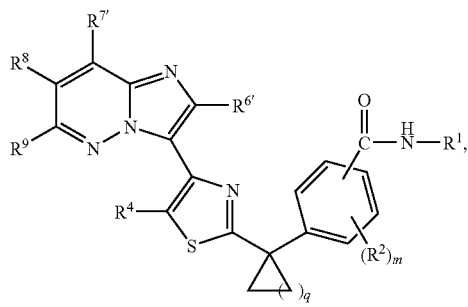

Formula (I-a'3)

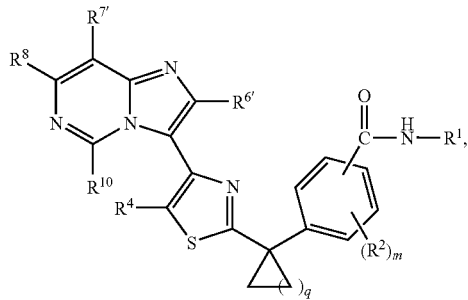

Formula (I-a'4)

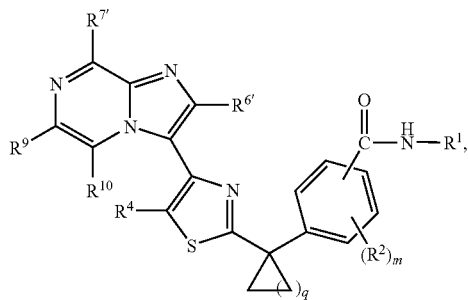

Formula (I-a'5)

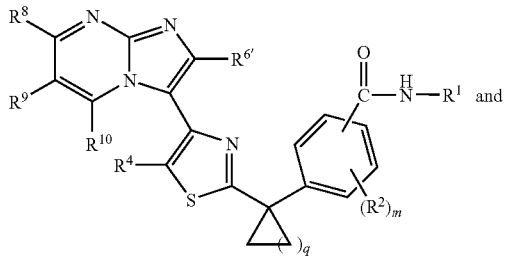

and

Formula (I-a'6)

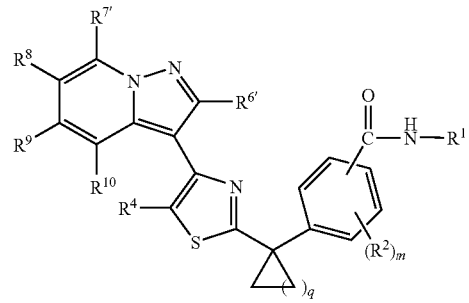

where the groups $R^{6'}$, $R^{7'}$, $R^8$, $R^9$, and $R^{10}$ are independently selected from H and the functional groups of $R^5$ defined herein, and wherein q is 2, 3, 4 or 5. In particular embodiments, for each value of q, the groups $R^1$, $R^2$, $R^4$, $R^{6'}$, $R^{7'}$, $R^8$, $R^9$ and $R^{10}$ are selected to have the same combination of substituents given in the table for Compounds a1-01 to a1-200. Non-limiting examples of such compounds include the following compounds and pharmaceutically acceptable salts thereof:

Compound a'1-27

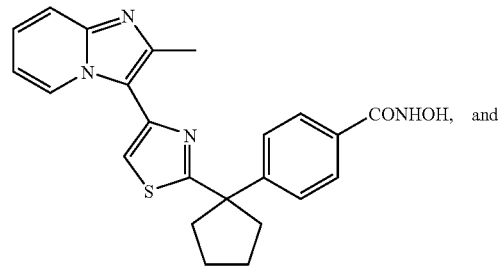

and

Compound a'1-29

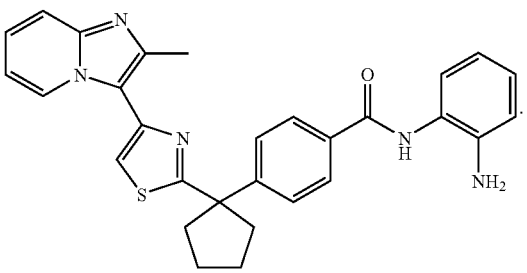

In yet another embodiment of Formula (I-a), $Cy^1$ is cyclobutylidene, cyclopentylidene, cyclohexylidene or cycloheptylidene and $Cy^2$ is substituted with a monocyclic ring. Further, $R^1$ is hydroxyl, aryl or heteroaryl, wherein aryl or heteroaryl is substituted with —$NH_2$ or —OH at a ring position adjacent to attachment of the —CONH-moiety, wherein $R^1$ is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl; $R^2$ is halo, alkyl or haloalkyl; m is 0 or 1 and $R^{12}$ is halo, alkyl or haloalkyl; n is 0, 1 or 2 and each $R^3$ is independently methyl, ethyl, bromo, trifluoromethyl; p is 1 or greater and one and only one $R^4$ is aryl, cycloalkyl or heterocyclyl, wherein aryl, cycloalkyl or heterocyclyl is a monocyclic ring and $R^4$ is optionally further substituted by one or more $R^5$ where such an optional substitution is chemically feasible; and $R^5$ is as defined above. In a particular embodiment, $Cy^1$ is cyclopentylidene.

Non-limiting examples of such compounds include compounds of Formulae (I-a'7) to (I-a'12) and pharmaceutically acceptable salts thereof:

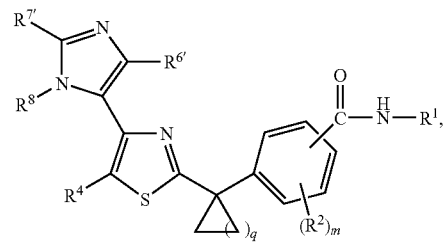

Formula (I-a'7)

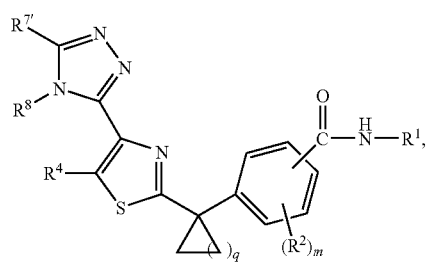

Formula (I-a'8)

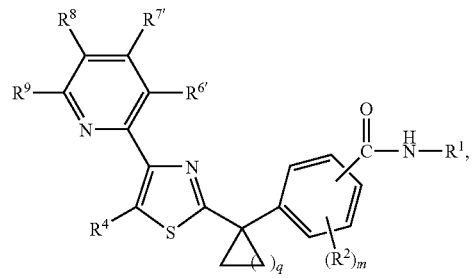

Formula (I-a'9)

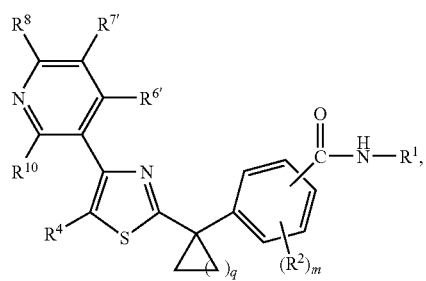

Formula (I-a'10)

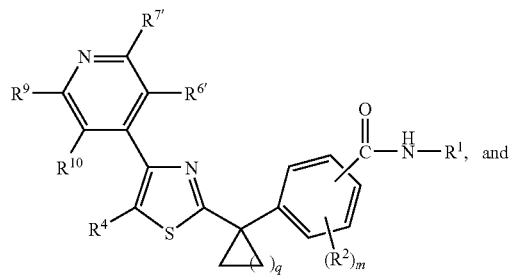

Formula (I-a'11)

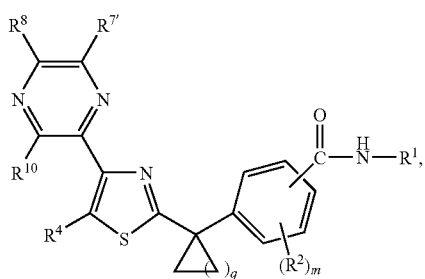

Formula (I-a'12)

where the groups $R^{6'}$, $R^{7'}$, $R^8$, $R^9$, and $R^{10}$ are independently selected from H and the functional groups of $R^5$ defined herein and q is 2, 3, 4, or 5. In various embodiments, the groups $R^1$, $R^4$, $R^{6'}$, $R^{7'}$, $R^8$, $R^9$ and $R^{10}$ are selected to have the same combination of substituents as those of Formulae (I-a7), (I-a8), (I-a9), (I-a10), (I-a11), and (I-a12). Non-limiting examples of such compounds include the following compounds and pharmaceutically acceptable salts thereof:

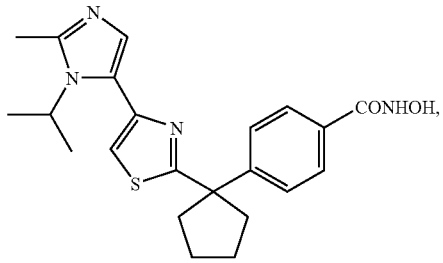

Compound a'7-01

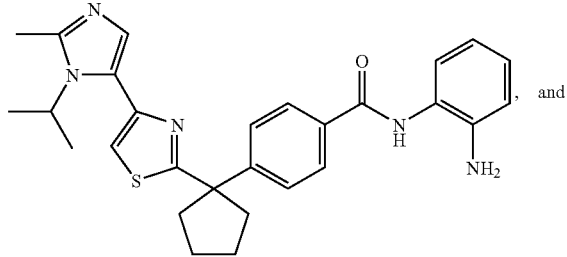

Compound a'7-02

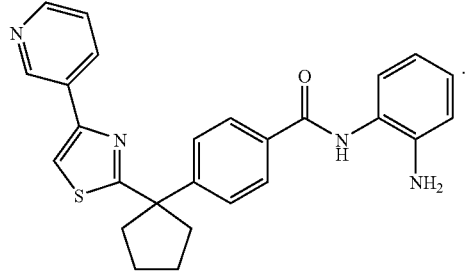

Compound a'10-02

In a further embodiment of Formula (I-a), $Cy^1$ is heterocycloalkylidene; $R^1$ is hydroxyl, aryl or heteroaryl, wherein aryl or heteroaryl is substituted with —$NH_2$ or —OH at a ring position adjacent to attachment of the —CONH-moiety, wherein $R^1$ is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl; $R^2$ is halo, alkyl or haloalkyl; m is 0 or 1 and $R^2$ is halo, alkyl or haloalkyl; n is 0, 1 or 2 and each $R^3$ is independently methyl, ethyl, bromo, trifluoromethyl; p is 0, 1 or 2 and each $R^4$ is independently selected from the group consisting of halo, nitro, cyano, hydroxyl, hydroxyalkyl, haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, $NH_2$—S(O)$_2$NH—, N—($C_{1-10}$ alkyl) sulphamoyl and N,N—($C_{1-10}$ alkyl)$_2$sulphamoyl, wherein each $R^4$ is optionally substituted by one or more $R^{15}$ where such an optional substitution is chemically feasible. In a particular embodiment, $Cy^1$ is

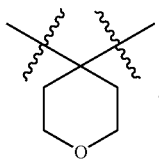

Non-limiting examples of such compounds include compounds of Formula (I-a″0) and pharmaceutically acceptable salts thereof:

Formula (I-a″0)

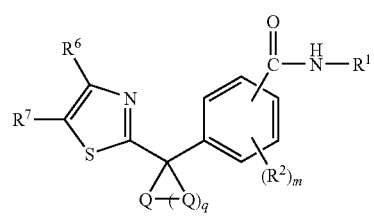

wherein $R^6$ and $R^7$ are independently selected from groups $R^4$; q is 2, 3, 4 or 5 and each Q is independently —$CH_2$— or a heteroatom selected from —NH—, —O— and —S—, and when Q is methylene (—$CH_2$—) or imino (—NH—), Q is optionally substituted with a group $R^3$. In various embodiments, Q adjacent the 1-position is not a heteroatom. In particular embodiments, q is 2, 3, 4 or 5; each Q is independently —$CH_2$— or a heteroatom selected from —NH—, —O— and —S—. In a particular embodiment, $Cy^1$ is

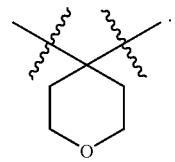

Table 4 provides non-limiting examples of compounds of Formula (I-a″0) where m is zero, q is four, and Q is oxygen at the 4-position, as shown in Structure (A″0):

TABLE 4

Examples of Structure (A″0).

Structure (A″0)

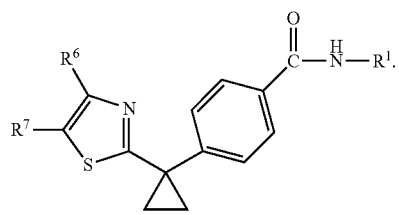

| Compound No. | $R^1$ | $R^6$ | $R^7$ |
|---|---|---|---|
| a″0-01 | 2-aminophenyl | $CH_3$— | $CH_3C(O)$— |
| a″0-02 | 2-aminophenyl | 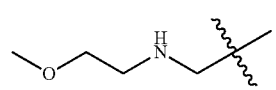 | H |
| a″0-03 | 2-aminophenyl | N-pyridin-2-ylaminomethyl | H |
| a″0-04 | 2-aminophenyl | pyridin-2-yloxymethyl | H |
| a″0-05 | 2-aminophenyl | 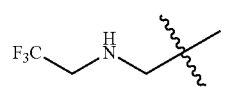 | H |

TABLE 4-continued
Examples of Structure (A″0).
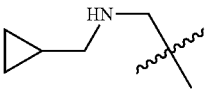
Structure (A″0)
| Compound No. | R¹ | R⁶ | R⁷ |
| --- | --- | --- | --- |
| a″0-06 | 2-aminophenyl | 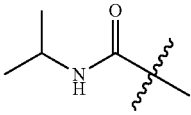 | H |
| a″0-07 | 2-aminophenyl | 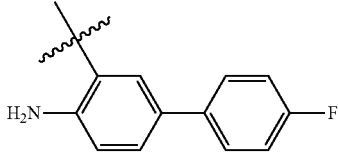 | H |
| a″0-08 | 2-aminophenyl | $CH_3$— | $(CH_3)_2NC(O)$— |
| a″0-09 | —OH | H | H |
| a″0-10 | 2-aminophenyl | H | H |
| a″0-11 | 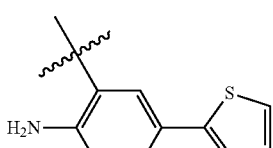 | H | H |
| a″0-12 | 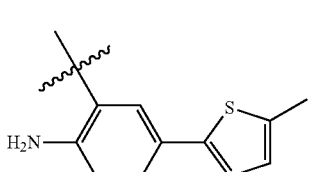 | H | H |
| a″0-13 | 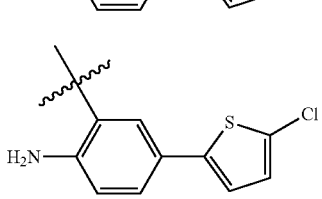 | H | H |
| a″0-14 | 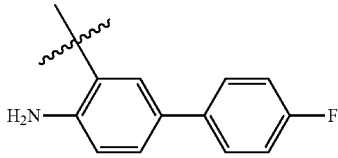 | H | H |
| a″0-15 | 2-aminophenyl | $CH_3$— | isopropyl |
| a″0-16 | 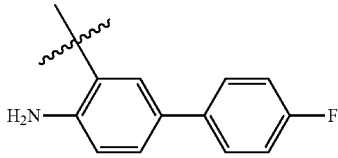 | $CH_3$— | isopropyl |

TABLE 4-continued
Examples of Structure (A″0).
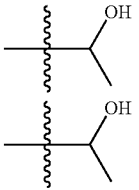
Structure (A″0)
| Compound No. | R¹ | R⁶ | R⁷ |
|---|---|---|---|
| a″0-17 | 2-aminophenyl | $CH_3$— | 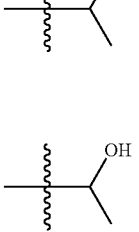 |
| a″0-18 | 2-amino-5-fluorophenyl | $CH_3$— | 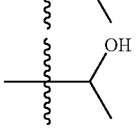 |
| a″0-19 | 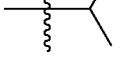 | $CH_3$— | 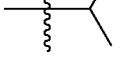 |
| a″0-20 | 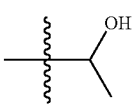 | $CH_3$— | 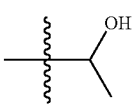 |
| a″0-21 | 2-aminophenyl | $CH_3$— | $CH_3$— |
| a″0-22 |  | $CH_3$— | $CH_3$— |
| a″0-23 | HO— | pyrrolidin-1-ylmethyl | H |
| a″0-24 | 2-aminophenyl | pyrrolidin-1-ylmethyl | H |
| a″0-25 | 2-amino-5-fluorophenyl | pyrrolidin-1-ylmethyl | H |
| a″0-26 | 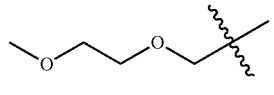 | pyrrolidin-1-ylmethyl | H |
| a″0-27 | 2-aminophenyl | 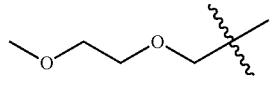 | H |
| a″0-28 |  |  | H |

TABLE 4-continued

Examples of Structure (A″0).

Structure (A″0)

| Compound No. | R¹ | R⁶ | R⁷ |
|---|---|---|---|
| a″0-29 | 2-aminophenyl | morpholin-4-ylmethyl | H |
| a″0-30 | 4-amino-3-(thiophen-2-yl)phenyl (H₂N-phenyl-thiophene) | morpholin-4-ylmethyl | H |
| a″0-31 | 2-aminophenyl | ethoxy | H |
| a″0-32 | 4-amino-3-(4-fluorophenyl)phenyl | ethoxy | H |
| a″0-33 | 4-amino-3-(thiophen-2-yl)phenyl | ethoxy | H |
| a″0-34 | 2-aminophenyl | 4-(4-methylpiperazin-1-yl)phenyl | H |
| a″0-35 | 2-amino-5-fluorophenyl | 4-(4-methylpiperazin-1-yl)phenyl | H |
| a″0-36 | 2-aminophenyl | H | CH₃— |
| a″0-37 | 4-amino-3-(4-fluorophenyl)phenyl | H | CH₃— |
| a″0-38 | 4-amino-3-(thiophen-2-yl)phenyl | H | CH₃— |

TABLE 4-continued

Examples of Structure (A"0).

Structure (A"0)

| Compound No. | R¹ | R⁶ | R⁷ |
| --- | --- | --- | --- |
| a"0-39 | 2-aminophenyl | H | pyridin-3-yl |
| a"0-40 | [3-(thiophen-2-yl)-4-aminophenyl] | H | pyridin-3-yl |
| a"0-41 | 2-aminophenyl | H | pyridin-3-yl |
| a"0-42 | 2-aminophenyl | H | 6-cyclopropyl pyridin-3-yl |
| a"0-43 | 2-aminophenyl | CH₃— | H |
| a"0-44 | [3-(4'-fluorobiphenyl-4-yl)-4-aminophenyl] | cyclopropyl | H |
| a"0-45 | 2-aminophenyl | cyclopropyl | H |
| a"0-46 | [3-(4'-fluorobiphenyl-4-yl)-4-aminophenyl] | CH₃— | CH₃C(O)— |
| a"0-47 | 2-aminophenyl | CH₃— | CH₃C(O)— |
| a"0-48 | 2-aminophenyl | 4,5,6,7-tetrahydrobenzothiazol-2-yl | |
| a"0-49 | 2-aminophenyl | 4,5,6,7-tetrahydrothiazolo[5,4-c]pyridin-2-yl | |
| a"0-50 | 2-aminophenyl | 5-methyl-4,5,6,7-tetrahydrothiazolo[5,4-c]pyridin-2-yl | |

TABLE 4-continued

Examples of Structure (A″0).

Structure (A″0)

| Compound No. | R¹ | R⁶ | R⁷ |
|---|---|---|---|
| a″0-51 | 2-aminophenyl | 5-ethyl-4,5,6,7-tetrahydrothiazolo[5,4-c]pyridine (N-ethyl) | |
| a″0-52 | 2-aminophenyl | 5-isopropyl-4,5,6,7-tetrahydrothiazolo[5,4-c]pyridine | |
| a″0-53 | 2-aminophenyl | 5-(2-methoxyethyl)-4,5,6,7-tetrahydrothiazolo[5,4-c]pyridine | |
| a″0-54 | 2-aminophenyl | 5-acetyl-4,5,6,7-tetrahydrothiazolo[5,4-c]pyridine | |
| a″0-55 | 2-aminophenyl | 5-(N,N-dimethylglycyl)-4,5,6,7-tetrahydrothiazolo[5,4-c]pyridine | |
| a″0-56 | 2-aminophenyl | 5-valyl-4,5,6,7-tetrahydrothiazolo[5,4-c]pyridine | |
| a″0-57 | 2-aminophenyl | 5-ethoxycarbonyl-4,5,6,7-tetrahydrothiazolo[5,4-c]pyridine | |
| a″0-58 | 2-aminophenyl | 5-tert-butoxycarbonyl-4,5,6,7-tetrahydrothiazolo[5,4-c]pyridine | |

TABLE 4-continued
Examples of Structure (A″0).
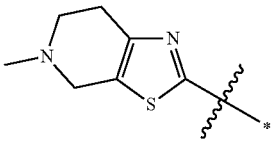
Structure (A″0)
| Compound No. | R¹ | R⁶ | R⁷ |
|---|---|---|---|
| a″0-59 | 2-amino-5-fluorophenyl | 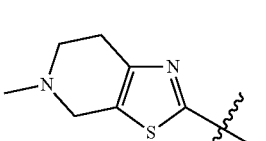 | |
| a″0-60 | 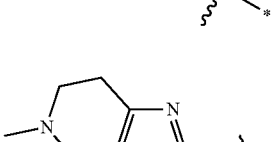 | 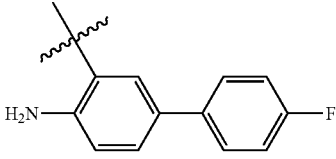 | |
| a″0-61 | 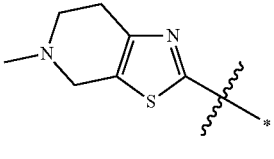 | 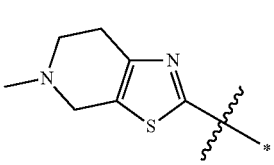 | |
| a″0-62 | 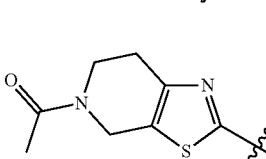 | 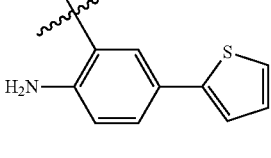 | |
| a″0-63 | 2-aminophenyl | 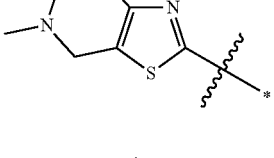 | |
| a″0-64 | 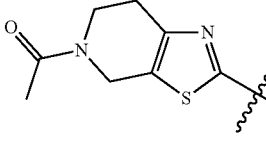 | 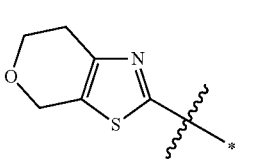 | |
| a″0-65 | 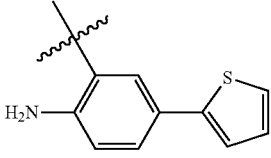 | 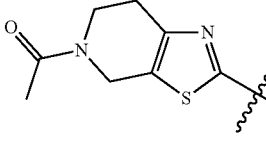 | |
*wherein R⁶ and R⁷ form a cyclic moiety. The groups R⁶ and R⁷ are illustrated with the thiazolyl group (Cy²) to show their attachments to the thiazolyl ring.

In another embodiment of Formula (I-a), $Cy^1$ is heterocycloalkylidene; $R^1$ is hydroxyl, aryl or heteroaryl, wherein aryl or heteroaryl is substituted with —$NH_2$ or —OH at a ring position adjacent to attachment of the —CONH-moiety, wherein $R^1$ is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl; $R^2$ is halo, alkyl or haloalkyl; m is 0 or 1 and $R^2$ is halo, alkyl or haloalkyl; n is 0, 1 or 2 and each $R^3$ is independently methyl, ethyl, bromo, trifluoromethyl; p is 1 or greater; and one and only one $R^4$ is aryl, cycloalkyl or heterocyclyl, wherein aryl, cycloalkyl or heterocyclyl is a fused ring and $R^4$ is optionally further substituted by one or more $R^5$ where such an optional substitution is chemically feasible; and $R^5$ is as defined above. Compounds of this embodiment include, but are not limited to, the following formulae and pharmaceutically acceptable salts thereof:

Formula (I-a"1)

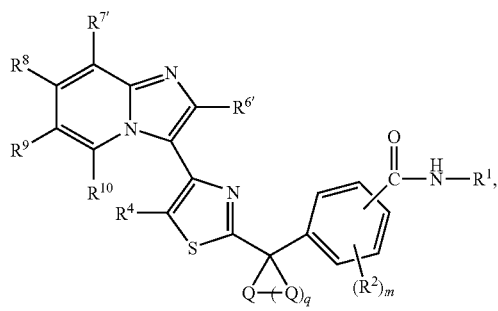

Formula (I-a"2)

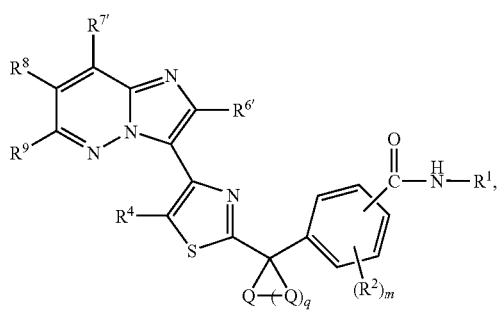

Formula (I-a"3)

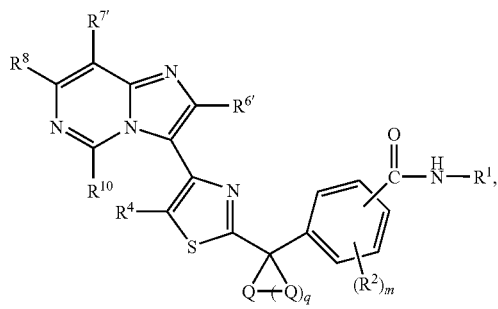

Formula (I-a"4)

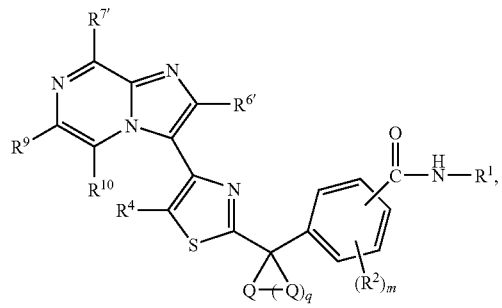

Formula (I-a"5)

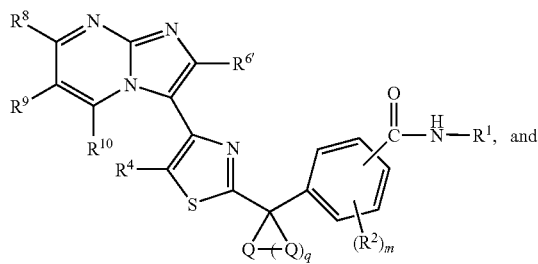

Formula (I-a"6)

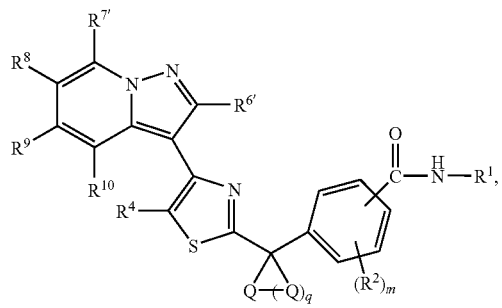

where the groups $R^{6'}$, $R^{7'}$, $R^8$, $R^9$, and $R^{10}$ are independently selected from H and the functional groups of $R^5$ defined herein. In non-limiting examples of such compounds, q is 2, 3, 4 or 5 and each Q is independently —$CH_2$— or a heteroatom selected from —NH—, —O— and —S—, and when Q is methylene (—$CH_2$—) or imino (—NH—), Q is optionally substituted with a group $R^3$. In various embodiments, Q adjacent the 1-position is not a heteroatom. In particular embodiments, q is 2, 3, 4 or 5; each Q is independently —$CH_2$— or a heteroatom selected from —NH—, —O— and —S—; and the groups $R^1$, $R^4$, $R^{6'}$, $R^{7'}$, $R^8$, $R^9$ and $R^{10}$ can be selected to have the same combination of substituents given in the table for Compounds a1-01 to a1-200. In a particular embodiment, $Cy^1$ is

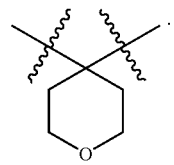

In yet another embodiment of Formula (I-a), $Cy^1$ is heterocycloalkylidene; and one and only one $R^4$ is a monocyclic group. Further, $R^1$ is hydroxyl, aryl or heteroaryl, wherein aryl or heteroaryl is substituted with —$NH_2$ or —OH at a ring position adjacent to attachment of the —CONH-moiety, wherein R¹ is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl; R² is halo, alkyl or haloalkyl; m is 0 or 1 and R² is halo, alkyl or haloalkyl; n is 0, 1 or 2 and each R³ is independently methyl, ethyl, bromo, trifluoromethyl; p is 1 or greater; and one and only one R⁴ is aryl, cycloalkyl or heterocyclyl, wherein aryl, cycloalkyl or heterocyclyl is a monocyclic ring and R⁴ is optionally further substituted by one or more R⁵ where such an optional substitution is chemically feasible; and R⁵ is as defined above. Heterocycloalkylidene-containing compounds of this embodiment include, but are not limited to, those of the following formulae and pharmaceutically acceptable salts thereof:

Formula (I-a"7)

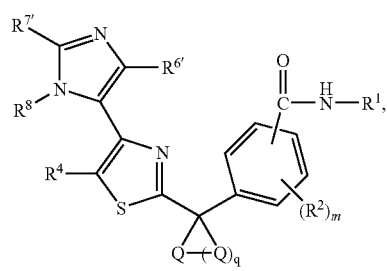

Formula (I-a"8)

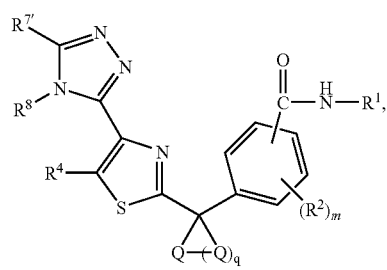

Formula (I-a"9)

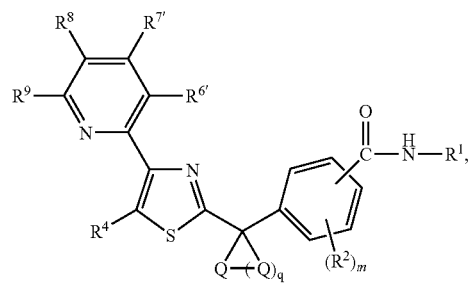

Formula (I-a"10)

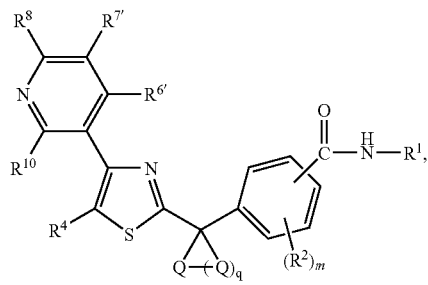

Formula (I-a"11)

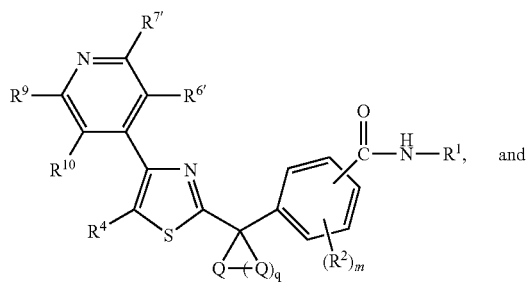

Formula (I-a"12)

wherein q is 2, 3, 4 or 5; each Q is independently —CH₂— or a heteroatom selected from —NH—, —O— and —S—; wherein R¹, R², and R⁴ are as defined for various embodiments above, and wherein R⁶', R⁷', R⁸, R⁹, and R¹⁰ are selected from H and the functional groups of R⁵ defined herein. In various embodiments, the groups R¹, R⁴, R⁶', R⁷', R⁸, R⁹ and R¹⁰ are selected to have the same combination of substituents as those of Formulae (I-a7), (I-a8), (I-a9), (I-a11), and (I-a12). In a particular embodiment, Cy¹ is

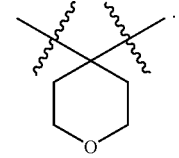

Table 5 provides non-limiting examples of compounds of Formula (I-a"10) where m is zero and R⁴, R⁶', R⁷', and R¹⁰ are H, as shown in Structure (A"10):

TABLE 5

Examples of Structure (A"10).

Structure (A"10)

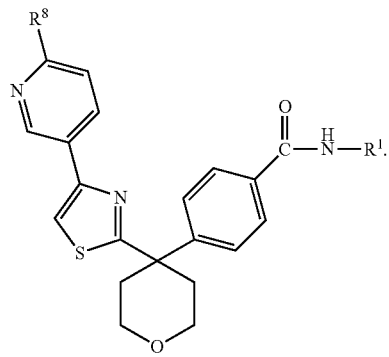

| Compound No. | R¹ | R⁸ |
| --- | --- | --- |
| a"10-01 | HO— | H |
| a"10-02 | 2-aminophenyl | H |
| a"10-03 | 2-amino-5-fluorophenyl | H |
| a"10-04 | 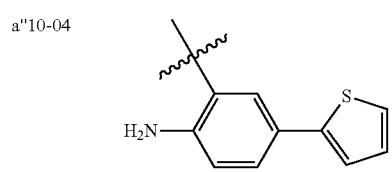 | H |
| a"10-05 | 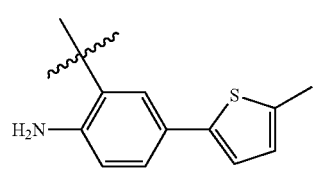 | H |
| a"10-06 | HO— | Cl— |
| a"10-07 | 2-aminophenyl | Cl— |
| a"10-08 | HO— | pyrrolidin-1-yl |
| a"10-09 | 2-aminophenyl | pyrrolidin-1-yl |
| a"10-10 | HO— | 2-methoxy-ethoxy |
| a"10-11 | 2-aminophenyl | 2-methoxy-ethoxy |
| a"10-12 | HO— | piperazin-1-yl |
| a"10-13 | 2-aminophenyl | piperazin-1-yl |
| a"10-14 | HO— | 4-methyl-piperazin-1-yl |
| a"10-15 | 2-aminophenyl | 4-methyl-piperazin-1-yl |
| a"10-16 | HO— | 4-cyclopropyl-piperazin-1-yl |
| a"10-17 | 2-aminophenyl | 4-cyclopropyl-piperazin-1-yl |

In one embodiment, the invention provides a compound of Formula (I-b) and a pharmaceutically acceptable salt thereof:

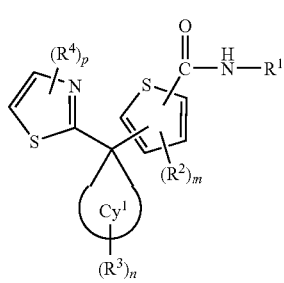

Formula (I-b)

wherein $Cy^1$, $R^1$, $R^2$, $R^3$ and $R^4$ are as defined above for various aspects of Formula (I).

In an embodiment of Formula (I-b), $Cy^1$ is cyclopropylidene; and $R^4$ is independently selected from the group consisting of H, halo, nitro, cyano, hydroxyl, hydroxyalkyl, haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—$(C_{1-10}$ alkyl)amino, N,N—$(C_{1-10}$ alkyl)$_2$amino, $C_{1-10}$ alkanoylamino, N—$(C_{1-10}$ alkyl)carbamoyl, N,N—$(C_{1-10}$ alkyl)$_2$ carbamoyl, $C_{1-10}$ alkyl-S(O)$_a$ wherein a is 0, 1 or 2, $C_{1-10}$ alkoxycarbonyl, NH$_2$—S(O)$_2$NH—, N—$(C_{1-10}$ alkyl)sulphamoyl and N,N—$(C_{1-10}$ alkyl)$_2$sulphamoyl, wherein each $R^4$ is optionally substituted by one or more B where such an optional substitution is chemically feasible. Non-limiting examples of such compounds include compounds of Formula (I-b0) and pharmaceutically acceptable salts thereof:

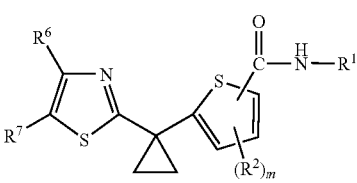

Formula (I-b0)

wherein $R^6$ and $R^7$ are selected from groups $R^4$.

In various embodiments, m is 0 and —CONH—$R^1$ is attached to the thiophene ring position adjacent the S atom. Illustratively, the groups $R^1$, $R^6$ and $R^7$ are selected to have the same combination of substituents given in the table for Compounds a0-01 to a0-126.

In an embodiment of Formula (I-b), $Cy^1$ is cyclopropylidene; and $R^4$ is aryl, cycloalkyl or heterocyclyl, wherein aryl, cycloalkyl or heterocyclyl is a fused ring and $R^4$ is optionally further substituted by one or more $R^5$ where such an optional substitution is chemically feasible; and $R^5$ is as defined above. Compounds of this embodiment include, but are not limited to, the following formulae:

Formula (I-b1)

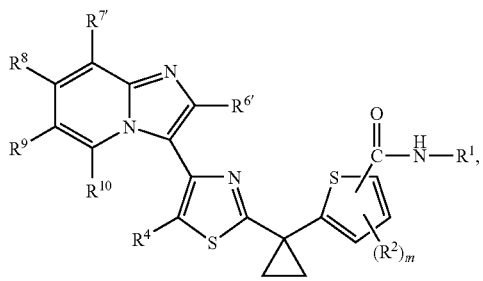

Formula (I-b2)

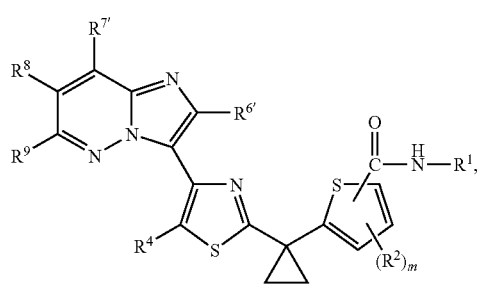

Formula (I-b3)

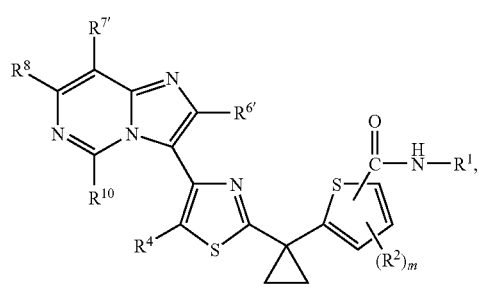

Formula (I-b4)

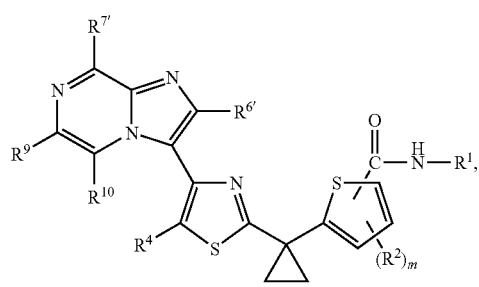

Formula (I-b5)

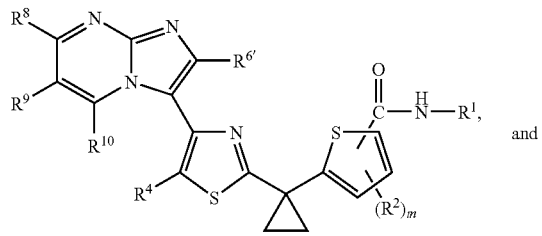

and

Formula (I-b6)

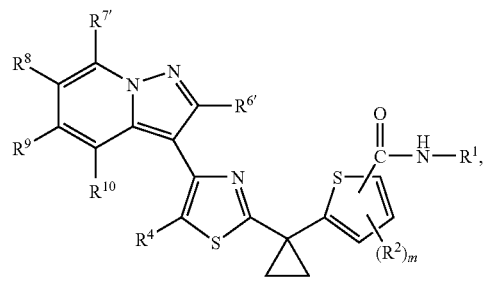

where the groups $R^{6\prime}$, $R^{7\prime}$, $R^8$, $R^9$, and $R^{10}$ are independently selected from H and the functional groups of $R^5$ defined herein. In non-limiting embodiments, m is 0 and —CONH—$R^1$ is attached to the thiophene at a ring position adjacent to the S atom. In various embodiments, the groups $R^1$, $R^4$, $R^{6\prime}$, $R^{7\prime}$, $R^8$, $R^9$ and $R^{10}$ are selected to have the same combination of substituents given in the table for Compounds a1-01 to a1-200.

In an embodiment of Formula (I-b), $Cy^1$ is cyclopropylidene; and one and only one $R^4$ is aryl, cycloalkyl or heterocyclyl, wherein aryl, cycloalkyl or heterocyclyl is a monocyclic ring optionally further substituted by one or more $R^5$ where such an optional substitution is chemically feasible; and $R^5$ is as defined above. Compounds of this embodiment include, but are not limited to, those of the following formulae:

Formula (I-b7)

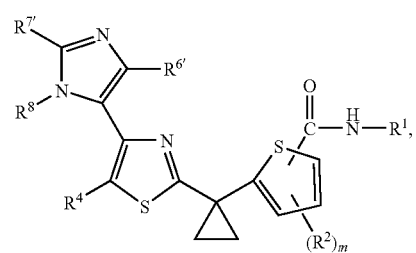

Formula (I-b8)

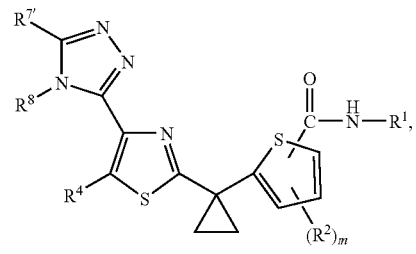

Formula (I-b9)

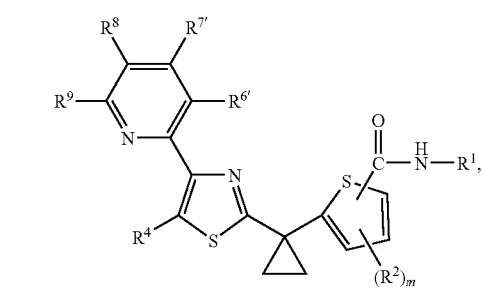

-continued

Formula (I-b10)

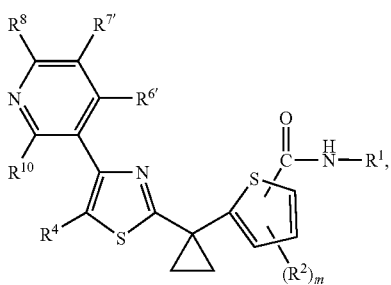

Formula (I-b11)

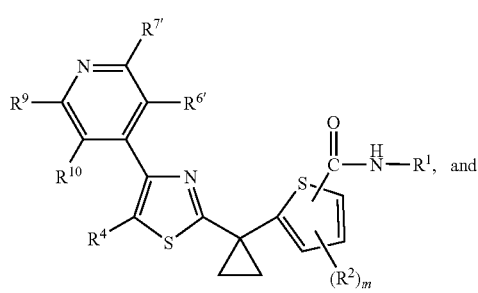

(Formula (I-b12))

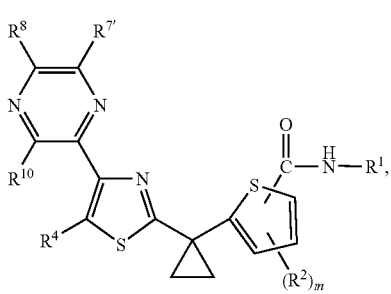

where the groups $R^{6'}$, $R^{7'}$, $R^8$, $R^9$, and $R^{10}$ are independently selected from H and the functional groups of $R^5$ defined herein. In particular embodiments, m is 0 and —CONH—$R^1$ is attached to the thiophene ring position adjacent the S atom. In various embodiments, the groups $R^1$, $R^4$, $R^{6'}$, $R^{7'}$, $R^8$, $R^9$ and $R^{10}$ are selected to have the same combination of substituents as those of Compounds a7-01 through a12-04. That is, Compounds b7-01 through b12-04 are like a7-01 through a12-04, except the former have thiophene where the latter have phenyl.

In one embodiment, the invention provides a compound of Formula (I-c) and a pharmaceutically acceptable salt thereof:

Formula (I-c)

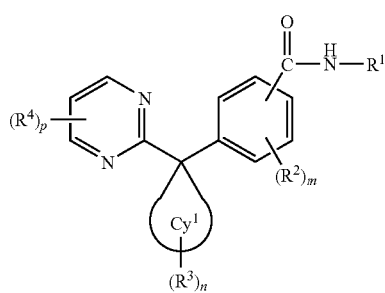

wherein $Cy^1$, $R^1$, $R^2$, $R^3$ and $R^4$ are as defined above for various aspects of Formula (I).

In an embodiment of Formula (I-c), $Cy^1$ is cyclopropylidene; and $R^4$ is independently selected from the group consisting of H, halo, nitro, cyano, hydroxyl, hydroxyalkyl, haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$ carbamoyl, $C_{1-10}$-alkyl-S(O)$_a$ wherein a is 0, 1 or 2, $C_{1-10}$ alkoxycarbonyl, NH$_2$—S(O)$_2$NH—, N—($C_{1-10}$ alkyl)sulphamoyl and N,N—($C_{1-10}$ alkyl)$_2$sulphamoyl, wherein each $R^4$ is optionally substituted by one or more B where such an optional substitution is chemically feasible. Non-limiting examples of such compounds include the following compounds and pharmaceutically acceptable salts thereof:

Formula (I-c0)

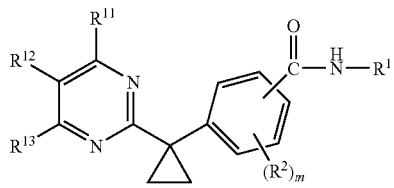

wherein $R^1$ and $R^2$ are as defined above; and $R^{11}$, $R^{12}$ and $R^{13}$ are independently selected from $R^4$ defined herein.

In an embodiment of Formula (I-c), $Cy^1$ is cyclopropylidene; and one and only one $R^4$ is aryl, cycloalkyl or heterocycloalkyl, wherein aryl, cycloalkyl or heterocyclyl is a fused ring optionally further substituted by one or more $R^5$ where such an optional substitution is chemically feasible; and $R^5$ is as defined above. Compounds of this embodiment include, but are not limited to, the following formulae:

Formula (I-c1)

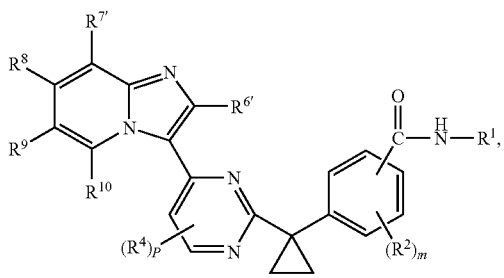

Formula (I-c2)

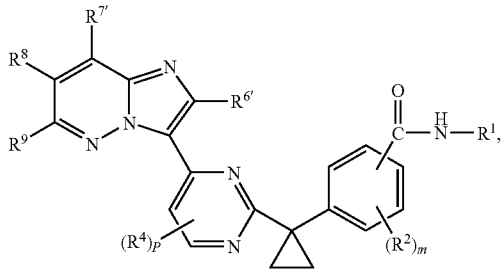

-continued

Formula (I-c3)
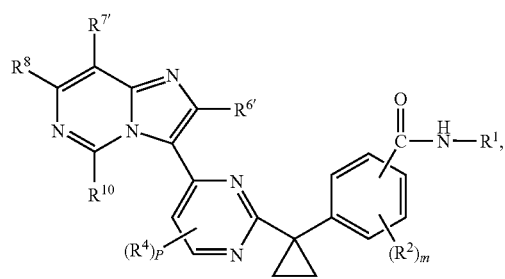

Formula (I-c4)

Formula (I-c5)

Formula (I-c6)

Formula (I-c7)
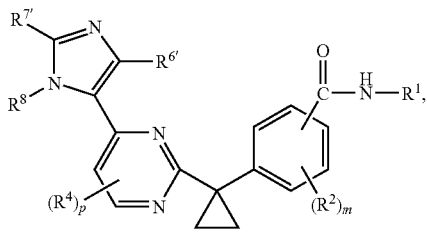

Formula (I-c8)

Formula (I-c9)
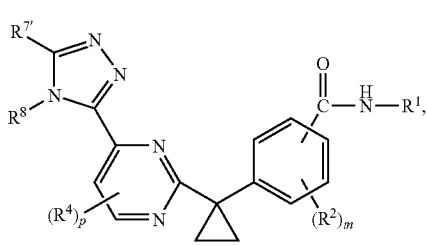

Formula (I-c10)
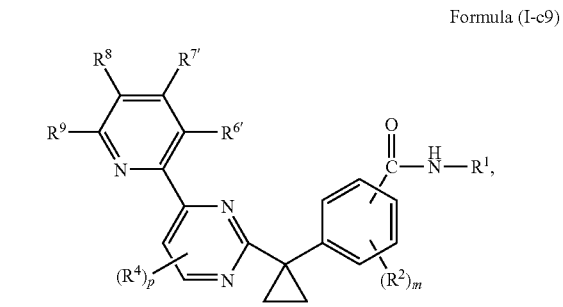

Formula (I-c11)
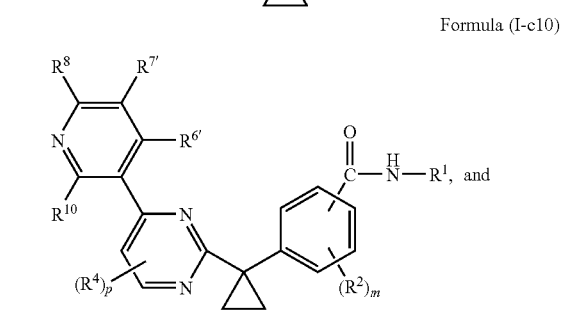

and

Formula (I-c12)
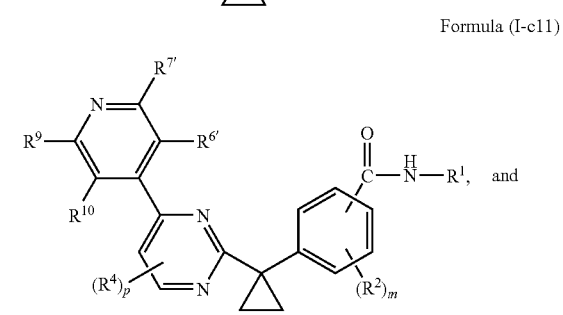

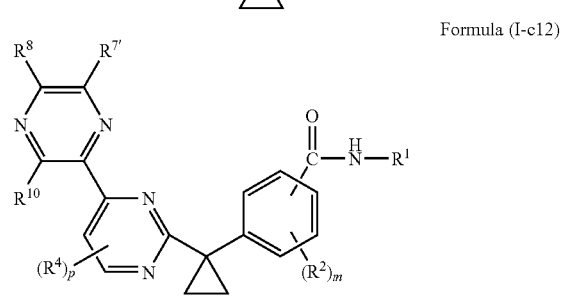

wherein p is 2; and $R^{6'}$, $R^{7'}$, $R^8$, $R^9$ and $R^{10}$ are selected from H and groups $R^5$. In specific embodiments, $R^1$, $R^2$, $R^{6'}$, $R^{7'}$, $R^8$, $R^9$ and $R^{10}$ are selected to have the same combination of substituents given in the table for Compounds a1-01 to a1-200.

In an embodiment of Formula (I-c), $Cy^1$ is cyclopropylidene; and $R^4$ is aryl, cycloalkyl or heterocyclyl, wherein aryl, cycloalkyl or heterocyclyl is a monocyclic ring optionally further substituted by one or more $R^5$ where such an optional substitution is chemically feasible; and $R^5$ is as defined above. Compounds of this embodiment include, but are not limited to, the following formulae:

where the groups $R^{6'}$, $R^{7'}$, $R^8$, $R^9$, and $R^{10}$ are independently selected from H and the functional groups of $R^5$ defined herein. In various embodiments, groups $R^4$ are H. In various embodiments, —C(O)NHR$^1$ is attached to the phenyl ring at a position para to cyclopropylidene. In illustrative embodiments, the groups $R^1$, $R^2$, $R^{6'}$, $R^{7'}$, $R^8$, $R^9$ and $R^{10}$ are selected to have the same combination of substituents as those of Compounds a7-01 through a12-04. That is, Compounds c7-01 through c12-04 are like a7-01 through a12-04, except the former have pyrimidine where the latter have thiazole.

In one embodiment, the invention provides a compound of Formula (I-d) and a pharmaceutically acceptable salt thereof:

Formula (I-d)

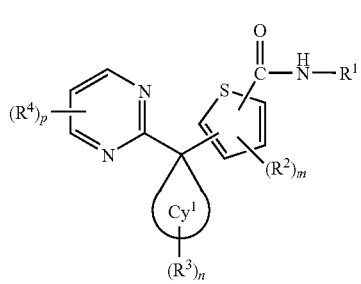

wherein Cy$^1$, $R^1$, $R^2$, $R^3$ and $R^4$ are as defined above for various aspects of Formula (I).

In an embodiment of Formula (I-d), Cy$^1$ is cyclopropylidene; and $R^4$ is independently selected from the group consisting of H, halo, nitro, cyano, hydroxyl, hydroxyalkyl, haloalkyl, haloalkoxy, amino, azido, carboxyl, carbamoyl, mercapto, sulphamoyl, C$_{1-10}$ alkyl, C$_{2-10}$ alkenyl, C$_{2-10}$ alkynyl, C$_{1-10}$ alkoxy, C$_{1-10}$ alkanoyl, C$_{1-10}$ alkanoyloxy, N—(C$_{1-10}$ alkyl)amino, N,N—(C$_{1-10}$ alkyl)$_2$amino, C$_{1-10}$ alkanoylamino, N—(C$_{1-10}$ alkyl)carbamoyl, N,N—(C$_{1-10}$ alkyl)$_2$ carbamoyl, C$_{1-10}$ alkyl-S(O)$_a$ wherein a is 0, 1 or 2, C$_{1-10}$ alkoxycarbonyl, NH$_2$—S(O)$_2$NH—, N—(C$_{1-10}$ alkyl) sulphamoyl and N,N—(C$_{1-10}$ alkyl)$_2$sulphamoyl, wherein each $R^4$ is optionally substituted by one or more B where such an optional substitution is chemically feasible. Non-limiting examples of such compounds include the following compounds and pharmaceutically acceptable salts thereof:

Formula (I-d0)

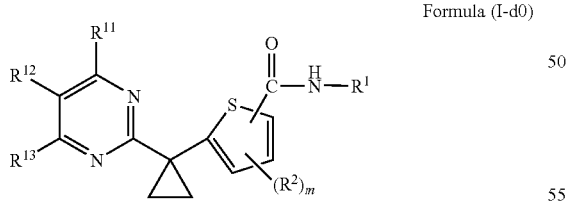

wherein $R^1$ and $R^2$ are as defined above; and $R^{11}$, $R^{12}$ and $R^{13}$ are independently selected from the functional groups of $R^4$ defined herein.

In an embodiment of Formula (I-d), Cy$^1$ is cyclopropylidene; and one and only one $R^4$ is aryl, cycloalkyl or heterocyclyl, wherein aryl, cycloalkyl or heterocyclyl is a fused ring and $R^4$ is optionally further substituted by one or more $R^5$ where such an optional substitution is chemically feasible; and $R^5$ is as defined above. Compounds of this embodiment include, but are not limited to, the following formulae:

Formula (I-d1)

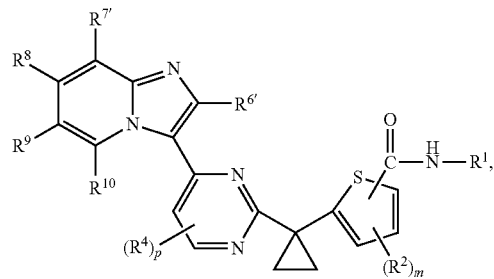

Formula (I-d2)

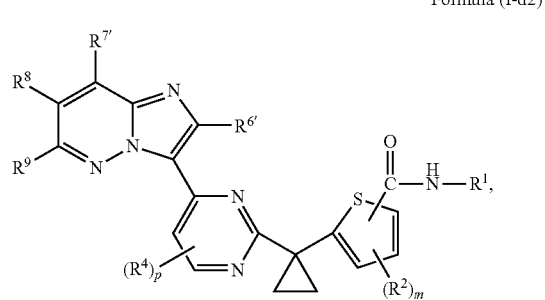

Formula (I-d3)

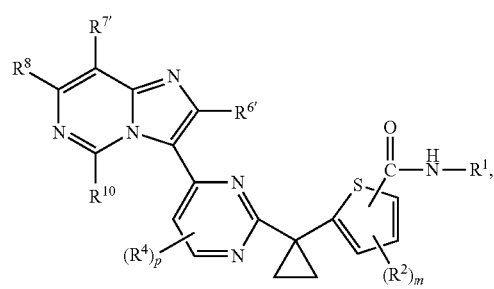

Formula (I-d4)

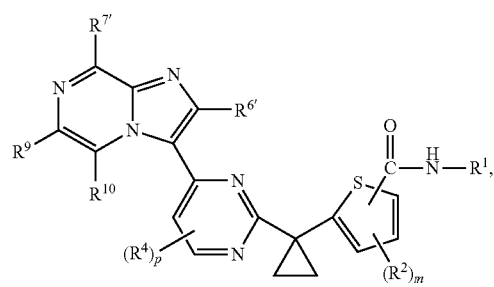

Formula (I-d5)

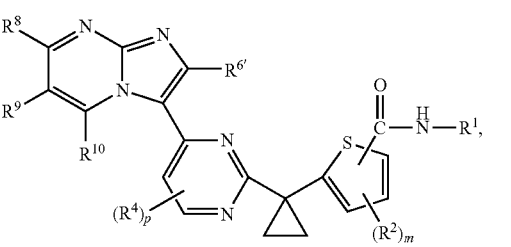

and

-continued

Formula (I-d6)

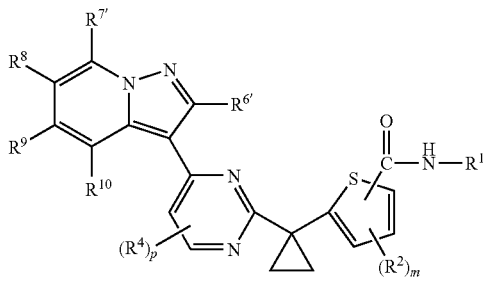

where the groups $R^{6'}$, $R^{7'}$, $R^8$, $R^9$, and $R^{10}$ are independently selected from H and the functional groups of $R^5$ defined herein. In various embodiments, m is 0; both groups $R^4$ are H; and/or —CONH—$R^1$ is attached to the thiophene ring position adjacent the S atom. In illustrative embodiments, the groups $R^1$, $R^{6'}$, $R^{7'}$, $R^8$, $R^9$ and $R^{10}$ are selected to have the same combination of substituents given in the table for each of Compounds a1-01 to a1-200.

In an embodiment of Formula (I-d), $Cy^1$ is cyclopropylidene; and one and only one $R^4$ is aryl, cycloalkyl or heterocyclyl, wherein aryl, cycloalkyl or heterocyclyl is a monocyclic ring optionally further substituted by one or more $R^5$ where such an optional substitution is chemically feasible; and $R^5$ is as defined above. Compounds of this embodiment include, but are not limited to, the following formulae:

Formula (I-d7)

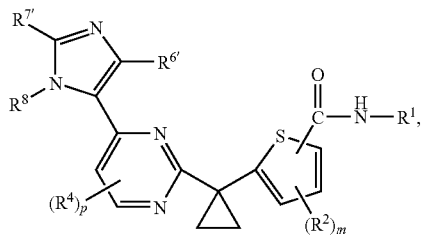

Formula (I-d8)

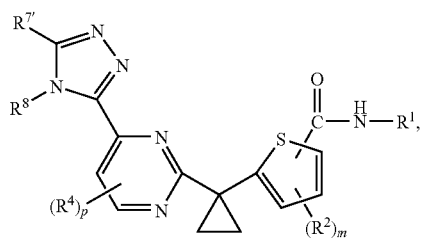

Formula (I-d9)

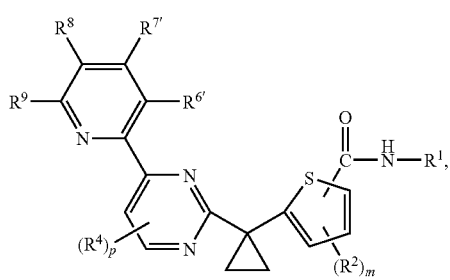

-continued

Formula (I-d10)

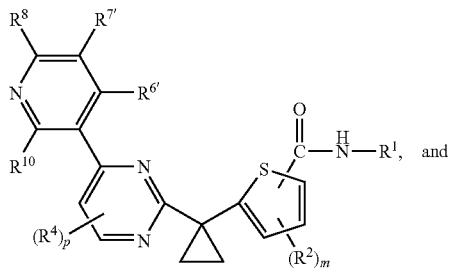
and

Formula (I-d11)

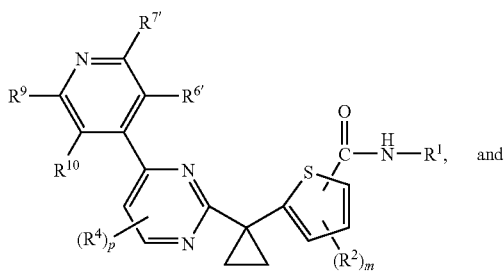
and

Formula (I-d12)

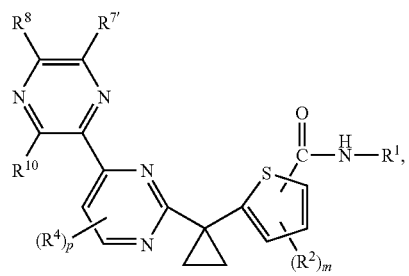

where the groups $R^{6'}$, $R^{7'}$, $R^8$, $R^9$, and $R^{10}$ are independently selected from H and the functional groups of $R^5$ defined herein. In particular embodiments, m is 0; both groups $R^4$ are H; and/or —CONH—$R^1$ is attached to the thiophene ring position adjacent the S atom. In various embodiments, the groups $R^1$, $R^{6'}$, $R^{7'}$, $R^8$, $R^9$ and $R^{10}$ are selected to have the same combination of substituents as those of Compounds a7-01 through a12-04. That is, Compounds d7-01 through d12-04 are like a7-01 through a12-04, except the former have pyrimidine and thiophene where the latter have thiazole and phenyl, respectively.

In one embodiment, the invention provides a compound selected from the group consisting of Formulae (I-e), (I-f), (I-g), (I-h), (I-i), (I-j), (I-k), (I-l), (I-m), (I-n), (I-o), (I-p), (I-q), and (I-r), and a pharmaceutically acceptable salt thereof:

Formula (I-e)

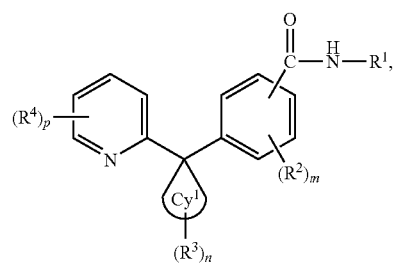

Formula (I-f)
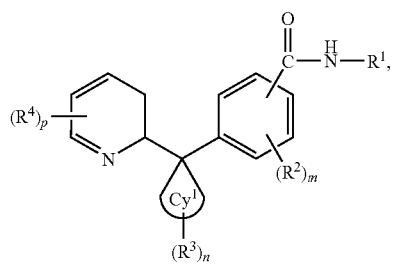
Formula (I-g)
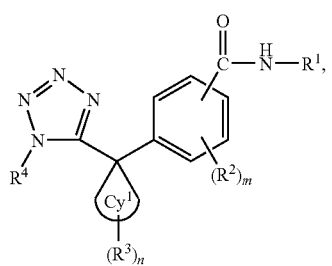
Formula (I-h)
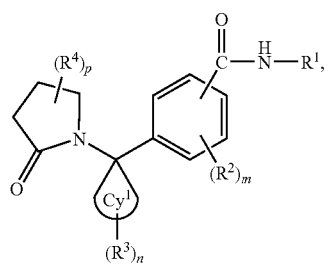
Formula (I-i)
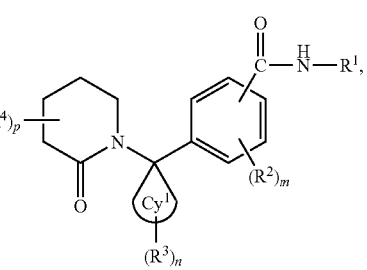
Formula (I-j)
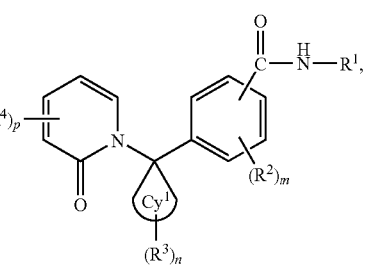
Formula (I-k)
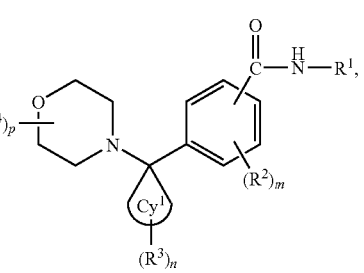
Formula (I-l)
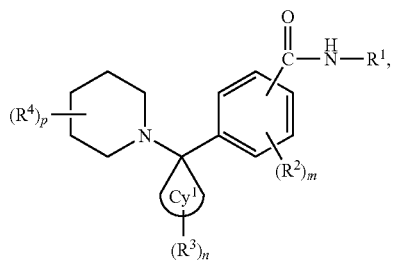
Formula (I-m)
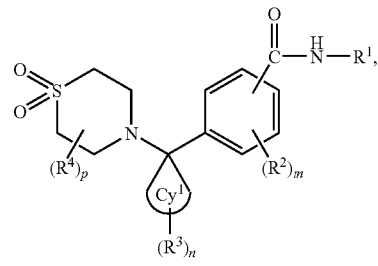
Formula (I-n)
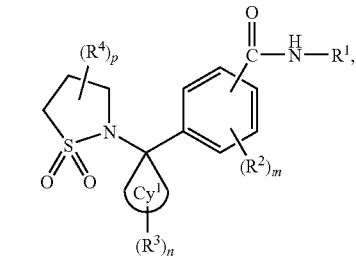
Formula (I-o)
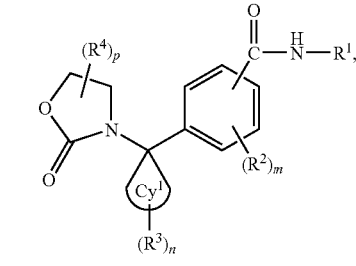
Formula (I-p)
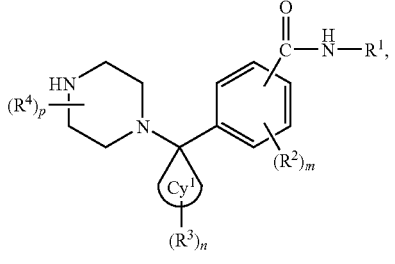
Formula (I-q)
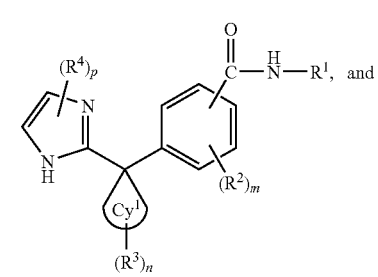
and Formula (I-r)
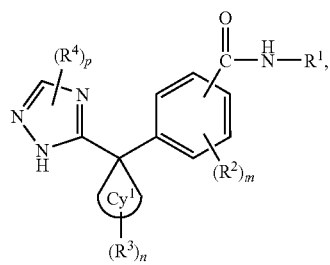
wherein Cy¹, R¹, R², R³ and R⁴ are as defined above for various aspects of Formula (I).
Non-limiting examples of such compounds include the following compounds and pharmaceutically acceptable salts thereof:
Compound e-01
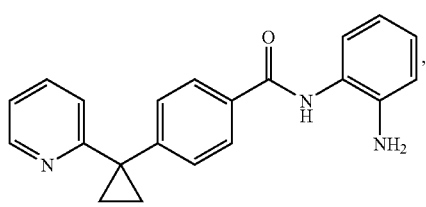
Compound e-02
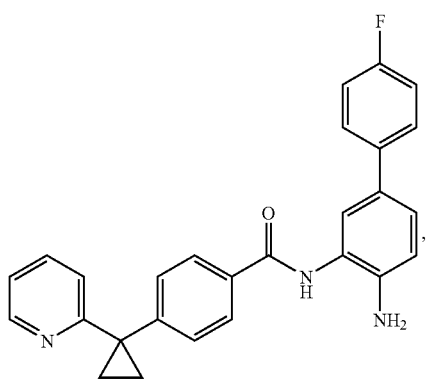
Compound e-03
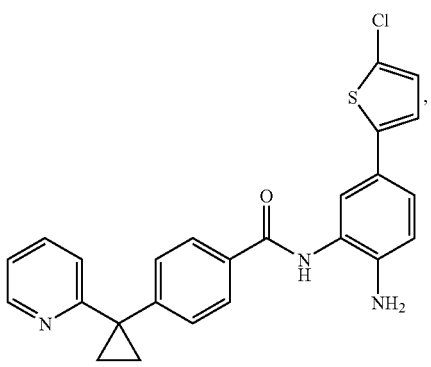
Compound e-04
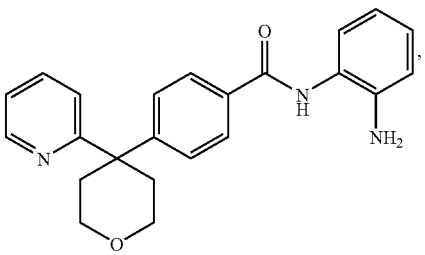
Compound e-05
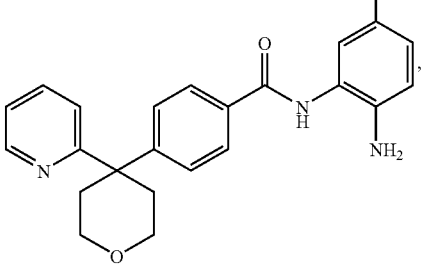
Compound e-06
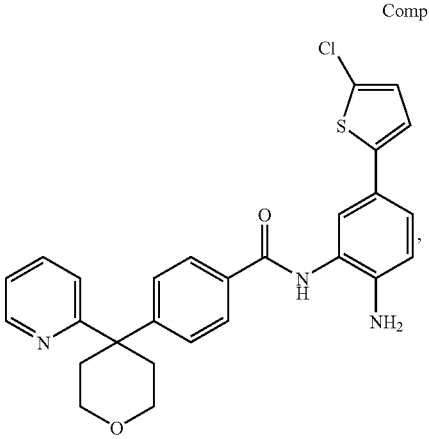
Compound e-07
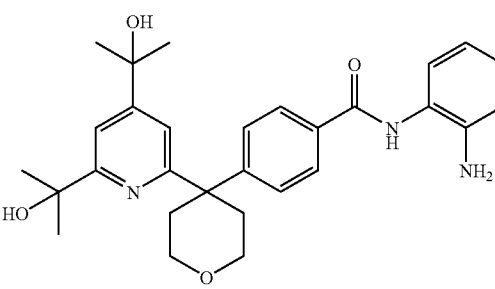

Compound e-08
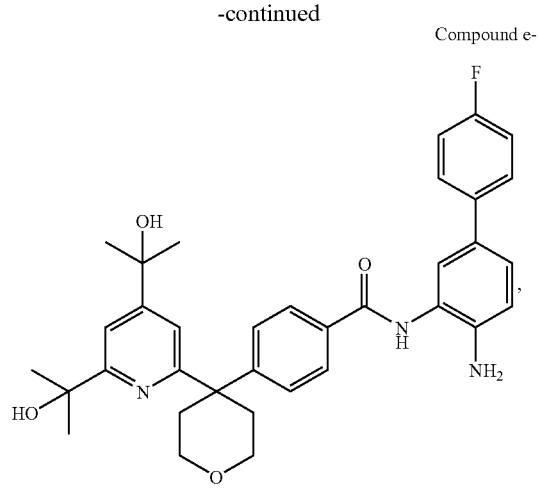
Compound e-09
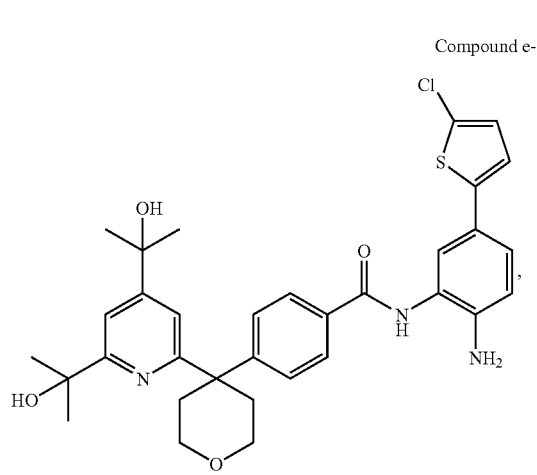
Compound f-01
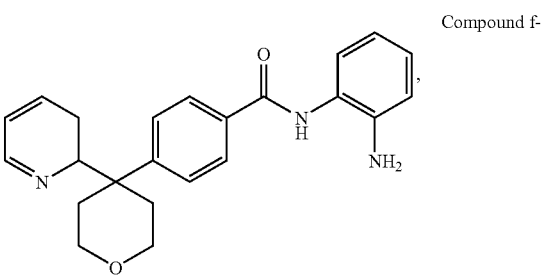
Compound f-02
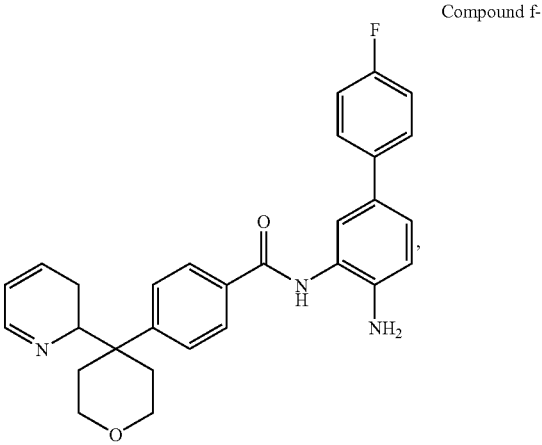
Compound f-03
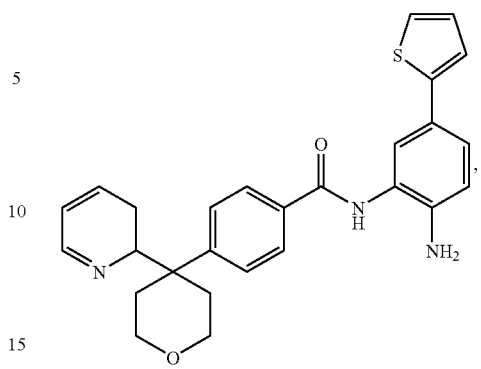
Compound g-01
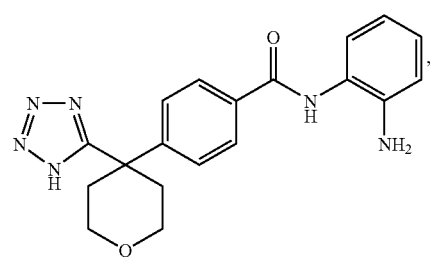
Compound g-02
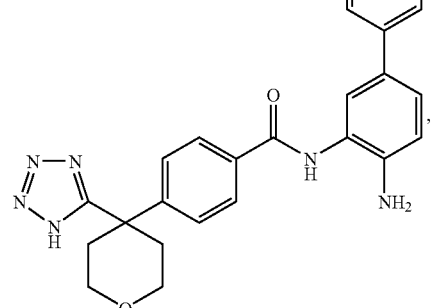
Compound g-03
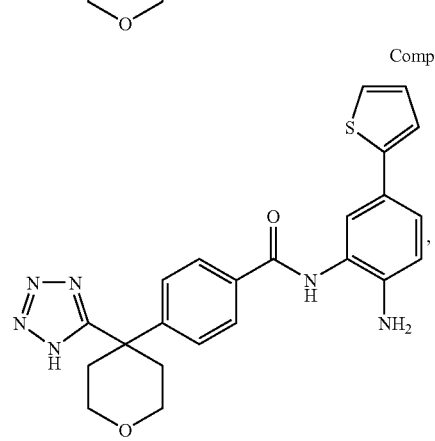

Compound q-01
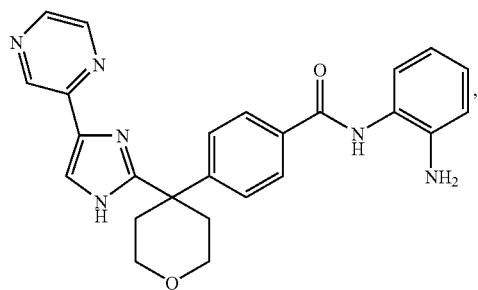
Compound q-02
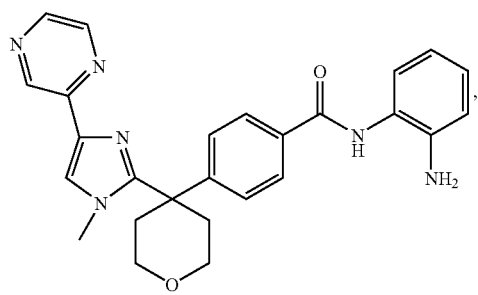
Compound q-03
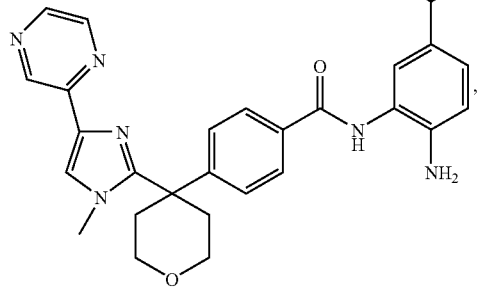
Compound q-04
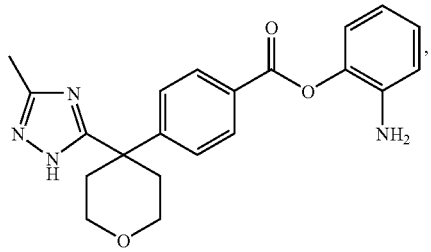
Compound q-05
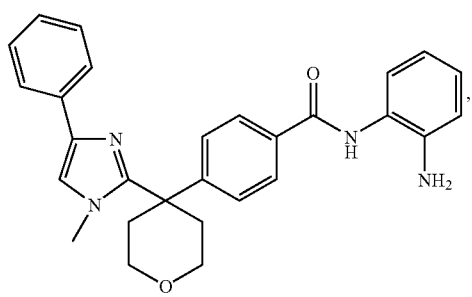
Compound q-06
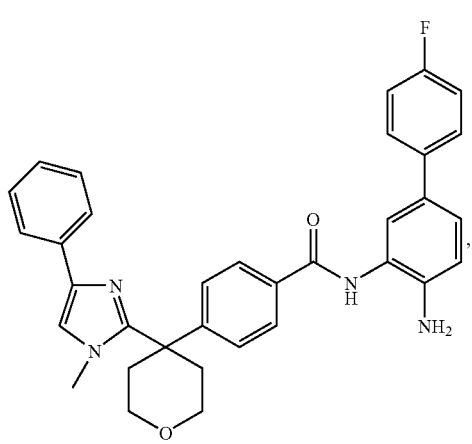
Compound r-01
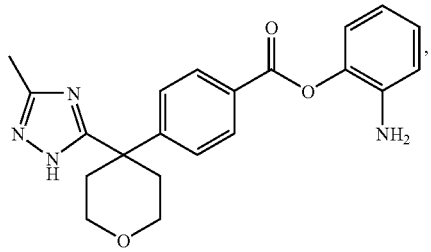
Compound r-02
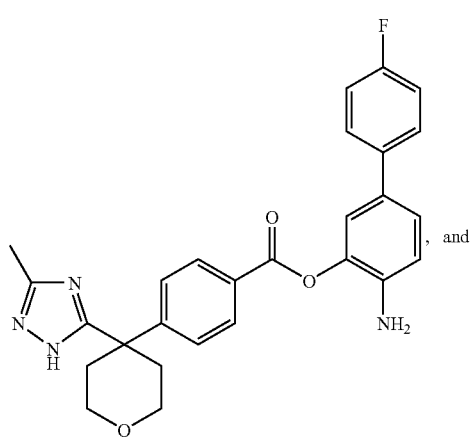

-continued

Compound r-03

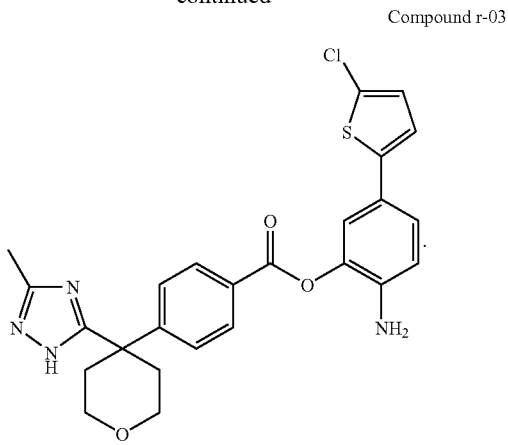

In yet another embodiment, the invention provides a compound of Formula (II) or a pharmaceutically acceptable salt thereof:

Formula (II)

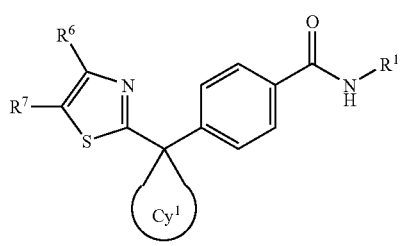

wherein $Cy^1$, $R^1$, $R^6$ and $R^7$ are as defined above.

In particular embodiments, the variables are further exemplified as follows:

$Cy^1$ is cyclopropylidene, cyclopentylidene or tetrahydropyran-4,4-diylidene;

$R^1$ is hydroxyl or phenyl substituted with —$NH_2$ or —OH at a ring position adjacent to attachment of the —CONH-moiety, wherein $R^1$ is optionally further substituted with one or more groups selected from amino, halo, alkyl, haloalkyl, cycloalkyl, heterocycloalkyl, aryl and heteroaryl;

$R^6$ is $C_{1-3}$ alkyl, $C_{2-3}$ alkenyl, $C_{2-3}$ alkynyl, $C_{1-3}$ alkoxy, $C_{1-3}$ alkanoyl, imidazopyridinyl or pyridinyl, wherein if $R^6$ is not imidazopyridinyl or pyridinyl, $R^6$ is optionally substituted by one or more B where such an optional substitution is chemically feasible, and if $R^6$ is imidazopyridinyl or pyridinyl, $R^6$ is optionally further substituted by one or more $R^5$;

$R^7$ is $C_{1-3}$ alkyl, $C_{2-3}$ alkenyl, $C_{2-3}$ alkynyl, $C_{1-3}$ alkoxy or $C_{1-3}$ alkanoyl;

$R^5$ is independently selected from the group consisting of halo, nitro, cyano, hydroxyl, oxo, hydroxyalkyl, haloalkyl, haloalkoxy, amino, azido, carboxyl, carbamoyl, mercapto, sulphamoyl, alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkyl-S(O)$_a$ wherein a is 0, 1 or 2, $C_{1-6}$ alkoxycarbonyl, $NH_2$—S(O)$_2$NH—, N—($C_{1-6}$ alkyl)sulphamoyl, N,N—($C_{1-6}$ alkyl)$_2$sulphamoyl, aryl, aryloxy, arylthio, cycloalkyl, cycloalkyloxy, heterocyclyl, heterocyclyl(C=O)—, heterocyclyloxy and heterocyclylthio; wherein $R^5$ is optionally substituted by one or more D where such an optional substitution is chemically feasible;

B and D are independently selected from halo, nitro, cyano, hydroxyl, oxo, hydroxyalkyl, haloalkyl, haloalkoxy, amino, azido, carboxyl, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkyl-S(O)$_a$ wherein a is 0, 1 or 2, $C_{1-6}$ alkoxycarbonyl, N—($C_{1-6}$ alkyl)sulphamoyl, N,N—($C_{1-6}$ alkyl)$_2$sulphamoyl, $H_2NS(O)_2NH$—, N—($C_{1-6}$ alkyl)NHS(O)$_2$NH—, N,N—($C_{1-6}$ alkyl)$_2$NS(O)$_2$NH—, aryl, aryloxy, arylthio, cycloalkyl, cycloalkyloxy, heterocyclyl, heterocyclyl(C=O)—, heterocyclyloxy and heterocyclylthio.

Examples of such compounds include, but are not limited to:

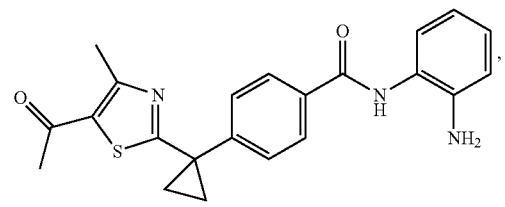

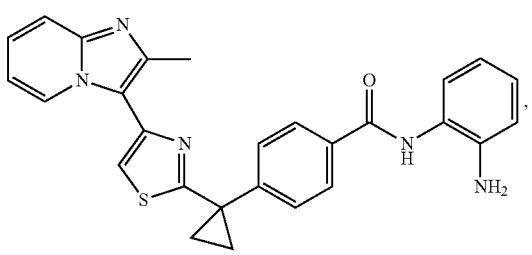

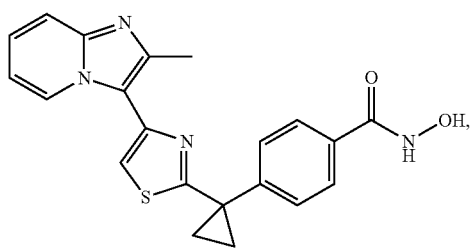

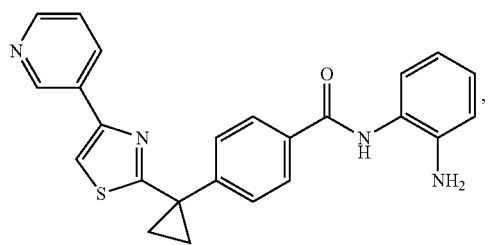

143
-continued

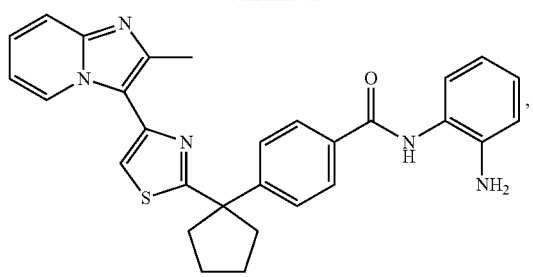

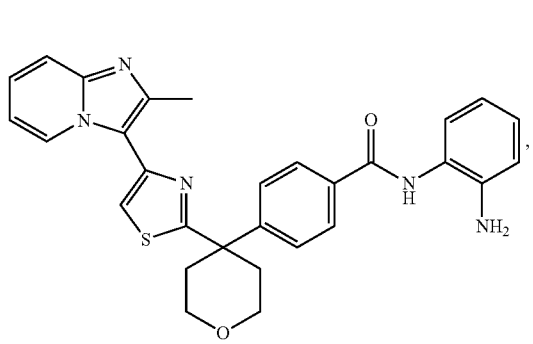

and pharmaceutically acceptable salts thereof.

Compound Preparation

A compound of the present invention such as those of Formulae (I), (I-a), (I-b), (I-c), (I-d), (I-e), (I-f), (I-g), (I-h), (I-i), (I-j), (I-k), (I-l), (I-m), (I-n), (I-o), (I-p), (I-q), and (I-r) can be prepared according to the schemes described below, but it shall be appreciated that modifications of the illustrated process or other processes can also be used.

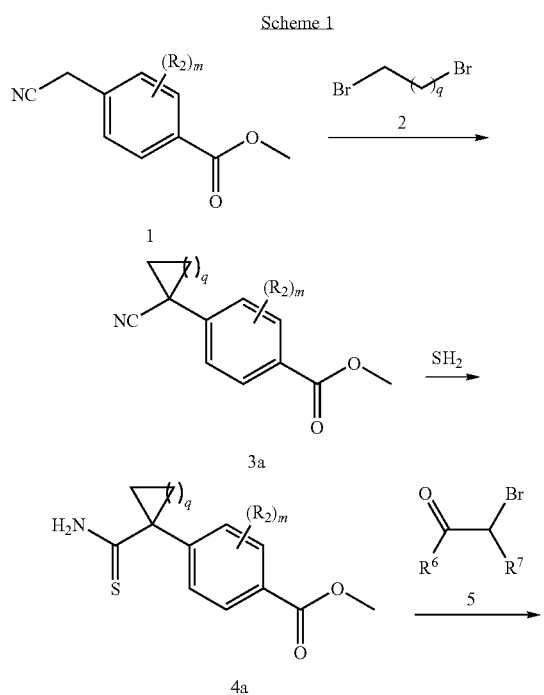

144
-continued

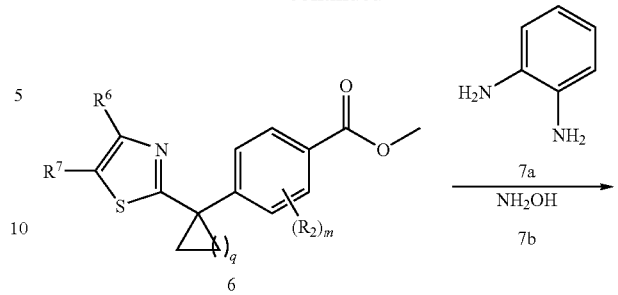

Cycloalkylidene linked HDAC inhibitors can be synthesized according to Scheme 1, showing preparation of inhibitors 8a and 8b where Ar is phenyl and where $Cy^2$ is a substituted thiazole. In Scheme 1, α-cyano-p-methylbenzoic acid ester 1 is reacted with dibromide 2 (q is an integer from 1 to 6) to form cyano intermediate 3a, which is in turn reacted with hydrogen sulfide to yield thioamide compound 4a. Thiazole intermediate 6 is prepared by reacting thioamide 4a with α-bromo carbonyl compound 5. Substituents $R^6$ and $R^7$ on intermediate 5 are selected from H and the functional groups of $R^4$ defined herein and become the substituents on ring $Cy^2$ of the inhibitors. Thiazole intermediate 6 is then reacted with 1,2-diamino aryl compound 7a to provide arylamide HDAC inhibitor 8a or with $NH_2OH$ to provide hydroxamate inhibitor 8b.

Scheme 1 can be genericized with respect to the group Ar of the HDAC inhibitors. In scheme 2, inhibitors 8' are synthesized from starting esters 1' by way of thioamide intermediate 4'.

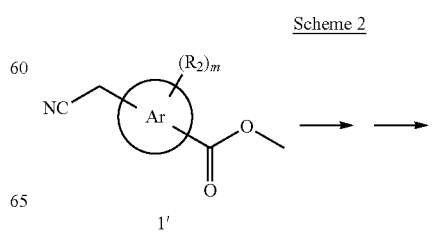

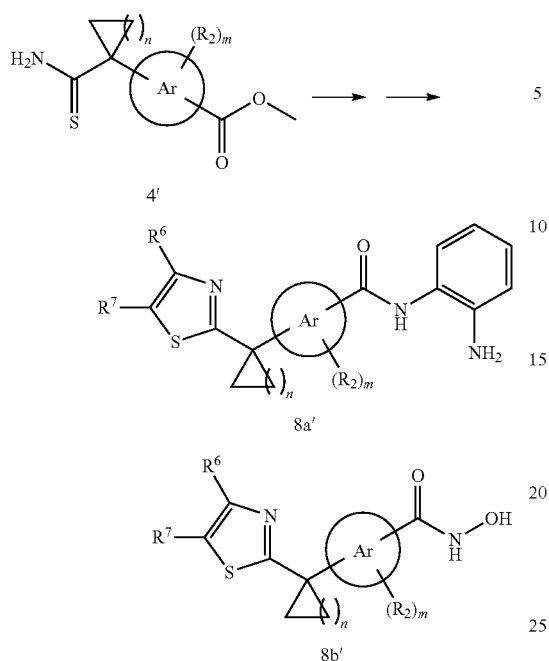

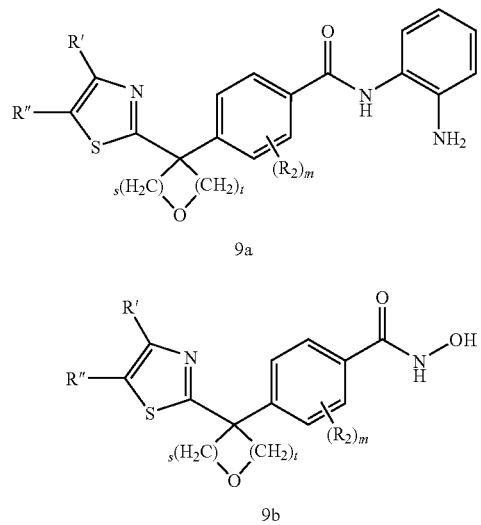

Inhibitors with heterocycloalkylidene linkers $Cy^1$ can be synthesized analogously to Schemes 1 and 2 by reaction of starting compounds 1 or 1' with a dibromoether 2' as in Scheme 3. Scheme 3 illustrates the synthesis when Ar in the inhibitor is a 1,4-substituted phenyl, with $Cy^1$ taken as position 1.

In one embodiment, intermediate 5 is prepared containing a ring substituent at R' according to Scheme 4. A first synthetic route begins with the reaction of an aminopyridine b with a chlorodiketone a to make an acyl imidazopyridine c, which is brominated to bromoketone 5.

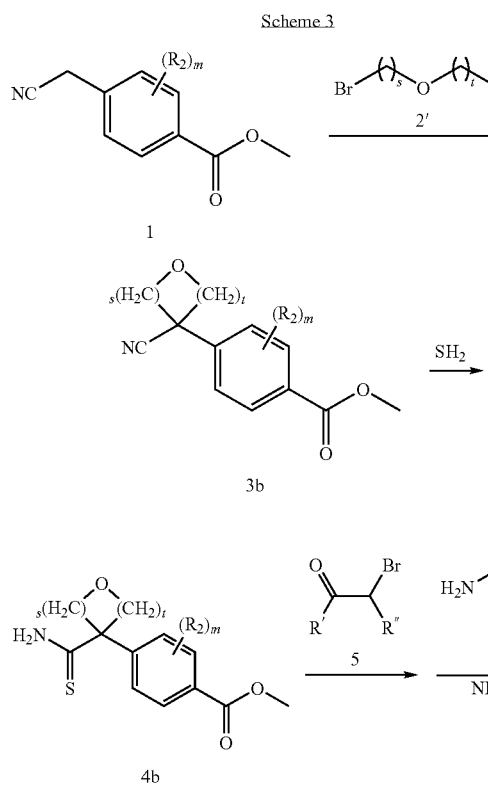

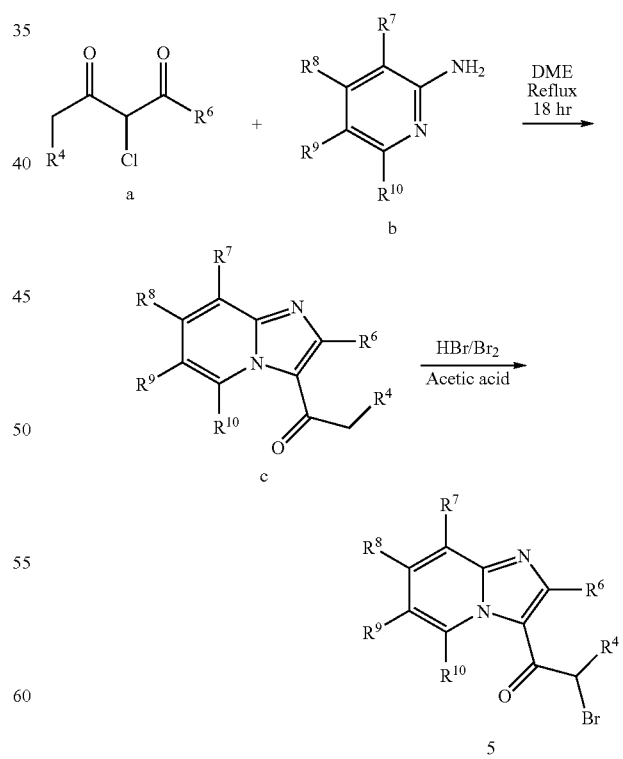

A second route to bromoketone 5 is given in Scheme 5, where the imidazopyridine is formed first and is then acylated and brominated.

Scheme 5

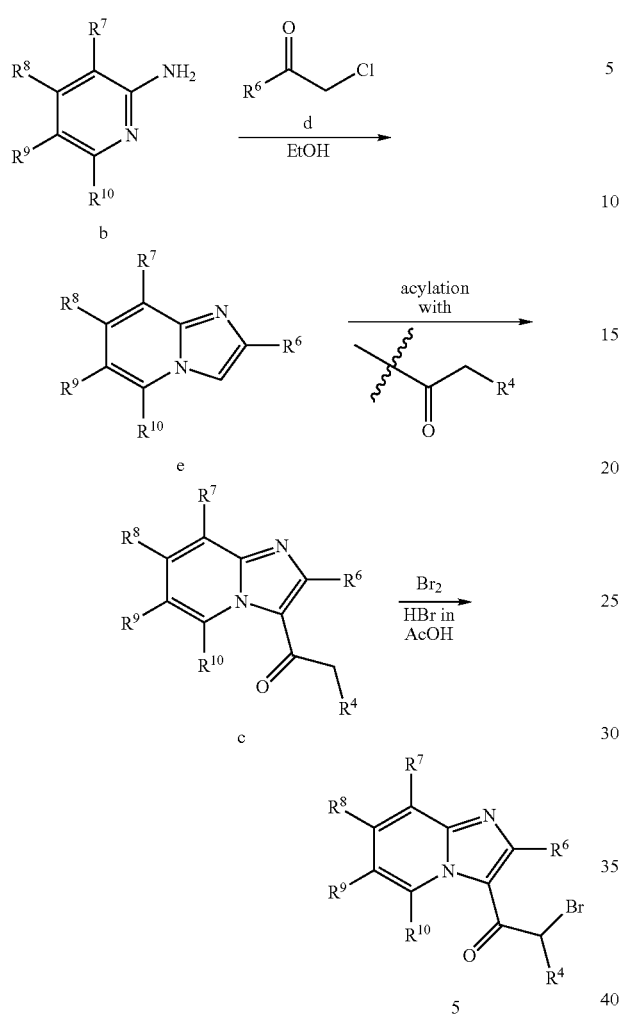

In Scheme 5, the imidazo ring is elaborated first, and then subjected to acylation to add the ketone side chain and group $R^4$, both of which will become part of the thiazole in subsequent synthetic steps. In one sense, this affords more flexibility in the choices of $R^6$ and $R^4$ than does Scheme 4. At the same time, the reaction of aminopyridine b with chloroketone or chloroaldehyde d occurs under similar conditions as in Scheme 4, and is permissive of the same broad range of substituents $R^7$, $R^8$, $R^9$, and $R^{10}$ on the aminopyridine starting material b.

Pyrimidine inhibitor compounds can be made as in Scheme 6.

Scheme 6

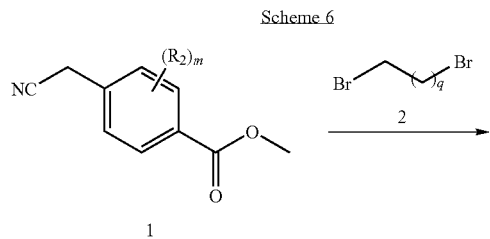

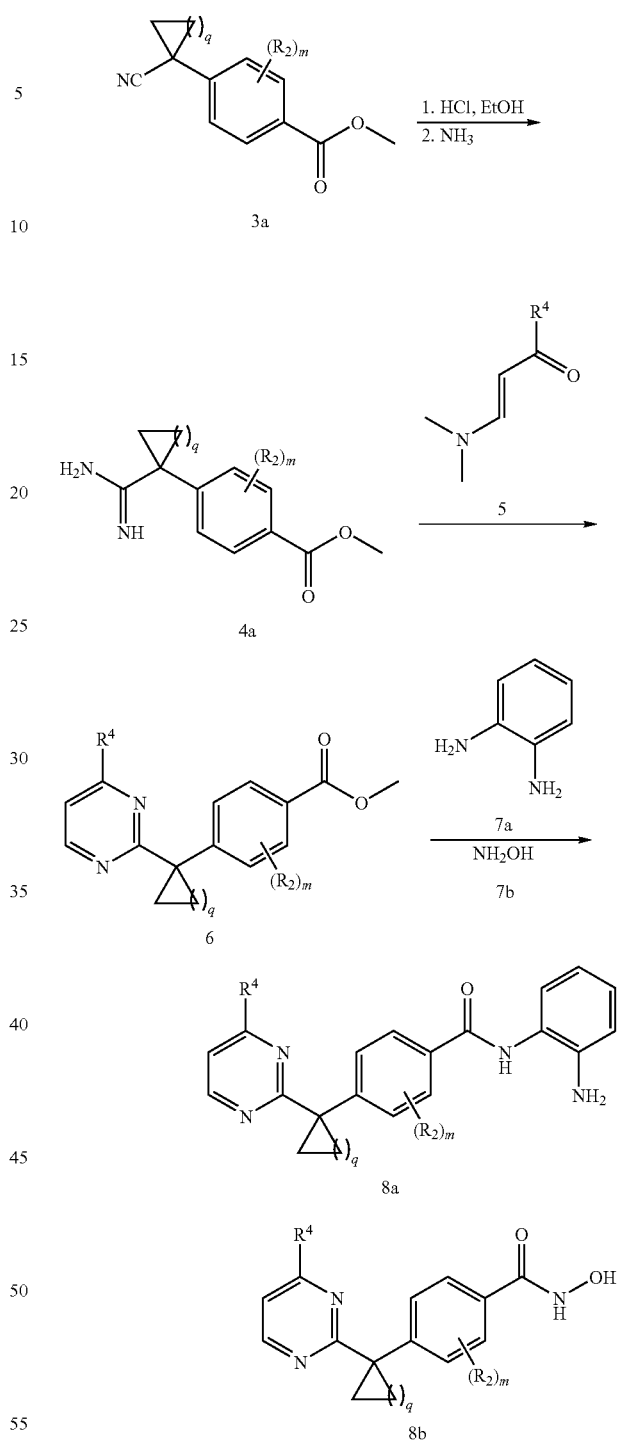

Cyanocycloalkylidene 3a is converted to urea compound 4a and reacted with aminoketone 5 to give ester 6. Ester 6 is converted to arylamide 8a or to hydroxamate 8b.

Alternatively, pyrimidine compounds can be synthesized according to Scheme 7, where intermediate 6 is alkylated to form cycloalkylidene 3 before reaction to the hydroxamate or arylamide. Alternatively, intermediate 6 of Scheme 7 can be alkylated as in Scheme 3 to form a heterocycloalkylidene analog of intermediate 3 (not shown).

Scheme 7

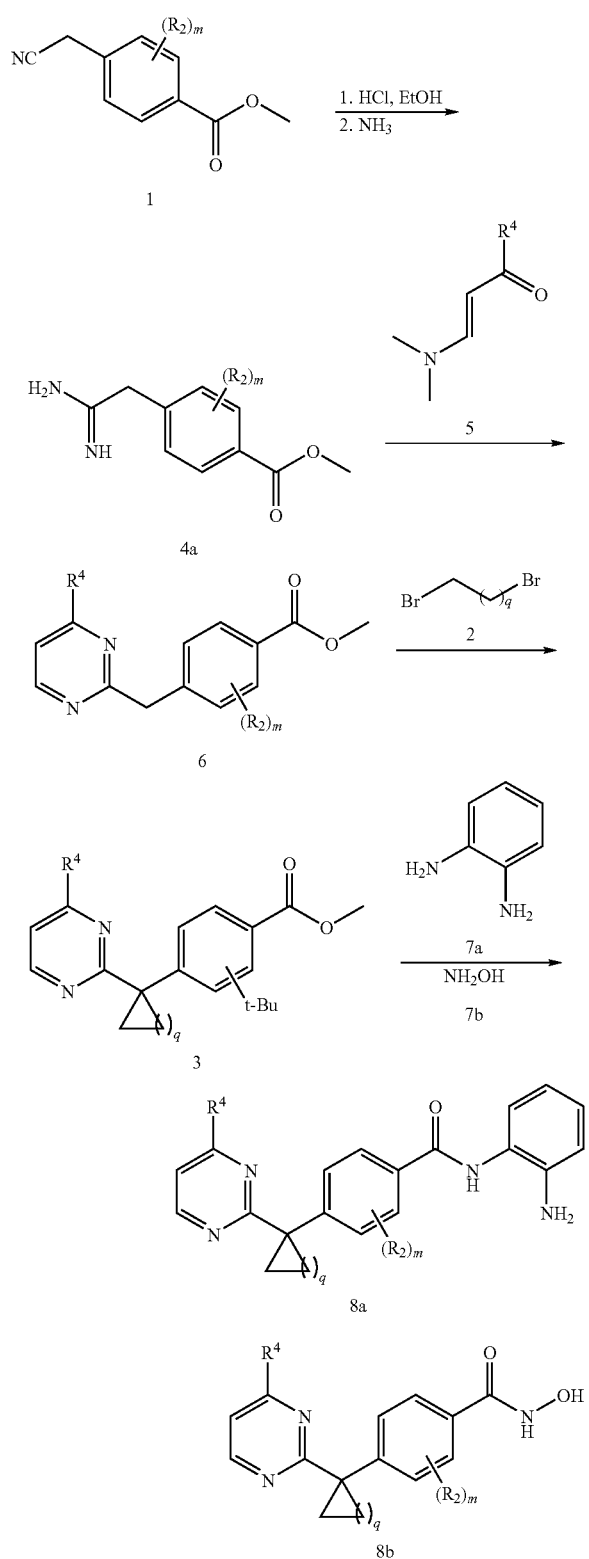

The compounds of the present invention inhibit histone deacetylase and are useful to treat or ameliorate diseases mediated directly or indirectly by HDAC. Therefore, another aspect of the present invention is to provide a pharmaceutical composition comprising an effective amount of one or more compounds as described above.

In one embodiment of the invention, a pharmaceutical composition is provided comprising, in addition to one or more compounds described herein, at least one pharmaceutically-acceptable diluent, adjuvant, excipient, or carrier. The composition can take any suitable form for the desired route of administration. Where the composition is to be administered orally, any suitable orally deliverable dosage form can be used, including without limitation tablets, capsules (solid- or liquid-filled), powders, granules, syrups and other liquids, elixirs, inhalants, troches, lozenges, and solutions. Injectable compositions or iv infusions are also provided in the form of solutions, suspensions, and emulsions.

A pharmaceutical composition according to the present invention may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by HDAC. Examples of such active ingredients are, without limitation, agents to treat or inhibit cancer, Huntington's disease, cystic fibrosis, liver fibrosis, renal fibrosis, pulmonary fibrosis, skin fibrosis, Rheumatoid arthritis, diabetes, stroke, amyotrophic lateral sclerosis, cardiac hypertrophy, heart failure or Alzheimer's disease.

In an embodiment, an additional therapeutic agent to be included is an anti-cancer agent. Examples of an anti-cancer agent include, but are not limited to, alkylating agents such as cyclophosphamide, dacarbazine, and cisplatin; antimetabolites such as methotrexate, mercaptopurine, thioguanine, fluorouracil, and cytarabine; plant alkaloids such as vinblastine, and paclitaxel; antitumor antibiotics such as doxorubicin, bleomycin, and mitomycin; hormones/antihormones such as prednisone, tamoxifen, and flutamide; other types of anticancer agents such as asparaginase, rituximab, trastuzumab, imatinib, retinoic acid and derivatives, colony-stimulating factors, amifostine, camptothecin, topotecan, thalidomide analogs such as lenalidomide, CDK inhibitor and other HDAC inhibitor such as histone deacetylase 1 inhibitors, histone deacetylase 2 inhibitors, histone deacetylase 3 inhibitors, histone deacetylase 4 inhibitors, histone deacetylase 5 inhibitors, histone deacetylase 6 inhibitors, histone deacetylase 7 inhibitors, histone deacetylase 8 inhibitors, histone deacetylase 9 inhibitors, histone deacetylase 10 inhibitors, and histone deacetylase 11 inhibitors.

Yet another aspect of the present invention is to provide a method of inhibiting or treating diseases arising from abnormal cell proliferation and/or differentiation in animal, comprising administering to said animal a therapeutically effective amount of one or more compounds according to the present invention. In one embodiment, the method of inhibiting or treating disease comprises administering to an animal a composition comprising an effective amount of one or more compounds of the invention and a pharmaceutically-acceptable carrier. The composition to be administered may further contain a therapeutic agent such as anti-cancer agent.

A method of the present invention is particularly suitable for use with humans, but may be used with other animals, particularly mammals, such as, for example, non-human primates, companion animals, farm animals, laboratory animals, and wild and zoo animals.

A method of the present invention is particularly useful to treat diseases mediated directly or indirectly by HDAC since the compounds of the present invention have inhibitory activity against those molecules. In some embodiments, therefore, a method of the present invention is used in inhibiting or treating HDAC-mediated diseases. Examples of such disease include, but are not limited to, cell proliferative diseases such as cancer, autosomal dominant disorders such as Huntington's disease, genetic related metabolic disorder such as cystic fibrosis, fibrosis such as liver fibrosis, renal fibrosis, pulmonary fibrosis and skin fibrosis, autoimmune diseases such as Rheumatoid arthritis, diabetes, acute and chronic neurological diseases such as stroke, hypertrophy such as cardiac hypertrophy, heart failure including congestive heart failure, amyotrophic lateral sclerosis, and Alzheimer's disease.

In an embodiment, a method according to the present invention is applied to a patient with cancer, cystic fibrosis, or pulmonary fibrosis. In some embodiments, a method using a compound according to the present invention is used to treat or inhibit a cancer selected from bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer.

EXAMPLES

The following examples are merely illustrative, and do not limit this disclosure in any way.

Example 1

N-(2-amino-phenyl)-4-{1-[4-(2-methyl-imidazo[1,2-a]pyridin-3-yl)-thiazol-2-yl]-cyclopropyl}-benzamide

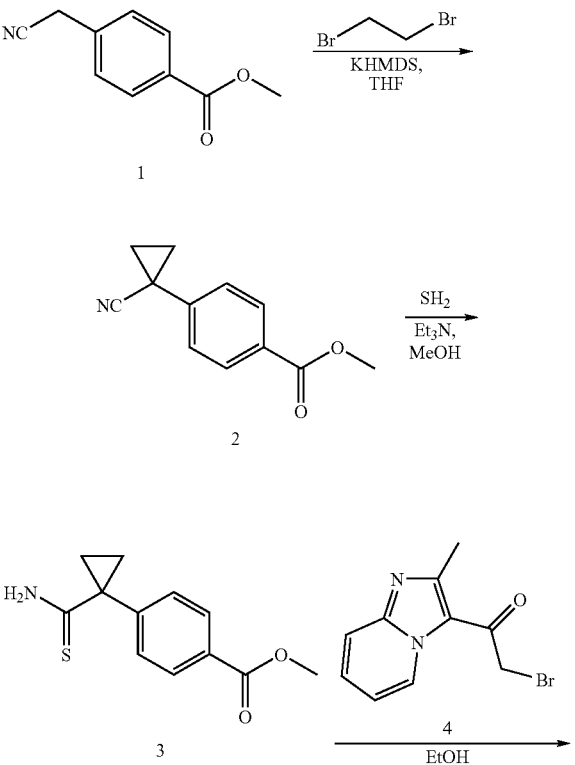

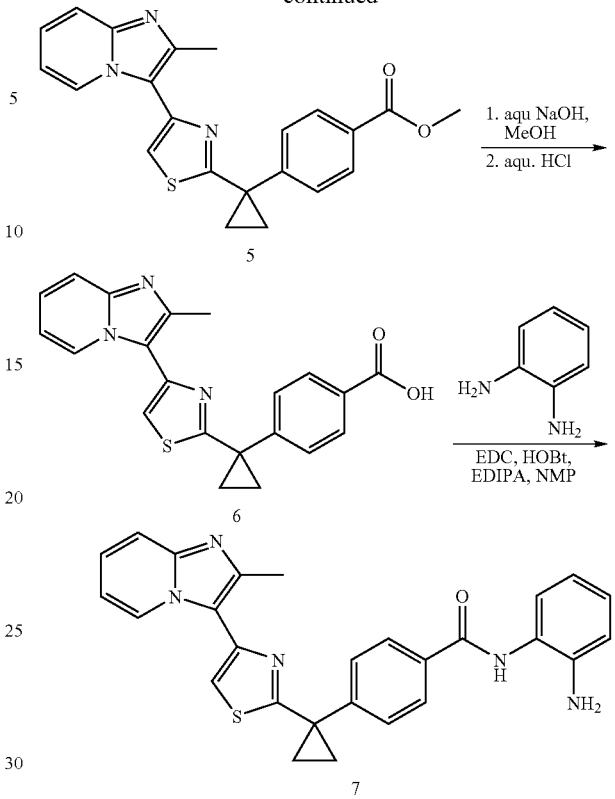

Example 1 (Compound a1-29)

Preparation of Intermediate (hereinafter "Int") 6: Int-1 (1.92 g, 11.01 mmol) and 1,2-dibromoethane (4.76 mL, 55.04 mmol) were combined in tetrahydrofuran (THF) (40 mL) and cooled down to 0° C. To this solution, potassium bis(trimethylsilyl)-amide (0.5M, 48.3 mL, 24.21 mmol) was added in a period of 15 minutes and then warmed up to room temperature and stirred overnight. The reaction mixture was partitioned between ethyl acetate and water. The organic phase were washed with aqueous solution of NaHCO$_3$ and brine, dried with MgSO$_4$ and evaporated under vacuum. The crude product was purified by chromatography on silica gel (25% EtOAc/hexanes) to afford Int-2 (1.55 g, 7.71 mmol, 70.33%). To a solution of Int-2 in MeOH (50 mL) was added Et$_3$N (2.5 mL). H$_2$S was bubbled into the solution. The reaction vessel was stirred at room temperature for 4 days. The reaction mixture was evaporated and purified by silica gel chromatography (33% EtOAc/hexanes) to Int-3 (1.23 g, 5.22 mmol, 67%). 1-(2-methyl-imidazo[1,2-a]pyridine-3-yl)-ethanone (0.25 g, 1.44 mmol) was dissolved in a mixture of HBr/AcOH (33%) (2 mL) and AcOH (4 mL). A solution of Br$_2$ (0.1 mL) in CHCl$_3$ (3 mL) was added at room temperature. After 10 minutes of stirring, the reaction mixture was completed. The solids were filtered out, dissolved in EtOAc, washed out with aqueous NaHCO$_3$, Na$_2$S$_2$O$_3$, dried with MgSO$_4$ and evaporated in vacuum to afford Int-4 (0.32 g, 1.26 mmol, 86%). Int-4 (0.11 g, 0.42 mmol) and Int-3 (00.10 g, 0.42 mmol) were dissolved in EtOH (10 mL) and heated to reflux under stirring for 20 minutes. The reaction mixture was evaporated under vacuum. The crude Int-5 (0.15 g) was used in the next step without further purification. Int-5 (0.15 g, 0.38 mmol) was dissolved in MeOH (6 mL) and treated with an aqueous solution of 1N NaOH (2 mL). The reaction mixture was stirred for 2 hours and then 1N aqueous HCl was added until reaching pH 5. The suspension was filtered out to have Int-6 (0.14 g, 0.36 mmol, 94%).

Preparation of Compound 7: A solution of Int-6 (00.10 g, 0.26 mmol), 1,2-phenylenediamine (57.67 mg, 0.53 mmol), hydroxybenzotriazole (HOBt) (36.03 mg, 0.26 mmol), EDC (102 mg, 0.53 mmol), in N-methyl-2-pyrrolidone (NMP) (5 mL) was stirred for 30 minutes and then N,N-diisopropyl-ethylamine (DIPEA) (74 μL) was added and the mixture was stirred for 2 hours. Water was added to precipitate the product. The solids were filtered and washed with more water, and dried on a filter to afford Compound 7 (0.1 g, 0.21 mmol, 80%). ¹H-NMR (dimethyl sulfoxide (DMSO)) δ: 8.90 (d, J=6.8 Hz, 1H), 8.04 (d, J=8.4 Hz, 2H), 7.71 (d, J=8 Hz, 2H), 7.53-7.50 (m, 3H), 7.34 (t, J=7.2 Hz, 1H), 7.21 (d, J=7.6 Hz, 1H), 7.09 (t, J=7.2 Hz, 1H), 6.98-6.91 (m, 2H), 6.78 (t, J=8.4 Hz, 1H), 2.55 (s, 3H), 1.91-1.88 (m, 2H), 1.61-1.58 (m, 2H). MS m/z: 466 (MH⁺).

Example 2

N-hydroxy-4-{1-[4-(2-methyl-imidazo[1,2-a]pyridin-3-yl)-thiazol-2-yl]-cyclopropyl}-benzamide

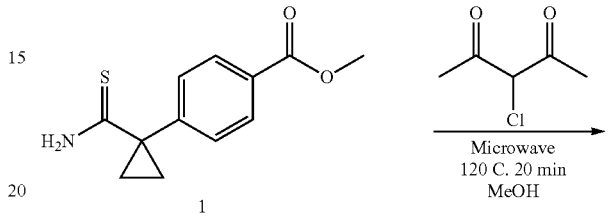

Example 2 (Compound a1-25)

Int-6 of Example 1 (0.24 g, 0.64 mmol), PyBOP (0.39 g, 0.76 mmol), NH₂OTBS (0.37 g, 2.56 mmol) and DIPEA (0.22 mL, 1.28 mmol) were mixed in NMP (5 mL) and stirred for 2 hours at room temperature. After the reaction was completed, 1N HCl 1 mL was added to the reaction mixture and stirred overnight. Once the hydrolysis was done, preparative high performance liquid chromatography (HPLC) purification was performed to obtain Compound 8.

¹H-NMR (DMSO) δ: 11.22 (s, 1H), 8.82 (d, J=6.8 Hz, 1H), 8.44 (s, 1H), 7.76 (d, J=8.2 Hz, 2H), 7.20-7.12 (m, 3H), 7.49 (d, J=8.8 Hz, 1H), 7.23 (t, J=6.8, 1H), 6.91 (t, J=6.1 Hz, 1H), 2.46 (s, 3H), 1.78-1.72 (m, 2H), 1.53-1.47 (m, 2H). m/z=390.12

Example 3

4-[1-(5-Acetyl-4-methyl-thiazol-2-yl)-cyclopropyl]-N-(2-amino-phenyl)-benzamide

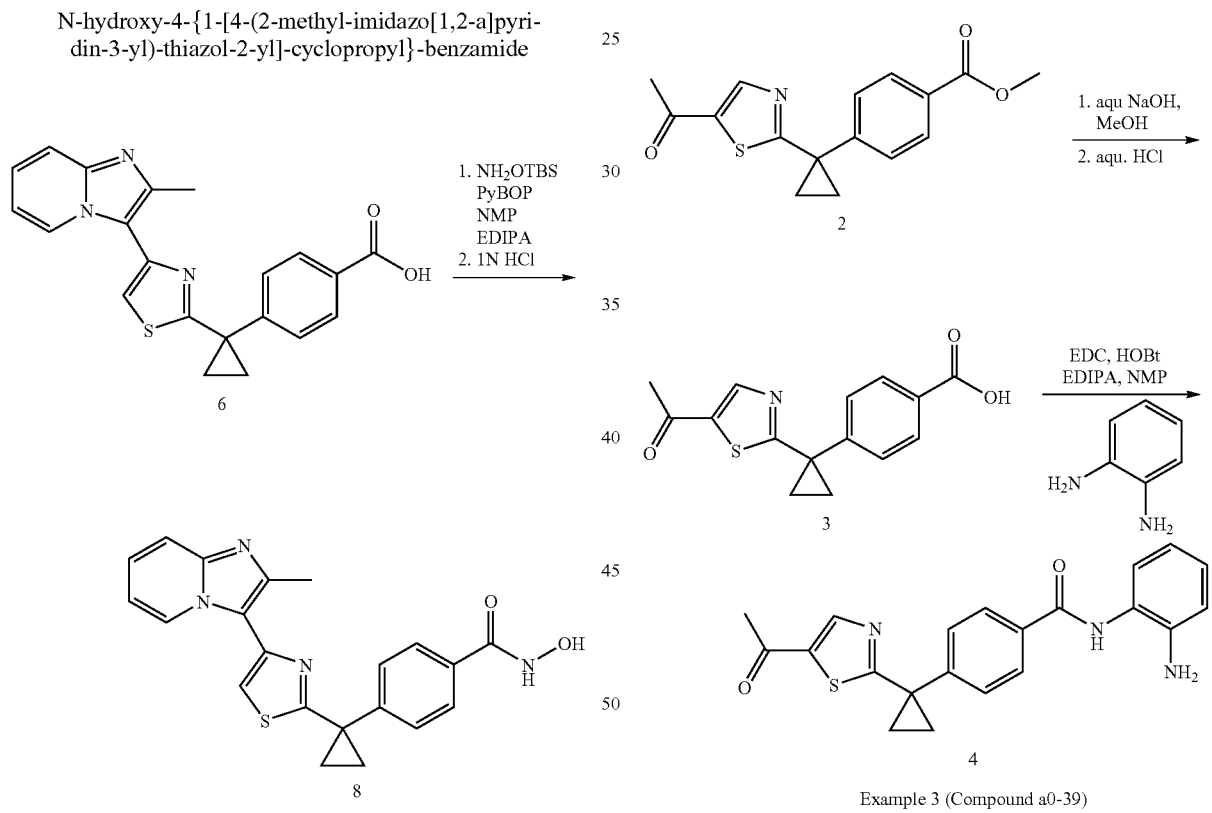

Example 3 (Compound a0-39)

3-Chloro-pentane-2,-4-dione (24, 0.37 mmol) and Int-1 (50 mg, 0.3719 mmol) were dissolved in MeOH (1 mL) and heated in the microwave to 120° C. for 30 minutes. The reaction mixture was evaporated and extracted with water and EtOAc. The organic phase were dried with MgSO₄ and evaporated under vacuum. The crude product Int-2 was used without further purification for ester hydrolysis. The same procedure to get Int-6 and Int-7 of Example 1 was used to synthesize Compound 4 from Int-2: ¹H-NMR (MeOD) δ: 8.30 (d, J=8.0 Hz, 2H), 7.64 (d, J=8.4 Hz, 2H), 7.20 (d, J=8.0 Hz, 1H), 7.08 (t, J=7.96 Hz, 1H), 6.92 (d, J=7.6 Hz, 1H), 6.78

(t, J=7.4 Hz, 1H), 2.62 (s, 3H), 2.41 (s, 3H), 1.88-1.84 (m, 2H), 1.58-1.54 (m, 2H). MS m/z: 392 (MH⁺).

Example 4

2-(1-(4-(2-aminophenylcarbamoyl)phenyl)cyclopropyl)-N,N-4-trimethylthiazole-5-carboxamide

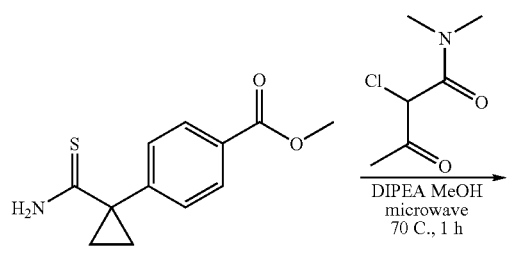

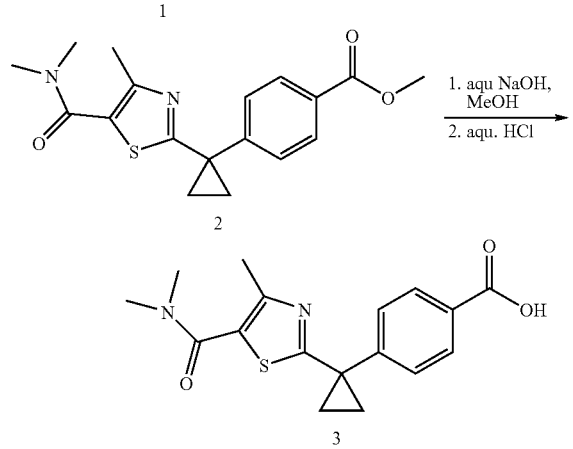

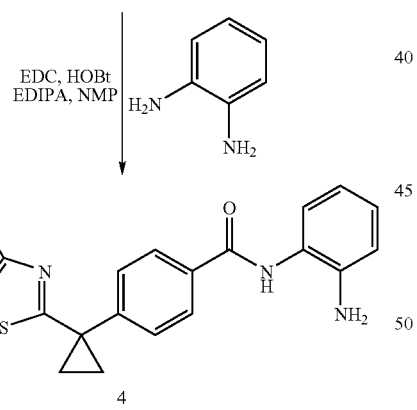

Example 4 (Compound a0-46)

Int-1 (200 mg, 0.85 mmol) and 2-chloro-N,N-dimethyl-3-oxo-butyramide 2-chloro-N,N-dimethyl-3-oxo-butyramide (0.46 mL, 1.70 mmol) were dissolved in MeOH (3 mL), and DIPEA (0.3 mL, 1.70 mmol) was added. The mixture was heated in the microwave for 30 minutes at 90° C. The reaction mixture was evaporated and extracted with water and EtOAc and saturated aqueous solution of NaHCO₃. The organic phase was dried with MgSO₄ and evaporated under vacuum. The crude product Int-2 was used without further purification for hydrolysis. The same procedure to get Int-6 and Int-7 of Example 1 was used to synthesize Compound 4 from Int-2.

¹H-NMR (MeOD) δ: 8.05 (d, J=6.4 Hz, 2H), 7.62 (d, J=8.0 Hz, 2H), 7.10 (d, J=7.6 Hz, 1H), 7.05 (t, J=7.6 Hz, 1H), 6.95 (d, J=7.6 Hz, 1H), 6.78 (t, J=7.2 Hz, 1H), 3.05 (s, 6H), 2.32 (s, 3H), 1.90-1.86 (m, 2H), 1.62-1.58 (m, 2H). MS m/z: 421 (MH⁺).

Example 5

N-(2-Amino-phenyl)-4-[1-(4-pyridin-3-yl-thiazol-2-yl)-cyclopropyl]-benzamide

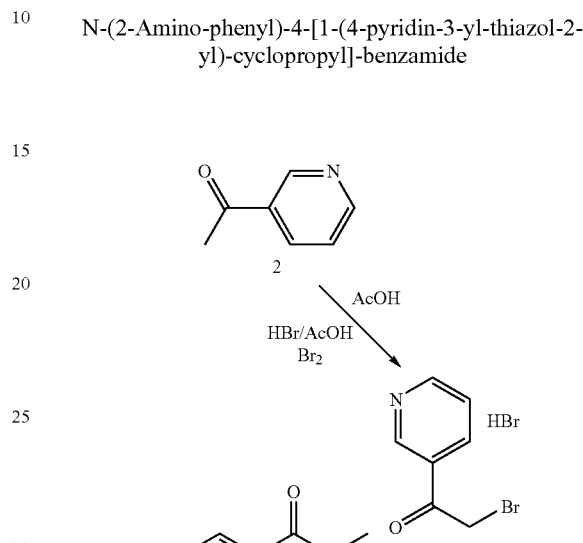

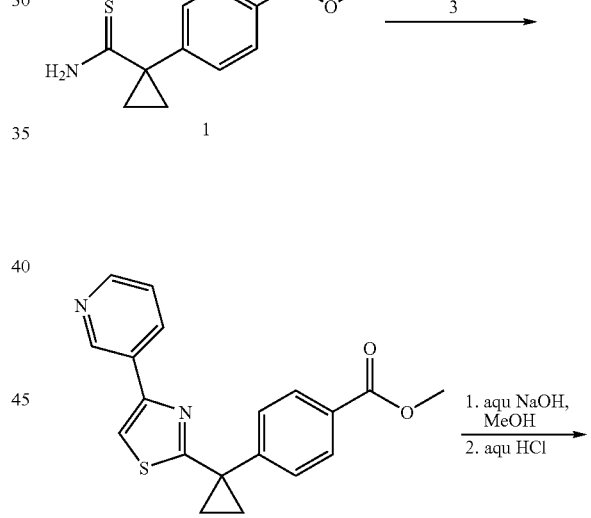

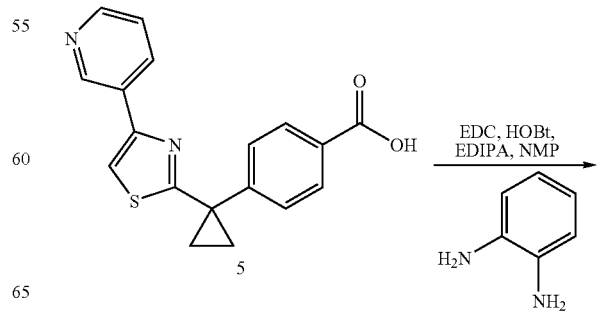

-continued

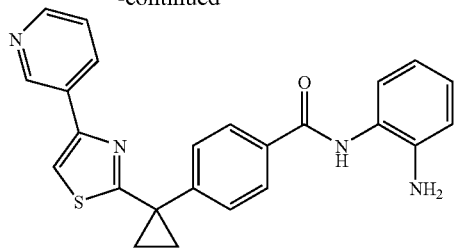

6
Example 5 (Compound a10-02)

Int-2 (0.2 g, 16.51 mmol) was dissolved in a mixture of HBr/AcOH 33% (2 mL) and AcOH (4 mL). 93.3 μL Br$_2$ (1.1 equivalents (eq)) in chloroform (3 mL) was added slowly to the solution at room temperature. After 5 minutes the crystals in suspension were filtered out and worked out with water and EtOAc. The organic phase was dried with MgSO$_4$ and evaporated under vacuum. The crude product was used without further purification for next step. The procedure to synthesize Int-5 of Example 1 was followed to synthesize Int-4 but using Int-3. The same procedure to get Int-6 and Int-7 of Example 1 was used to synthesize Compound 6 from Int-4. $^1$H-NMR (DMSO) δ: 9.66 (s, 1H), 9.08 (s, 1H), 8.48 (m, 1H), 8.20 (d, J=8.4 Hz, 1H), 7.95 (s, 1H), 7.92 (d, J=8.0 Hz, 2H), 7.60 (d, J=8.4 Hz, 2H), 7.40-7.44 (m, 1H), 7.13 (d, J=7.6 Hz, 1H), 6.92 (t, J=7.20 Hz, 1H), 6.72 (d, J=7.6 Hz, 1H), 6.55 (t, J=7.2 Hz, 1H), 4.85 (s, 1H), 1.79-1.75 (m, 2H), 1.52-1.48 (m, 2H). MS m/z: 413 (MH$^+$).

Examples 6 and 7

Example 6

N-(2-Amino-phenyl)-4-[1-(4-pyridin-3-yl-thiazol-2-yl)-cyclopentyl]-benzamide

Example 7

N-(2-Amino-phenyl)-4-{1-[4-(2-methyl-imidazo[1,2-a]pyridin-3-yl)-thiazol-2-yl]-cyclopentyl}-benzamide

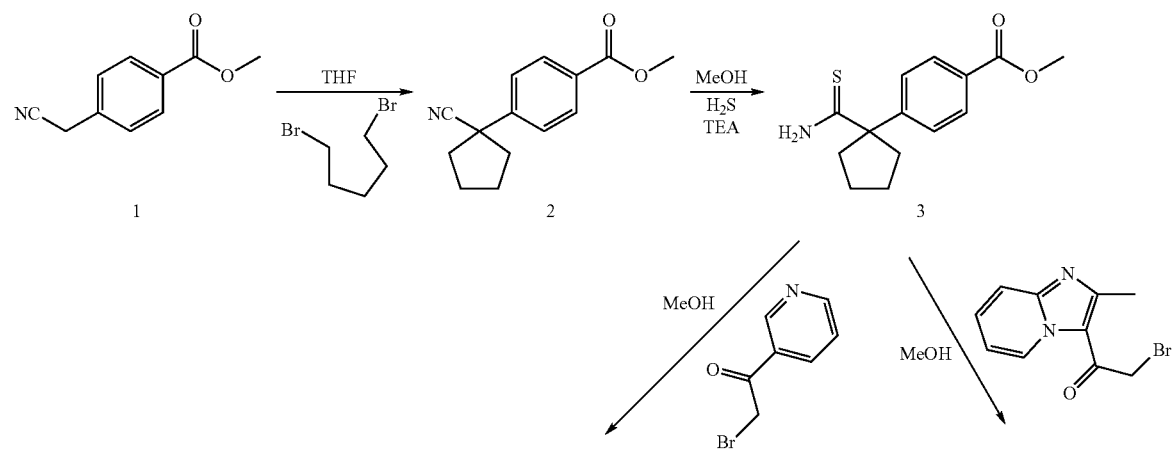

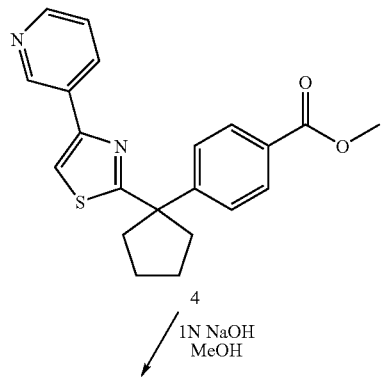

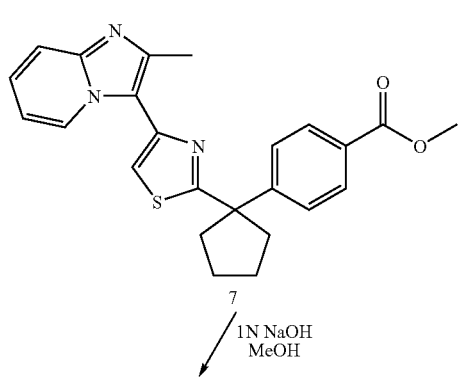

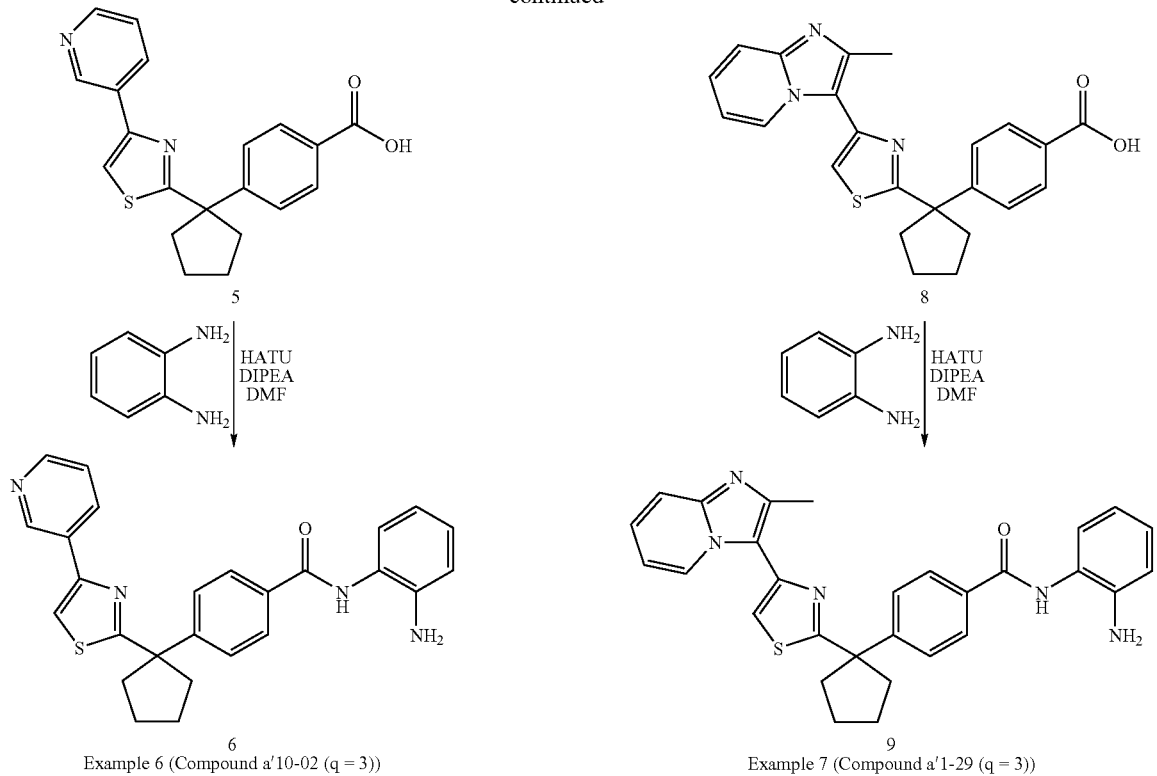

Example 6 (Compound a'10-02 (q = 3))

Example 7 (Compound a'1-29 (q = 3))

The same procedure to get Int-2 and Int-3 of Example 1 was used to synthesize Int-3. Then the procedure to get Int-5 of Example 1 was followed for the synthesis of Int-4 and Int-7 but using 2-bromo-1-pyridin-3-yl-ethanone and 2-bromo-1-(2-methyl-imidazo[1,2-a]pyridin-3-yl)-ethanone. Following the procedure to get Int-6 of Example 1, Int-5 and Int-8 were synthesized.

Preparation of Compounds 6 and 9: The same procedure to get Int-6 and Compound 7 of Example 1 was used to synthesize Compound 6 and Compound 9 from Int-5 and Int-8, respectively. Compound 6: $^1$H-NMR (DMSO) δ: 9.58 (s, 1H), 8.82 (d, J=6.8 Hz, 1H), 7.79 (d, J=8.4 Hz, 2H), 7.75 (d, J=8.0 Hz 2H), 7.50 (d, J=7.6 Hz, 1H), 7.32 (t, J=7.0 Hz, 1H), 7.12 (d, J=7.2 Hz, 1H), 6.98-6.90 (m, 2H), 6.74 (d, J=7.6 Hz, 1H), 6.52 (t, J=7.2 Hz, 1H), 4.80 (s, 2H), 2.82-2.74 (m, 2H), 2.34-2.30 (m, 2h), 1.84-1.78 (m, 4H). MS m/z: 494 (MH$^+$). Compound 9: $^1$H-NMR (DMSO) δ: 9.60 (s, 1H), 9.18 (s, 1H), 8.48 (d, J=8.0 Hz, 1H), 8.23 (d, J=8.4 Hz, 1H), 8.18 (s, 1H), 7.95 (d, J=8.4 Hz, 2H), 7.59 (d, J=8.2, 2H), 7.43 (t, J=7.6 Hz, 1H), 7.18 (d, J=8.0 Hz, 1H), 6.95 (t, J=7.2 Hz, 1H), 6.78 (d, J=7.6 Hz, 1H), 6.49 (t, J=7.2 Hz, 1H), 2.72-2.80 (m, 2H), 2.32-2.20 (m, 2H), 1.80-1.75 (m, 4H), 1.80-1.75 (m, 4H). MS m/z: 441 (MH$^+$).

Examples 8 and 9

Example 8

N-(2-Amino-phenyl)-4-[4-(4-pyridin-3-yl-thiazol-2-yl)-tetrahydro-pyran-4-yl]-benzamide Example 9

N-(2-Amino-phenyl)-4-{4-[4-(2-methyl-imidazo[1,2-a]pyridin-3-yl)-thiazol-2-yl]-tetrahydro-pyran-4-yl}-benzamide

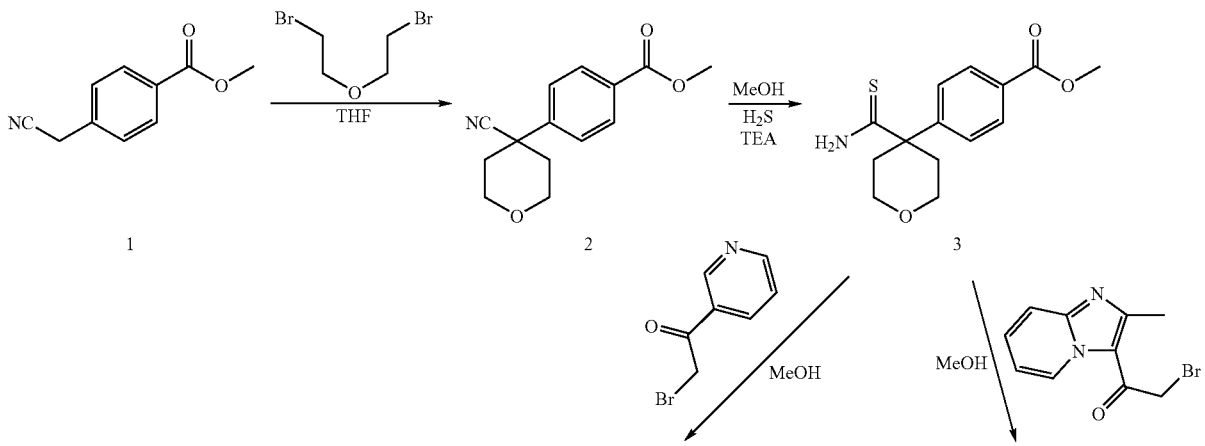

161
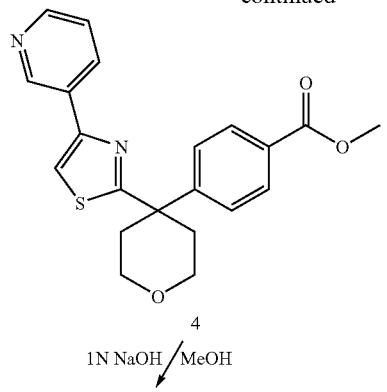
4
1N NaOH / MeOH ↓
162
-continued
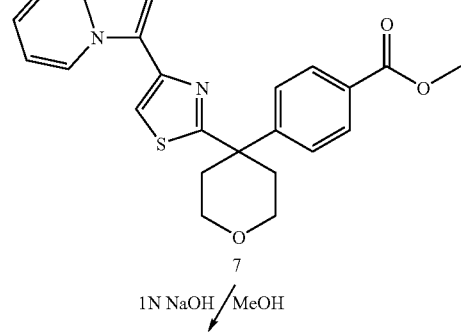
7
1N NaOH / MeOH ↓
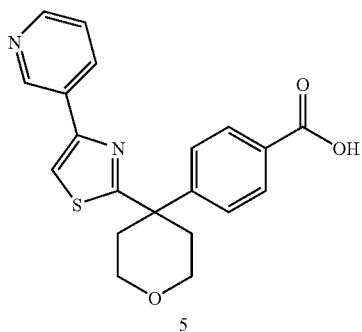
5
HATU
DIPEA
DMF ↓
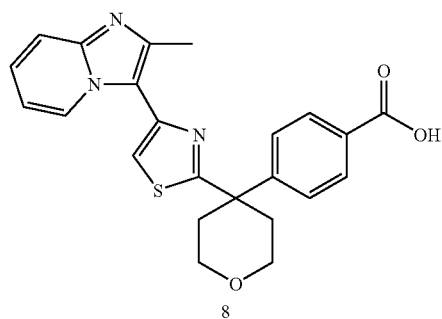
8
HATU
DIPEA
DMF ↓
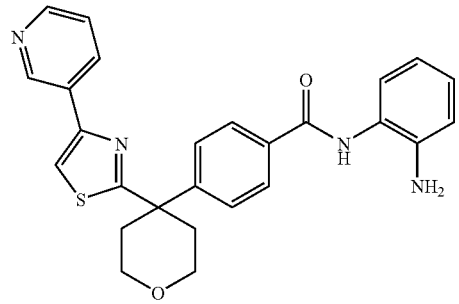
6
Example 8 (Compound a"10-02)
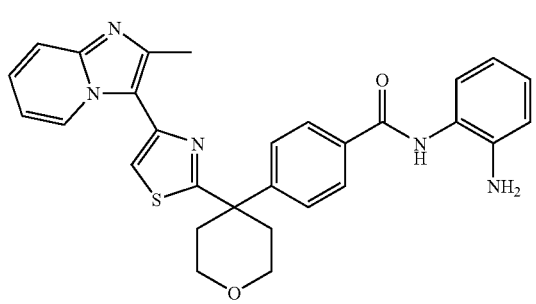
9
Example 9 (Compound a"1-29)

Preparation of Int-3: The procedure to get Int-2 of Example 1 was followed to synthesize Int-2 and Int-3 but using 1-bromo-2-(2-bromo-ethoxy)-ethane.

Preparation of Compounds 6 and 9: The procedure to get Int-5 of Example 1 was followed for the synthesis of Int-4 and Int-7 but using 2-bromo-1-pyridin-3-yl-ethanone and 2-bromo-1-(2-methyl-imidazo[1,2-a]pyridin-3-yl)-ethanone. The same procedure to get Int-6 and Compound 7 of Example 1 was used to synthesize Compound 6 and Compound 9 from Int-4 and Int-7, respectively. Compound 6: $^1$H-NMR (DMSO) δ: 9.58 (s, 1H), 9.18 (s, 1H), 8.54 (d, J=8.0 Hz, 1H), 8.28 (d, J=8.4 Hz, 1H), 8.21 (s, 1H), 7.9 (d, J=8.4 Hz, 2H), 7.6 (d, J=8.0, 2H), 7.42 (t, J=7.4 Hz, 1H), 7.10 (d, J=7.0 Hz, 1H), 6.95 (t, J=7.2 Hz, 1H), 6.70 (d, J=7.6 Hz, 1H), 6.55 (t, J=7.2 Hz, 1H), 4.82 (s, 2H), 3.78-3.65 (m, 2H), 3.68-3.60 (m, 2H), 2.70-2.62 (m, 2H), 2.42-2.38 (m, 2H). MS m/z: 457 (MH$^+$). Compound 9: $^1$H-NMR (DMSO) δ: 9.60 (s, 1H), 8.84 (d, J=6.4 Hz, 1H), 7.96 (d, J=8.2 Hz, 2H), 7.82 (s, 1H), 7.65 (d, J=8.0 Hz, 2H), 7.56 (d, J=7.8 Hz, 1H), 7.32 (t, J=7.6 Hz, 1H), 7.18 (d, J=7.0 Hz, 1H), 7.0-6.92 (m, 2H), 6.76 (d, J=7.0 Hz, 1H), 6.58 (t, J=7.2 Hz, 1H), 4.88 (s, 2H), 3.75-3.65 (m, 4h), 2.78-2.65 (m, 2H), 2.58-2.50 (m, 2H). MS m/z: 510 (MH$^+$).

Example 10

2-(1-(4-(2-aminophenylcarbamoyl)phenyl)cyclopropyl)-N-isopropylthiazole-4-carboxamide

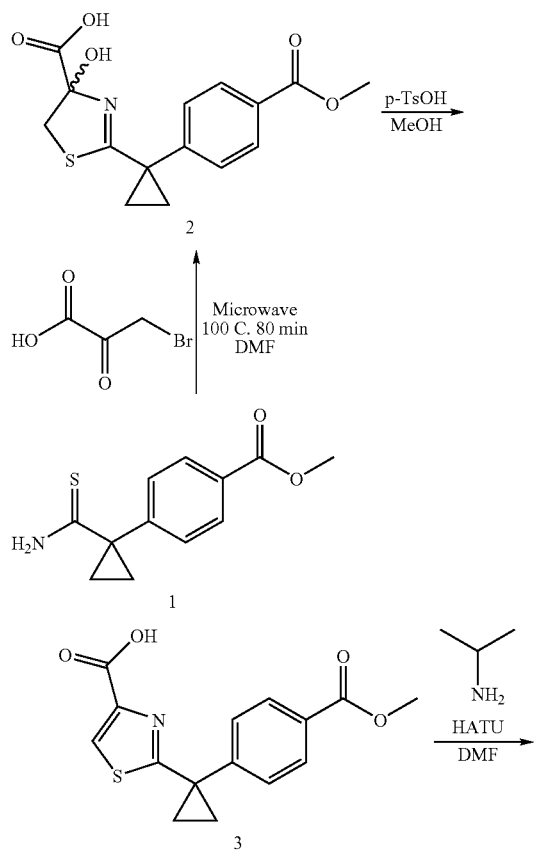

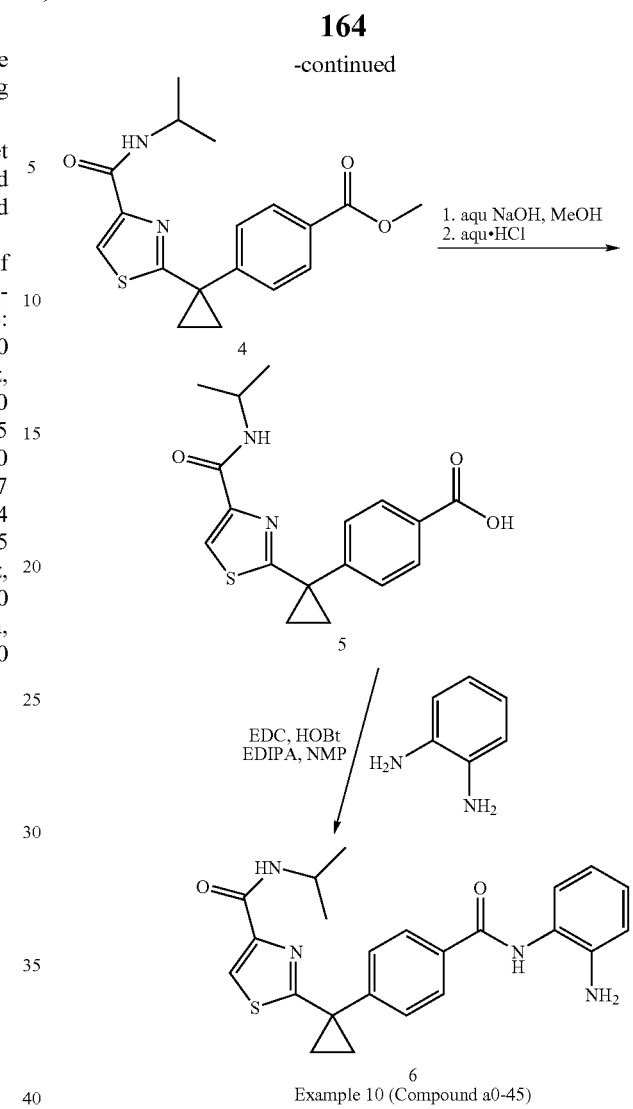

Example 10 (Compound a0-45)

3-Bromo-2-oxo-propionic acid (142 mg, 0.85 mmol) and Int-1 (100 mg, 0.4255 mmol) were dissolved in dimethylformamide (DMF). DIPEA (0.15 mL, 0.84 mmol) was added and the whole mixture heated in microwave at 100° C. for 80 minutes. The reaction mixture was evaporated and extracted with EtOAc, water, and saturated aqueous solution of NaHCO$_3$. The organic phase was dried with MgSO$_4$ and evaporated under vacuum. The crude product Int-2 was used without further purification for ester hydrolysis. p-TsOH was added in excess to a solution of Int-2 (100 mg, 0.31 mmol) in MeOH and heated in microwave for 30 minutes at 80° C. The reaction mixture was evaporated and extracted with EtOAc, water and a saturated aqueous solution of NaHCO$_3$. The organic phase was dried with MgSO$_4$ and evaporated to yield Int-3. A solution of Int-3 (0.2 g, 0.85 mmol), isopropylamine (0.1 g, 1.70 mmol), HOBt (0.32 g, 0.85), and DIPEA (0.28 mL, 1.70 mmol) were dissolved in DMF (3 mL) and stirred at room temperature for 2 hours. The reaction mixture was crushed out with water and saturated solution of NaHCO$_3$ to the solution to have pure Int-4. This compound was used without further purification for next step. The same procedure to get Int-6 and Compound 7 of Example 1 was used to synthesize Compound 6 from Int-4. $^1$H-NMR (MeOD) δ: 8.03 (d, J=6.4 Hz, 2H), 7.91 (s, 1H), 7.64 (d, J=8.0 Hz, 2H), 7.25 (d, J=8.0 Hz, 1H), 7.16 (t, J=7.6 Hz, 1H), 7.02 (d, J=7.2 Hz, 1H), 6.93 (t, J=7.6 Hz, 1H), 1.88-1.82 (m, 2H), 1.59-1.53 (m, 2H), 1.27 (s, 3H), 1.25 (s, 3H). MS m/z: 421 (MH$^+$).

Example 11

N-(2-amino-phenyl)-4-[1-(4,5,6,7-tetrahydro-benzothiazol-2-yl)-cyclopropyl]-benzamide

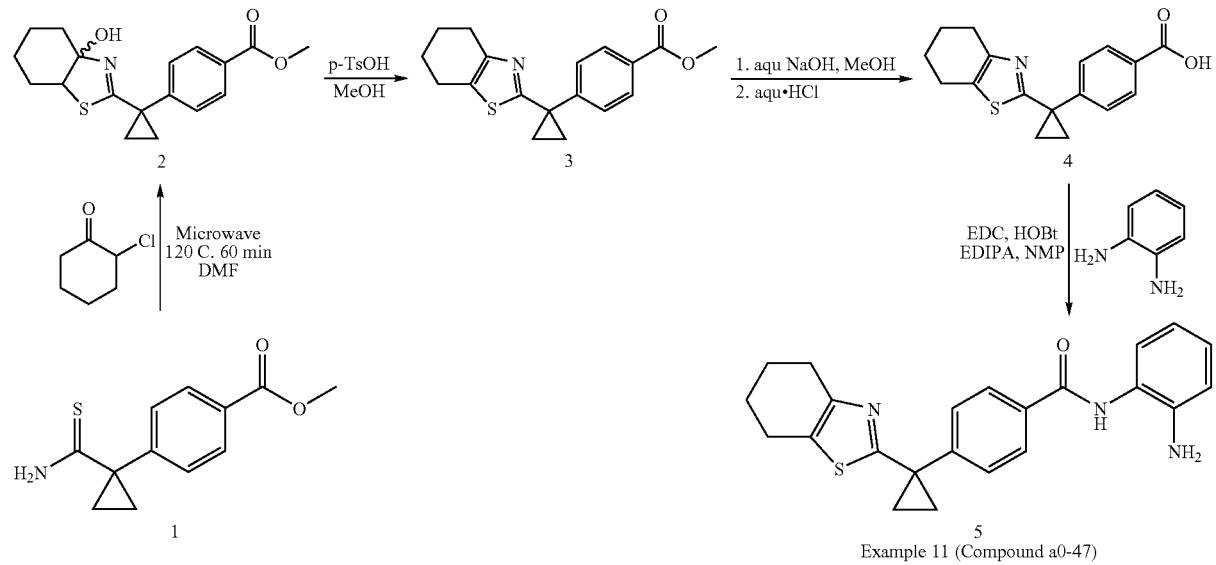

2-Chloro-cyclohexanone (0.5 mL, 8.52 mmol) and Int-1 (0.5 g, 2.13 mmol) were dissolved in DMF and (0.72 mL, 4.26 mmol) of DIPEA was added. The whole mixture heated in microwave at 120° C. for 10 minutes. The reaction mixture was evaporated and extracted with EtOAc, water, and saturated aqueous solution of $NaHCO_3$. The organic phase was dried with $MgSO_4$ and evaporated under vacuum. The crude product Int-2 was used without further purification for dehydration. The same procedures to get Int-3 of Example 3 and Int-6 and Compound 7 of Example 1 were used to synthesize Compound 5 from Int-2. $^1$H-NMR (MeOD) δ: 7.95 (d, J=8.2 Hz, 2H), 7.50 (d, J=8.4 Hz, 2H), 7.2 (d, J=7.6 Hz, 1H), 7.10 (d, J=7.2 Hz, 1H), 7.88 (d, J=7.2 Hz, 1H), 6.78 (t, J=7.4 Hz, 1H), 2.70-2.65 (m, 4H), 1.70-1.65 (m, 4H), 1.50-1.42 (m, 2H). MS m/z: 390 (MH$^+$).

Examples 12, 13 and 14

Example 12

Ethyl-2-(1-(4-(2-aminophenylcarbamoyl)phenyl)cyclopropyl)-6,7-dihydrothiazolo[5,4-c]pyridine-5(4H)-carboxylate

Example 13

N-(2-amino-phenyl)-4-[1-(4,5,6,7-tetrahydro-thiazolo[5,4-c]pyridin-2-yl)-cyclopropyl]-benzamide

Example 14 tert-butyl 2-(1-(4-(2-aminophenylcarbamoyl)phenyl)cyclopropyl)-6,7-dihydrothiazolo[5,4-c]pyridine-5(4H)-carboxylate

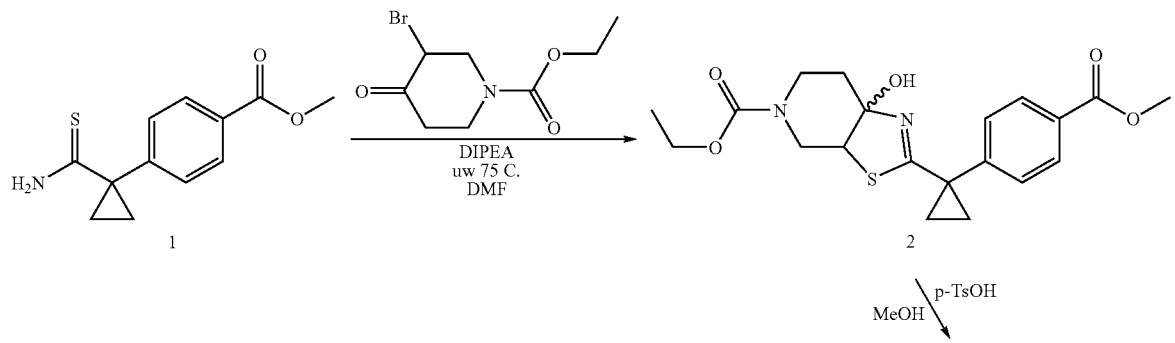

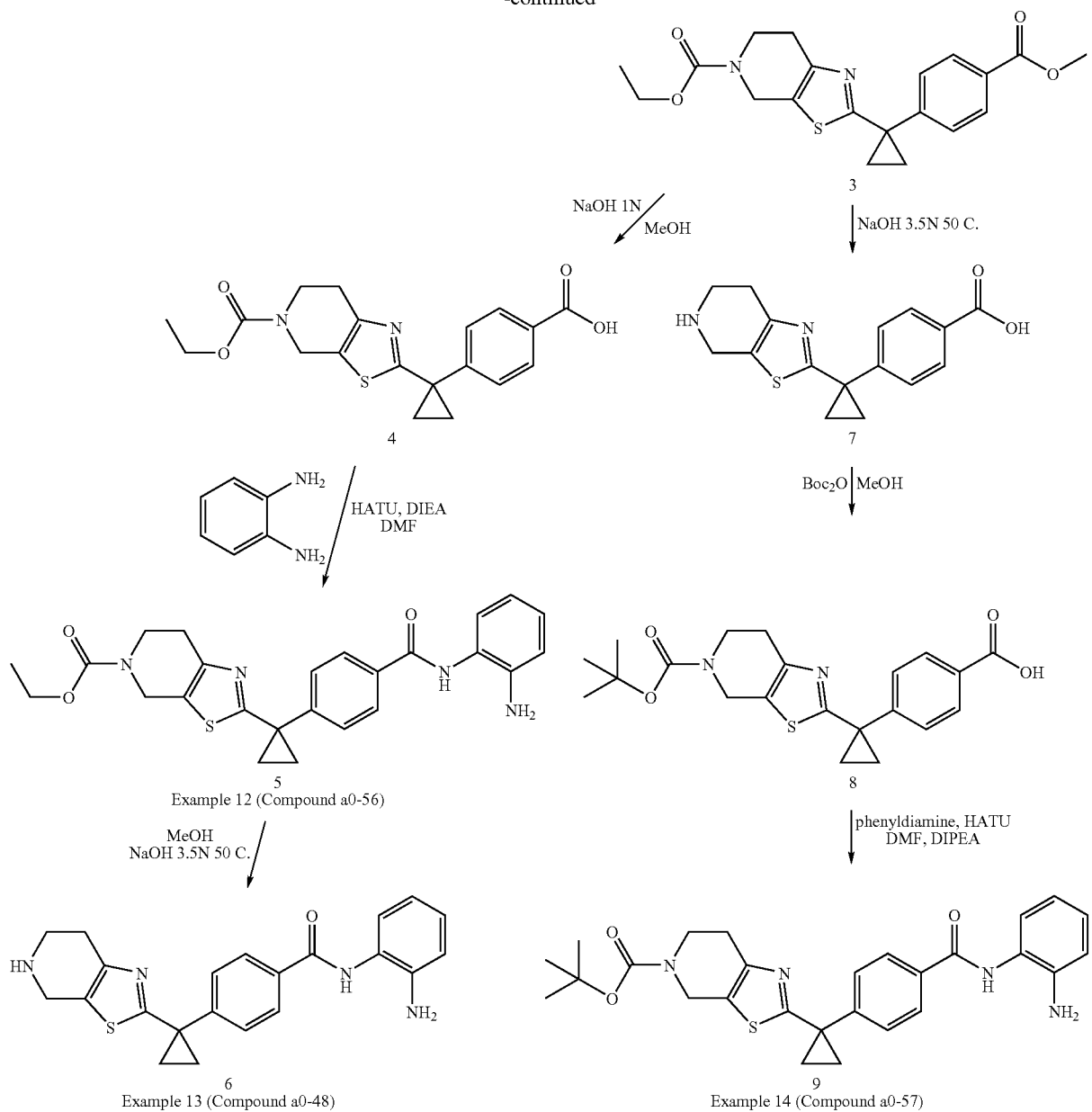

Preparation of Compound 5: 3-Bromo-4-oxo-piperidine-1-carboxylic acid ethyl ester (1.06 g, 4.24 mmol) and Int-1 (500 mg, 2.12 mmol) were dissolved in DMF. DIPEA (0.72 mL, 4.24 mmol) was added and the whole mixture heated in microwave at 75° C. for 60 minutes. The reaction mixture was extracted with EtOAc, water, and saturated aqueous solution of $NaHCO_3$. The organic phase were dried with $MgSO_4$ and evaporated under vacuum to yield Int-2. The procedures to get Int-3 of Example 3 and Int-6 and Compound 7 of Example 1 were followed in order to synthesize Int-3, Int-4 and Compound 5, respectively. Compound 5: $^1$H-NMR (DMSO) δ: 9.62 (s, 1H), 7.95 (d, J=6.4 Hz, 2H), 7.45 (d, J=8.4 Hz, 2H), 7.05 (d, J=7.6 Hz, 1H), 6.92 (t, J=7.2 Hz, 1H), 6.65 (d, J=7.6 Hz, 1H), 6.52 (t, J=7.2 Hz, 1H), 4.82 (s, 2H), 4.42 (s, 2H), 4.02-3.98 (m, 2H), 3.62-3.58 (m, 2H), 2.66-2.60 (m, 2H), 2.58-2.52 (m, 2H), 1.39-1.32 (m, 2H), 1.08-1.05 (m, 2H). MS m/z: 463 ($MH^+$).

Preparation of Compound 6: Int-5 (0.2 g, 0.43 mmol) was added in MeOH (3 mL) and treated with an aqueous solution of 3.5N NaOH (1 mL). The reaction mixture was stirred overnight at 50° C. and then 1N of aqueous HCl was added until reaching a neutral pH. The reaction mixture was extracted with EtOAc and water. The organic phase dried over $MgSO_4$ and evaporated. Further purification was done to have Compound 6. $^1$H-NMR (DMSO) δ: 9.62 (s, 1H), 8.15 (s, 1H), 7.92 (d, J=8.4 Hz, 2H), 7.48 (d, J=8.2 Hz, 2H), 7.10 (d, J=7.6 Hz, 1H), 6.90 (t, J=7.0 Hz, 1H), 6.72 (d, J=7.2 Hz, 1H), 6.55 (t, J=7.0 Hz, 1H), 4.85 (s, 2H), 3.70-3.66 (m, 2H), 2.90-2.85 (m, 2H), 2.55-2.50 (m, 2H), 1.55-1.50 (m, 2H), 1.35-1.32 (m, 2H). MS m/z: 391 ($MH^+$).

Preparation of Compound 9: Int-7 (0.2 mg, 0.52 mmol) was dissolved in MeOH and treated with a 2.5 equivalents of an aqueous 3.5N solution of NaOH. The reaction mixture were stirred overnight at 50° C. and then evaporated to be use on next step without further purification. Int-8 (0.15 g, 0.5 mmol) was dissolved in MeOH and di-tert-butyl dicarbonate (BOC$_2$O) (0.543 mg, 2.5 mmol) at 0° C. and stirred for 2 hours until the reaction was completed. The reaction mixture was evaporated and extracted with EtOAc and water. The organic phase was evaporated and used without further purification for the next step. Procedure to get Compound 7 of Example 1 was followed in order to get Compound 9. $^1$H-NMR (MeOD) δ: 7.96 (d, J=8.4 Hz, 2H), 7.56 (d, J=8.2 Hz, 2H), 7.17 (d, J=7.0 Hz, 1H), 7.06 (t, J=7.6 Hz, 1H), 6.89 (d, J=7.6 Hz, 1H), 6.76 (t, J=7.0 Hz, 1H), 4.52-4.49 (m, 2H), 3.72-3.65 (m, 2H), 2.79-2.75 (m, 2H), 1.72-1.68 (m, 2H), 1.50-1.45 (m, 2H), 1.44 (s, 9H). MS m/z: 491 (MH$^+$).

Example 15

N-(2-amino-cyclohexa-1,5-dienyl)-4-(4-thiazol-2-yl-tetrahydro-pyran-4-yl)-benzamide

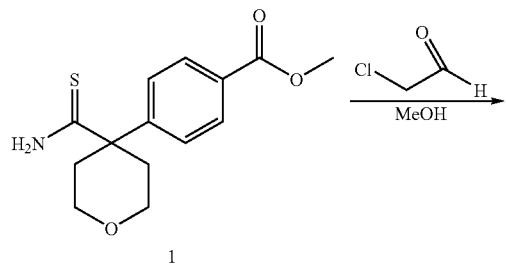

1

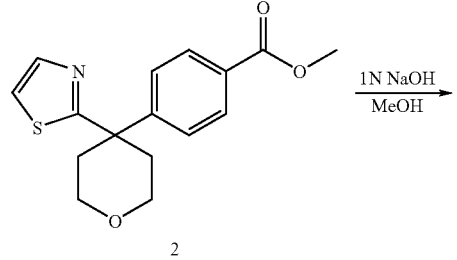

2

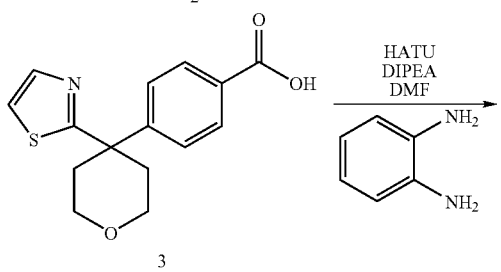

3

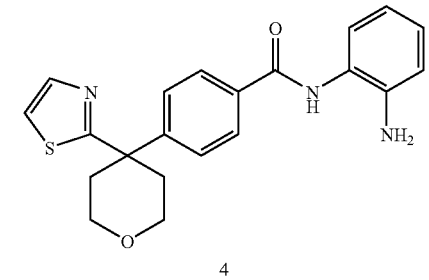

4
Example 15 (Compound a″0-10)

The same procedure to synthesize Int-5 of Example 10 was followed to synthesize Int-2 but using chloro-acetaldehyde in methanol. The same procedure to get Int-6 and Compound 7 of Example 1 was used to synthesize Compound 4. $^1$H-NMR (MeOD) δ: 9.62 (s, 1H), 7.95 (d, J=8.4 Hz, 2H), 7.75 (d, J=7.6 Hz, 1H), 7.63 (d, J=7.2 Hz, 1H), 7.52 (d, J=8.4 Hz, 2H), 7.05 (d, J=7.6 Hz, 1H), 6.95 (t, J=7.2 Hz, 1H), 6.78 (d, J=7.6 Hz, 1H), 6.58 (t, J=7.2 Hz, 1H), 3.80-3.72 (m, 2H), 3.50-3.45 (m, 2H), 2.64-2.60 (m, 2H), 2.40-2.32 (m, 2H). MS m/z: 380 (MH$^+$).

Example 16

N-(2-aminophenyl)-4-(1-(4-methylthiazol-2-yl)cyclopropyl)benzamide

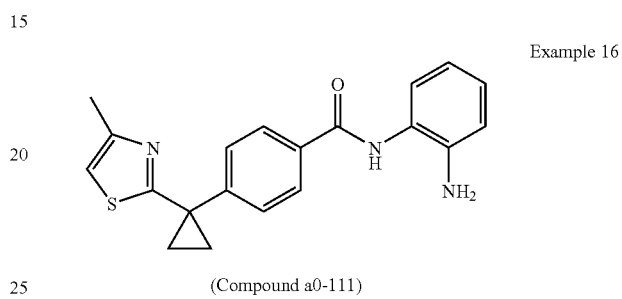

(Compound a0-111)

Similar procedure from Example 1 was followed to obtain the title compound using 1-bromopropan-2-one. MS found for $C_{20}H_{19}N_3OS$ as (M+H)$^+$ 350.19. $^1$H NMR (400 MHz, dmso-d$_6$): δ: 9.65 (s, 1H), 7.95 (d, J=6.4 Hz, 2H), 7.53 (d, J=7.6 Hz, 2H), 7.13 (d, J=7.2 Hz, 1H), 6.97-6.92 (m, 2H), 6.74 (d, J=8.4 Hz, 1H), 6.57 (d, J=6.8 Hz, 1H), 4.88 (s, 2H), 2.26 (s, 3H), 1.62-1.60 (m, 2H), 1.42-1.40 (m, 2H).

Example 17

(S)-4-(1-(5-(2-amino-3-methylbutanoyl)-4,5,6,7-tetrahydrothiazolo[5,4-c]pyridin-2-yl)cyclopropyl)-N-(2-aminophenyl)benzamide

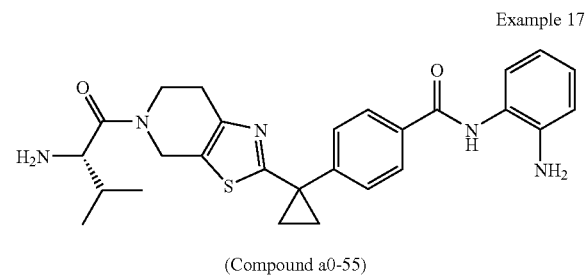

(Compound a0-55)

To a solution of 4-[1-(4,5,6,7-tetrahydro-thiazolo[5,4-c]pyridin-2-yl)-cyclopropyl]-benzoic acid (100 mg, 0.333 mmol) in MeOH (3 mL), tert-Butoxycarbonyl-L-valine N-hydroxysuccinimide ester (Boc-VAL-OSu) (1.0 eq) was added and heated at reflux for 2 hours. After reaction was completed it was extracted with EtOAc. The organic phase was dried and evaporated.

O-(7-azabenzotriazol-1-yl)-N,N,N',N'-tetramethyluronium hexafluorophosphate (HATU) coupling was carried out following the same procedures from Example 1. The resulting compound was dissolved in 1N HCl and stirred for 1 hour. The resulting mixture was evaporated and purified by reverse phase chromatography to afford title compound. MS found for $C_{27}H_{31}N_5O_2S$ as $(M+H)^+$ 490.49. $^1H$ NMR (400 MHz, dmso-d$_6$): δ: 9.64 (s, 1H), 7.95 (d, J=8.4 Hz, 2H), 7.53 (d, J=8.4 Hz, 2H), 7.13 (d, J=7.2 Hz, 1H), 6.96-6.92 (m, 1H), 6.75 (d, J=8.0 Hz, 1H), 6.56 (t, J=6.4 Hz, 1H), 4.86 (s, 2H), 4.73-4.61 (m, 2H), 4.44-4.40 (m, 1H), 3.82-3.49 (m, 3H), 1.59-1.58 (m, 2H), 1.42-1.41 (m, 2H), 0.86 (d, J=6.8 Hz, 3H), 0.78 (d, J=6.8 Hz, 3H), 0.75-0.73 (m, 2H).

Example 18

N-(2-aminophenyl)-4-(4-(4-(6-chloropyridin-3-yl)thiazol-2-yl)tetrahydropyran-4-yl)benzamide Example 18

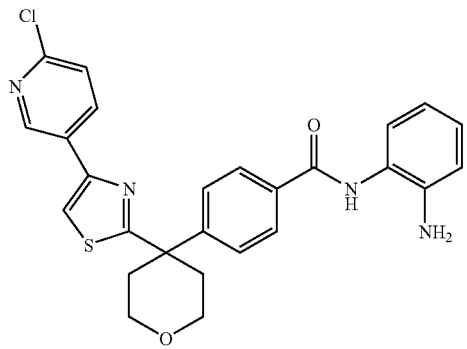

(Compound a″10-07)

Similar procedure from Example 15 was followed to obtain the title compound using 2-bromo-1-(5-chloropyridin-3-yl)ethanone. MS found for $C_{26}H_{23}ClN_4O_2S$ as $(M+H)^+$ 491.35. $^1H$ NMR (400 MHz, dmso-d$_6$): δ: 8.94 (d, J=2.4 Hz, 1H), 8.34 (dd, J=8.4, 6.0 Hz, 1H), 7.97-7.93 (m, 4H), 7.61 (d, J=8.8 Hz, 2H), 7.50 (d, J=8.8 Hz, 1H), 7.15 (d, J=8.0 Hz, 1H), 7.07-7.02 (m, 1H), 6.86 (t, J=6.4 Hz, 1H), 6.76-6.71 (m, 1H), 4.82 (s, 2H), 3.91-3.86 (m, 2H), 3.80-3.71 (m, 2H), 2.81-2.78 (m, 2H), 2.53-2.46 (m, 2H).

Example 19

N-(2-Amino-5-fluoro-phenyl)-4-[1-(4-pyridin-3-yl-thiazol-2-yl)-cyclopropyl]-benzamide Example 19

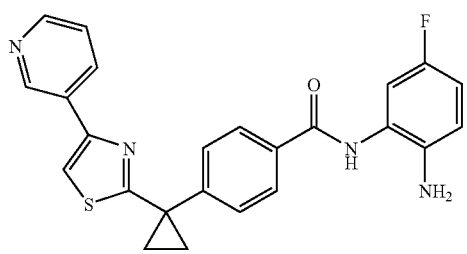

(Compound a10-03)

Similar procedure from Example 22 was followed to obtain the title compound using (2-amino-4-fluoro-phenyl)-carbamic acid tert-butyl ester. MS found for $C_{24}H_{19}FN_4OS$ as $(M+H)^+$ 431.43. $^1H$ NMR (400 MHz, dmso-d$_6$): δ: 9.68 (s, 1H), 9.09 (d, J=1.6 Hz, 1H), 8.49 (dd, J=4.8, 3.2 Hz, 1H), 8.23-8.20 (m, 1H), 8.01-7.97 (m, 3H), 7.63 (dd, J=6.4, 1.6 Hz, 2H), 7.44-7.41 (m, 2H), 7.14 (dd, J=8.8, 7.6 Hz, 1H), 6.83-6.72 (m, 2H), 4.83 (s, 2H), 1.78-1.75 (m, 2H), 1.52-1.49 (m, 2H).

Example 20

N-(2-aminophenyl)-4-(4-(4-(6-(pyrrolidin-1-yl)pyridin-3-yl)thiazol-2-yl)tetrahydropyran-4-yl)benzamide Example 20

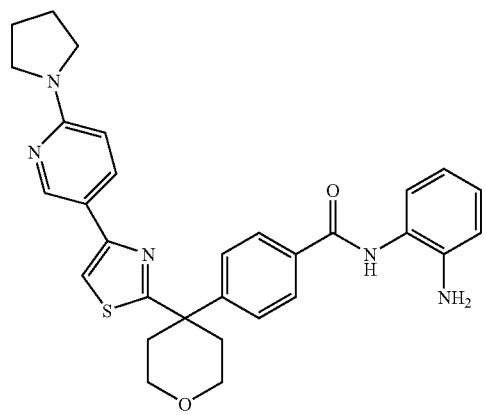

(Compound a″10-09)

Similar procedure from Example 34 was followed to obtain the title compound using pyrrolidine instead of 1-cyclopropyl-piperazine. MS found for $C_{30}H_{31}N_5O_2S$ as $(M+H)^+$ 526.36. $^1H$ NMR (400 MHz, dmso-d$_6$): δ: 9.53 (s, 1H), 8.62 (dd, J=2.4, 2.2 Hz, 1H), 7.93 (dd, J=8.8, 6.4 Hz, 1H), 7.88 (d, J=8.4 Hz, 2H), 7.69 (s, 1H), 7.53 (d, J=8.4 Hz, 2H), 7.07 (dd, J=7.6, 6.8 Hz, 1H), 6.90-6.86 (m, 1H), 6.69 (dd, J=8.0, 6.8 Hz, 1H), 6.53-6.49 (m, 1H), 6.43 (d, J=8.0 Hz, 1H), 4.81 (s, 2H), 3.72-3.68 (m, 2H), 3.62-3.57 (m, 2H), 3.37-3.33 (m, 4H), 2.60-2.59 (m, 2H), 2.39-2.33 (m, 2H), 1.90-1.87 (m, 4H).

Example 21

N-(2-amino-5-(thiophen-2-yl)phenyl)-4-(4-(5-methyl-4,5,6,7-tetrahydrothiazolo[5,4-c]pyridin-2-yl)tetrahydropyran-4-yl)benzamide (Compound a″0-61)

Example 21

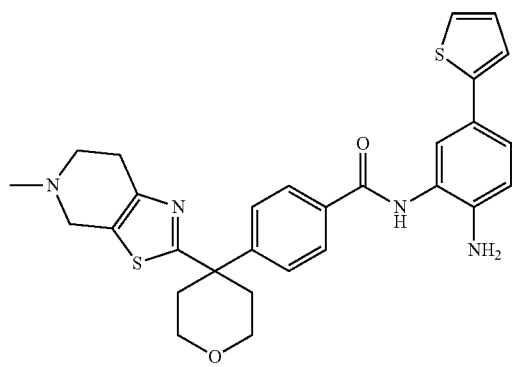

Similar procedure from Example 29 was followed to obtain the title compound using (2-amino-4-thiophen-2-yl-phenyl)- carbamic acid tert-butyl ester De-protection was carried out with a mixture of dichloromethane/trifluoroacetic acid (DCM/TFA) (1:1) at room temperature. MS found for $C_{29}H_{30}N_4O_2S_2$ as $(M+H)^+$ 531.02. $^1H$ NMR (400 MHz, dmso-$d_6$): δ: 9.63 (s, 1H), 7.90 (d, J=8.4 Hz, 2H), 7.49 (d, J=8.4 Hz, 2H), 7.39 (d, J=2.0 Hz, 1H), 7.28 (dd, J=4.8, 4.0 Hz, 1H), 7.23 (dd, J=8.0, 4.8 Hz, 1H), 7.16-7.15 (m, 1H), 6.99-6.96 (m, 1H), 6.73 (d, J=8.4 Hz, 1H), 5.09 (s, 2H), 3.82-3.52 (m, 6H), 2.98-2.96 (m, 2H), 2.85-2.81 (m, 2H), 2.42 (s, 3H), 2.51-2.34 (m, 4H).

Example 22

N-(2-amino-5-(thiophen-2-yl)phenyl)-4-(4-(4-(pyridin-3-yl)thiazol-2-yl)tetrahydropyran-4-yl)benzamide (Compound a″10-04)

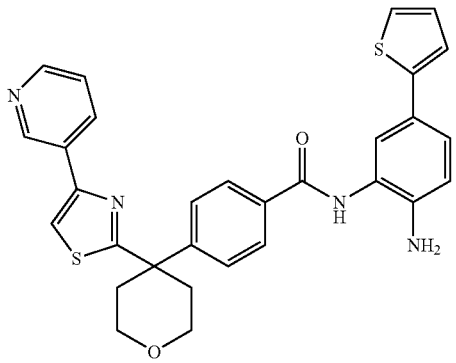

Example 22

1-Pyridin-3-yl-ethanone (2 g, 16.52 mmol) was dissolved in a mixture of AcOH (8 mL) and HBr (4 mL). After stirring for 20 minutes, $Br_2$ (1.0 eq) in $CHCl_3$ (3 mL) was added in a period of 5 minutes. When the reaction was completed, the solids were filtered out and washed with water and extracted with EtOAc. The organic phase was dried, evaporated, and used for next step. Compound 4-(4-thiocarbamoyl-tetrahydro-pyran-4-yl)-benzoic acid methyl ester (300 mg, 1.075 mmol) was dissolved in MeOH (7 mL) and 2-Bromo-1-pyridin-3-yl-ethanone (1.2 eq) was added and refluxed at 85° C. for 30 minutes. The reaction mixture was washed with saturated aqueous solution of $NaHCO_3$ and then extracted with EtOAc. The organic phase was dried, evaporated and used for next step without any purification. Compound 4-[4-(4-pyridin-3-yl-thiazol-2-yl)-tetrahydro-pyran-4-yl]-benzoic acid methyl ester (200 mg, 0.52 mmol) was dissolved in MeOH and 1N NaOH was added. After reaction was complete, the mixture was evaporated and acidified slowly with 1N HCl. The formed solid was filtered out and used for next step without purification. Compound 4-[4-(4-Pyridin-3-yl-thiazol-2-yl)-tetrahydro-pyran-4-yl]-benzoic acid HATU (171 mg, 1.1 eq), (2-amino-4-thiophen-2-yl-phenyl)-carbamic acid tert-butyl ester (136 mg, 1.1 eq), and DIPEA (0.14 mL, 2.0 eq) were dissolved in DMF and heated at 50° C. overnight. The reaction mixture was washed with water and extracted with EtOAc. The organic phase was dried, evaporated, and re-dissolved in a mixture of DCM and TFA (1:1). After stirring for 1 hour at room temperature the mixture was evaporated and purified by reverse phase chromatography to give Example 22. MS found for $C_{30}H_{26}N_4O_2S_2$ as $(M+H)^+$ 539.12. $^1H$ NMR (400 MHz, dmso-$d_6$): δ: 9.64 (s, 1H), 9.12 (d, J=1.6 Hz, 1H), 8.49 (dd, J=4.8, 3.2 Hz, 1H), 8.26-8.23 (m, 1H), 8.17 (s, 1H), 7.92 (d, J=8.4 Hz, 2H), 7.57 (d, J=8.8 Hz, 2H), 7.43-7.28 (m, 2H), 7.27 (t, J=4.4 Hz, 1H), 7.22 (dd, J=8.4, 6.1 Hz, 1H), 7.16-7.15 (m, 1H), 6.97 (dd, J=5.2, 1.6 Hz, 1H), 6.72 (d, J=8.4 Hz, 1H), 5.09 (s, 2H), 3.73-3.70 (m, 2H), 3.63-3.58 (m, 2H), 2.67-2.64 (m, 2H), 2.42-2.36 (m, 2H).

Example 23

N-(2-amino-5-fluorophenyl)-4-(4-(4-(pyridin-3-yl)thiazol-2-yl)tetrahydropyran-4-yl)benzamide (Compound a″10-03)

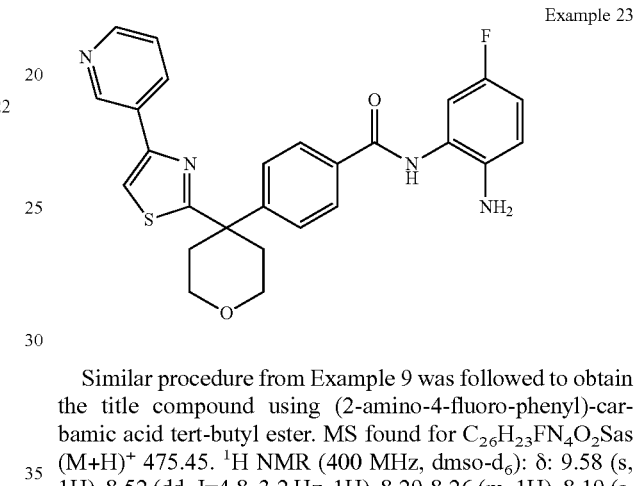

Example 23

Similar procedure from Example 9 was followed to obtain the title compound using (2-amino-4-fluoro-phenyl)-carbamic acid tert-butyl ester. MS found for $C_{26}H_{23}FN_4O_2S$ as $(M+H)^+$ 475.45. $^1H$ NMR (400 MHz, dmso-$d_6$): δ: 9.58 (s, 1H), 8.52 (dd, J=4.8, 3.2 Hz, 1H), 8.29-8.26 (m, 1H), 8.19 (s, 1H), 8.13 (s, 1H), 7.91 (d, J=8.4 Hz, 2H), 7.60 (d, J=8.8 Hz, 2H), 7.45 (dd, J=4.4, 2.8 Hz, 1H), 7.11 (dd, J=8.4, 7.6 Hz, 1H), 6.82-6.72 (m, 2H), 4.78 (s, 2H) 3.76-3.73 (m, 2H), 3.66-3.61 (m, 2H), 2.70-2.63 (m, 2H), 2.43-2.40 (m, 2H).

Example 24

N-(2-aminophenyl)-4-(4-(4-(6-(2-methoxyethoxy)pyridin-3-yl)thiazol-2-yl)tetrahydropyran-4-yl)benzamide (Compound a″10-11)

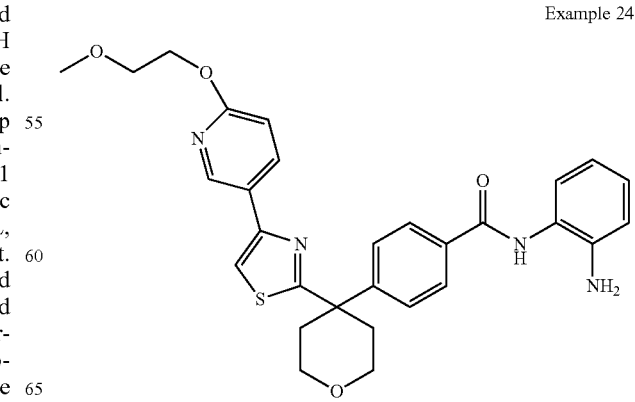

Example 24

Similar procedure from Example 34 was followed to obtain the title compound using 2-methoxy-ethanol instead of 1-cyclopropyl-piperazine. MS found for $C_{29}H_{30}N_4O_4S$ as $(M+H)^+$ 531.08. $^1H$ NMR (400 MHz, dmso-$d_6$): δ: 9.58 (s, 1H), 8.72 (d, J=2.0 Hz, 1H), 8.20 (dd, J=8.4, 6.0 Hz, 1H), 7.98 (s, 1H), 7.92 (d, J=8.4 Hz, 2H), 7.57 (d, J=8.4 Hz, 2H), 7.11 (d, J=7.2 Hz, 1H), 6.95-6.87 (m, 2H), 6.73 (d, J=7.6 Hz, 1H), 6.56 (t, J=7.2 Hz, 1H), 4.39-4.36 (m, 2H), 3.75-3.72 (m, 2H), 3.65-3.60 (m, 4H), 2.27 (s, 3H), 2.69-2.65 (m, 2H), 2.43-2.38 (m, 2H).

Example 25

N-(2-aminophenyl)-4-(4-(4-(6-(4-methylpiperazin-1-yl)pyridin-3-yl)thiazol-2-yl)tetrahydropyran-4-yl) benzamide (Compound a″10-15)

Example 25

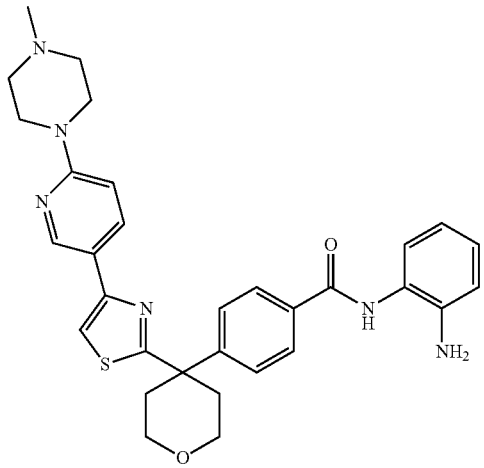

Similar procedure from Example 34 was followed to obtain the title compound using 1-methyl-piperazine instead of 1-cyclopropyl-piperazine. MS found for $C_{31}H_{34}N_6O_2S$ as $(M+H)^+$ 555.23. $^1H$ NMR (400 MHz, dmso-$d_6$): δ: 9.53 (s, 1H), 8.66 (d, J=2.0 Hz, 1H), 7.89 (dd, J=8.4, 7.2 Hz, 1H), 7.88 (d, J=8.0 Hz, 1H), 7.78 (s, 1H), 7.53 (d, J=8.4 Hz, 2H), 7.07 (t, J=8.0 Hz, 1H), 6.90-6.83 (m, 2H), 6.71 (d, J=8.0 Hz, 1H), 6.51 (t, J=7.6 Hz, 1H), 3.71-3.49 (m, 12H), 2.63-2.60 (m, 2H), 2.39-2.34 (m, 2H), 2.22 (s, 3H).

Example 26

N-(2-aminophenyl)-4-(4-(6,7-dihydropyrano[4,3-d] thiazol-2-yl)tetrahydropyran-4-yl)benzamide (Compound a″0-63)

Example 26

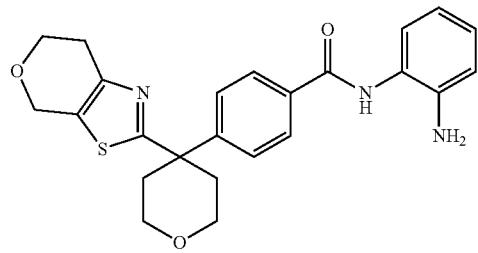

Tetrahydro-pyran-4-one (100 mg, 1.0 mmol), triethylamine (TEA) (0.139 mL, 1.0 eq), and trimethylchlorosilane (TMSCl) (0.127 mL, 1.0 eq) were mixed together in DMF and heated at 80° C. for 2 hours. After the reaction was done, the mixture was evaporated and re-dissolved in THF NaOAc (16.3 mg) and N-bromosuccinimide (NBS) (177 mg, 1.0 eq) was added at −78° C. and stirred for 1 hour. When the reaction was done the mixture was extracted with EtOAc and the organic phase was dried and evaporated to give 3-bromo-tetrahydro-pyran-4-one that was used for next step without further purification. Following similar procedure for cyclization, hydrolysis and HATU coupling from Example 9 gave the title compound. MS found for $C_{24}H_{25}N_3O_3S$ as $(M+H)^+$ 436.23. $^1H$ NMR (400 MHz, dmso-$d_6$): δ: 9.53 (s, 1H), 7.86 (d, J=8.4 Hz, 2H), 7.47 (d, J=8.4 Hz, 2H), 7.08 (d, J=7.2 Hz, 1H), 6.91-6.87 (m, 1H), 6.69 (dd, J=8.0, 6.8 Hz, 1H), 6.50 (t, J=6.4 Hz, 1H), 4.81 (s, 2H), 4.62 (s, 2H), 3.85-3.82 (m, 2H), 3.68-3.52 (m, 4H), 2.73-2.70 (m, 2H), 2.54-2.18 (m, 4H).

Example 27

4-(4-(5-acetyl-4,5,6,7-tetrahydrothiazolo[5,4-c]pyridin-2-yl)tetrahydropyran-4-yl)-N-(2-aminophenyl) benzamide (Compound a″0-54)

Example 27

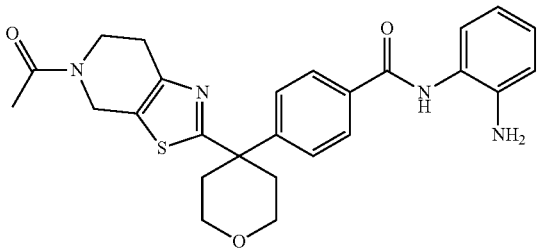

4-[4-(4,5,6,7-tetrahydro-thiazolo[5,4-c]pyridin-2-yl)-tetrahydro-pyran-4-yl]-benzoic acid (40 mg, 0.116 mmol) in pyridine, catalytic amount of 4-dimethylaminopyridine (DMAP), and excess $Ac_2O$ were mixed together at room temperature. After the reaction was complete, the mixture was evaporated, washed with water, and extracted with EtOAc. The organic phase was dried and evaporated to give 4-[4-(5-acetyl-4,5,6,7-tetrahydro-thiazolo[5,4-c]pyridin-2-yl)-tetrahydro-pyran-4-yl]-benzoic acid. Similar HATU coupling procedure from Example 9 was followed to obtain the title compound. MS found for $C_{26}H_{28}N_4O_3S$ as $(M+H)^+$ 477.58. $^1H$ NMR (400 MHz, dmso-$d_6$): δ: 9.53 (s, 1H), 7.89 (d, J=8.4 Hz, 2H), 7.51 (t, J=8.4 Hz, 2H), 7.10 (d, J=7.2 Hz, 1H), 6.92 (t, J=7.6 Hz, 1H), 6.72 (d, J=8.0 Hz, 1H), 6.54 (t, J=7.6 Hz, 1H), 4.84 (s, 2H), 4.61-4.57 (m, 2H), 3.69-3.57 (m, 6H), 2.80-2.29 (m, 6H), 2.05-1.98 (m, 3H).

Example 28

4-(4-(5-acetyl-4,5,6,7-tetrahydrothiazolo[5,4-c]pyridin-2-yl)tetrahydropyran-4-yl)-N-(2-amino-5-(thiophen-2-yl)phenyl)benzamide (Compound a″0-62)

Example 28

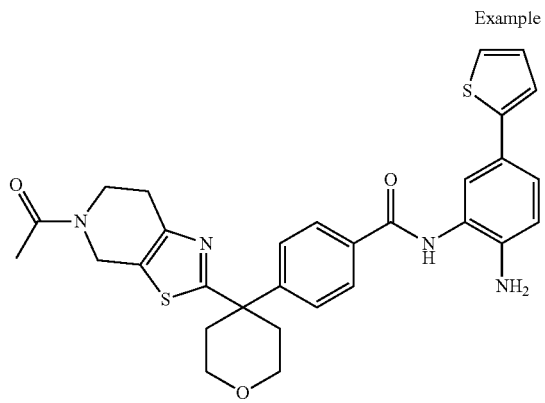

Similar procedure from Example 27 was followed to obtain the title compound using (3-amino-4'-fluoro-biphenyl-4-yl)-carbamic acid tert-butyl ester. MS found for $C_{30}H_{30}N_4O_3S_2$ as $(M+H)^+$ 559.56. $^1H$ NMR (400 MHz, dmso-$d_6$): δ: 9.63 (s, 1H), 7.92 (d, J=8.2 Hz, 2H), 7.52 (t, J=7.2 Hz, 2H), 7.40 (s, 1H), 7.31 (d, J=5.2 Hz, 1H), 7.25 (d, J=8.0 Hz, 1H), 7.19 (d, J=3.6 Hz, 1H), 7.00 (dd, J=5.2, 1.6 Hz, 1H), 6.76 (d, J=8.4 Hz, 1H), 5.10 (s, 2H), 4.62-4.58 (m, 2H), 3.71-3.55 (m, 6H), 2.85-2.69 (m, 2H), 2.57-2.33 (m, 4H), 2.06-2.00 (m, 3H).

Example 29

N-(2-aminophenyl)-4-(4-(5-methyl-4,5,6,7-tetrahydrothiazolo[5,4-c]pyridin-2-yl)tetrahydropyran-4-yl)benzamide (Compound a″0-50)

Example 29

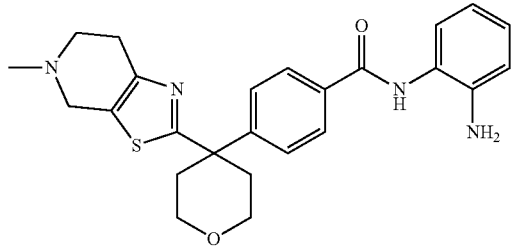

A methanolic solution of 4-(4-thiocarbamoyl-tetrahydro-pyran-4-yl)-benzoic acid methyl ester (500 mg, 1.87 mmol) and 3-bromo-4-oxo-piperidine-1-carboxylic acid ethyl ester (1.0 gr, 2.0 eq) was added and heated in the microwave at 75° C. for 30 minutes. The reaction mixture was evaporated, washed with water, and extracted with EtOAc. The organic phase was dried and evaporated to be used for next step without further purification.

2-[4-(4-methoxycarbonyl-phenyl)-tetrahydro-pyran-4-yl]-6,7-dihydro-4H-thiazolo[5,4-c]pyridine-5-carboxylic acid ethyl ester was dissolved in MeOH and 4N NaOH was added. The mixture was stirred at 50° C. for 24 hours. After hydrolysis was complete the solution was evaporated and suspended in water. Aqueous HCl was added slowly to permit the formation of precipitates that were filtered out.

To 1 mL of an aqueous solution of 4-[4-(4,5,6,7-tetrahydro-thiazolo[5,4-c]pyridin-2-yl)-tetrahydro-pyran-4-yl]-benzoic acid (40 mg, 0.116 mmol) p-formaldehyde was added. The mixture was heated at 50° C. and stirred for 20 minutes. This mixture was cooled down at 0° C. and alpha-picoline-borane (15 mg, 1.2 eq) was added, followed by stirring overnight. The mixture was evaporated and purified by reverse phase chromatography. HATU coupling was carried out following the procedure from Example 9 using benzene-1,2-diamine, followed by reverse phase purification gave the title compound. MS found for $C_{25}H_{28}N_4O_2S$ as $(M+H)^+$ 449.10. $^1H$ NMR (400 MHz, dmso-$d_6$): δ: 9.55 (s, 1H), 7.89 (d, J=8.8 Hz, 2H), 7.49 (d, J=8.4 Hz, 2H), 7.10 (d, J=8.0 Hz, 1H), 6.91 (d, J=7.2 Hz, 1H), 6.72 (d, J=6.8 Hz, 1H), 6.54 (t, J=7.2 Hz, 1H), 4.84 (s, 2H), 3.70-3.67 (m, 2H), 3.59-3.54 (m, 2H), 3.46 (s, 2H), 2.71-2.62 (m, 4H), 2.55-2.52 (m, 2H), 2.34-2.30 (m, 5H).

Example 30

N-(2-amino-5-fluorophenyl)-4-(4-(5-methyl-4,5,6,7-tetrahydrothiazolo[5,4-c]pyridin-2-yl)tetrahydropyran-4-yl)benzamide (Compound a″0-59)

Example 30

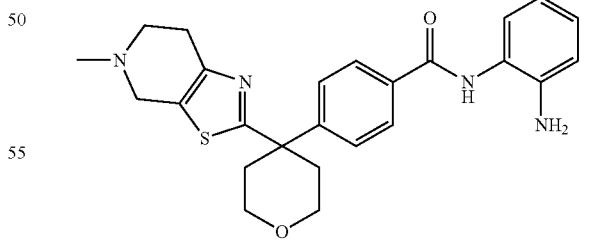

Similar procedure from Example 29 was followed to obtain the title compound using (2-amino-4-fluoro-phenyl)-carbamic acid tert-butyl ester De-protection was carried out with a mixture of DCM/TFA (1:1) at room temperature. MS found for $C_{25}H_{27}FN_4O_2S$ as (M+H)+ 467.23. 1H NMR (400 MHz, dmso-d6): δ: 9.54 (s, 1H), 7.84 (d, J=8.4 Hz, 2H), 7.47 (d, J=8.4 Hz, 2H), 7.08 (dd, J=8.8, 7.6 Hz, 1H), 6.75-6.67 (m, 2H), 4.77 (s, 2H), 3.67-3.64 (m, 2H), 3.56-3.53 (m, 2H), 2.67-2.60 (m, 6H), 2.52-2.29 (m, 4H), 2.27 (s, 3H).

Example 31

N-(2-amino-5-(thiophen-2-yl)phenyl)-4-(4-(4-(pyrrolidin-1-ylmethyl)thiazol-2-yl)tetrahydropyran-4-yl)benzamide (Compound a″0-26)

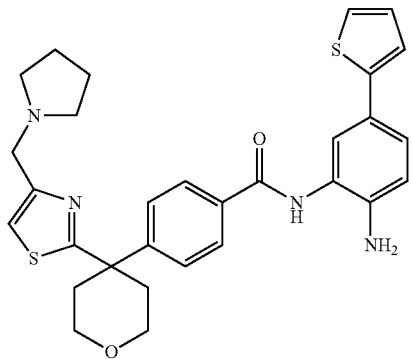

Example 31

Similar procedure from Example 32 was followed to obtain the title compound using pyrrolidine instead of 2-methoxyethanol. MS found for $C_{30}H_{32}N_4O_2S_2$ as $(M+H)^+$ 545.32. $^1$H NMR (400 MHz, dmso-d$_6$): δ: 9.64 (s, 1H), 7.93 (d, J=8.4 Hz, 2H), 7.51 (d, J=8.6 Hz, 2H), 7.41 (s, 1H) 7.35-7.31 (m, 2H), 7.26 (dd, J=8.2-5.4 Hz, 1H), 7.20 (d, J=3.2 Hz, 1H), 7.05-7.00 (m, 1H), 6.77 (d, J=8.0 Hz, 1H), 5.11 (s, 2H), 3.76-3.70 (m, 2H), 3.63 (s, 2H), 3.61-3.52 (m, 2H), 2.62-2.53 (m, 2H), 2.41-2.31 (m, 2H), 1.69-1.61 (m, 4H).

Example 32

N-(2-amino-5-(thiophen-2-yl)phenyl)-4-(4-(4-((2-methoxyethoxy)methyl)thiazol-2-yl)tetrahydropyran-4-yl)benzamide (Compound a″0-28)

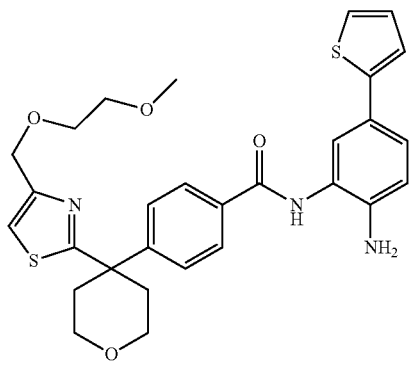

Example 32

To a solution of 4-(4-thiocarbamoyl-tetrahydro-pyran-4-yl)-benzoic acid methyl ester (5.0 gr, 17.92 mmol) in DMF was added acetic acid 3-chloro-2-oxo-propyl ester (6.32 mL, 3.0 eq) and DIPEA (6.24 mL, 2.0 eq). The reaction mixture was heated at 90° C. for 30 minutes in the microwave. Said mixture was then partitioned between ethyl acetate and water. The organic phase was dried with MgSO$_4$ and evaporated under vacuum. The solid was used for next step without purification.

The solid 4-[4-(4-acetoxymethyl-4-hydroxy-4,5-dihydro-thiazol-2-yl)-tetrahydro-pyran-4-yl]-benzoic acid methyl ester was dissolved in MeOH and excess of p-TsOH was added and heated in the microwave for 20 minutes at 65° C. The reaction mixture was washed with saturated of NaHCO$_3$ and extracted with EtOAc. The organic phase was dried with MgSO$_4$ and evaporated under vacuum.

Compound 4-[4-(4-hydroxymethyl-thiazol-2-yl)-tetrahydro-pyran-4-yl]-benzoic acid methyl ester (2.0 gr, 6.00 mmol) was dissolved in DCM and then MsCl (1.67 mL 3.5 eq) and TEA (1.80 mL, 2.0 eq) were added at 0° C. and stirred for 2 hours. When the reaction was complete, 1N aqueous HCl was added to the reaction mixture. The organic phase was separated and dried over MgSO$_4$ and evaporated under vacuum conditions to have the solid 4-[4-(4-methanesulfonyloxymethyl-thiazol-2-yl)-tetrahydro-pyran-4-yl]-benzoic acid methyl ester that was used for next step without further purification.

Compound 4-[4-(4-methanesulfonyloxymethyl-thiazol-2-yl)-tetrahydro-pyran-4-yl]-benzoic acid methyl ester (50 mg, 0.121 mmol) was dissolved in excess 2-methoxy-ethanol (1 mL), and potassium tert-butoxide (13 mg, 1.0 eq) was added to the solution. The mixture was heated at 90° C. for 30 minutes in the microwave. The reaction mixture was evaporated extracted with EtOAc. The organic phase was dried over MgSO$_4$ and evaporated to give a solid that was used for next step without further purification. Hydrolysis and HATU coupling was carried out following the same procedures from Example 64. MS found for $C_{29}H_{31}N_3O_4S_2$ as $(M+H)^+$ 550.09. $^1$H NMR (400 MHz, dmso-d$_6$): δ: 9.64 (s, 1H), 7.93 (d, J=8.4 Hz, 2H), 7.53 (d, J=8.4 Hz, 2H), 7.48 (s, 1H) 7.42 (s, 1H), 7.31 (d, J=5.2 Hz, 1H), 7.25 (dd, J=8.0-6.2 Hz, 1H), 7.20 (d, J=3.2 Hz, 1H), 7.05-7.00 (m, 1H), 6.73 (d, J=8.0 Hz, 1H), 5.12 (s, 2H) 3.73-3.68 (m, 2H), 3.61-3.51 (m, 6H), 3.46-3.40 (m, 2H), 2.21 (s, 3H) 2.62-2.53 (m, 2H), 2.42-2.32 (m, 2H).

Example 33

N-(2-amino-5-(thiophen-2-yl)phenyl)-4-(4-(4-(morpholinomethyl)thiazol-2-yl)tetrahydropyran-4-yl)benzamide (Compound a″0-30)

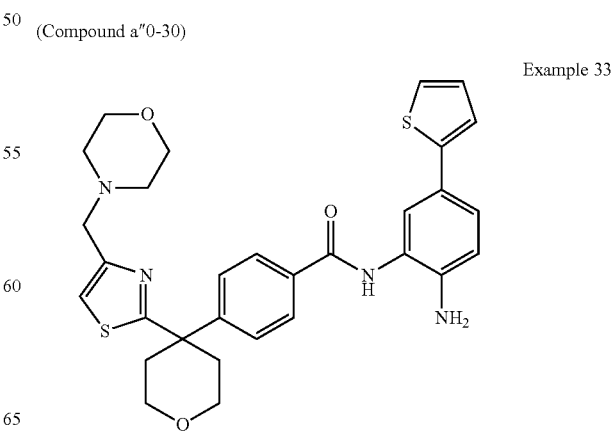

Example 33

Similar procedure from Example 32 was followed to obtain the title compound using morpholine instead of 2-methoxyethanol. MS found for $C_{30}H_{32}N_4O_3S_2$ as $(M+H)^+$ 561.20. $^1$H NMR (400 MHz, dmso-$d_6$): δ: 9.65 (s, 1H), 7.92 (d, J=8.2 Hz, 2H), 7.51 (d, J=8.4 Hz, 2H), 7.41 (s, 1H) 7.32 (d, J=5.4 Hz, 1H), 7.25 (dd, J=8.6, 6.1 Hz, 1H), 7.19 (d, J=3.2 Hz, 1H), 7.01 (t, J=5.4 Hz, 1H), 6.78 (d, J=8.0 Hz, 1H), 5.1 (s, 2H), 3.74-3.70 (m, 2H), 3.61-3.52 (m, 6H), 2.65-2.54 (m, 2H), 2.45-2.30 (m, 6H).

Example 34

N-(2-aminophenyl)-4-(4-(4-(6-(4-cyclopropylpiperazin-1-yl)pyridin-3-yl)thiazol-2-yl)tetrahydropyran-4-yl)benzamide (Compound a″10-17)

Example 34

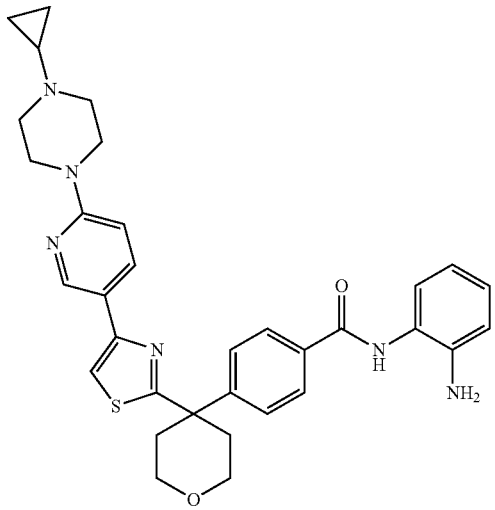

4-(4-thiocarbamoyl-tetrahydro-pyran-4-yl)-benzoic acid methyl ester (700 mg, 2.50 mmol), in MeOH was combined with 2-Bromo-1-(6-chloro-pyridin-3-yl)-ethanone (800 mg, 1.1 eq) and heated at 65° C. for 2 hours. After reaction was complete, the reaction mixture was evaporated, diluted with EtOAc, and washed with a saturated aqueous NaHCO$_3$ and brine. The organic phase was dried over MgSO$_4$ and evaporated.

4-{4-[4-(6-chloro-pyridin-3-yl)-thiazol-2-yl]-tetrahydro-pyran-4-yl}-benzoic acid methyl ester was dissolved in MeOH and 1N NaOH was added. After the reaction was done, the reaction mixture was evaporated, suspended in water, and neutralized with 1N HCl. The formed solids were collected by filtration. The solids were then suspended in acetonitrile and filtered to have a clean product 4-{4-[4-(6-chloro-pyridin-3-yl)-thiazol-2-yl]-tetrahydro-pyran-4-yl}-benzoic acid. Compound 4-{4-[4-(6-chloro-pyridin-3-yl)-thiazol-2-yl]-tetrahydro-pyran-4-yl}-benzoic acid (150 mg, 0.375 mmol) was dissolved in DMF. Then, 1-cyclopropyl-piperazine (82 mg, 1.1 eq), and DIPEA (0.2 mL, 3.2 eq) were added, and the reaction mixture was heated in the microwave at 90° C. for 30 minutes. After reaction was done, the reaction mixture was extracted with EtOAc. The organic phase was dried with MgSO$_4$ and evaporated to have the solid material 4-(4-{4-[6-(4-cyclopropyl-piperazin-1-yl)-pyridin-3-yl]-thiazol-2-yl}-tetrahydro-pyran-4-yl)-benzoic acid.

4-(4-{4-[6-(4-cyclopropyl-piperazin-1-yl)-pyridin-3-yl]-thiazol-2-yl}-tetrahydro-pyran-4-yl)-benzoic acid (60 mg, 0.122 mmol), benzene-1,2-diamine (26 mg, 2.0 eq), HATU (56 mg, 1.2 eq), and DIPEA (0.042 mL, 2.1 eq) were dissolved in DMF and stirred at room temperature for 2 hours. After the reaction was complete, the reaction mixture was extracted with EtOAc and water. The organic phase was dried with MgSO$_4$ and evaporated. The solid was purified by reverse phase chromatography to afford title compound. MS found for $C_{33}H_{36}N_6O_2S$ as $(M+H)^+$ 581.56. $^1$H NMR (400 MHz, dmso-$d_6$): δ: 9.24 (s, 1H), 8.35 (s, 1H), 7.68 (d, J=6.2 Hz, 1H), 7.60 (d, J=8.2 Hz, 2H), 7.51 (s, 1H), 7.23 (d, J=8.4 Hz, 2H), 6.79 (d, J=7.2 Hz, 1H), 6.62-6.51 (m, 2H), 6.41 (d, J=7.4 Hz, 1H), 6.22 (t, J=5.2 Hz, 1H), 4.51 (s, 2H), 3.45-3.38 (m, 2H), 3.32-3.25 (m, 2H), 3.18-3.11 (m, 4H), 2.38-2.22 (m, 6H), 2.15-2.05 (m, 2H), 1.31-1.23 (m, 1H), 0.12-0.1 (m, 4H).

Example 35

N-(2-aminophenyl)-4-(4-(4-(6-(piperazin-1-yl)pyridin-3-yl)thiazol-2-yl)tetrahydropyran-4-yl)benzamide (Compound a″10-13)

Example 35

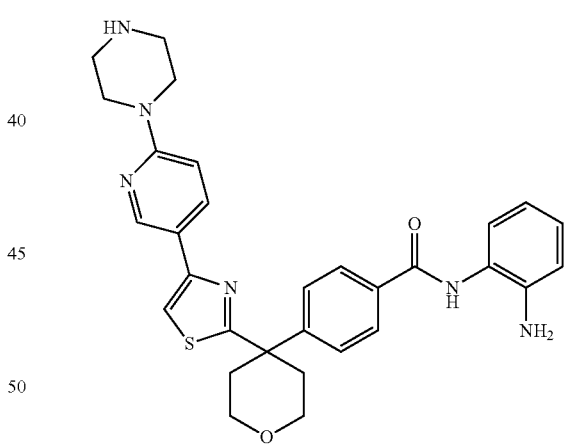

Similar procedure from Example 34 was followed to obtain the title compound using piperazine-1-carboxylic acid tert-butyl ester instead of 1-cyclopropyl-piperazine. An additional step was taken here. The amine was de-protected with a 1:1 mixture of TFA and DCM at room temperature and purified by reverse phase chromatography to have N-(2-amino-phenyl)-4-{4-[4-(6-piperazin-1-yl-pyridin-3-yl)-thiazol-2-yl]-tetrahydro-pyran-4-yl}-benzamide. MS found for $C_{30}H_{32}N_6O_2S$ as $(M+H)^+$ 541.16. $^1$H NMR (400 MHz, dmso-$d_6$): δ: 9.54 (s, 1H), 8.67 (d, J=2.0 Hz, 1H), 8.00 (dd, J=8.8, 2.4 Hz, 1H), 7.88 (d, J=8.4 Hz, 2H), 7.79 (s, 1H), 7.53

(d, J=8.8 Hz, 2H), 7.07 (d, J=8.0 Hz, 1H), 6.91-6.84 (m, 2H), 6.69 (d, J=6.8 Hz, 1H), 6.51 (t, J=8.4 Hz, 1H), 4.81 (s, 2H), 3.71-3.68 (m, 2H), 3.61-3.57 (m, 2H), 3.52-3.49 (m, 4H), 2.89-2.87 (m, 4H), 2.64-2.60 (m, 2H), 2.42-2.34 (m, 2H).

Example 36

N-(4-amino-4'-fluorobiphenyl-3-yl)-4-(4-(thiazol-2-yl)tetrahydropyran-4-yl)benzamide Example 36 (Compound a″0-11)

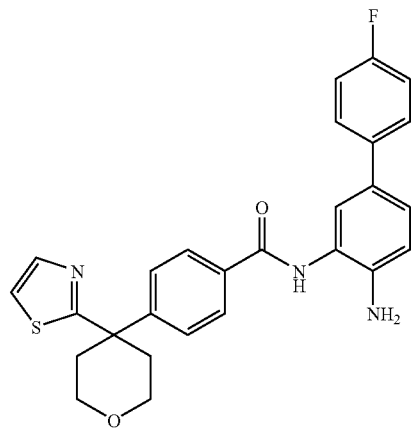

Similar procedure from Example 64 was followed to obtain the title compound using (3-amino-4'-fluoro-biphenyl-4-yl)-carbamic acid tert-butyl ester instead of (2-amino-4-thiophen-2-yl-phenyl)-carbamic acid tert-butyl ester. MS found for $C_{27}H_{24}FN_3O_2S$ as $(M+H)^+$ 474.32. $^1$H NMR (400 MHz, dmso-$d_6$): δ: 9.63 (s, 1H), 7.92 (d, J=8.4 Hz, 2H), 7.74 (d, J=3.2 Hz, 1H), 7.64 (d, J=7.2 Hz, 1H), 7.55-7.50 (m, 6H), 7.45 (s, 1H), 7.26 (dd, J=8.4, 6.4 Hz, 1H), 7.15 (t, J=8.4 Hz, 2H), 6.80 (d, J=8.4 Hz, 1H), 5.06 (s, 2H), 3.71-3.70 (m, 2H), 3.60-3.49 (m, 2H), 2.64-2.60 (m, 2H), 2.42-2.32 (m, 2H).

Example 37

N-(2-amino-5-(thiophen-2-yl)phenyl)-4-(4-(4-ethoxythiazol-2-yl)tetrahydropyran-4-yl)benzamide

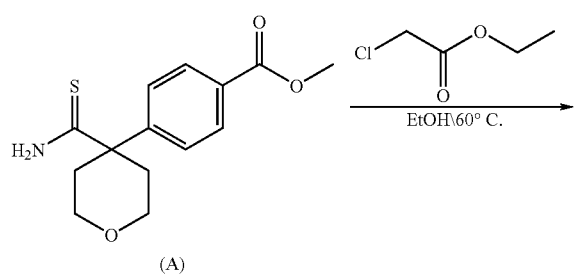

(A)

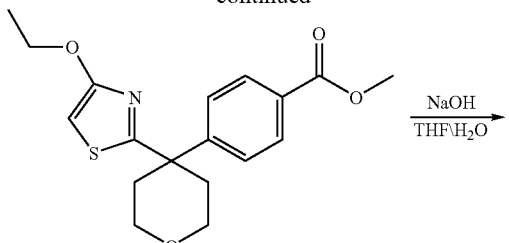

(B)

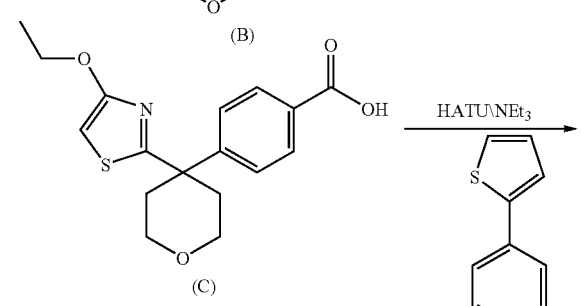

(C)

(D)

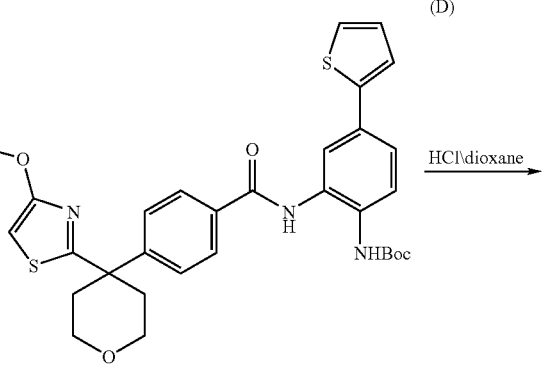

(E)

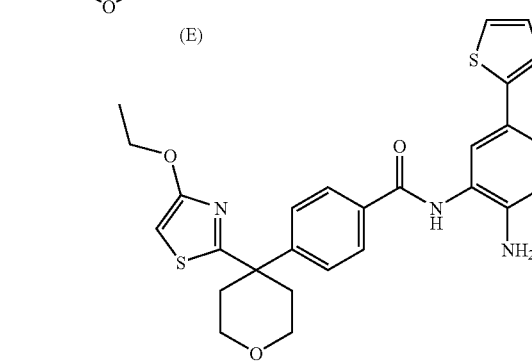

Example 37 (Comopund a″0-33)

Compound A (0.49 g, 1.8 mmol) and ethyl chloroacetate (1.11 mL, 10.4 mmol) were dissolved in EtOH (15 mL). The resulting mixture was heated at 60° C. overnight, concentrated, and purified by silica gel chromatography (1% MeOH/DCM) to afford Compound B (0.35 g, 58%). MS m/z: 348 (MH$^+$). Compound B (0.35 g, 1.0 mmol) was hydrolyzed with 2N aqueous NaOH (5 mL) and THF (2 mL) to afford corresponding acid Compound C (0.30 g, 90%). MS m/z: 334 (MH$^+$). Compound C (0.20 g, 0.6 mmol) was coupled with amine Compound D (0.18 g, 0.6 mmol) in the presence of HATU (0.46 g, 1.2 mmol) and triethylamine (0.25 mL, 1.8 mmol) in DMF (10 mL) to afford crude amide Compound E. MS m/z: 606 (MH$^+$). Crude Compound E was treated with 4N HCl/dioxane, concentrated and purified by preparative HPLC to afford Example 37 (0.041 g, 13% for two steps). MS ($C_{27}H_{27}N_3O_3S_2$) m/z: 506 (MH$^+$). NMR $^1$H NMR (dmso-d$_6$): δ 9.66 (s, 1H), 7.94 (d, J=8.4 Hz, 2H), 7.52 (d, J=8.4 Hz, 2H), 7.42 (s, 1H), 7.31 (d, J=5.2 Hz, 1H), 7.25 (d, J=8.4 Hz, 1H), 7.18 (d, J=2.4 Hz, 1H), 7.02 (t, J=3.2 Hz, 1H), 6.87 (d, J=8.4 Hz, 1H), 6.41 (s, 1H), 5.12 (s, 2H), 4.01 (q, J=7.2 Hz, 2H), 3.68 (m, 2H), 3.58 (m, 2H), 2.53 (m, 2H), 2.31 (m, 2H), 1.28 (t, J=7.2 Hz, 3H).

Example 38

4-(4-(1H-tetrazol-5-yl)tetrahydropyran-4-yl)-N-(2-amino-5-(thiophen-2-yl)phenyl)benzamide Example 38 (Compound g-03)

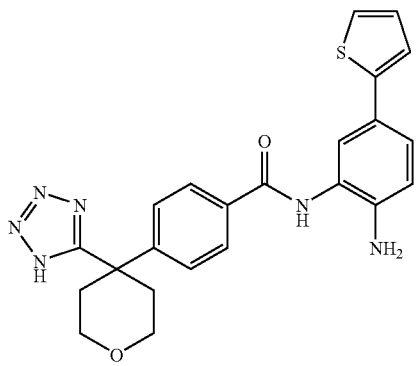

A solution of 4-(4-cyano-tetrahydro-pyran-4-yl)-benzoic acid methyl ester (400 mg, 1.63 mmol), trimethylsilyl azide (TMSN$_3$) (40 mg, 2.1 eq), and Bu$_2$Sn(O) (40 mg, 1.0 eq) in DME was heated in the microwave at 150° C. for 4 hours. After the reaction was done the mixture was washed with water and extracted with EtOAc. The organic phase was dried and evaporated to give 4-[4-(1H-tetrazol-5-yl)-tetrahydro-pyran-4-yl]-benzoic acid methyl ester.

Hydrolysis HATU coupling and amine de-protection were carried out following the same procedures from Example 64. MS found for $C_{23}H_{22}N_6O_2S$ as (M+H)$^+$ 447.56. $^1$H NMR (400 MHz, dmso-d$_6$): δ: 9.64 (s, 1H), 7.92 (d, J=8.4 Hz, 2H), 7.42-7.35 (m, 3H), 7.28 (d, J=5.4 Hz, 1H), 7.22 (dd, J=4.0, 3.6 Hz, 1H), 7.15 (t, J=6.0 Hz, 1H), 6.95 (dd, J=8.4, 6.4 Hz, 1H), 6.73 (d, J=6.4 Hz, 1H), 5.08 (s, 2H), 3.83-3.73 (m, 2H), 3.33-3.25 (m, 2H), 2.66-2.60 (m, 2H), 2.32-2.22 (m, 2H), 1.4 (s, 1H).

Example 39

4-(4-(1H-tetrazol-5-yl)tetrahydropyran-4-yl)-N-(4-amino-4'-fluorobiphenyl-3-yl)benzamide Example 39 (Compound g-02)

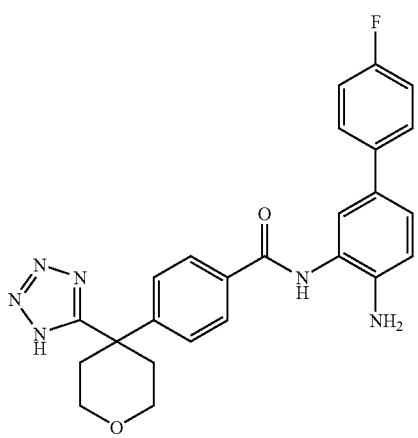

Similar procedure from Example 38 was followed to obtain the title compound using (3-amino-4'-fluoro-biphenyl-4-yl)-carbamic acid tert-butyl ester instead of (2-amino-4-thiophen-2-yl-phenyl)-carbamic acid tert-butyl ester. MS found for $C_{25}H_{23}FN_6O_2$ as (M+H)$^+$ 459.41. $^1$H NMR (400 MHz, dmso-d$_6$): δ: 9.65 (s, 1H), 8.93 (d, J=8.4 Hz, 2H), 7.55-7.50 (m, 2H), 7.45-7.35 (m, 3H), 7.25 (d, J=7.2 Hz, 1H), 7.15 (t, J=8.0 Hz, 2H), 6.81 (d, J=8.4 Hz, 1H), 5.05 (s, 2H), 3.85-3.78 (m, 2H), 3.35-3.28 (m, 2H), 2.70-2.62 (m, 2H), 2.33-2.28 (m, 2H), 2.42 (s, 1H).

Example 40

N-(4-amino-4'-fluorobiphenyl-3-yl)-4-(4-(4-ethoxythiazol-2-yl)tetrahydropyran-4-yl)benzamide

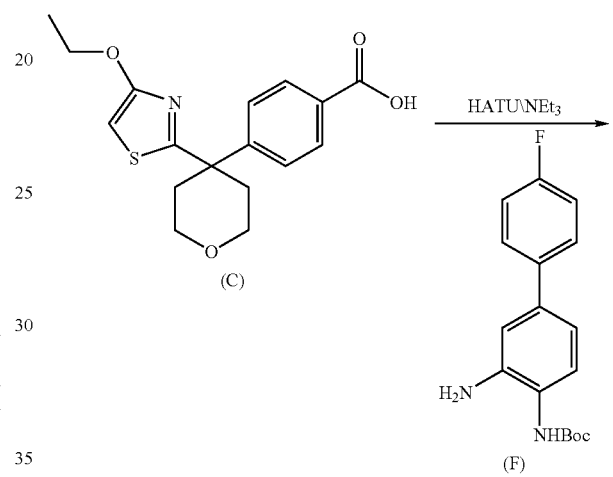

-continued

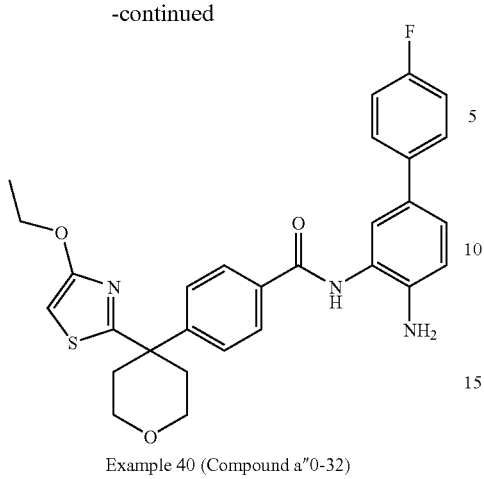

Example 40 (Compound a″0-32)

Compound C (0.10 g, 0.3 mmol) was coupled with amine Compound F (0.092 g, 0.3 mmol) in the presence of HATU (0.23 g, 0.6 mmol), and triethylamine (0.15 mL, 1.1 mmol) in DMF (5 mL) to afford crude amide Compound G. MS m/z: 618 (MH$^+$). Crude Compound G was treated with 4N HCl/dioxane, concentrated and purified by preparative HPLC to afford Example 40. (0.021 g, 14% for two steps). MS ($C_{29}H_{28}FN_3O_3S$) m/z: 518 (MH$^+$). NMR $^1$H NMR (dmso-d6): δ 9.67 (s, 1H), 7.93 (d, J=8.4 Hz, 2H), 7.52 (m, 4H), 7.43 (s, 1H), 7.25 (d, J=8.0 Hz, 1H), 7.17 (t, J=8.8 Hz, 2H), 6.82 (d, J=8.4 Hz, 1H), 6.41 (s, 1H), 5.18 (s, 2H), 4.00 (q, J=7.2 Hz, 2H), 3.68 (m, 2H), 3.55 (m, 2H), 2.50 (m, 2H), 2.32 (m, 2H), 1.28 (t, J=7.2 Hz, 3H).

Example 41

N-(2-aminophenyl)-4-(4-(4-(pyrazin-2-yl)thiazol-2-yl)tetrahydropyran-4-yl)benzamide Example 41 (Compound a″12-01)

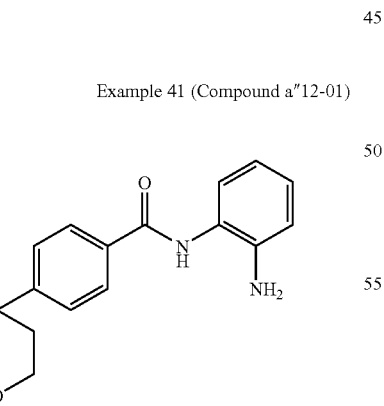

Similar procedure from Example 9 was followed to obtain the title compound using 2-bromo-1-(pyrazin-2-yl)ethanone. MS found for $C_{25}H_{23}N_5O_2S$ as (M+H)$^+$ 458.25. $^1$H NMR (400 MHz, dmso-d$_6$): δ: 9.59 (s, 1H), 9.29 (s, 1H), 8.64 (s, 1H), 8.59 (s, 1H), 8.32 (s, 1H), 7.93 (d, J=8.0 Hz, 2H), 7.60 (d, J=8.2 Hz, 2H), 7.11 (d, J=7.6 Hz, 1H), 6.92 (t, J=6.8 Hz, 1H), 6.73 (d, J=7.6 Hz, 2H), 6.54 (t, J=7.2 Hz, 1H), 4.85 (s, 2H), 3.74-3.62 (m, 4H), 2.72-2.50 (m, 4H).

Example 42

N-hydroxy-4-(4-(4-(pyridin-3-yl)thiazol-2-yl)tetrahydropyran-4-yl)benzamide

Example 42 (Compound a″10-01)

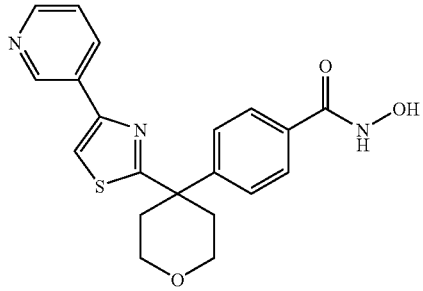

Similar procedure from Example 22 was followed to obtain the title compound using O-(1,1,2,2-tetramethyl-propyl)-hydroxylamine. De-protection of TBS group was done by heating the protected hydroxylamine with 1N HCl for 30 minutes. MS found for $C_{20}H_{19}N_3O_3S$ as (M+H)$^+$ 382.65. $^1$H NMR (400 MHz, dmso-d$_6$): δ: 11.14 (s, 1H), 9.14 (d, J=1.6 Hz, 1H), 8.99 (s, 1H), 8.51 (dd, J=4.8-3.2 Hz, 1H), 8.28-8.19 (m, 1H), 7.69 (d, J=8.4 Hz, 2H), 7.52 (d, J=8.4 Hz, 2H), 7.46-7.43 (m, 1H), 3.75-3.73 (m, 2H), 3.62-3.58 (m, 2H), 2.67-2.64 (m, 2H), 2.40-2.33 (m, 2H).

Example 43

N-hydroxy-4-(4-(thiazol-2-yl)tetrahydropyran-4-yl)benzamide

Example 43 (Compound a″0-09)

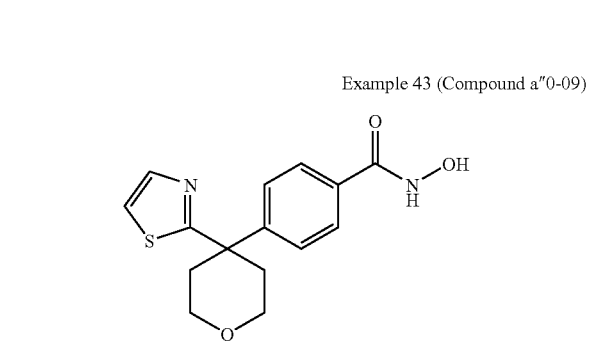

Similar procedure from Example 64 was followed to obtain the title compound using O-(1,1,2,2-tetramethyl-propyl)-hydroxylamine instead of (2-amino-4-thiophen-2-yl-phenyl)-carbamic acid tert-butyl ester. De-protection of TBS group was done by heating the protected hydroxylamine with 1N HCl for 30 minutes. MS found for $C_{15}H_{16}N_2O_3S$ as (M+H)$^+$ 305.12. $^1$H NMR (400 MHz, dmso-d$_6$): δ: 11.08 (s, 1H), 8.94 (s, 1H), 7.68 (d, J=3.2 Hz, 1H), 7.63 (d, J=8.8 Hz, 2H), 7.60

(d, J=3.2 Hz, 1H), 7.39 (d, J=8.4 Hz, 2H), 3.69-3.64 (m, 2H), 3.50-3.45 (m, 2H), 2.56-2.52 (m, 2H), 2.32-2.25 (m, 2H).

Example 44

N-hydroxy-4-(4-(4-(6-(4-methylpiperazin-1-yl)pyridin-3-yl)thiazol-2-yl)tetrahydropyran-4-yl)benzamide Example 44 (Compound a″10-14)

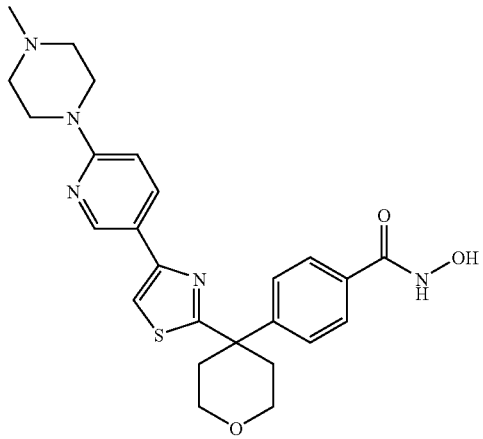

4-(4-{4-[6-(4-methyl-piperazin-1-yl)-pyridin-3-yl]-thiazol-2-yl}-tetrahydro-pyran-4-yl)-benzoic acid (200 mg, 0.215 mmol), HATU (90 mg, 1.1 eq), H$_2$N-OTBS (2.0 eq), and TEA (0.1 mL, 3 eq) were mixed in DMF and stirred for 2 hours. The reaction mixture was washed with water and then extracted with EtOAc. The organic phase was evaporated, suspended in 1N HCl, and slowly evaporated at 50° C. for 30 minutes to give title compound. MS found for C$_{25}$H$_{29}$N$_5$O$_3$S as (M+H)$^+$ 480.15. $^1$H NMR (400 MHz, dmso-d$_6$): δ: 11.13 (s, 1H), 8.99 (s, 1H), 8.68 (d, J=2.4 Hz, 1H), 8.00 (dd, J=8.8, 6.4 Hz, 1H), 7.81 (s, 1H), 7.68 (d, J=8.4 Hz, 2H), 7.50 (d, J=8.4 Hz, 2H), 6.87 (d, J=8.8 Hz, 1H), 3.73-3.70 (m, 2H), 3.61-3.56 (m, 2H), 3.53-3.50 (m, 4H), 2.65-2.60 (m, 2H), 2.44-2.20 (m, 4H), 2.38-2.32 (m, 2H), 2.22 (s, 3H).

Example 45

N-(2-amino-5-(5-chlorothiophen-2-yl)phenyl)-4-(4-(thiazol-2-yl)tetrahydropyran-4-yl)benzamide Example 45 (Compound a″0-14)

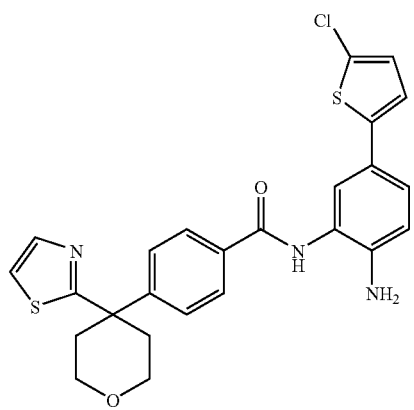

Similar procedure from Example 64 was followed to obtain the title compound using [2-amino-4-(5-chloro-thiophen-2-yl)-phenyl]-carbamic acid tert-butyl ester instead of (2-amino-4-thiophen-2-yl-phenyl)-carbamic acid tert-butyl ester. MS found for C$_{27}$H$_{24}$FN$_3$O$_2$S as (M+H)$^+$ 474.22. $^1$H NMR (400 MHz, dmso-d$_6$): δ: 9.64 (s, 1H), 7.92 (d, J=8.4 Hz, 2H), 7.73 (d, J=3.2 Hz, 1H), 7.65 (d, J=3.2 Hz, 1H), 7.51 (d, J=8.4 Hz, 2H), 7.35 (s, 1H), 7.20 (dd, J=8.4, 6.4 Hz, 1H), 7.06 (d, J=4.0 Hz, 1H), 7.01 (d, J=4.1 Hz, 1H), 6.75 (d, J=8.4 Hz, 1H), 5.21 (s, 2H), 3.73-3.70 (m, 2H), 3.57-3.52 (m, 2H), 2.63-2.59 (m, 2H), 2.40-2.35 (m, 2H).

Example 46

N-(2-amino-5-(5-methylthiophen-2-yl)phenyl)-4-(4-(thiazol-2-yl)tetrahydropyran-4-yl)benzamide Example 46 (Compound a″0-13)

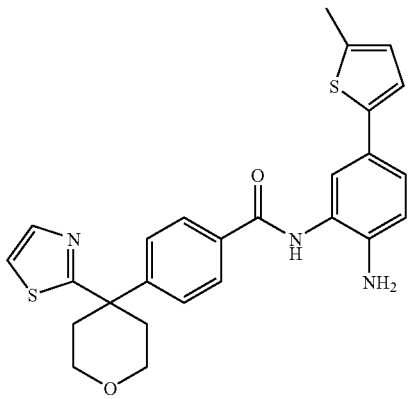

Similar procedure from Example 64 was followed to obtain the title compound using [2-amino-4-(5-methyl-thiophen-2-yl)-phenyl]-carbamic acid tert-butyl ester instead of (2-amino-4-thiophen-2-yl-phenyl)-carbamic acid tert-butyl ester. MS found for C$_{26}$H$_{25}$N$_3$O$_2$S$_2$ as (M+H)$^+$ 476.07. $^1$H NMR (400 MHz, dmso-d$_6$): δ: 9.61 (s, 1H), 7.92 (d, J=8.4 Hz, 2H), 7.72 (d, J=3.4 Hz, 1H), 7.61 (d, J=3.4 Hz, 1H), 7.51 (d, J=8.4 Hz, 2H), 7.32 (s, 1H), 7.18 (d, J=5.4 Hz, 1H), 6.95 (d, J=4.2 Hz, 1H), 6.72 (d, J=8.2 Hz, 1H), 6.68 (s, 1H), 5.06 (s, 2H) 3.74-3.68 (m, 2H), 3.58-3.50 (m, 2H), 2.66-2.56 (m, 2H), 2.38 (s, 3H) 2.42-2.33 (m, 2H).

Example 47

N-(2-aminophenyl)-4-(4-(4-(4-(4-methylpiperazin-1-yl)phenyl)thiazol-2-yl)tetrahydropyran-4-yl)benzamide

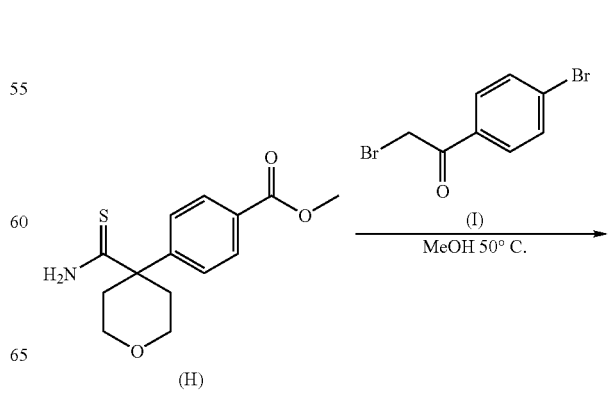

-continued

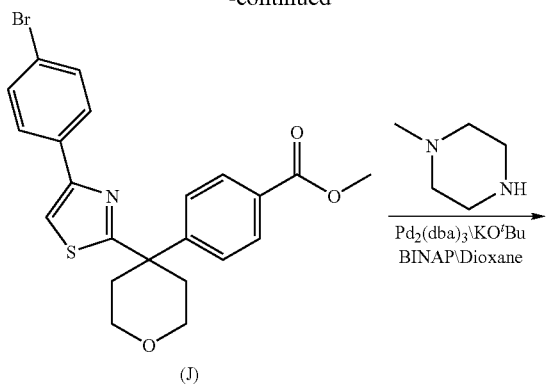

(J)

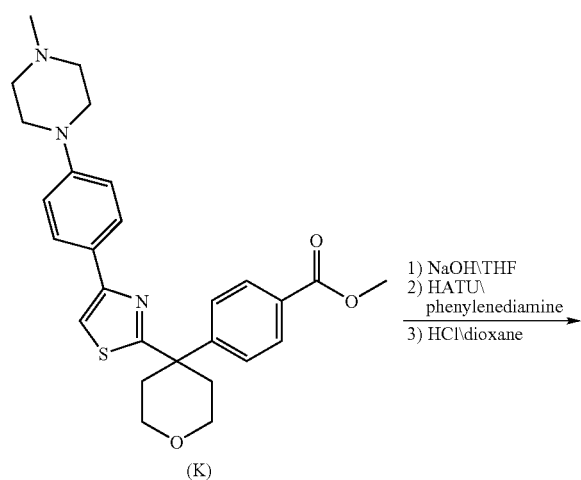

(K)

Example 47 (Compound a″0-34)

Compound H (0.62 g, 2.2 mmol), and Compound I (0.65 g, 2.3 mmol) were dissolved in MeOH (10 mL). The resulting mixture was stirred overnight, concentrated, and purified by preparative HPLC to afford Compound J (0.54 g, 54%). MS m/z: 458, 460 (MH$^+$). A solution of tris(dibenzylideneacetone)dipalladium (0) (Pd$_2$(dba)$_3$, 0.054 g, 0.059 mmol) and 2,2'-bis(diphenylphosphino)-1,1'-binaphthyl (BINAP, 0.11 g, 0.18 mmol) in dioxane (10 mL) under nitrogen atmosphere was stirred for 10 minutes before the addition of Compound J (0.54 g, 1.2 mmol) and N-methylpiperazine (0.27 mL, 2.4 mmol). After the sample was stirred for 10 minutes, the resultant solution was treated with KO$^t$Bu (0.20 g, 1.8 mmol). The mixture was stirred and heated at 80° C. overnight, then cooled down, and treated with EtOAc and filtered. The solution was washed with brine, dried, concentrated and purified by preparative HPLC to afford Compound K (0.18 g, 31%). MS m/z: 478 (MH$^+$). Compound K (0.18 g, 0.4 mmol) was hydrolyzed with 2N aqueous NaOH (5 mL) and THF (2 mL). It was then coupled with phenylenediamine (0.062 g, 0.6 mmol) in the presence of HATU (0.28 g, 0.7 mmol) and TEA (0.16 mL, 1.1 mmol) in DMF (5 mL). The resultant mixture was purified by preparative HPLC to afford title compound (0.018 g, 9%). MS (C$_{32}$H$_{35}$N$_5$O$_2$S) m/z: 555 (MH$^+$). $^1$H NMR (dmso-d6): δ 9.57 (s, 1H), 7.90 (d, J=8.4 Hz, 2H), 7.78 (d, J=8.8 Hz, 2H), 7.75 (s, 1H), 7.55 (d, J=8.4 Hz, 2H), 7.11 (d, J=6.8 Hz, 1H), 6.95 (d, J=8.8 Hz, 2H), 6.91 (t, J=7.2 Hz, 1H), 6.72 (d, J=8.0 Hz, 1H), 6.54 (t, J=8.4 Hz, 1H), 4.85 (s, 2H), 3.74 (m, 2H), 3.64 (m, 2H), 3.28 (m, 4H), 3.17 (m, 4H), 2.65 (m, 2H), 2.40 (m, 2H), 2.23 (s, 3H).

Example 48

N-(4-amino-4'-fluorobiphenyl-3-yl)-4-(1-(thiazol-2-yl)cyclopropyl)benzamide

Example 48 (Compound a0-79)

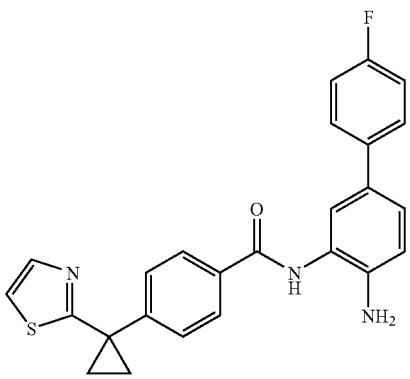

Similar procedure from Example 64 was followed to obtain the title compound using 4-(1-cyano-cyclopropyl)-benzoic acid methyl ester instead of 4-(4-cyano-tetrahydro-pyran-4-yl)-benzoic acid methyl ester. MS found for C$_{25}$H$_{20}$FN$_3$OS as (M+H)$^+$ 430.21. $^1$H NMR (400 MHz, dmso-d$_6$): δ: 9.73 (s, 1H), 7.99 (d, J=8.4 Hz, 2H), 7.64 (d, J=3.2 Hz, 1H), 7.57-7.52 (m, 4H), 7.47-7.44 (m, 2H), 7.26 (dd, J=8.0-6.0 Hz, 1H), 7.18 (t, J=8.8 Hz, 2H), 6.83 (d, J=8.4 Hz, 1H), 5.08 (s, 2H), 1.65-1.62 (m, 2H), 1.46-1.43 (m, 2H).

Example 49

N-(2-amino-5-(thiophen-2-yl)phenyl)-4-(4-(2,3-dihydropyridin-2-yl)tetrahydropyran-4-yl)benzamide Example 49 (Compound f-03)

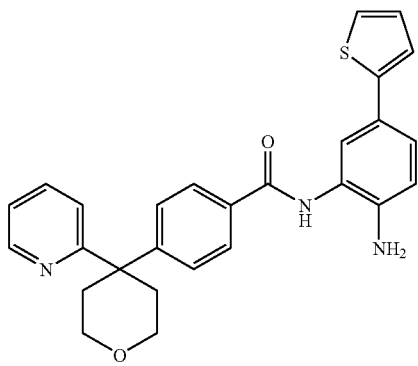

To 4-(4-cyano-tetrahydro-pyran-4-yl)-benzoic acid methyl ester (200 mg, 0.81 mmol) in toluene was added ethynyl-trimethyl-silane (800 mg, 10 eq) and CpCo(CO)$_2$ (0.2 eq). The mixture was irradiated with light of 400 nm under stirring conditions for 2 days. Toluene was removed by evaporation. The solids were washed with water and the compound was extracted with EtOAc. The organic phase was dried and evaporated. 4-[4-(4,6-bis-trimethylsilanyl-pyridin-2-yl)-tetrahydro-pyran-4-yl]-benzoic acid methyl ester was dissolved in THF and TBAF was added in excess. The reaction mixture was stirred overnight at room temperature. After the reaction was done, it was extracted with EtOAc. The organic phase was evaporated to be used for next step. Hydrolysis, HATU coupling, and amine de-protection were carried out following the same procedures from Example 64 using (2-amino-4-thiophen-2-yl-phenyl)-carbamic acid tert-butyl ester instead of (3-amino-4'-fluoro-biphenyl-4-yl)-carbamic acid tert-butyl ester. MS found for $C_{27}H_{25}N_3O_2S$ as (M+H)$^+$ 456.26. $^1$H NMR (400 MHz, dmso-d$_6$): δ: 9.59 (s, 1H), 8.51 (t, J=4.8 Hz, 1H), 7.87 (d, J=8.4 Hz, 2H), 7.70-7.66 (m, 1H), 7.47 (d, J=8.8 Hz, 2H), 7.39 (d, J=8.8 Hz, 2H), 7.30 (t, J=4.0 Hz, 1H), 7.24 (dd, J=8.4, 6.0 Hz, 1H), 7.18-7.14 (m, 2H), 7.01-6.99 (m, 1H), 6.75 (d, J=8.4 Hz, 1H), 5.09 (s, 2H), 3.64-3.67 (m, 2H), 3.58-3.46 (m, 2H), 2.72-2.69 (m, 2H), 2.34-2.29 (m, 2H).

Example 50

N-(2-amino-5-(thiophen-2-yl)phenyl)-4-(1-(thiazol-2-yl)cyclopropyl)benzamide

Example 50 (Compound a0-80)

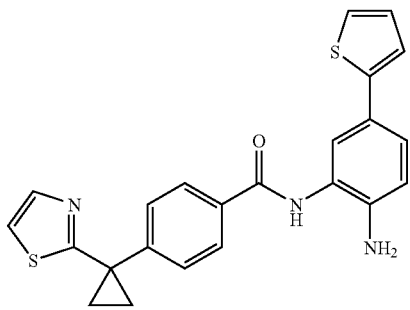

Similar procedure from Example 64 was followed to obtain the title compound using 4-(1-cyano-cyclopropyl)-benzoic acid methyl ester instead of 4-(4-cyano-tetrahydro-pyran-4-yl)-benzoic acid methyl ester. MS found for $C_{23}H_{19}N_3OS_2$ as (M+H)$^+$ 418.20. $^1$H NMR (400 MHz, dmso-d$_6$): δ: 9.73 (s, 1H), 7.99 (d, J=8.4 Hz, 2H), 7.64 (d, J=3.2 Hz, 1H), 7.56 (d, J=8.4 Hz, 2H), 7.45-7.35 (m, 2H), 7.22 (dd, J=5.2, 4.4 Hz, 1H), 7.21 (d, J=2.8 Hz, 1H), 6.78 (d, J=8.4 Hz, 1H), 5.13 (s, 2H), 1.65-1.62 (m, 2H), 1.46-1.43 (m, 2H).

Example 51

N-(2-amino-5-(thiophen-2-yl)phenyl)-4-(4-(5-(pyridin-3-yl)thiazol-2-yl)tetrahydropyran-4-yl)benzamide Example 51 (Compound a″0-40)

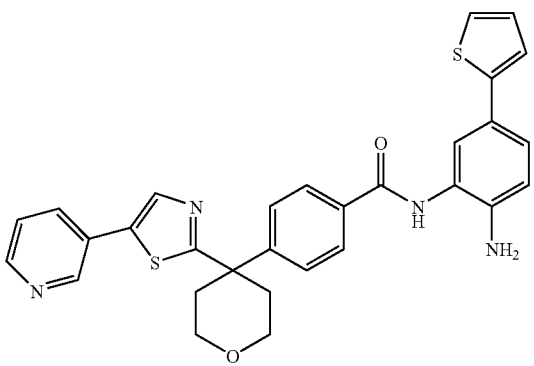

To the mixture of methyl 4-(4-(thiazol-2-yl)-tetrahydro-2H-pyran-4-yl)benzoate (570 mg, 1.88 mmol) in DMF (5 mL) was added a 1M solution of bromine in DMF (1.9 mL, 1.88 mmol). After 2 hours, additional 1M solution of bromine in DMF (1.9 mL, 1.88 mmol) was added. The reaction mixture was then concentrated to half its volume and poured into water (25 mL). The resulting solid was filtered and washed with water and dried to give methyl 4-(4-(5-bromothiazol-2-yl)-tetrahydro-2H-pyran-4-yl)benzoate. $^1$H NMR (400 MHz, dmso-d$_6$): δ 7.99 (d, J=8.0 Hz, 2H); 7.58 (s, 1H); 7.41 (d, J=8.0 Hz, 2H); 3.87 (s, 3H); 3.91-3.84 (m, 2H); 3.73-3.68 (m, 2H); 2.63-2.59 (m, 2H); 2.41-2.37 (m, 2H); MS found for $C_{16}H_{16}BrNO_3S$ (m/z): 3840.3 [M$^+$+1].

A mixture pyridin-3-ylboronic acid (128 mg, 1.05 mmol), methyl 4-(4-(5-bromothiazol-2-yl)-tetrahydro-2H-pyran-4-yl)benzoate (200 mg, 0.52 mmol), potassium carbonate (144 mg, 1.05 mmol), and PdCl$_2$(dppf) (76 mg, 0.11 mmol) in toluene/ethanol/water (2 mL/1 mL/1 mL) was heated in microwave (Emry's Optimizer) at 100° C. for 20 minutes. The reaction mixture was then poured into EtOAc/hexanes mixture and the resultant solid was filtered and dried. The dried solid was used for next step without purification. MS found for $C_{21}H_{20}N_2O_3S$ (m/z): 381.20 [M$^+$+1]. To the above crude ester in methanol (5 mL) and THF (2 mL), NaOH (1.0 M, 5.0 mL) was added and stirred at room temperature for 16 hours. The reaction mixture was then diluted with water and acidified with 1N HCl to about pH 7. The aqueous solution was then concentrated and diluted with methanol. The solids were filtered. The filtrate was then concentrated and used for next step. MS found for $C_{20}H_{18}N_2O_3S$ (m/z): 367.39 [M$^+$+1]. To the above crude carboxylic acid in NMP (3 mL), was added HATU (300 mg, 0.76 mmol), tert-butyl 2-amino-4-(thiophen-2-yl)phenylcarbamate (303 mg, 1.05 mmol) and N-methylmorpholine (NMM) (0.3 mL, 2.62 mmol) and stirred at 50° C. for 16 hours. The reaction mixture was then diluted with water and acetonitrile/methanol and the resulting solid was filtered and washed with water and dried to give tert-butyl 2-(4-(4-(5-(pyridin-3-yl)thiazol-2-yl)-tetrahydro-2H-pyran-4-yl)benzamido)-4-(thiophen-2-yl)phenylcarbamate. MS found for $C_{35}H_{34}N_4O_4S_2$ as (M+H)⁺ 639.17. To the above butoxycarbonyl (Boc) protected compound was added 4.0 M HCl dioxane (6.0 mL) and stirred at room temperature for 1 hour. The reaction mixture was then concentrated and diluted with water and acetonitrile and directly purified by preparative HPLC followed by lyophilization to give the title compound. MS found for $C_{30}H_{26}N_4O_2S_2$ as (M+H)⁺ 538.91. ¹H NMR (400 MHz, dmso-d₆): δ 9.68 (s, 1H); 8.82 (s, 1H); 8.50 (d, J=3.6 Hz, 1H); 8.25 (s, 1H); 7.99-7.95 (m, 3H); 7.59 (d, J=8.8 Hz, 2H) 7.41-7.39 (m, 2H); 7.32-7.19 (m, 4H); 7.02-7.00 (m, 1H); 6.77 (d, J=8.4 Hz, 1H); 5.12 (brs, 2H); 3.76-3.73 (m, 2H); 3.65-3.60 (m, 2H); 2.66-2.63 (m, 2H); 2.41-2.39 (m, 2H).

Example 52

N-(2-amino-5-(5-methylthiophen-2-yl)phenyl)-4-(1-(thiazol-2-yl)cyclopropyl)benzamide Example 52 (Compound a0-81)

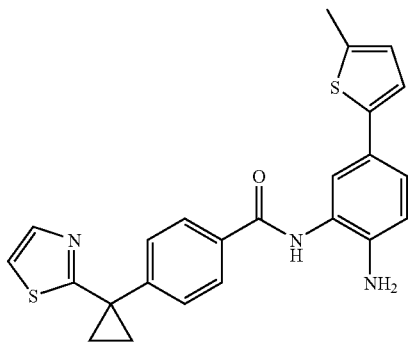

Similar procedure from Example 64 was followed to obtain the title compound using 4-(1-cyano-cyclopropyl)-benzoic acid methyl ester instead of 4-(4-cyano-tetrahydro-pyran-4-yl)-benzoic acid methyl ester. MS found for $C_{24}H_{21}N_3OS_2$ as (M+H)⁺ 432.23. ¹H NMR (400 MHz, dmso-d₆): δ: 9.71 (s, 1H), 7.98 (d, J=8.0 Hz, 2H), 7.64 (d, J=3.6 Hz, 1H), 7.56 (d, J=8.4 Hz, 2H), 7.45 (d, J=2.8 Hz, 1H), 7.36 (s, 1H), 7.18 (dd, J=8.4, 6.4 Hz, 1H), 6.98 (d, J=3.6 Hz, 1H), 6.75 (d, J=8.4 Hz, 1H), 6.69-6.68 (m, 1H), 5.08 (s, 2H), 2.39 (s, 3H), 1.64-1.62 (m, 2H), 1.46-1.44 (m, 2H).

Example 53

N-hydroxy-4-(4-(4-(pyrazin-2-yl)thiazol-2-yl)tetrahydropyran-4-yl)benzamide

Example 53 (Compound a″12-02)

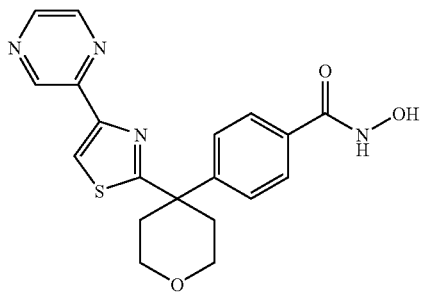

Similar procedure from Example 22 was followed to obtain the title compound using 2-bromo-1-(pyrazin-2-yl)ethanone. MS found for $C_{19}H_{18}N_4O_3S$ as (M+H)⁺ 383.85. ¹H NMR (400 MHz, dmso-d₆): δ: 11.09 (s, 1H), 9.24 (d, J=1.2 Hz, 1H), 8.61-8.55 (m, 2H), 8.28 (s, 1H), 7.66 (d, J=8.4 Hz, 2H), 7.50 (d, J=8.4 Hz, 2H), 3.72-3.70 (m, 2H), 3.60-3.55 (m, 2H), 2.66-2.62 (m, 2H), 2.38-2.33 (m, 2H).

Example 54

N-(4-amino-4'-fluorobiphenyl-3-yl)-4-(4-(4-(pyrazin-2-yl)thiazol-2-yl)tetrahydropyran-4-yl)benzamide (Compound a″12-03)

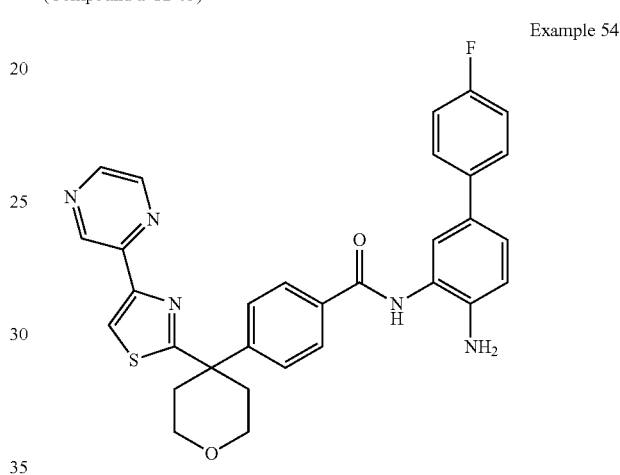

Similar procedure from Example 22 was followed to obtain the title compound using 1-pyrazin-2-yl-ethanone. MS found for $C_{31}H_{26}FN_5O_2S$ as (M+H)⁺ 552.22. ¹H NMR (400 MHz, dmso-d₆): δ: 9.65 (s, 1H), 9.29 (d, J=1.2 Hz, 1H), 8.65 (t, J=2.8 Hz, 1H), 8.60 (d, J=2.4 Hz, 1H), 8.33 (s, 1H), 7.95 (d, J=8.4 Hz, 2H), 7.62 (d, J=8.8 Hz, 2H), 7.54-7.50 (m, 2H), 7.44 (s, 1H), 7.25 (dd, J=8.4, 5.6 Hz, 1H), 7.17 (t, J=9.2 Hz, 2H), 6.80 (d, J=8.4 Hz, 1H), 5.05 (s, 2H), 3.77-3.74 (m, 2H), 3.68-3.63 (m, 2H), 2.73-2.63 (m, 2H), 2.47-2.46 (m, 2H).

Example 55

N-(2-aminophenyl)-4-(1-(4-(pyrazin-2-yl)thiazol-2-yl)cyclopropyl)benzamide (Compound a12-01)

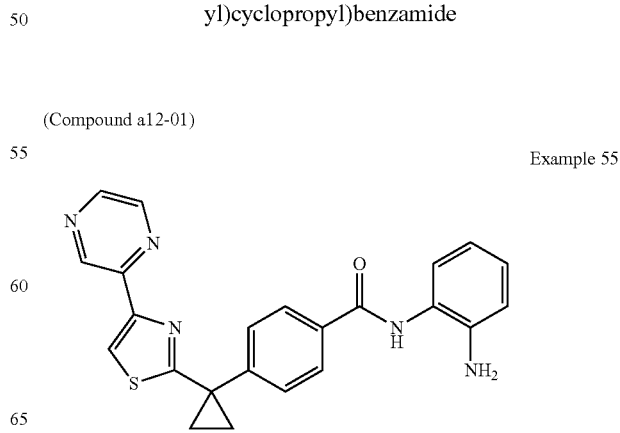

Similar procedure from Example 22 was followed to obtain the title compound using 4-(1-cyano-cyclopropyl)-benzoic acid methyl ester instead of 4-(4-cyano-tetrahydro-pyran-4-yl)-benzoic acid methyl ester. MS found for $C_{23}H_{19}N_5OS$ as $(M+H)^+$ 414.65. $^1H$ NMR (400 MHz, dmso-$d_6$): δ: 9.76 (s, 1H), 9.19 (d, J=1.6 Hz, 1H), 8.64 (t, J=4.4 Hz, 1H), 8.58 (d, J=2.8 Hz, 1H), 8.15 (s, 1H), 8.00 (d, J=8.0 Hz, 2H), 7.63 (d, J=8.0 Hz, 2H), 7.18 (d, J=7.2 Hz, 1H), 6.99 (t, J=7.6 Hz, 1H), 6.82 (d, J=7.2 Hz, 1H), 6.68-6.66 (m, 1H), 1.82-1.79 (m, 2H), 1.54-1.51 (m, 2H).

Example 56

N-(4-amino-4'-fluorobiphenyl-3-yl)-4-(1-(5-methyl-4,5,6,7-tetrahydrothiazolo[5,4-c]pyridine-2-yl)cyclopropyl)benzamide (Compound a0-117)

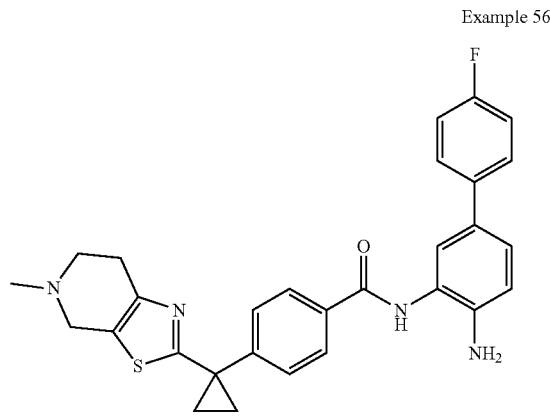

Example 56

Similar procedure from Example 29 was followed to obtain the title compound using 4-(1-cyano-cyclopropyl)-benzoic acid methyl ester instead of 4-(4-cyano-tetrahydro-pyran-4-yl)-benzoic acid methyl ester. MS found for $C_{29}H_{27}FN_4OS$ as $(M+H)^+$ 499.19. $^1H$ NMR (400 MHz, dmso-$d_6$): δ: 9.71 (s, 1H), 7.97 (d, J=8.0 Hz, 2H), 7.56-7.52 (m, 4H), 7.46 (s, 1H), 7.27 (dd, J=8.4-6.4 Hz, 1H), 7.18 (t, J=8.8 Hz, 2H), 6.83 (d, J=8.4 Hz, 1H), 5.07 (s, 2H), 3.41 (s, 2H), 2.64-2.61 (m, 4H), 2.29 (s, 3H), 1.59-1.57 (m, 2H), 1.41-1.38 (m, 2H).

Example 57

N-(2-amino-5-fluorophenyl)-4-(4-(4-(pyrazin-2-yl)thiazol-2-yl)tetrahydropyran-4-yl)benzamide (Compound a″12-04)

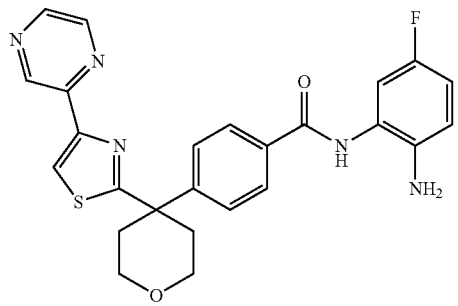

Example 57

Similar procedure from Example 22 was followed to obtain the title compound using (2-amino-4-fluoro-phenyl)-carbamic acid tert-butyl ester MS found for $C_{25}H_{22}FN_5O_2S$ as $(M+H)^+$ 476.41. $^1H$ NMR (400 MHz, dmso-$d_6$): δ: 9.58 (s, 1H), 9.29 (d, J=1.2 Hz, 1H), 8.65 (t, J=2.4 Hz, 1H), 8.60 (d, J=2.4 Hz, 1H), 8.33 (s, 1H), 7.91 (d, J=8.4 Hz, 2H), 7.61 (d, J=8.4 Hz, 2H), 7.11 (dd, J=8.4, 7.6 Hz, 1H), 4.79 (s, 2H) 3.77-3.74 (m, 2H), 3.67-3.62 (m, 2H), 2.72-2.69 (m, 2H), 2.47-2.41 (m, 2H).

Example 58

N-(4-amino-4'-fluorobiphenyl-3-yl)-4-(1-(6,7-dihydropyrano[4,3-d]thiazol-2-yl)cyclopropyl)benzamide (Compound a0–122)

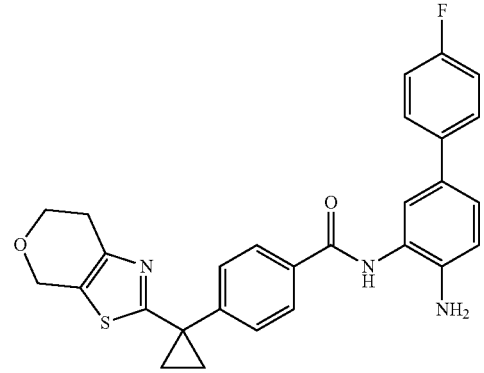

Example 58

Similar procedure from Example 26 was followed to obtain the title compound using 4-(1-cyano-cyclopropyl)-benzoic acid methyl ester and (3-amino-4'-fluoro-biphenyl-4-yl)-carbamic acid tert-butyl ester. MS found for $C_{28}H_{24}FN_3O_2S$ as $(M+H)^+$ 486.54. $^1H$ NMR (400 MHz, dmso-$d_6$): δ: 9.71 (s, 1H), 7.97 (d, J=8.4 Hz, 2H), 7.55-7.47 (m, 5H), 7.28-7.25 (m, 1H), 7.18 (t, J=8.8 Hz, 2H), 6.82 (d, J=8.0 Hz, 1H), 5.07 (s, 2H), 4.61 (s, 2H), 3.85 (t J=5.6 Hz, 2H), 2.69 (t, J=5.6 Hz, 2H), 1.61-1.58 (m, 2H), 1.43-1.42 (m, 2H).

Example 59

N-(4-amino-4'-fluorobiphenyl-3-yl)-4-(4-(pyridin-2-yl)tetrahydropyran-4-yl)benzamide (Compound e–05)

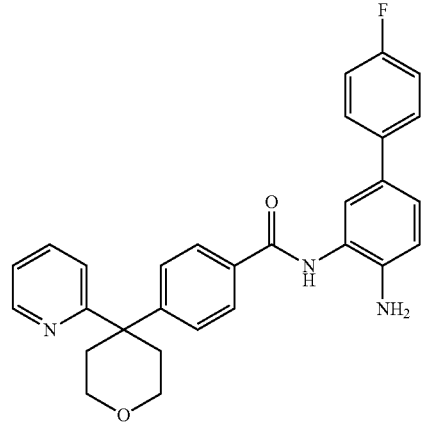

Example 59

Similar procedure from Example 49 was followed to obtain the title compound using (3-amino-4'-fluoro-biphenyl-4-yl)-carbamic acid tert-butyl ester. MS found for $C_{29}H_{26}FN_3O_2$ as $(M+H)^+$ 468.20. $^1$H NMR (400 MHz, dmso-d$_6$): δ: 9.59 (s, 1H), 8.52 (dd, J=4.8, 3.6 Hz, 1H), 7.87 (d, J=8.8 Hz, 2H), 7.71-7.66 (m, 1H), 7.53-7.38 (m, 6H), 7.24 (dd, J=8.4, 6.0 Hz, 1H), 7.19-7.14 (m, 3H), 6.80 (d, J=8.0 Hz, 1H), 5.03 (s, 2H), 3.68-3.64 (m, 2H), 3.51-3.46 (m, 2H), 2.72-2.68 (m, 2H), 2.34-2.24 (m, 2H).

Example 60

N-(2-amino-5-(5-chlorothiophen-2-yl)phenyl)-4-(4-(pyridin-2-yl)tetrahydropyran-4-yl)benzamide (Compound e–06)

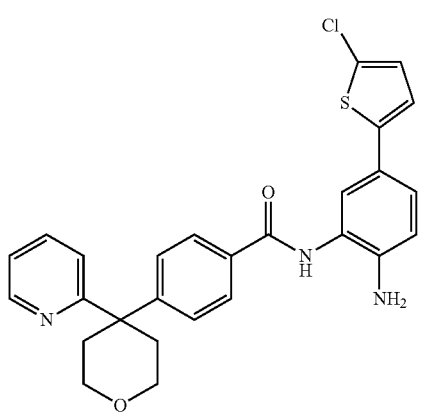

Similar procedure from Example 49 was followed to obtain the title compound using [2-amino-4-(5-chloro-thiophen-2-yl)-phenyl]-carbamic acid tert-butyl ester instead of (2-amino-4-thiophen-2-yl-phenyl)-carbamic acid tert-butyl ester. MS found for $C_{27}H_{24}ClN_3O_2S$ as $(M+H)^+$ 490.63. $^1$H NMR (400 MHz, dmso-d$_6$): δ: 9.58 (s, 1H), 8.52 (d, J=4.0 Hz, 1H), 7.86 (d, J=8.8 Hz, 2H), 7.71-7.66 (m, 1H), 7.46 (d, J=8.8 Hz, 2H), 7.39-7.34 (m, 2H), 7.20-7.14 (m, 2H), 7.06-7.00 (m, 2H), 6.75 (d, J=8.4 Hz, 1H), 5.18 (s, 2H), 3.67-3.64 (m, 2H), 3.51-3.46 (m, 2H), 2.72-2.63 (m, 2H), 2.34-2.22 (m, 2H).

Example 61

N-(4-amino-4'-fluorobiphenyl-3-yl)-4-(4-(5-(1-hydroxyethyl)-4-methylthiazol-2-yl)tetrahydropyran-4-yl)benzamide (Compound a″0–20)

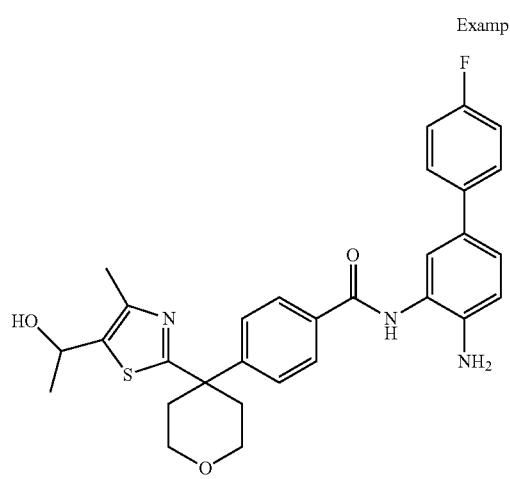

To a solution of 4-[4-(5-Acetyl-4-methyl-thiazol-2-yl)-tetrahydro-pyran-4-yl]-benzoic acid (100 mg, 0.289 mmol) in MeOH was added NaBH$_4$ (22 mg, 2 eq) at 0° C. and stirred for 1 hour. After reaction was done, it was quenched with aqueous HCl and stirred for 1 more hour. Reaction mixture was evaporated and purified by reverse phase chromatography to have pure 4-{4-[5-(1-hydroxy-ethyl)-4-methyl-thiazol-2-yl]-tetrahydro-pyran-4-yl}-benzoic acid. HATU coupling and amine de-protection was carried out following the procedure from Example 64 to afford title compound. MS found for $C_{30}H_{30}FN_3O_3S$ as $(M+H)^+$ 532.25. $^1$H NMR (400 MHz, dmso-d$_6$): δ: 9.64 (s, 1H), 7.92 (d, J=8.4 Hz, 2H), 7.54-7.51 (m, 4H), 7.45 (d, J=1.2 Hz, 1H), 7.25 (dd, J=8.4, 6.4 Hz, 1H), 7.17 (t, J=8.2 Hz, 2H), 6.81 (d, J=8.4 Hz, 1H), 5.44 (d, J=3.6 Hz, 1H), 5.06 (s, 2H), 4.91-4.89 (m, 1H), 3.69-3.66 (m, 2H), 3.59-3.54 (m, 2H), 2.57-2.54 (m, 2H), 2.35-2.29 (m, 2H), 2.23 (s, 3H), 1.26 (d, J=6.4 Hz, 3H).

Example 62

N-(4-amino-4'-fluorobiphenyl-3-yl)-4-(4-(4,5-dimethylthiazol-2-yl)tetrahydropyran-4-yl)benzamide (Compound a″0–22)

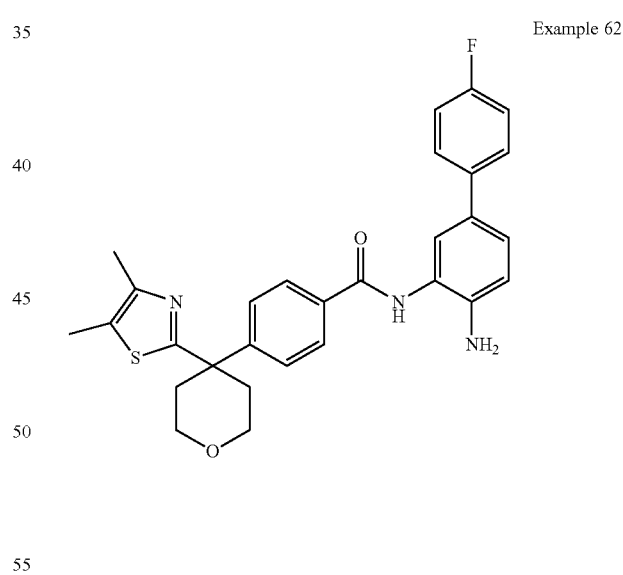

Similar procedure from Example 9 was followed to obtain the title compound using 3-chloro-butan-2-one and (3-amino-4'-fluoro-biphenyl-4-yl)-carbamic acid tert-butyl ester. MS found for $C_{29}H_{28}FN_3O_2S$ as $(M+H)^+$ 502.24. $^1$H NMR (400 MHz, dmso-d$_6$): δ: 9.63 (s, 1H), 7.91 (d, J=8.4 Hz, 2H), 7.54-7.44 (m, 5H), 7.25 (dd, J=8.4, 6.4 Hz, 1H), 7.17 (t, J=8.8 Hz, 2H), 6.81 (d, J=8.2 Hz, 1H), 5.05 (s, 2H), 3.71-3.68 (m, 2H), 3.59-3.54 (m, 2H), 2.54-2.50 (m, 2H), 2.31-2.26 (m, 2H), 2.22 (s, 3H), 2.20 (s, 3H).

Example 63

N-(4-amino-4'-fluorobiphenyl-3-yl)-4-(4-(5-methylthiazol-2-yl)tetrahydropyran-4-yl)benzamide (Compound a"0-37)

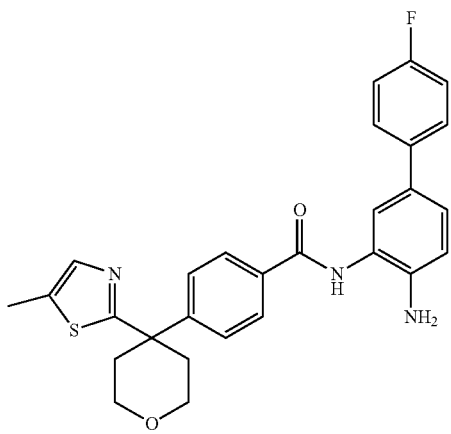

Example 63

Similar procedure from Example 9 was followed to obtain the title compound using 2-chloro-1,1-dimethoxy-propane. MS found for $C_{28}H_{26}FN_3O_2S$ as $(M+H)^+$ 488.35. $^1H$ NMR (400 MHz, dmso-$d_6$): δ: 9.63 (s, 1H), 7.91 (d, J=8.4 Hz, 2H), 7.54-7.44 (m, 5H), 7.38 (s, 1H), 7.26-7.23 (m, 1H), 7.17 (t, J=8.8 Hz, 2H), 6.81 (d, J=8.4 Hz, 1H), 5.05 (s, 2H), 3.73-3.70 (m, 2H), 3.58-3.53 (m, 2H), 2.57-2.53 (m, 2H), 2.34 (s, 3H), 2.31-12.29 (m, 2H).

Example 64

N-(2-amino-5-thiophen-2-yl-phenyl)-4-(4-thiazol-2-yl-tetrahydro-pyran-4-yl)-benzamide (Compound a"0-12)

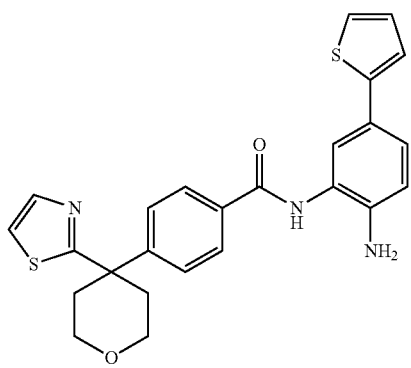

Example 64

Methyl 4-(cyanomethyl)-benzoic acid methyl ester (1.92 g, 11.01 mmol) and 1-bromo-2-(2-bromo-ethoxy)-ethane (12.56 mL, 55.04 mmol) were combined in THF (15 mL) and cooled down to 0° C. Potassium bis(trimethylsilyl)-amide (0.5M in toluene, 48.3 mL, 24.21 mmol, 2.2 eq) was added over a period of 15 minutes and then warmed up to room temperature and stirred for 2 hours. The reaction mixture was partitioned between ethyl acetate and water. The organic phase was dried with $MgSO_4$ and evaporated under vacuum. The crude product was purified by chromatography on silica gel (25% EtOAc/hexanes) to afford 4-(4-cyano-tetrahydro-pyran-4-yl)-benzoic acid methyl ester. To a solution of 4-(4-cyano-tetrahydro-pyran-4-yl)-benzoic acid methyl ester (1.55 g 6.32 mmol) in MeOH (10 mL) was added $Et_3N$ (3 mL). $H_2S$ was bubbled into the solution. The reaction vessel was stirred at room temperature for 3 days. The reaction mixture was then evaporated and purified by silica gel chromatography (33% EtOAc/hexanes) to afford 4-(4-thiocarbamoyl-tetrahydro-pyran-4-yl)-benzoic acid methyl ester.

The above compound was dissolved in DMF. Chloro-acetaldehyde in water (1.2 eq) was added and heated with microwave at 85° C. for 1 hour. The reaction mixture was partitioned between ethyl acetate and water. The organic phase was dried with $MgSO_4$ and evaporated under vacuum. This product was used for next step without purification. The solid 4-[4-(4-hydroxy-4,5-dihydro-thiazol-2-yl)-tetrahydro-pyran-4-yl]-benzoic acid methyl ester was dissolved in MeOH and an excess of p-TsOH was added and heated in the microwave for 20 minutes at 70° C. The reaction mixture was diluted with EtOAc and washed with saturated $NaHCO_3$ solution. The organic phase was dried with $MgSO_4$, evaporated under vacuum and purified by silica gel chromatography (33% EtOAc/hexanes).

Compound 4-(4-thiazol-2-yl-tetrahydro-pyran-4-yl)-benzoic acid methyl ester (1.00 g, 3.3 mmol) was dissolved in MeOH (5 mL) and treated with 1N NaOH. The reaction mixture was stirred at room temperature for 2 hours. After the reaction was complete, the solution mixture was evaporated, suspended in water, and acidified with 1N HCl. 4-(4-thiazol-2-yl-tetrahydro-pyran-4-yl)-benzoic acid was collected as precipitate, dried under vacuum, and used for next step without further purification.

A solution of 4-(4-thiazol-2-yl-tetrahydro-pyran-4-yl)-benzoic acid (0.9 g, 3.11 mmol), 2-Amino-4-thiophen-2-yl-phenyl-carbamic acid tert-butyl ester (1.08 g, 1.1 eq), HATU (1.42 g, 1.2 eq), and DIPEA (1.04 mL, 2.0 eq) were dissolved in DMF and stirred at 45° C. overnight. After the reaction was complete, it was cooled down and precipitated with water and a saturated solution of $NaHCO_3$. The solid formed was collected and used for next step without further purification. Solid {2-[4-(4-thiazol-2-yl-tetrahydro-pyran-4-yl)-benzoylamino]-4-thiophen-2-yl-phenyl}-carbamic acid tert-butyl ester was re-dissolved in DCM/TFA (1:1) and stirred for 1 hour. After the reaction was complete, the reaction mixture was evaporated and purified by reverse phase chromatography to afford title compound, Example 64. MS found for $C_{28}H_{26}N_7FOS$ as $(M+H)^+$ 461.12. $^1H$ NMR (400 MHz, dmso-$d_6$): $^1$H-NMR (DMSO) δ: 9.74 (s, 1H), 8.04 (d, J=8.0 Hz, 2H), 7.67 (d, J=8.8 Hz, 2H), 7.44 (s, 1H), 7.32 (d, J=5.2 Hz, 1H), 7.27 (d, J=8.4 Hz, 1H), 7.21 (d, J=3.6 Hz, 1H), 7.01 (q, J=3.6, 4.8 Hz, 1H), 6.78 (d, J=8.4 Hz, 1H), 5.14 (s, 1H), 4.02-4.00 (m, 2H), 3.69-3.65 (m, 2H), 2.11-2.08 (m, 4H).

Example 65

N-(4-amino-4'-fluoro-biphenyl-3-yl)-4-[4-(4-cyclopropyl-thiazol-2-yl)-tetrahydro-pyran-4-yl]-benzamide (Compound a″0–44)

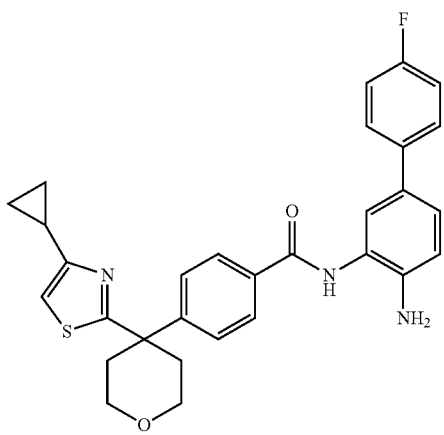

Similar procedure from Example 64 was followed to obtain the title compound using 2-bromo-1-cyclopropyl-ethanone instead of 3-chloro-butan-2-one. MS found for $C_{30}H_{28}FN_3O_2S$ as $(M+H)^+$ 514.35. $^1H$ NMR (400 MHz, dmso-$d_6$): δ: 9.84 (s, 1H), 7.93 (d, J=8.0 Hz, 2H), 7.58-7.54 (m, 2H), 7.52-7.51 (m, 3H), 7.34 (dd, J=8.4, 6.4 Hz, 1H), 7.20 (t, J=8.8 Hz, 2H), 7.13 (s, 1H) 6.96 (d, J=8.4 Hz, 1H), 3.71-3.68 (m, 2H), 3.57-3.52 (m, 2H), 2.56-2.52 (m, 2H), 2.35-2.29 (m, 2H), 2.03-1.98 (m, 1H), 0.89-0.84 (m, 2H), 0.77-0.74 (m, 2H).

Example 66

4-[4-(5-acetyl-4-methyl-thiazol-2-yl)-tetrahydro-pyran-4-yl]-N-(4-amino-4'-fluoro-biphenyl-3-yl)-benzamide (Compound a″0–46)

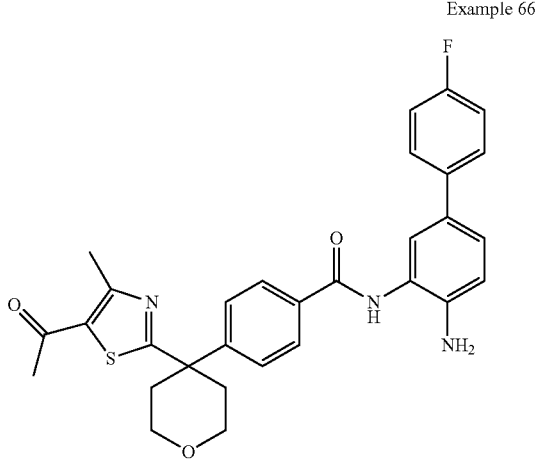

Similar procedure from Example 64 was followed to obtain the title compound using 3-chloro-pentane-2,4-dione instead of 3-chloro-butan-2-one. MS found for $C_{30}H_{28}FN_3O_3S$ as $(M+H)^+$ 530.41. $^1H$ NMR (400 MHz, dmso-$d_6$): δ: 9.66 (s, 1H), 7.95 (d, J=8.4 Hz, 2H), 7.58-7.51 (m, 4H), 7.44 (s, 1H), 7.26 (dd, J=8.4, 6.4 Hz, 1H), 7.17 (t, J=8.8 Hz, 2H), 6.81 (d, J=8.4 Hz, 1H), 5.06 (s, 2H), 3.70-3.67 (m, 2H), 3.62-3.57 (m, 2H), 2.62-2.47 (m, 2H), 2.61 (s, 3H), 2.42 (s, 3H).

Example 67

4-[4-(5-methyl-2H-[1,2,4]triazol-3-yl)-tetrahydro-pyran-4-yl]-benzoic acid 4-amino-4'-fluoro-biphenyl-3-yl ester (Compound r–02)

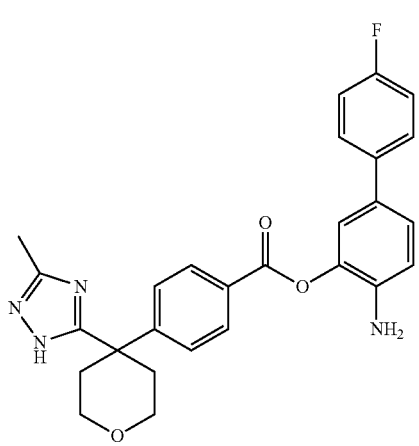

4-(4-cyano-tetrahydro-pyran-4-yl)-benzoic acid methyl ester (300 mg, 1.22 mmol) was suspended in water and then 4N NaOH was added and heated at 110° C. for 15 minutes. To this solution 2N HCl was added to precipitate the product. The solid was filtered out and used for next step without further purification. 4-(4-carbamoyl-tetrahydro-pyran-4-yl)-benzoic acid (200 mg, 0.80 mmol) was dissolved in DMF and then DMA-acetal in excess was added. The mixture was heated at 50° C. for 20 minutes. The reaction mixture was evaporated and used for next step without further purification. 4-[4-(1-dimethylamino-ethylidenecarbamoyl)-tetrahydro-pyran-4-yl]-benzoic acid methyl ester (50 mg, 0.150 mmol) and hydrazine hydrate (0.015 mL, 2 eq) were dissolved in AcOH and heated at 50° C. for 20 minutes. The reaction mixture was evaporated and used for next step without further purification. Hydrolysis HATU coupling, and amine de-protection was carried out following the same procedures from Example 64 using (3-amino-4'-fluoro-biphenyl-4-yl)-carbamic acid tert-butyl ester instead of (2-amino-4-thiophen-2-yl-phenyl)-carbamic acid tert-butyl ester. MS found for $C_{27}H_{25}FN_4O_3$ as $(M+H)^+$ 473.21. $^1H$ NMR (400 MHz, dmso-$d_6$): δ: 13.31 (s, 1H), 9.55 (s, 1H), 7.82 (d, J=7.6 Hz, 2H), 7.50 (dd, J=8.8, 5.2 Hz, 2H), 7.41 (s, 1H), 7.35 (d, J=8.4 Hz, 2H), 7.20 (dd, J=8.0-2.4 Hz, 1H), 7.14 (t, J=8.8 Hz, 2H), 6.77 (d, J=6.77 Hz, 1H), 5.00 (s, 2H), 3.73-3.71 (m, 2H), 3.37-3.31 (m, 2H), 2.58-2.55 (m, 2H), 2.24 (s, 3H), 2.06-2.03 (m, 2H).

Example 68

N-(4-amino-4'-fluoro-biphenyl-3-yl)-4-(1-pyridin-2-yl-cyclopropyl)-benzamide (Compound e-01)

Example 68

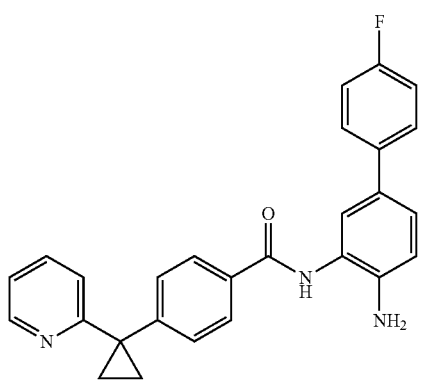

Similar procedure from Example 49 was followed to obtain the title compound using 4-(1-cyano-cyclopropyl)-benzoic acid methyl ester instead of 4-(4-cyano-tetrahydro-pyran-4-yl)-benzoic acid methyl ester. MS found for $C_{27}H_{22}FN_3Oas$ $(M+H)^+$ 424.31. $^1$H NMR (400 MHz, dmso-$d_6$): δ: 9.57 (s, 1H), 8.34 (dd, J=4.8, 1.2 Hz, 1H), 7.86 (d, J=8.0 Hz, 2H), 7.44-7.40 (m, 3H), 7.35-7.33 (m, 3H), 7.15 (dd, J=8.0-2.0 Hz, 1H), 7.08-6.99 (m, 3H), 6.72-6.67 (m, 2H), 4.95 (s, 2H), 1.46-1.43 (m, 2H), 1.17-1.15 (m, 2H).

Example 69

4-[1-(5-acetyl-4-methyl-thiazol-2-yl)-cyclopropyl]-N-(2-amino-phenyl)-benzamide (Compound a0-115)

Example 69

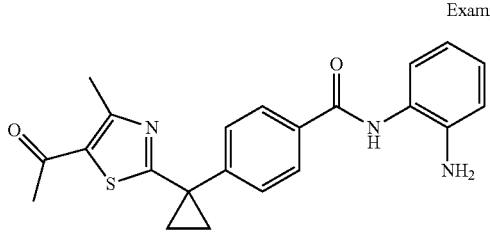

Similar procedure from Example 64 and Example 66 was followed to obtain the title compound. MS found for $C_{22}H_{21}N_3O_2S$ as $(M+H)^+$ 392.28. $^1$H NMR (400 MHz, CD$_3$OD): $^1$H-NMR (CD$_3$OD) δ: 8.03 (d, J=8.2 Hz, 2H), 7.64 (d, J=8.4 Hz, 2H), 7.20 (d, J=7.6 Hz, 1H), 7.08 (d, J=8.4 Hz, 1H), 6.91 (d, J=8.0 Hz, 1H), 6.77 (t, J=7.2 Hz, 1H), 2.62 (s, 3H), 2.40 (s, 3H), 1.85-1.84 (m, 2H), 1.57-1.56 (m, 2H).

Example 70

N-(2-amino-phenyl)-4-[1-(5-methyl-4,5,6,7-tetrahydro-thiazolo[5,4-c]pyridin-2-yl)-cyclopropyl]-benzamide (Compound a0-49)

Example 70

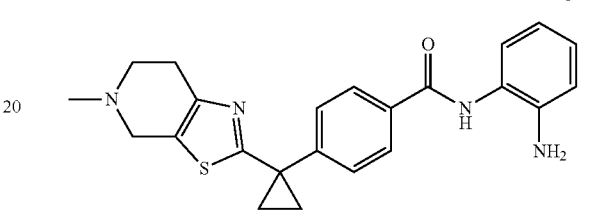

Similar procedure from Example 29 was followed to obtain the title compound using 4-(1-cyano-cyclopropyl)-benzoic acid methyl ester instead of 4-(4-cyano-tetrahydro-pyran-4-yl)-benzoic acid methyl ester. MS found for $C_{23}H_{24}N_4OS$ as $(M+H)^+$ 405.32. $^1$H NMR (400 MHz, dmso-$d_6$): $^1$H-NMR (CD$_3$OD) δ: 8.32 (s, 1H), 7.97 (d, J=8.8 Hz, 2H), 7.56 (d, J=8.4 Hz, 2H), 7.17 (d, J=6.4 Hz, 1H), 7.08-7.04 (m, 1H), 6.89 (dd, J=8.0, 7.2 Hz, 1H), 6.77-6.73 (m, 1H), 3.74 (s, 2H), 2.99-2.96 (m, 2H), 2.89-2.86 (m, 2H), 2.56 (s, 3H), 1.70-1.68 (m, 2H), 1.49-1.46 (m, 2H).

Example 71

4-[1-(5-acetyl-4,5,6,7-tetrahydro-thiazolo[5,4-c]pyridin-2-yl)-cyclopropyl]-N-(2-amino-phenyl)-benzamide (Compound a0-53)

Example 71

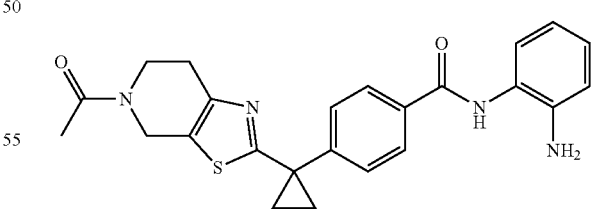

Similar procedure from Example 27 was followed to obtain the title compound using 4-(1-cyano-cyclopropyl)-benzoic acid methyl ester instead of 4-(4-cyano-tetrahydro-pyran-4-yl)-benzoic acid methyl ester. MS found for $C_{24}H_{24}N_4O_2S$ as $(M+H)^+$ 433.18. $^1$H NMR (400 MHz, CD$_3$OD): δ: 7.95 (d, J=8.2 Hz, 2H), 7.55 (d, J=8.2 Hz, 2H), 7.18 (d, J=7.2 Hz, 1H), 7.08 (t, J=7.0 Hz, 1H), 6.88 (d, J=7.6 Hz, 1H), 6.76 (t, J=6.0

Hz, 1H), 4.63 (s, 3H), 3.91-3.76 (m, 2H), 2.85-2.73 (m, 2H), 2.19-2.11 (m, 2H), 1.73-1.67 (m, 2H), 1.50-1.43 (m, 2H).

Example 72

N-(4-amino-4'-fluoro-biphenyl-3-yl)-4-{4-[4,6-bis-(1-hydroxy-1-methyl-ethyl)-pyridin-2-yl]-tetrahydro-pyran-4-yl}-benzamide (Compound e-08)

Example 72

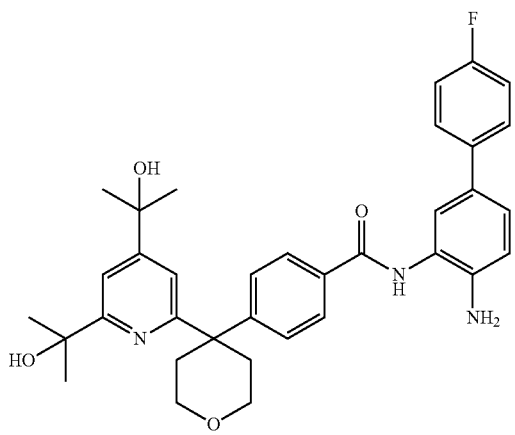

Similar procedure from Example 49 was followed to obtain the title compound using 2-methyl-but-3-yn-2-ol and (3-amino-4'-fluoro-biphenyl-4-yl)-carbamic acid tert-butyl ester instead of ethynyl-trimethyl-silane and (2-amino-4-thiophen-2-yl-phenyl)-carbamic acid tert-butyl ester respectively. MS found for $C_{35}H_{38}FN_3O_4$ as $(M+H)^+$ 584.36. $^1$H NMR (400 MHz, dmso-$d_6$): δ: 9.58 (s, 1H), 7.86 (d, J=8.4 Hz, 2H), 7.53-7.48 (m, 5H), 7.43 (s, 1H), 7.25-7.23 (m, 2H), 7.16 (t, J=9.2 Hz, 2H), 6.81 (d, J=8.4 Hz, 1H), 5.12 (s, 2H), 5.10 (s, 1H), 5.03 (s, 2H), 3.69-3.65 (m, 2H), 3.47-3.42 (m, 2H), 2.76-2.73 (m, 2H), 2.31-2.26 (m, 2H), 1.41 (s, 6H), 1.32 (s, 6H).

Example 73

N-(2-Amino-phenyl)-4-[1-(5-isopropyl-4,5,6,7-tetrahydro-thiazolo[5,4-c]pyridin-2-yl)-cyclopropyl]-benzamide (Compound a0-51)

Example 73

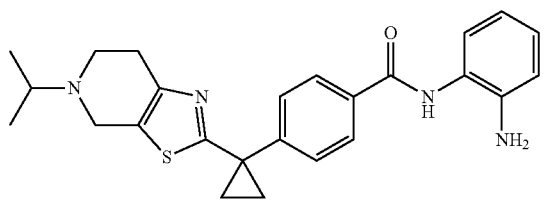

Similar procedure from Example 29 was followed to obtain the title compound using 4-(1-cyano-cyclopropyl)-benzoic acid methyl ester and acetone instead of 4-(4-cyano-tetrahydro-pyran-4-yl)-benzoic acid methyl ester and p-formaldehyde, respectively. MS found for $C_{25}H_{28}N_4OSas$ $(M+H)^+$ 433.65. $^1$H NMR (400 MHz, CD$_3$OD): δ: 8.43 (s, 1H), 7.96 (d, J=8.4 Hz, 2H), 7.55 (d, J=8.4 Hz, 2H), 7.17 (d, J=8.2 Hz, 1H), 7.08-7.04 (m, 1H), 6.90 (d, J=8.0 Hz, 1H), 6.77 (t, J=1.6 Hz, 1H), 3.82 (s, 2H), 3.11-3.02 (m, 2H), 2.86-2.83 (m, 2H), 1.70-1.67 (m, 2H), 1.49-1.46 (m, 2H), 1.17 (d, J=6.4 Hz, 6H).

Example 74

N-(2-aminophenyl)-4-(4-(5-(pyridin-3-yl)thiazol-2-yl)-tetrahydro-2H-pyran-4-yl)benzamide (Compound a"0-39)

Example 74

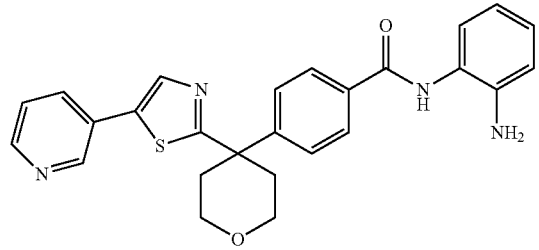

Similar procedure from Example 51 was followed to obtain the title compound using tert-butyl-2-(4-(4-(5-(pyridin-3-yl)thiazol-2-yl)-tetrahydro-2H-pyran-4-yl)benzamido)-4-(thiophen-2-yl)phenylcarbamate and 1,2-phenylenediamine. MS found for $C_{26}H_{24}N_4SO_2$ as $(M+H)^+$ 456.98. $^1$H NMR (400 MHz, dmso-$d_6$): δ 9.59 (brs, 1H); 8.81 (d, J=2.0 Hz, 1H); 8.49 (d, J=3.2 Hz, 1H); 8.24 (s, 1H); 7.99 (d, J=8.4 Hz, 1H); 7.94 (d, J=8.4 Hz, 2H); 7.57 (d, J=8.4 Hz, 2H); 7.42-7.41 (m, 1H); 7.12 (d, J=7.6 Hz, 1H); 6.94 (t, J=7.2 Hz, 1H); 6.74 (d, J=7.2 Hz, 1H); 6.55 (t, J=7.2 Hz, 1H); 3.76-3.73 (m, 2H); 3.65-3.60 (m, 2H); 2.65-2.62 (m, 2H); δ 2.43-2.38 (m, 2H).

Example 75

N-(2-aminophenyl)-4-(4-(5-(6-cyclopropylpyridin-3-yl)thiazol-2-yl)-tetrahydro-2H-pyran-4-yl)benzamide (Compound a"0-42)

Example 75

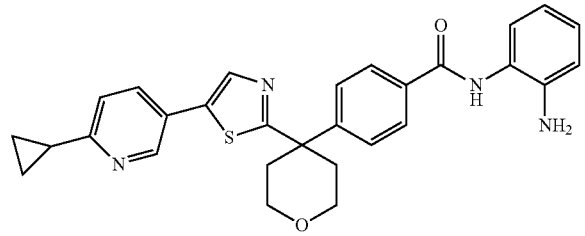

A mixture of 2-cyclopropyl-5-(4,4,5,5-tetramethyl-1,3,2-dioxaborolan-2-yl)pyridine (490 mg, 2.00 mmol), methyl 4-(4-(5-bromothiazol-2-yl)-tetrahydro-2H-pyran-4-yl)benzoate (382 mg, 1.00 mmol), potassium carbonate (276 mg, 2.0 mmol), and 1,1'-bis(diphenylphosphino)ferrocene]

dichloropalladium(II) (PdCl₂(dppf), 146 mg, 0.20 mmol) in toluene/ethanol/water (2 mL/1 mL/1 mL) was heated in microwave (Emry's Optimizer) at 110 C for 20 minutes. The reaction mixture was cooled to room temperature and then diluted with EtOAc and filtered. The filtrate was concentrated and purified by Flash Chromatography (SiO₂, 95% EtOAC: 5% MeOH) to give methyl 4-(4-(5-(6-cyclopropylpyridin-3-yl)thiazol-2-yl)-tetrahydro-2H-pyran-4-yl)benzoate. MS found for $C_{24}H_{24}N_2O_3S$ as $(M+H)^+$ 421.42. To the above ester in MeOH/THF/dioxane (1:1:1) (9 mL) was added 3N NaOH (5.0 mL) and stirred at 55° C. After 14 hours, the reaction mixture was concentrated, diluted with water, and neutralized with 6N HCl. The formed solids were filtered and washed with water and dried. MS found for $C_{23}H_{22}N_2O_3S$ as $(M+H)^+$ 407.04. The acid was used further without purification.

To the above carboxylic acid (406 mg, 1.0 mmol) in DMF (3 mL), was added HATU (570 mg, 1.5 mmol), 1,2-phenylenediamine (162 mg, 1.5 mmol) and NMM (0.4 mL) and stirred at room temperature for 1 hour. The reaction mixture was diluted with water and acetonitrile and directly purified by preparative HPLC affording the title compound, after lyophilization. MS found for $C_{29}H_{28}N_4SO_2$ as $(M+H)^+$ 496.92. ¹H NMR (400 MHz, dmso-d₆): δ 9.58 (s, 1H); 8.60 (d, J=2.0 Hz, 1H); 8.13 (s, 1H); 7.93 (d, J=8.4 Hz, 2H); 7.83 (dd, J=8.0, 2.0 Hz, 2H); 7.56 (d, J=8.4 Hz, 2H); 7.30 (d, J=8.0 Hz, 2H); 7.12 (d, J=7.6 Hz, 1H); 6.93 (d, J=7.2 Hz, 1H); 6.74 (d, J=7.6 Hz, 1H); 6.57 (d, J=7.2 Hz, 1H); 4.90 (brs, 2H); 3.75-3.72 (m, 2H); 3.63-3.59 (m, 2H); 2.64-2.62 (m, 2H); 2.46-2.36 (m, 2H); 2.09-2.05 (m, 1H); 0.96-0.88 (m, 4H).

Example 76

N-(2-amino-phenyl)-4-[4-(4-pyrazin-2-yl-1H-imidazol-2-yl)-tetrahydro-pyran-4-yl]-benzamide (Compound q-01)

Example 76

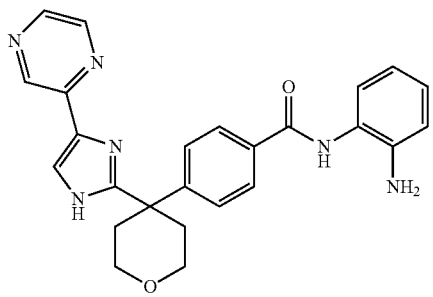

4-(4-Cyano-tetrahydro-pyran-4-yl)-benzoic acid methyl ester (1.0 g, 4.08 mmol) was suspended in 4.0N NaOH and heated at 110° C. for 1 hour. After the reaction was complete, 2N HCl was slowly added to form a precipitate. The precipitate was then filtered, dried under vacuum, and used for next step without purification. 4-(4-Carboxy-phenyl)-tetrahydro-pyran-4-carboxylic acid (0.4 g, 1.6 mmol) was dissolved in NMP. HATU (1.28 g, 2.1 eq) and DIPEA (0.8 mL, 3.0 eq) were added and stirred at 50° C. for 1 hour. The reaction mixture was cooled down to room temperature and benzyl alcohol (172 mg, 1.0 eq) was added. The reaction mixture was stirred at room temperature overnight. Saturated aqueous solution of NaHCO₃ was added to the mixture and was then extracted with EtOAc. The organic phase was dried, evaporated and used for next step without further purification.

To a solution of 4-(4-benzyloxycarbonyl-phenyl)-tetrahydro-pyran-4-carboxylic acid (0.3 g, 0.88 mmol) and 2-bromo-1-pyrazin-2-yl-ethanone (210 mg, 1.2 eq) in acetonitrile, TEA (0.18 mL, 1.2 eq) was added and heated in the microwave at 80° C. for 1 hour. The reaction mixture was evaporated and purified by silica gel chromatography (Hex: EtOAc 25:75). 4-(4-benzyloxycarbonyl-phenyl)-tetrahydro-pyran-4-carboxylic acid 2-oxo-2-pyrazin-2-yl-ethyl ester (0.3 g, 0.65 mmol), NH₄OAc (110 mg, 2.2 eq) and 3 Å molecular sieves were mixed together in xylene and heated in the microwave at 160° C. for 1 hour. After the reaction was done, it was extracted with EtOAc and the organic phase was dried and evaporated to be used in the next step without further purifications.

Hydrogenation of 4-[4-(4-pyrazin-2-yl-1H-imidazol-2-yl)-tetrahydro-pyran-4-yl]-benzoic acid benzyl ester (0.2 mg, 0.45 mmol) in EtOH, was carried out in the presence of excess Pd/C (10%, dry basis) at a pressure of 1 atmosphere. After 16 hours, the reaction mixture was filtered through a celite pad and washed with hot ethanol. The solution was evaporated and used for next step without further purification.

The above acid was then coupled with 1,2-phenylenediamine in the presence of HATU and DIPEA in DMF and purified by reverse phase chromatography to give the title compound. MS found for $C_{25}H_{24}N_6O_2$ as $(M+H)^+$ 441.21 ¹H NMR (400 MHz, dmso-d₆): ¹H-NMR (DMSO) δ: 10.42 (s, 1H), 9.32 (s, 1H), 8.68-8.64 (m, 2H), 8.37 (s, 1H), 8.07 (d, J=8.4 Hz, 2H), 7.54 (d, J=8.4 Hz, 2H), 7.46-7.28 (m, 5H), 3.82-3.79 (m, 2H), 3.52-3.46 (m, 2H), 2.98-2.95 (m, 2H), 2.40-2.29 (m, 2H).

Example 77

N-(2-amino-phenyl)-4-[4-(4-phenyl-1H-imidazol-2-yl)-tetrahydro-pyran-4-yl]-benzamide (Compound q-04)

Example 77

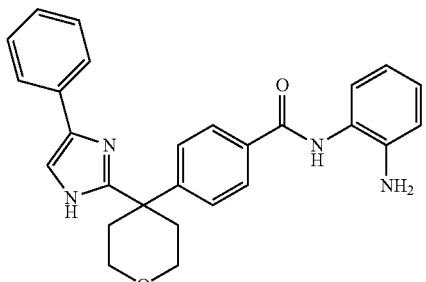

Similar procedure from Example 76 was followed to obtain the title compound using 2-bromo-1-phenyl-ethanone. MS found for $C_{27}H_{26}N_4O_2$ as $(M+H)^+$ 439.04 ¹H NMR (400 MHz, dmso-d₆): ¹H-NMR (DMSO) δ: 10.15 (s, 1H), 8.09 (s, 1H), 8.05 (d, J=8.4 Hz, 2H), 7.86 (d, J=7.2 Hz, 2H), 7.55 (d, J=8.4 Hz, 2H), 7.49-7.33 (m, 4H), 7.15 (d, J=6.4 Hz, 2H), 7.04 (s, 1H), 3.82-3.79 (m, 2H), 3.53-3.48 (m, 2H), 2.97-2.90 (m, 2H), 2.41-2.38 (m, 2H).

Example 78

N-(2-amino-phenyl)-4-[4-(1-methyl-4-pyrazin-2-yl-1H-imidazol-2-yl)-tetrahydro-pyran-4-yl]-benzamide (Compound q-02)

Example 78

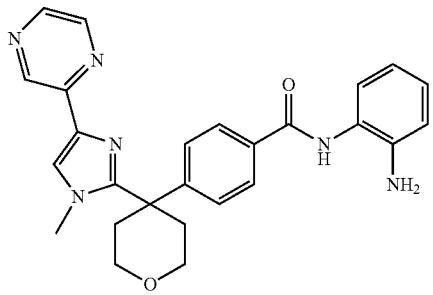

4-(4-Cyano-tetrahydro-pyran-4-yl)-benzoic acid methyl ester (1.0 g, 4.08 mmol) was suspended in 4.0N NaOH and heated at 110° C. for 1 hour. After the reaction was completed, 2N HCl was slowly added to form a precipitate. The precipitate was then filtered, dried under vacuum, and used for next step without purification.

4-(4-carboxy-phenyl)-tetrahydro-pyran-4-carboxylic acid (0.4 g, 1.6 mmol) was dissolved in NMP and then HATU (1.28 g, 2.1 eq) and DIPEA (0.8 mL, 3.0 eq) were added and stirred at 50° C. for 1 hour. The reaction mixture was cooled down to room temperature and benzyl alcohol (172 mg, 1.0 eq) was added. The reaction mixture was stirred at room temperature overnight. A saturated aqueous solution of NaHCO$_3$ was added to the mixture and was then extracted with EtOAc. The organic phase was dried, evaporated and used for next step without further purification.

To a solution of 4-(4-benzyloxycarbonyl-phenyl)-tetrahydro-pyran-4-carboxylic acid (0.3 g, 0.88 mmol) and 2-bromo-1-pyrazin-2-yl-ethanone (210 mg, 1.2 eq) in acetonitrile, TEA (0.18 mL, 1.2 eq) was added and heated in the microwave at 80° C. for 1 hour. The reaction mixture was evaporated and purified by silica gel chromatography (Hex:EtOAc 25:75). 4-(4-benzyloxycarbonyl-phenyl)-tetrahydro-pyran-4-carboxylic acid 2-oxo-2-pyrazin-2-yl-ethyl ester (0.3 g, 0.65 mmol), NH$_4$OAc (110 mg, 2.2 eq) and 3 Å molecular sieves were mixed together in xylene and heated in the microwave at 160° C. for 1 hour. After the reaction was done, it was extracted with EtOAc and the organic phase was dried and evaporated to be used in the next step without further purifications.

4-[4-(4-pyrazin-2-yl-1H-imidazol-2-yl)-tetrahydro-pyran-4-yl]-benzoic acid benzyl ester (168 mg, 0.38 mmol) was dissolved in THF (3 mL). MeI (0.26 mL, 1.1 eq) and NaH (10 mg, 1.1 eq) were added at room temperature under vigorous stirring. After one hour, the mixture was evaporated under vacuum and then extracted in EtOAc. The organic phase was dried and evaporated to be used for next step. Hydrogenation of 4-[4-(1-methyl-4-pyrazin-2-yl-1H-imidazol-2-yl)-tetrahydro-pyran-4-yl]-benzoic acid benzyl ester (0.2 mg, 0.44 mmol) in EtOH was carried out in the presence of excess Pd/C (10%, dry basis) at a pressure of 1 atmosphere. After 16 hours, the reaction mixture was filtered through a celite pad and washed with hot ethanol. The solution was evaporated and used for next step without further purification.

The above acid was then coupled with 1,2-phenylenediamine in the presence of HATU and DIPEA in DMF and purified by reverse phase chromatography to give the title compound. MS found for $C_{26}H_{26}N_6O_2$ as (M+H)$^+$ 455.08 $^1$H NMR (400 MHz, dmso-d$_6$): $^1$H-NMR (DMSO) δ: 10.44 (s, 1H), 9.14 (d, J=1.6 Hz, 1H), 8.54-8.53 (m, 1H), 8.44 (d, J=2.4 Hz, 1H), 8.05 (d, J=8.4 Hz, 2H), 7.82 (s, 1H), 7.47-7.29 (m, 6H), 3.79-3.78 (m, 4H), 3.20 (s, 3H), 2.56-2.20 (m, 4H).

Example 79

N-(2-amino-phenyl)-4-[4-(1-methyl-4-phenyl-1H-imidazol-2-yl)-tetrahydro-pyran-4-yl]-benzamide (Compound q-05)

Example 79

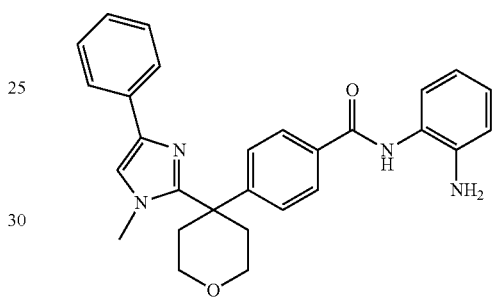

Similar procedure from Example 78 was followed to obtain the title compound using 2-bromo-1-phenyl-ethanone. MS found for $C_{28}H_{28}N_4O_2$ as (M+H)$^+$ 453.17 $^1$H NMR (400 MHz, dmso-d$_6$): $^1$H-NMR (DMSO) δ: 10.49 (s, 1H), 8.11 (d, J=8.4 Hz, 2H), 7.81-7.79 (m, 3H), 7.48-7.25 (m, 9H), 3.74-3.66 (m, 4H), 3.32 (s, 3H), 2.66-2.43 (m, 4H).

Example 80

Biological Assays

HDAC inhibitory activity of the compound of Example 1 was measured by two types of assays in which HDAC 1 and 6 were used as a target molecule. The first assay was carried out without preincubation after addition of the enzyme. The test compound was suspended in and titrated in DMSO. It was then spotted into a 384-well test plate. The enzyme, HDAC 1 or 6, was diluted in assay buffer containing 25 mM Tris-HCl (pH 8.0), 137 mM NaCl, 2.7 mM KCl, and 0.01% Tween-20 and added to the pre-spotted compound. The peptide substrate containing a fluorophore/quencher pair was diluted in the same assay buffer and added to the compound/enzyme mix initiating the reaction. The reaction incubated at room temperature for about 45 minutes. A concentrated developer solution was diluted in the assay buffer, and added to the reaction. The reaction was incubated at room temperature for about 15 minutes and relative fluorescence was read on an instrument reader.

The second assay is similar to the first assay described above, except that preincubation is carried out for about 3 hours after the enzyme is introduced. The test compound was suspended in, and titrated in DMSO. It was then spotted into a 384-well test plate. The enzyme, HDAC 1 or 6, was diluted in the same assay buffer as used in the previous assay and added to the pre-spotted compound. The enzyme/compound mix was incubated at room temperature for about 3 hours. The peptide substrate containing a fluorophore/quencher pair was diluted in the assay buffer and added to the compound/enzyme mix initiating the reaction. The reaction incubated at room temperature for 45 minutes. A concentrated developer solution was diluted in the assay buffer, and added to the reaction. The reaction was incubated at room temperature for about 15 minutes and relative fluorescence was read on an instrument reader.

Table 6 shows $IC_{50}$ data for the compound tested with the protocols described above.

TABLE 6

$IC_{50}$ of HDAC inhibitor compounds

| Compound | HDAC 1 inhibitory activity ($IC_{50}$ [μM]) (3-hour preincubation) |
| --- | --- |
| Example 1 | 0.0239 |
| Example 2 | 0.024 |
| Example 3 | 0.065 |
| Example 4 | 0.331 |
| Example 5 | 0.012 |
| Example 6 | 0.012 |
| Example 7 | 0.008 |
| Example 8 | 0.037 |
| Example 9 | 0.003 |
| Example 10 | 0.279 |
| Example 11 | 0.069 |
| Example 12 | 0.016 |
| Example 15 | 0.119 |
| Example 16 | 0.0988 |
| Example 17 | 0.0982287 |
| Example 18 | 0.0139298 |
| Example 19 | 0.0518244 |
| Example 20 | 0.0189882 |
| Example 21 | 0.006 |
| Example 22 | 0.014 |
| Example 23 | 0.032 |
| Example 24 | 0.013 |
| Example 25 | 0.006 |
| Example 26 | 0.017 |
| Example 27 | 0.019 |
| Example 28 | 0.0026 |
| Example 29 | 0.032 |
| Example 30 | 0.067 |
| Example 31 | 0.001 |
| Example 32 | 0.0025 |
| Example 33 | 0.0029 |
| Example 34 | 0.0066 |
| Example 35 | 0.0033 |
| Example 36 | 0.0029 |
| Example 37 | 0.00388 |
| Example 38 | 0.003112 |
| Example 39 | 0.003326 |
| Example 40 | 0.006387 |
| Example 41 | 0.0070215 |
| Example 42 | 0.0350785 |
| Example 43 | 0.3625015 |
| Example 44 | 0.0070965 |
| Example 45 | 0.0060575 |
| Example 46 | 0.007488 |
| Example 47 | 0.005758 |
| Example 48 | 0.002944 |
| Example 49 | 0.002474 |
| Example 50 | 0.002621 |
| Example 51 | 0.003895 |
| Example 52 | 0.007922 |
| Example 53 | 0.0979 |
| Example 54 | 0.00625 |
| Example 55 | 0.04445 |
| Example 56 | 0.003246 |
| Example 57 | 0.00774 |
| Example 58 | 0.020776 |

TABLE 6-continued $IC_{50}$ of HDAC inhibitor compounds

| Compound | HDAC 1 inhibitory activity ($IC_{50}$ [μM]) (3-hour preincubation) |
| --- | --- |
| Example 59 | 0.002309 |
| Example 60 | 0.006157 |
| Example 61 | 0.002092 |
| Example 62 | 0.00896 |
| Example 63 | 0.004277 |

The results indicate that the compounds have inhibitory activity against HDAC and thus can be useful to treat or inhibit diseases caused by abnormal activities of HDAC.

All patents and publications cited herein are incorporated by reference into this application in their entirety.

What is claimed is:

1. A compound selected from those of Formula (I) or a pharmaceutically acceptable salts thereof:

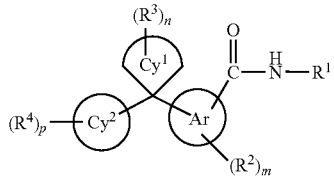

Formula (I)

wherein
$Cy^1$ is heterocycloalkylidene;
$Cy^2$ is thiazol-2-yl;
Ar is phenyl;
m is an integer from 0 to the maximum number of substitutable positions on Ar;
n is an integer from 0 to the maximum number of substitutable positions on $Cy^1$;
p is an integer equal to the number of substitutable positions on $Cy^2$;
$R^1$ is hydroxyl, aryl or heteroaryl, wherein aryl or heteroaryl is substituted with —$NH_2$ or —OH, and aryl or heteroaryl is optionally further substituted with one or more groups selected from amino, halo, cyano, alkyl, alkenyl, alkynyl, haloalkyl, cycloalkyl, heterocyclyl, aryl, haloaryl and haloheterocyclyl, wherein alkyl, alkenyl or alkynyl is optionally further substituted with one or more groups selected from halo, hydroxyl, alkyl, haloalkyl, cycloalkyl, halophenyl, heterocyclyl, and trialkylsilyl;
$R^2$ is independently selected from the group consisting of halo, hydroxyl, oxo, nitro, cyano, trifluoromethyl, trifluoromethoxy, amino, carboxyl, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—($C_{1-10}$ alkyl)amino, N,N—($C_{1-10}$ alkyl)$_2$ amino, $C_{1-10}$ alkanoylamino, N—($C_{1-10}$ alkyl)carbamoyl, N,N—($C_{1-10}$ alkyl)$_2$ carbamoyl, $C_{1-10}$ alkyl-S(O)$_a$ wherein a is 0, 1 or 2, $NH_2$—S(O)$_2$NH—, N—($C_{1-10}$ alkyl)sulphamoyl, N,N—($C_{1-10}$ alkyl)$_2$sulphamoyl, cycloalkyl, heterocyclyl and aryl;
$R^3$ is independently selected from the group consisting of halo, hydroxyl, oxo, nitro, cyano, trifluoromethyl, trifluoromethoxy, amino, carboxyl, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—($C_{1-10}$ alkyl)amino, N,N—($C_{1-10}$ alkyl)$_2$ amino, $C_{1-10}$ alkanoylamino, N—($C_{1-10}$ alkyl)carbamoyl, N,N—($C_{1-10}$ alkyl)$_2$ carbamoyl, $C_{1-10}$ alkyl-S(O)$_a$ wherein a is 0, 1 or 2, NH$_2$—S(O)$_2$NH—, N—($C_{1-10}$ alkyl)sulphamoyl, N,N—($C_{1-10}$ alkyl)$_2$sulphamoyl, cycloalkyl, heterocyclyl and aryl, wherein each $R^3$ is optionally substituted by one or more A; or two groups $R^3$ are substituted on the same carbon ring atom of $Cy^1$ and together with the carbon ring atom of $Cy^1$ form a ring situated on $Cy^1$ in a spiro configuration, wherein the spiro ring is cycloalkyl or heterocycloalkyl; $R^4$ is independently selected from the group consisting of H, halo, nitro, cyano, hydroxyl, oxo, hydroxy($C_{1-10}$ alkyl), amino($C_{1-10}$ alkyl), haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, hydroxy($C_{1-10}$ alkoxy)($C_{1-10}$ alkoxy), ($C_{1-10}$ alkoxy)($C_{1-10}$ alkoxy), ($C_{1-10}$ alkoxy)($C_{1-10}$ alkyl), $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, NH$_2$—S(O)$_2$NH—, NH$_2$—CO—NH—, N—($C_{1-10}$ alkyl)sulphamoyl, N,N—($C_{1-10}$ alkyl)$_2$sulphamoyl, aryl, arylalkyl, aryloxy, arylthio, cycloalkyl, cycloalkylalkyl, cycloalkyloxy, heterocyclyl, heterocyclylalkyl, heterocyclyl(C=O)—, heterocyclyloxy and heterocyclylthio, wherein if $R^4$ is not aryl, cycloalkyl or heterocyclyl, each $R^4$ is optionally substituted by one or more B, and if $R^4$ is aryl, cycloalkyl or heterocyclyl, $R^4$ is optionally further substituted by one or more $R^5$, or when p is 2 or greater, two $R^4$ groups form a 5- or 6-membered cyclic moiety to make a fused ring with $Cy^2$ ring, wherein the cyclic moiety can contain one or more heteroatoms selected from N, O and S and the fused ring is optionally substituted by one or more $R^5$;

$R^5$ is independently selected from halo, nitro, cyano, hydroxyl, oxo, hydroxy($C_{1-10}$ alkyl), amino($C_{1-10}$ alkyl), haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, hydroxy($C_{1-10}$ alkoxy)($C_{1-10}$ alkoxy), ($C_{1-10}$ alkoxy)($C_{1-10}$ alkoxy), ($C_{1-10}$ alkoxy)($C_{1-10}$ alkyl), $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O), wherein a is 0, 1 or 2, $C_{1-10}$ alkoxycarbonyl, NH$_2$—S(O)$_2$NH—, NH$_2$—CO—NH—, N—($C_{1-10}$ alkyl)sulphamoyl, N,N—($C_{1-10}$ alkyl)$_2$sulphamoyl, aryl, arylalkyl, aryloxy, arylthio, cycloalkyl, cycloalkylalkyl, cycloalkyloxy, heterocyclyl, heterocyclylalkyl, heterocyclyl(C=O)—, heterocyclyloxy and heterocyclylthio, wherein each $R^5$ is optionally substituted by one or more D; and A, B and D are independently selected from halo, nitro, cyano, hydroxyl, oxo, hydroxyalkyl, haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, N—($C_{1-10}$ alkyl)sulphamoyl, N,N—($C_{1-10}$ alkyl)$_2$sulphamoyl, H$_2$NS(O)$_2$NH—, N—($C_{1-10}$ alkyl)NHS(O)$_2$NH—, N,N—($C_{1-10}$ alkyl)$_2$NS(O)$_2$NH—, aryl, aryloxy, arylthio, cycloalkyl, cycloalkyloxy, heterocyclyl, heterocyclyl(C=O)—, heterocyclyloxy and heterocyclylthio.

2. The compound or pharmaceutically acceptable salt thereof of claim 1, wherein $R^1$ is hydroxyl, phenyl or 5-membered or 6-membered heteroaryl, wherein phenyl or heteroaryl is substituted with —NH$_2$ or —OH at a ring position adjacent to attachment of the —CONH-moiety, and phenyl or heteroaryl is optionally further substituted with one or more substituent selected from amino, halo, alkyl, alkenyl, alkynyl, haloalkyl, cycloalkyl, heterocyclyl, aryl, haloaryl, and haloheterocyclyl, wherein alkyl, alkenyl, or alkynyl is optionally further substituted with one or more groups selected from halo, hydroxyl, alkyl, haloalkyl and cycloalkyl.

3. The compound or pharmaceutically acceptable salt thereof of claim 1, wherein $Cy^1$ is $C_{3-7}$ heterocycloalkylidene having from 3 to 7 ring members.

4. The compound or pharmaceutically acceptable salt thereof of claim 1 having the structure of Formula (I-a):

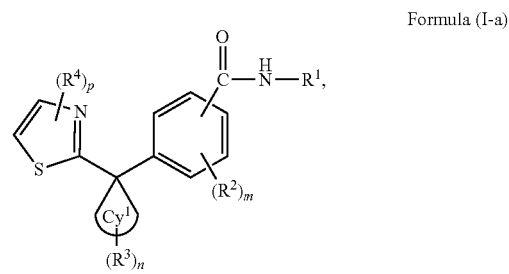

Formula (I-a)

wherein m is 0, 1, 2, 3 or 4;

$Cy^1$ is $C_{3-7}$ heterocycloalkylidene;

$R^1$ is hydroxyl, aryl or heteroaryl, wherein aryl or heteroaryl is substituted with —NH$_2$ or —OH at a ring position adjacent to attachment of the —CONH-moiety, and aryl or heteroaryl is optionally further substituted with one or more substituent selected from amino, halo, cyano, alkyl, alkenyl, alkynyl, haloalkyl, cycloalkyl, heterocyclyl, aryl, haloaryl, and haloheterocyclyl, wherein alkyl, alkenyl, or alkynyl is optionally further substituted with one or more groups selected from halo, hydroxyl, alkyl, haloalkyl, cycloalkyl, halophenyl, heterocyclyl, and trialkylsilyl; and each $R^4$ is independently selected from H, halo, nitro, cyano, hydroxyl, hydroxy($C_{1-10}$ alkyl), haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, NH$_2$—S(O)$_2$ NH—, N—($C_{1-10}$ alkyl)sulphamoyl, N,N—($C_{1-10}$ alkyl)$_2$sulphamoyl, aryl, cycloalkyl and heterocyclyl wherein if $R^4$ is not aryl, cycloalkyl or heterocyclyl, each $R^4$ is optionally substituted by one or more B, and if $R^4$ is aryl, cycloalkyl or heterocyclyl, $R^4$ is optionally further substituted by one or more $R^5$, or when the compound is selected from Formula (I-a) and (I-b), p is 2 and two $R^4$ groups are substituted at positions 4 and 5 of the thiazole ring and form a 5- or 6-membered cyclic moiety to make a fused ring with the thiazole ring, wherein the cyclic moiety can contain one or more heteroatoms selected from N, O and S and the fused ring is optionally substituted by one or more R⁵.

5. The compound or pharmaceutically acceptable salt thereof of claim 4 which has a formula selected from the group consisting of:

Formula (I-a″0)

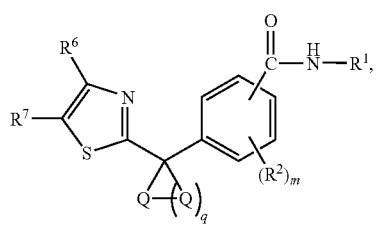

Formula (I-a″1)

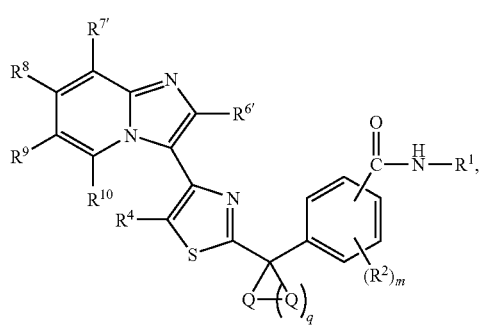

Formula (I-a″2)

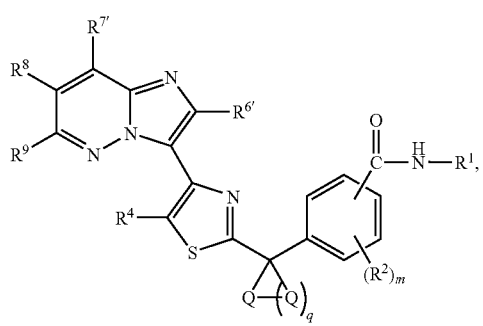

Formula (I-a″3)

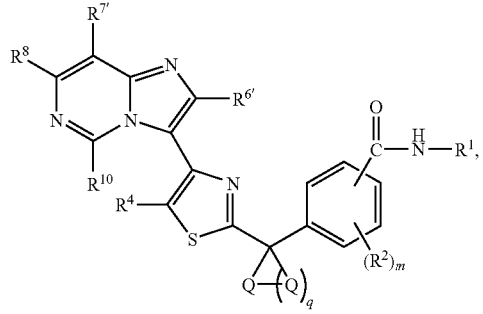

Formula (I-a″4)

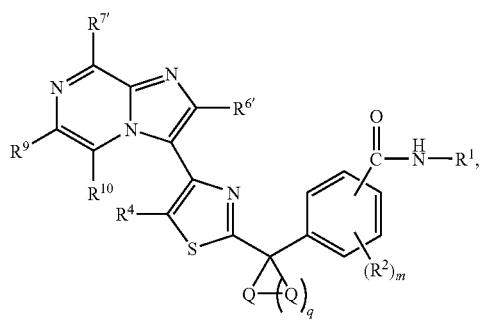

Formula (I-a″5)

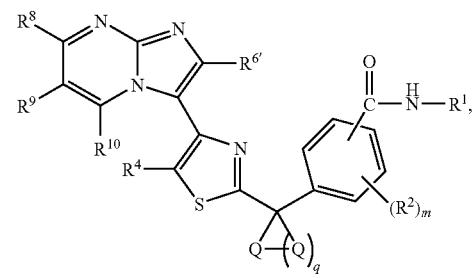

Formula (I-a″6)

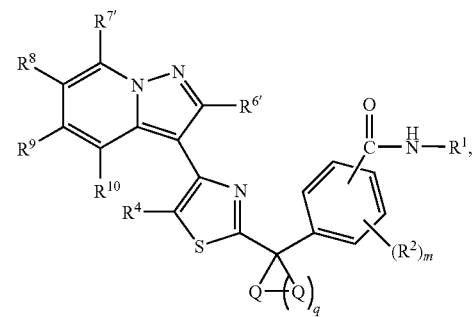

Formula (I-a″7)

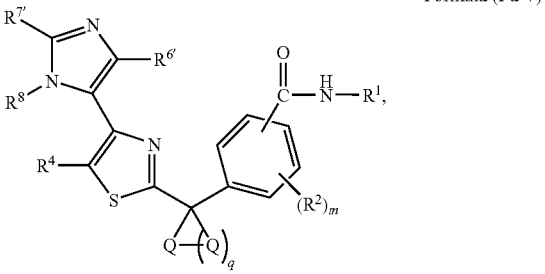

Formula (I-a″8)

Formula (I-a″9)

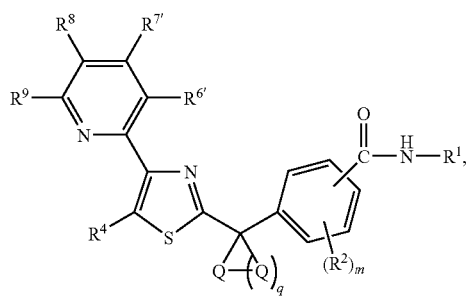

Formula (I-a″10)

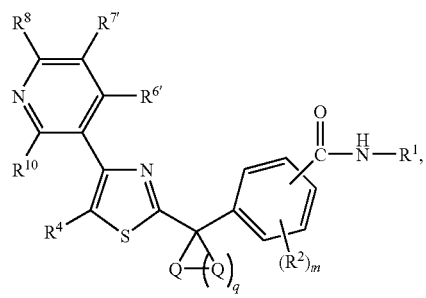

Formula (I-a″11)

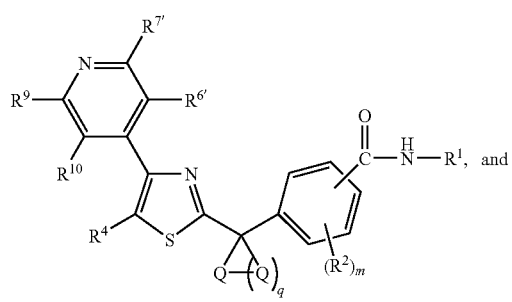

Formula (I-a″12)

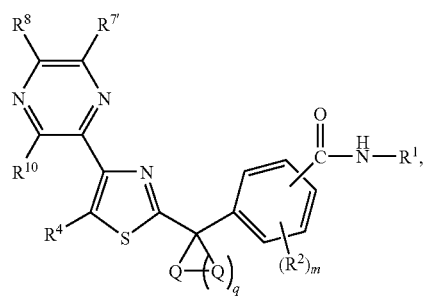

wherein
q is 2, 3, 4, or 5;
Q is a ring atom independently selected from C, N, O, and S, wherein at least one Q is a hetero ring atom selected from N, O and S;
$R^6$ and $R^7$ are independently selected from H, halo, nitro, cyano, hydroxyl, hydroxyalkyl, haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$ carbamoyl, $C_{1-10}$ alkyl-S(O)$_a$ wherein a is 0, 1 or 2, $C_{1-10}$ alkoxycarbonyl, NH$_2$—S(O)$_2$NH—, N—($C_{1-10}$ alkyl)sulphamoyl and N,N—($C_{1-10}$ alkyl)$_2$sulphamoyl, or form a 5- or 6-membered cyclic moiety to make a fused ring with the thiazole ring, wherein the cyclic moiety can contain one or more heteroatoms selected from N, O and S; wherein each $R^6$ and $R^7$ is optionally substituted by one or more B; and $R^{6\prime}$, $R^{7\prime}$, $R^8$, $R^9$ and $R^{10}$ are independently selected from H and the functional groups of $R^5$; wherein each $R^{6\prime}$, $R^{7\prime}$, $R^8$, $R^9$ and $R^{10}$ is optionally substituted by one or more D.

6. The compound or pharmaceutically acceptable salt thereof of claim 5 which is selected from those of Structures (A″0) and (A″10):

Structure (A″0)

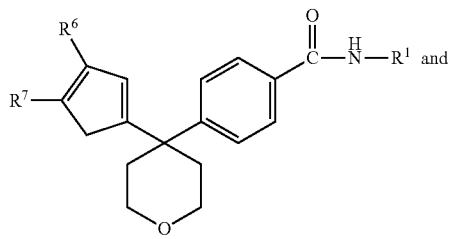

and

Structure (A″10)

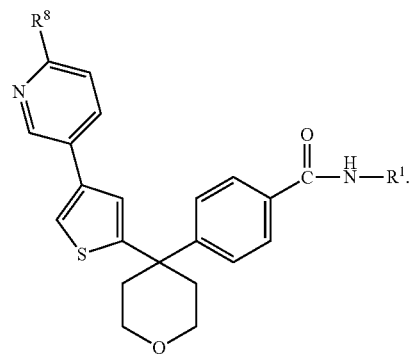

7. The compound of claim 5 which is selected from the group consisting of:
N-hydroxy-4-(4-(4-(imidazo[1,2-a]pyridin-3-yl)thiazol-2-yl)tetrahydropyran-4-yl)benzamide;
N-hydroxy-4-(4-(4-(imidazo[1,2-a]pyridin-3-yl)-5-methylthiazol-2-yl)tetrahydropyran-4-yl)benzamide;
N-(2-aminophenyl)-4-(4-(4-(imidazo[1,2-a]pyridin-3-yl)thiazol-2-yl)tetrahydropyran-4-yl)benzamide;
N-(2-aminophenyl)-4-(4-(4-(imidazo[1,2-a]pyridin-3-yl)-5-methylthiazol-2-yl)tetrahydropyran-4-yl)benzamide;
N-hydroxy-4-(4-(4-(2-methylimidazo[1,2-a]pyridin-3-yl)thiazol-2-yl)tetrahydropyran-4-yl)benzamide;
N-hydroxy-4-(4-(5-methyl-4-(2-methylimidazo[1,2-a]pyridin-3-yl)thiazol-2-yl)tetrahydropyran-4-yl)benzamide;
N-(2-aminophenyl)-4-(4-(4-(2-methylimidazo[1,2-a]pyridin-3-yl)thiazol-2-yl)tetrahydropyran-4-yl)benzamide;
N-(2-aminophenyl)-4-(4-(5-methyl-4-(2-methylimidazo[1,2-a]pyridin-3-yl)thiazol-2-yl)tetrahydropyran-4-yl)benzamide;
4-(4-(4-(6-chloro-2-methylimidazo[1,2-a]pyridin-3-yl)thiazol-2-yl)tetrahydropyran-4-yl)-N-hydroxybenzamide;
N-(2-aminophenyl)-4-(4-(4-(6-chloro-2-methylimidazo[1,2-a]pyridin-3-yl)thiazol-2-yl)tetrahydropyran-4-yl)benzamide;

N-hydroxy-4-(4-(4-(7-methoxy-2-methylimidazo[1,2-a]pyridin-3-yl)thiazol-2-yl)tetrahydropyran-4-yl)benzamide;
N-(2-aminophenyl)-4-(4-(4-(7-methoxy-2-methylimidazo[1,2-a]pyridin-3-yl)thiazol-2-yl)tetrahydropyran-4-yl)benzamide;
4-(4-(4-(7-((dimethylamino)methyl)imidazo[1,2-a]pyridin-3-yl)thiazol-2-yl)tetrahydropyran-4-yl)-N-hydroxybenzamide;
N-(2-aminophenyl)-4-(4-(4-(7-((dimethylamino)methyl)imidazo[1,2-a]pyridin-3-yl)thiazol-2-yl)tetrahydropyran-4-yl)benzamide;
N-hydroxy-4-(4-(4-(7-(pyrrolidin-1-ylmethyl)imidazo[1,2-a]pyridin-3-yl)thiazol-2-yl)tetrahydropyran-4-yl)benzamide;
N-(2-aminophenyl)-4-(4-(4-(7-(pyrrolidin-1-ylmethyl)imidazo[1,2-a]pyridin-3-yl)thiazol-2-yl)tetrahydropyran-4-yl)benzamide;
N-hydroxy-4-(4-(4-(7-(morpholinomethyl)imidazo[1,2-a]pyridin-3-yl)thiazol-2-yl)tetrahydropyran-4-yl)benzamide;
N-(2-aminophenyl)-4-(4-(4-(7-(morpholinomethyl)imidazo[1,2-a]pyridin-3-yl)thiazol-2-yl)tetrahydropyran-4-yl)benzamide;
N-hydroxy-4-(4-(4-(2-methyl-6-(trifluoromethyl)imidazo[1,2-a]pyridin-3-yl)thiazol-2-yl)tetrahydropyran-4-yl)benzamide;
N-(2-aminophenyl)-4-(4-(4-(2-methyl-6-(trifluoromethyl)imidazo[1,2-a]pyridin-3-yl)thiazol-2-yl)tetrahydropyran-4-yl)benzamide;
N-hydroxy-4-(4-(4-(2-methyl-7-(trifluoromethyl)imidazo[1,2-a]pyridin-3-yl)thiazol-2-yl)tetrahydropyran-4-yl)benzamide;
N-(2-aminophenyl)-4-(4-(4-(2-methyl-7-(trifluoromethyl)imidazo[1,2-a]pyridin-3-yl)thiazol-2-yl)tetrahydropyran-4-yl)benzamide;
3-(2-(4-(4-(hydroxycarbamoyl)phenyl)tetrahydropyran-4-yl)thiazol-4-yl)-N-(2-methoxyethyl)-2-methylimidazo[1,2-a]pyridine-7-carboxamide;
3-(2-(4-(4-(2-aminophenylcarbamoyl)phenyl)tetrahydropyran-4-yl)thiazol-4-yl)-N-(2-methoxyethyl)-2-methyl imidazo[1,2-a]pyridine-7-carboxamide;
4-(4-(4-(7-cyano-2-methylimidazo[1,2-a]pyridin-3-yl)thiazol-2-yl)tetrahydropyran-4-yl)-N-hydroxybenzamide;
N-(2-aminophenyl)-4-(4-(4-(7-cyano-2-methylimidazo[1,2-a]pyridin-3-yl)thiazol-2-yl)tetrahydropyran-4-yl)benzamide;
3-(2-(4-(4-(hydroxycarbamoyl)phenyl)tetrahydropyran-4-yl)thiazol-4-yl)-2-methyl-N-(2-morpholinoethyl)imidazo[1,2-a]pyridine-7-carboxamide;
3-(2-(4-(4-(2-aminophenylcarbamoyl)phenyl)tetrahydropyran-4-yl)thiazol-4-yl)-2-methyl-N-(2-morpholinoethyl)imidazo[1,2-a]pyridine-7-carboxamide;
methyl 3-(2-(4-(4-(hydroxycarbamoyl)phenyl)tetrahydropyran-4-yl)thiazol-4-yl)-2-methylimidazo[1,2-a]pyridine-7-carboxylate;
methyl 3-(2-(4-(4-(2-aminophenylcarbamoyl)phenyl)tetrahydropyran-4-yl)thiazol-4-yl)-2-methyl imidazo[1,2-a]pyridine-7-carboxylate;
N-hydroxy-4-(4-(4-(2-methyl-7-(4-methylpiperazine-1-carbonyl)imidazo[1,2-a]pyridin-3-yl)thiazol-2-yl)tetrahydropyran-4-yl)benzamide;
N-(2-aminophenyl)-4-(4-(4-(2-methyl-7-(4-methylpiperazine-1-carbonyl)imidazo[1,2-a]pyridin-3-yl)thiazol-2-yl)tetrahydropyran-4-yl)benzamide;
3-(2-(4-(4-(hydroxycarbamoyl)phenyl)tetrahydropyran-4-yl)thiazol-4-yl)-2-methylimidazo[1,2-a]pyridine-7-carboxylic acid;
3-(2-(4-(4-(2-aminophenylcarbamoyl)phenyl)tetrahydropyran-4-yl)thiazol-4-yl)-2-methylimidazo[1,2-a]pyridine-7-carboxylic acid;
N-hydroxy-4-(4-(4-(2-methyl-7-(2-morpholinoethoxy)imidazo[1,2-a]pyridin-3-yl)thiazol-2-yl)tetrahydropyran-4-yl)benzamide;
N-(2-aminophenyl)-4-(4-(4-(2-methyl-7-(2-morpholinoethoxy)imidazo[1,2-a]pyridin-3-yl)thiazol-2-yl)tetrahydropyran-4-yl)benzamide;
4-(4-(4-(7-(2-(dimethylamino)ethoxy)-2-methylimidazo[1,2-a]pyridin-3-yl)thiazol-2-yl)tetrahydropyran-4-yl)-N-hydroxybenzamide;
N-(2-aminophenyl)-4-(4-(4-(7-(2-(dimethylamino)ethoxy)-2-methylimidazo[1,2-a]pyridin-3-yl)thiazol-2-yl)tetrahydropyran-4-yl)benzamide;
N-hydroxy-4-(4-(4-(7-(2-methoxyethoxy)-2-methylimidazo[1,2-a]pyridin-3-yl)thiazol-2-yl)tetrahydropyran-4-yl)benzamide;
N-(2-aminophenyl)-4-(4-(4-(7-(2-methoxyethoxy)-2-methylimidazo[1,2-a]pyridin-3-yl)thiazol-2-yl)tetrahydropyran-4-yl)benzamide;
4-(4-(4-(7-(2-(dimethylamino)ethylamino)-2-methylimidazo[1,2-a]pyridin-3-yl)thiazol-2-yl)tetrahydropyran-4-yl)-N-hydroxybenzamide;
N-(2-aminophenyl)-4-(4-(4-(7-(2-(dimethylamino)ethylamino)-2-methylimidazo[1,2-a]pyridin-3-yl)thiazol-2-yl)tetrahydropyran-4-yl)benzamide;
3-(2-(4-(4-(hydroxycarbamoyl)phenyl)tetrahydropyran-4-yl)thiazol-4-yl)-N-(2-methoxyethyl)-2-methylimidazo[1,2-a]pyridine-6-carboxamide;
3-(2-(4-(4-(2-aminophenylcarbamoyl)phenyl)tetrahydropyran-4-yl)thiazol-4-yl)-N-(2-methoxyethyl)-2-methylimidazo[1,2-a]pyridine-6-carboxamide;
N-hydroxy-4-(4-(4-(2-methyl-6-(4-methylpiperazine-1-carbonyl)imidazo[1,2-a]pyridin-3-yl)thiazol-2-yl)tetrahydropyran-4-yl)benzamide;
N-(2-aminophenyl)-4-(4-(4-(2-methyl-6-(4-methylpiperazine-1-carbonyl)imidazo[1,2-a]pyridin-3-yl)thiazol-2-yl)tetrahydropyran-4-yl)benzamide;
3-(2-(4-(4-(hydroxycarbamoyl)phenyl)tetrahydropyran-4-yl)thiazol-4-yl)-2-methyl-N-(2-morpholinoethyl)imidazo[1,2-a]pyridine-6-carboxamide;
3-(2-(4-(4-(2-aminophenylcarbamoyl)phenyl)tetrahydropyran-4-yl)thiazol-4-yl)-2-methyl-N-(2-morpholinoethyl)imidazo[1,2-a]pyridine-6-carboxamide;
N-hydroxy-4-(4-(4-(6-(2-methoxyethoxy)-2-methylimidazo[1,2-a]pyridin-3-yl)thiazol-2-yl)tetrahydropyran-4-yl)benzamide;
N-(2-aminophenyl)-4-(4-(4-(6-(2-methoxyethoxy)-2-methylimidazo[1,2-a]pyridin-3-yl)thiazol-2-yl)tetrahydropyran-4-yl)benzamide;
N-hydroxy-4-(4-(4-(6-methoxy-2-methylimidazo[1,2-a]pyridin-3-yl)thiazol-2-yl)tetrahydropyran-4-yl)benzamide;
N-(2-aminophenyl)-4-(4-(4-(6-methoxy-2-methylimidazo[1,2-a]pyridin-3-yl)thiazol-2-yl)tetrahydropyran-4-yl)benzamide;
4-(4-(4-(8-fluoro-2-methylimidazo[1,2-a]pyridin-3-yl)thiazol-2-yl)tetrahydropyran-4-yl)-N-hydroxybenzamide;
N-(2-aminophenyl)-4-(4-(4-(8-fluoro-2-methylimidazo[1,2-a]pyridin-3-yl)thiazol-2-yl)tetrahydropyran-4-yl)benzamide;

4-(4-(4-(7-((dimethylamino)methyl)-2-methyl imidazo[1,2-a]pyridin-3-yl)thiazol-2-yl)tetrahydropyran-4-yl)-N-hydroxybenzamide;

N-(2-aminophenyl)-4-(4-(4-(7-((dimethylamino)methyl)-2-methylimidazo[1,2-a]pyridin-3-yl)thiazol-2-yl)tetrahydropyran-4-yl)benzamide;

4-(4-(4-(6-bromo-2-methylimidazo[1,2-a]pyridin-3-yl)thiazol-2-yl)tetrahydropyran-4-yl)-N-hydroxybenzamide;

N-(2-aminophenyl)-4-(4-(4-(6-bromo-2-methylimidazo[1,2-a]pyridin-3-yl)thiazol-2-yl)tetrahydropyran-4-yl)benzamide;

N-hydroxy-4-(4-(4-(7-methoxy-2-(trifluoromethyl)imidazo[1,2-a]pyridin-3-yl)thiazol-2-yl)tetrahydropyran-4-yl)benzamide;

N-(2-aminophenyl)-4-(4-(4-(7-methoxy-2-(trifluoromethyl)imidazo[1,2-a]pyridin-3-yl)thiazol-2-yl)tetrahydropyran-4-yl)benzamide;

N-(2-Amino-phenyl)-4-[4-(4-pyridin-3-yl-thiazol-2-yl)-tetrahydro-pyran-4-yl]-benzamide;

N-(2-Amino-cyclohexa-1,5-dienyl)-4-(4-(4-thiazol-2-yl-tetrahydro-pyran-4-yl)-benzamide;

N-(2-aminophenyl)-4-(4-(4-(6-chloropyridin-3-yl)thiazol-2-yl)tetrahydropyran-4-yl)benzamide;

N-(2-aminophenyl)-4-(4-(4-(6-(pyrrolidin-1-yl)pyridin-3-yl)thiazol-2-yl)tetrahydropyran-4-yl)benzamide;

N-(2-amino-5-(thiophen-2-yl)phenyl)-4-(4-(5-methyl-4,5,6,7-tetrahydrothiazolo[5,4-c]pyridin-2-yl)tetrahydropyran-4-yl)benzamide;

N-(2-amino-5-(thiophen-2-yl)phenyl)-4-(4-(4-(pyridin-3-yl)thiazol-2-yl)tetrahydropyran-4-yl)benzamide;

N-(2-amino-5-fluorophenyl)-4-(4-(4-(pyridin-3-yl)thiazol-2-yl)tetrahydropyran-4-yl)benzamide;

N-(2-aminophenyl)-4-(4-(4-(6-(2-methoxyethoxy)pyridin-3-yl)thiazol-2-yl)tetrahydropyran-4-yl)benzamide;

N-(2-aminophenyl)-4-(4-(4-(6-(4-methylpiperazin-1-yl)pyridin-3-yl)thiazol-2-yl)tetrahydropyran-4-yl)benzamide;

N-(2-aminophenyl)-4-(4-(6,7-dihydropyrano[4,3-d]thiazol-2-yl)tetrahydropyran-4-yl)benzamide;

4-(4-(5-acetyl-4,5,6,7-tetrahydrothiazolo[5,4-c]pyridin-2-yl)tetrahydropyran-4-yl)-N-(2-aminophenyl)benzamide;

4-(4-(5-acetyl-4,5,6,7-tetrahydrothiazolo[5,4-c]pyridin-2-yl)tetrahydropyran-4-yl)-N-(2-amino-5-(thiophen-2-yl)phenyl)benzamide;

N-(2-aminophenyl)-4-(4-(5-methyl-4,5,6,7-tetrahydrothiazolo[5,4-c]pyridin-2-yl)tetrahydropyran-4-yl)benzamide;

N-(2-amino-5-fluorophenyl)-4-(4-(5-methyl-4,5,6,7-tetrahydrothiazolo[5,4-c]pyridin-2-yl)tetrahydropyran-4-yl)benzamide;

N-(2-amino-5-(thiophen-2-yl)phenyl)-4-(4-(4-(pyrrolidin-1-ylmethyl)thiazol-2-yl)tetrahydropyran-4-yl)benzamide;

N-(2-amino-5-(thiophen-2-yl)phenyl)-4-(4-(4-((2-methoxyethoxy)methyl)thiazol-2-yl)tetrahydropyran-4-yl)benzamide;

N-(2-amino-5-(thiophen-2-yl)phenyl)-4-(4-(4-(morpholinomethyl)thiazol-2-yl)tetrahydropyran-4-yl)benzamide;

N-(2-aminophenyl)-4-(4-(4-(6-(4-cyclopropylpiperazin-1-yl)pyridin-3-yl)thiazol-2-yl)tetrahydropyran-4-yl)benzamide;

N-(2-aminophenyl)-4-(4-(4-(6-(piperazin-1-yl)pyridin-3-yl)thiazol-2-yl)tetrahydropyran-4-yl)benzamide;

N-(4-amino-4'-fluorobiphenyl-3-yl)-4-(4-(thiazol-2-yl)tetrahydropyran-4-yl)benzamide;

N-(2-amino-5-(thiophen-2-yl)phenyl)-4-(4-(4-ethoxythiazol-2-yl)tetrahydropyran-4-yl)benzamide;

N-(4-amino-4'-fluorobiphenyl-3-yl)-4-(4-(4-ethoxythiazol-2-yl)tetrahydropyran-4-yl)benzamide;

N-(2-aminophenyl)-4-(4-(4-(pyrazin-2-yl)thiazol-2-yl)tetrahydropyran-4-yl)benzamide;

N-hydroxy-4-(4-(4-(pyridin-3-yl)thiazol-2-yl)tetrahydropyran-4-yl)benzamide;

N-hydroxy-4-(4-(thiazol-2-yl)tetrahydropyran-4-yl)benzamide;

N-hydroxy-4-(4-(4-(6-(4-methylpiperazin-1-yl)pyridin-3-yl)thiazol-2-yl)tetrahydropyran-4-yl)benzamide;

N-(2-amino-5-(5-chlorothiophen-2-yl)phenyl)-4-(4-(thiazol-2-yl)tetrahydropyran-4-yl)benzamide;

N-(2-amino-5-(5-methylthiophen-2-yl)phenyl)-4-(4-(thiazol-2-yl)tetrahydropyran-4-yl)benzamide;

N-(2-aminophenyl)-4-(4-(4-(4-(4-methylpiperazin-1-yl)phenyl)thiazol-2-yl)tetrahydropyran-4-yl)benzamide;

N-(2-amino-5-(thiophen-2-yl)phenyl)-4-(4-(5-(pyridin-3-yl)thiazol-2-yl)tetrahydropyran-4-yl)benzamide;

N-hydroxy-4-(4-(4-(pyrazin-2-yl)thiazol-2-yl)tetrahydropyran-4-yl)benzamide;

N-(4-amino-4'-fluorobiphenyl-3-yl)-4-(4-(4-(pyrazin-2-yl)thiazol-2-yl)tetrahydropyran-4-yl)benzamide;

N-(2-amino-5-fluorophenyl)-4-(4-(4-(pyrazin-2-yl)thiazol-2-yl)tetrahydropyran-4-yl)benzamide;

N-(4-amino-4'-fluorobiphenyl-3-yl)-4-(4-(5-(1-hydroxyethyl)-4-methylthiazol-2-yl)tetrahydropyran-4-yl)benzamide;

N-(4-amino-4'-fluorobiphenyl-3-yl)-4-(4-(4,5-dimethylthiazol-2-yl)tetrahydropyran-4-yl)benzamide; and N-(4-amino-4'-fluorobiphenyl-3-yl)-4-(4-(5-methylthiazol-2-yl)tetrahydropyran-4-yl)benzamide; or a pharmaceutically acceptable salts thereof.

8. A pharmaceutical composition comprising an effective amount of one or more compounds according to claim 1 and a pharmaceutically-acceptable carrier.

9. The pharmaceutical composition according to claim 8, further comprising one or more anti-cancer agents selected from the group consisting of cyclophosphamide, dacarbazine, cisplatin, methotrexate, mercaptopurine, thioguanine, fluorouracil, cytarabine, vinblastine, paclitaxel, doxorubicin, bleomycin, mitomycin, prednisone, tamoxifen, flutamide, asparaginase, rituximab, trastuzumab, imatinib, retinoic acid, colony-stimulating factor, amifostine, lenalidomide, HDAC inhibitor, CDK inhibitor, camptothecin and topotecan.

* * * * *